United States Patent [19]

Hansen, Jr. et al.

[11] Patent Number: 6,011,028

[45] Date of Patent: Jan. 4, 2000

[54] CYCLIC AMIDINO AGENTS USEFUL AS NITRIC OXIDE SYNTHASE INHIBITORS

[75] Inventors: Donald W. Hansen, Jr., Skokie; E. Ann. Hallinan, Evanston; Timothy J. Hagen, Gurnee; Steven W. Kramer, Des Plaines, all of Ill.; Suzanne Metz, Chesterfield, Mo.; Karen B. Peterson, Vernon Hills; Dale P. Spangler, Deerfield, both of Ill.; Mihaly V. Toth; Kam F. Fok, both of St. Louis, Mo.; Arija A. Bergmanis, Des Plaines, Ill.; R. Keith Webber, St. Peters, Mo.; Mahima Trivedi, Glenview, Ill.; Foe S. Tjoeng, Manchester, Mo.; Barnett S. Pitzele, Skokie, Ill.

[73] Assignee: G.D. Searle & Co., Chicago, Ill.

[21] Appl. No.: 08/913,838

[22] PCT Filed: Apr. 19, 1996

[86] PCT No.: PCT/US96/05315

§ 371 Date: Mar. 27, 1998

§ 102(e) Date: Mar. 27, 1998

[87] PCT Pub. No.: WO96/33175

PCT Pub. Date: Oct. 24, 1996

Related U.S. Application Data

[63] Continuation-in-part of application No. 08/425,831, Apr. 20, 1995, abandoned.

[51] Int. Cl.$^7$ ...................... C07D 267/06; C07D 281/02; A61K 31/33; A61K 31/395

[52] U.S. Cl. .................. 514/184; 514/183; 514/188; 514/218; 514/222.2; 514/226.8; 514/228.8; 514/247; 514/227.5; 546/22; 546/184; 548/215; 548/300.1; 548/400; 548/412; 540/467; 540/470; 540/480; 540/544; 540/596; 540/598; 540/602; 540/606

[58] Field of Search ...................... 540/605, 604, 540/602, 603, 470, 480–482; 514/212, 183, 210, 211, 218, 227.2, 228.2, 256

[56] References Cited

U.S. PATENT DOCUMENTS 5,854,234  12/1998  Hansen, Jr. et al. .................... 540/605

*Primary Examiner*—Mukund J. Shah
*Assistant Examiner*—Pavanaram K Sripada
*Attorney, Agent, or Firm*—Alan L. Scrivner; Dennis A. Bennet

[57] ABSTRACT

The current invention discloses useful amidino derivative useful as nitric oxide synthase inhibitors.

24 Claims, No Drawings

CYCLIC AMIDINO AGENTS USEFUL AS NITRIC OXIDE SYNTHASE INHIBITORS

This application is a 371 of PCT/US96/05315 Apr. 19, 1996 and a CIP of U.S. Ser. No. 08/425,831 filed Apr. 20, 1995 now abandoned, contents of which are herein incorporated by reference.

FIELD OF THE INVENTION

The present invention relates to amidino derivative compounds, pharmaceutical compositions containing these novel compounds, and to their use in therapy, in particular their use as nitric oxide synthase inhibitors.

BACKGROUND OF THE INVENTION

It has been known since the early 1980's that the vascular relaxation brought about by acetycholine is dependent on the presence of the endothelium and this activity was ascribed to a labile humoral factor termed endothelium-derived relaxing factor (EDRF). The activity of nitric oxide (NO) as a vasodilator has been known for well over 100 years and NO is the active component of amylnitrite, glyceryltrinitrite and other nitrovasoadaaors. The recent identification of EDRF as NO has coincided with the discovery of a biochemical pathway by which NO is synthesized from the amino acid L-arginine by the enzyme NO synthase.

NO is the endogenous stimulator of the soluble guanylate cyclase and is involved in a number of biological actions in addition to endothelium-dependent relaxation including cytotoxicity of phagocytic cells and cell-to-cell communication in the central nervous system (see Moncada et al. *Biochemical Pharmacology.* 38, 1709–1715 (1989) and Moncada et al. *Pharmacological Reviews.* 43, 109–142 (1991). It is now thought that excess NO production may be involved in a number of conditions, particularly conditions which involve systemic hypotension such as toxic shock and therapy with certain cytokines.

The synthesis of NO from L-arginine can be inhibited by the L-arginine analogue, L-N-monomethyl-arginine (L-NMMA) and the therapeutic use of L-NMMA for the treatment of toxic shock and other types of systemic hypotension has been proposed (WO 91/04024 and GB-A-2240041). The therapeutic use of certain other NO synthase inhibitors apart from L-NMMA for the same purpose has also been proposed in WO 91/04024 and EP-A-0446099.

It has recently become apparent that there are at least three types of NO synthase as follows:

(i) a constitutive, $Ca^{++}$/calmodulin dependent enzyme, located in the endothelium, that releases NO in response to receptor or physical stimulation.

(ii) a constitutive, $Ca^{++}$/calmodulin dependent enzyme, located in the brain, that releases NO in response to receptor or physical stimulation.

(iii) a $Ca^{++}$ independent enzyme which is induced after activation of vascular smooth muscle, macrophages, endothelial cells, and a number of other cells by endotoxin and cytokines. Once expressed this inducible NO synthase synthesizes NO for long periods.

The NO released by the constitutive enzymes acts as a transduction mechanism underlying several physiological responses. The NO produced by the inducible enzyme is a cytotoxic molecule for tumor cells and invading microorganisms. It also appears that the adverse effects of excess NO production, in particular pathological vasodilation and tissue damage, may result largely form the effect of NO synthesized by the inducible NO synthase.

There is also a growing body of evidence that NO may be involved in the degeneration of cartilage which takes place in certain conditions such as arthritis and it is also known that NO synthesis is increased in rheumatoid arthritis. Accordingly, further conditions in which there is an advantage in inhibiting NO production from L-arginine include autoimmune and/or inflammatory conditions affecting the joints, for example arthritis, inflammatory bowel disease, cardiovascular ischemia, diabetes, hyperalgesia (allodynia), cerebral ischemia (both focal ischemia, thrombotic stroke and global ischemia, secondary to cardiac arrest), and other CNS disorders mediated by NO.

Further conditions in which there is an advantage in inhibiting NO production from L-arginine include systemic hypotension associated with septic and/or toxic shock induced by a wide variety of agents; therapy with cytokines such as TNF, IL-1 and IL-2; and as an adjuvant to short term immunosuppression in transciant therapy. Further conditions in which there is an advantage in inhibiting NO production from L-arginine include autoimmune diseases and/or inflammatory conditions such as those affecting the joints, for example arthritis or ARDS or inflammatory bowel disease, or asthma, cardiovascular ischemia, congestive heart failure, mycoarditits, artherosclerosis, migraine, reflux esophagitis, diarrhea, irritable bowel syndrome, cystic fibrosis, emphysema, diabetes, hyperalgesia (allodynia) cerebral ischmeia (both focal ischemia, thrombotic stroke and global ischemia, secondary to cardiac arrest) and other CNS disorders mediated by NO, including opiate tolerance in patients needing protracted opiate analgesics, benzodiazepine tolerance in patients taking benzodiazepines, an other addictive behaviors for example nicotine and eating disorder.

Some of the NO synthase inhibitors proposed for therapeutic use so far, and in particular L-NMMA, are non-selective in that they inhibit both the constitutive and the inducible NO synthase. Use of such a non-selective NO synthase inhibitor requires that great care be taken in order to avoid the potentially serious consequences of over-inhibition of the constitutive NO-synthase including hypertension and possible thrombosis and tissue damage. In particular, in the case of the therapeutic use of L-NMMA for the treatment of toxic shock it has been recommended that the patient must be subject to continuous blood pressure monitoring throughout the treatment. Thus, while non-selective NO synthase inhibitors have therapeutic utility provided that appropriate precautions are taken, NO synthase inhibitors which are selective in the sense that they inhibit the inducible NO synthase to a considerably greater extent than the constitutive isoforms of NO synthase would be of even greater therapeutic benefit and easier to use.

WO94/12165, WO94/14780, WO93/13055, EPO440699A1 and U.S. Pat. No. 5,132,453 disclose compounds that inhibit nitric oxide synthesis and preferentially inhibit the inducible isoform of nitric oxide synthase. The disclosures of which are hereby incorporated by reference in their entirety as if written herein.

SUMMARY OF THE INVENTION

In accordance with the present invention novel amidino derivatives are provided. These novel inhibitor compounds can be represented by the following chemical formula (I):

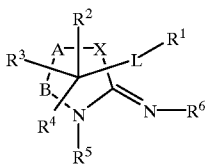
(I)

$R^1$ is selected from the group consisting of cycloalkyl, heterocycolyl, aryl, and heteroaryl which may optionally be substituted by one or more of the following: lower alkyl, lower alkenyl, lower alkynyl, hydroxy, lower alkoxy, thiol, lower thioalkoxy, $S(O)R^9$, $S(O)_2R^9$, halogen, nitro, amino, alkylamino, dialkylamino, aminoalkyl, dialkylaminoalkyl, arylamino, aminoaryl, alkylaminoaryl, acylamino, carboxyl, carboalkoxy, carboaryloxy, carboarylalkyloxy cyano, aminocarbonylalkoxy, aminocarbonylamino, aminocarbonylaminoalkyl, haloalkyl, $SO_2NR^7R^9$, wherein all said substitutions may be optionally substituted with one or more of the following: halogen, lower alkyl, amino, alkylamino, dialkylamino, aminoalkyl, aminoacyl, carboxyl, carboalkoxy, carboaryloxy, carboalkylaryloxy, hydroxy, lower alkoxy;

L is selected from the group consisting of lower alkylene, lower alkenylene, lower alkenylene, and —$(CH_2)_m$—D—$(CH_2)_n$—;

D is selected from the group consisting of O, S, SO, $SO_2$, $SO_2NR^7$, $NR^7SO_2$, $NR^8$, $POOR^7$, $PON(R^7)_2$, $POOR^7NR^7$, $NR^7POOR^7$, C(O), C(O)O:

$R^7$ is hydrogen, lower alkyl, or aryl;

$R^8$ is hydrogen, lower alkyl, $COR^9$, or $CO_2R^9$;

$R^9$ is lower alkyl, or aryl;

m=0 to about 7;

n=0 to about 5;

wherein L may optionally be substituted by one or more of the following lower alkyl, lower alkenyl: lower alkynyl, hydroxy, lower alkoxy, thiol, lower thioalkoxy, $S(O)R^9$, $S(O)_2R^9$, halogen, nitro, amino, alkylamino, dialkylamino, aminoalkyl, dialkylaminoalkyl, arylamino, aminoaryl, alkylaminoaryl, acylamino, carboxyl, carboalkoxy, carboaryloxy, carboarylalkyloxy, cyano, aminocarbonylalkoxy, aminocarbonylamino, aminocarbonylaminoalkyl, haloalkyl, $SO_2NR^7R^9$, cycloalkyl, heterocyclyl, aryl, heteroaryl, lactonyl, lactamyl, amidino, isourea, isothiourea, guanidino, substituted guanidino, wherein all said substitutions may be optionally substituted with one or more of the following: lower alkyl, amino, alkylamino, dialkylamino, aminoalkyl, aminoacyl, carboxyl, carboalkoxy, carboaryloxy, carboalkylaryloxy, hydroxy, lower alkoxy, nitro, amidino, guandino, substituted guanidino and X is selected from the group consisting of NH, O, S, $(CH_2)_p$, and CH=CH;

p=0 to about 4;

A is selected from the group consisting of $(CH_2)_q$, CH=CH;

q=1 to about 2;

B is selected from the group consisting of $(CH_2)_v$, CH=CH;

v=1 to about 2;

$R^2$, $R^3$, and $R^4$ are independently selected from hydrogen, lower alkyl, lower alkenyl, lower alkynyl, hydroxy, lower alkoxy, thiol, lower thioalkoxy, $S(O)R^9$, $S(O)_2R^9$, halogen, nitro, amino, alkylamino, dialkylamino, aminoalkyl, dialkylaminoalkyl, arylamino, aminoaryl, alkylaminoaryl, acylamino, carboxyl, carboalkoxy, carboaryloxy, carboarylalkyloxy, cyano, aminocarbonylalkoxy, aminocarbonylamino, aminocarbonylaminoalkyl, haloalkyl, $SO_2NR^7R^9$, wherein all said substitutions may be optionally substituted with one or more of the following: halogen, lower alkyl, amino, alkylamino, dialkylamino, aminoalkyl, aminoacyl, carboxyl, carboalkoxy, carboaryloxy, carboalkylaryloxy, hydroxy, lower alkoxy, and and $R^2$, $R^3$, may optionally be taken together to form an exocyclic double bond, alicyclic hydrocarbon, heterocyclyl or aromatic hydrocarbon and said optionally formed unit may be optionally substituted with one or more of the following:

lower alkyl, lower alkenyl, lower alkynyl which may be optionally substituted with carboxyl, carboalkoxy, carboaryloxy, carboxyalkylaryloxy and lower alkoxy; and $R^5$, $R^6$ are independently selected from the group consisting of hydrogen, hydroxy, and alkyloxy.

In another broad aspect, the present invention is directed to inhibiting nitric oxide synthesis in a subject in need of such inhibition or treatment by administering a compound of Formula (I) which preferentially inhibits the inducible isoform of nitric oxide synthase over the constitutive isoform of nitric oxide synthase, in a nitric oxide synthesis inhibiting amount to such subject.

The invention further relates to a pharmaceutical composition comprising a compound from Formula (I).

Compounds and compositions defined above have usefulness as inhibitors of nitric oxide synthase. These compounds also preferentially inhibit the inducible form.

Conditions in which there is an advantage in inhibiting NO production from L-arginine in disorders mediated by nitric oxide including amongst others, systemic hypotension associated with septic and/or toxic shock induced by a wide variety of agents; therapy with cytokines such as TNF, IL-1 and IL-2; and as an adjuvant to short term immunosuppression in transplant therapy. Further conditions in which there is an advantage in inhibiting NO production from L-arginine include autoimmune diseases and/or inflammatory conditions such as those affecting the joints, For example arthritis or inflammatory bowel disease, cardiovascular ischemia, diabetes, congestive heart failure, mycoarditits, artherosclerosis, migraine, reflux esophagitis, diarrhea, irritable bowel syndrome, cystic fibrosis, emphysema, hyperalgesia (allodynia) cerebral ischemia (both focal ischemia, thrombotic stroke and global ischemia, secondary to cardiac arrest) and other CNS disorder mediated by NO, including opiate tolerance in patients needing protracted opiate analgesics, benzodiazepine tolerance in patients taking benzodiazepines, and other addictive behaviors for example nicotine and eating disorder.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable salts may be of utility in the preparation and purification of the compound in question. Thus, preferred salts include those formed from hydrochloric, hydrobromic, sulfuric, citric, tartaric, phosphoric, lactic, acetic, succinic, fumaric, maleic, methanesulfonic, ethanesulfonic, p-toluenesulfonic, benzenesulfonic and the like. (See, for example, S. M. Berge et al., Pharmaceutical Salts, *J. Pharm. Sci.*, 1977, 66, 1–19.) Salts of the compounds of formula (I) can be made by reacting the appropriate compound in the form of the free base with the appropriate acid.

While it may be possible for the compounds of formula (I) to be administered as the raw chemical, it is preferable to present them as a pharmaceutical formulation. According to a further aspect, the present invention provides a pharmaceutical formulation comprising a compound of formula (I) or a pharmaceutically acceptable salt or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine she active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be store: in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Formulations for administration by inhalation can be prepared for use as an aerolized medicaments such as in a manner recited in U.S. Pat. No. 5,458,135 and U.S. Pat. No. 5,447,150.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.001 to 2500 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The compounds of formula (I) are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

As utilized herein, the term "lower alkyl", alone or in combination, means an acyclic alkyl radical containing from 1 to about 10, preferably from 1 to about 8 carbon atoms and more preferably 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "lower alkenyl" refers to an unsaturated acyclic hydrocarbon radical in so much as it contains at least one double bond. Such radicals containing from about 2 to about 10 carbon atoms, preferably from about 2 to about 8 carbon atoms and more preferably 2 to about 6 carbon atoms. Examples of suitable alkenyl radicals include propylenyl, buten-1-yl, isobutenyl, penzenylen-1-yl, 2-2-methylbuten-1-yl, 3-methylbuten-1-yl, hexen-1-yl, hepten-1-yl, and octen-1-yl, and the like.

The term "lower alkynyl" refers to an unsaturated acyclic hydrocarbon radical in so much as it contains one or more triple bonds, such radicals containing about 2 to about 10 carbon atoms, preferably having from about 2 to about 8 carbon atoms and more preferably having 2 to about 6 carbon atoms. Examples of suitable alkynyl radicals include ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "alicyclic hydrocarbon" or "cycloalkyl" means a aliphatic radical in a ring with 3 to about 10 carbon atoms, and preferably from 3 to about 6 carbon atoms. Examples of suitable alicyclic radicals include cyclopropyl, cyclobutyl, cyclopentyl, cyclohexyl, cyclohexenyl and the like.

The term "aromatic hydrocarbon radical" means 4 to about 16 carbon atoms, preferably 6 to about 12 carbon atoms, more preferably 6 to about 10 carbon atoms. Examples of suitable aromatic hydrocarbon radicals include phenyl,nachthyl, and the like.

The term "aryl" as used herein means 5- and 6-membered single-aromatic radicals which may include from zero to four heteroatoms. Representative aryls include phenyl, thienyl, furanyl, pyridinyl, (is)oxazoyl and the like.

The term DCM means dichloromethane.

The term DEAD means diethyl azodicarboxylate.

The term DIBAL-H means diisobutylaluminum hydride.

The term DMAP means dimethylaminopyridine.

The term DMSO means dimethylsulfoxide.

The term EDC means 1-(3-dimethylaminopropyl)-3-ethylcarbodiimide hydrochloride.

The term "heterocyclyl radical" means a saturated or unsaturated cyclic hydrocarbon radical including aromatic systems with 4 to about 10 carbon atoms, preferably about 5 to about 6; wherein 1 to about 4 carbon atoms are replaced by nitrogen, oxygen, sulfur, or carbonyl. The "heterocyclic radical" may be fused to an aromatic hydrocarbon radical. Suitable examples include pyrrolyl, pyridinyl, pyrazolyl, triazolyl, pyrimidinyl, pyridazinyl, oxazolyl, isoxazolyl, thiazolyl, imidazolyl, indolyl, thienyl, furanyl, tetrazolyl, 2-pyrrolinyl, 3-pyrrolinyl, pyrrolindinyl, 1,3-dioxolanyl, 2-imidazolinyl, imidazolidinyl, 2-pyrazolinyl, pyrazolidinyl, isoxazolinyl, isothiazolyl, oxadiazolyl, triazolyl, thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, triazinyl, 1,3,5-trithianyl, benzo(b)thiophenyl, benzimidazolyl, uinolinyl, and the like.

The term HOBT means N-hydroxybenzotriazole.

The term "lower alkoxy", alone or in combination, means an alkyl ether radical wherein the term alkyl is as defined above and most preferably containing 1 to about 4 carbon atoms. Examples of suitable alkyl ether radicals include methoxy, ethoxy, n-propoxy, isopropcoxy, n-bntoxy, iso-butoxy, sec-butoxy, tert-butoxy and the like.

The term "lower thioalkoxy", alone or in combination, means an alkyl thioether radical wherein the term alkyl is as defined above and most preferably containing 1 to about 4 carbon atoms. Examples of suitable alkyl thioether radicals include thiomethoxy, thioethoxy, thio-n-propcoxy, thio-i-propoxy, thio-n-butoxy, thio-iso-butoxy, thio-sec-butoxy, thio-ter-butoxy and the like.

The term alkoxycarbonyl as used herein means an alkoxy group, as defined above, having a carbonyl (C=O) group attached.

The term "halogen" means fluorine, chlorine, bromine or iodine.

The term mcpba means m-chloroperbenzoic acid.

The term NMM means N-methylmorpholine.

The term NMMO means 4-methylmorpholine N-oxide.

The term "prodrug" refers to a compound that is made more active in vivo.

The term sulfinyl means SO.

The term sulfonyl means $SO_2O$.

The term TEA means triethylamine.

The term $TMSN_3$ means azidotrimethylsilane.

As used herein, reference to "treatment" of a patient is intended to include prophylaxis.

All references, patents or applications, U.S. or foreign, cited in the application are hereby incorporated by reference as if written herein.

Compounds of the present invention can exist in geometric or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof, as falling within the scope of the invention.

Disclosed are nineteen general synthetic processes useful in the preparation of the compounds of the present invention.

Scheme 1:

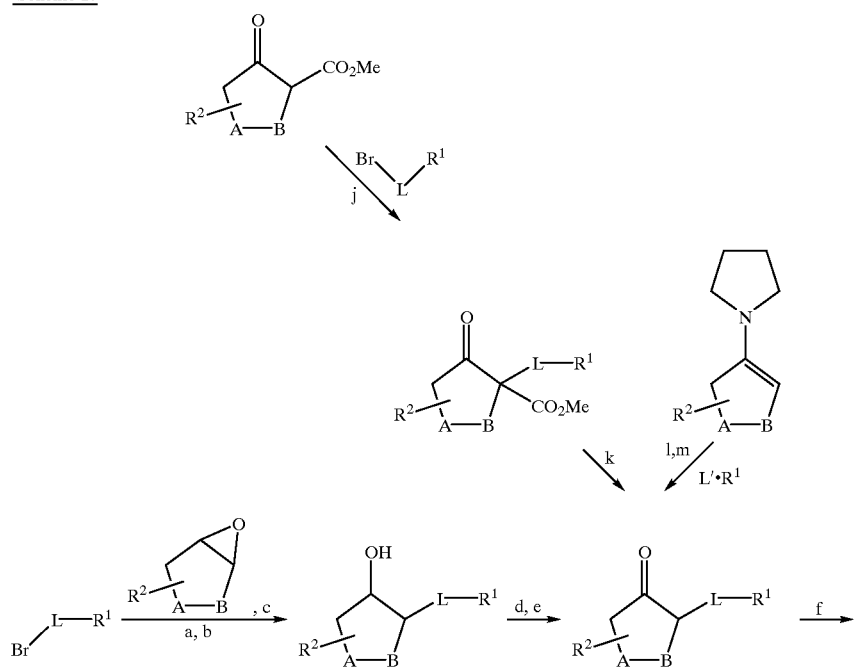

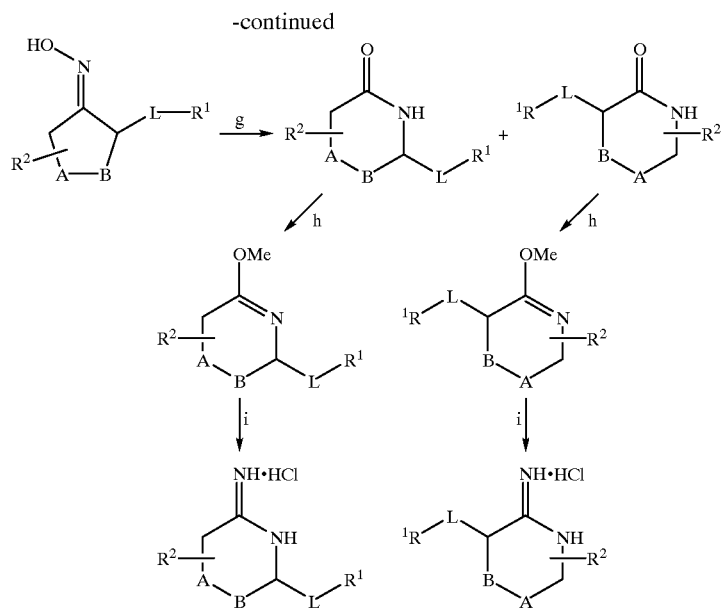
a) Mg, THF;
b) CuI, -30° C.;
c) -30° C. to 0° C. or r.t.;
d) DMSO, oxalyl chloride, CH$_2$Cl$_2$, -70° C.;
e) Et$_3$N, -70° C. to 0° C.;
f) NH$_2$OH, NaOAc, EtOH;
g) PhSO$_2$Cl, NaOH, H$_2$O, acetone [followed by resolution and or H$_2$, Pd/C reduction where R$^1$ = phenyl];
h) Me$_3$O$^+$BF$_4^-$;
i) NH$_4$Cl;
j) K$_2$CO$_3$ or NaH, DMF;
k) NaCN DMSO, H$_2$O, heat;
l) DMF, L-R$^1$ (where L'-R$^1$ is CH$_2$=CHCO—R$^1$);
m) 1N LiOH, MeOH.
Scheme 2:
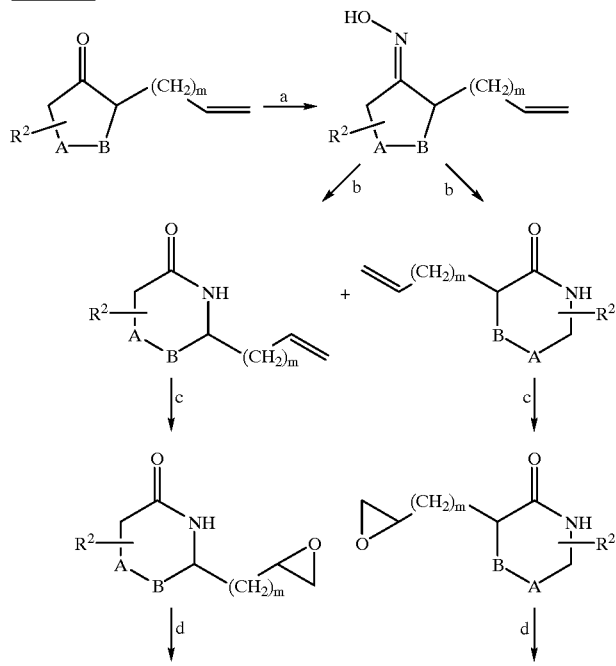

-continued
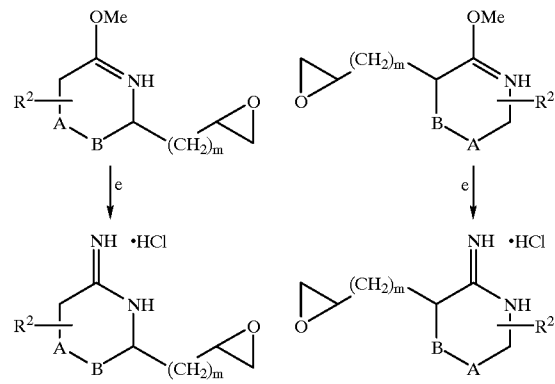
a) NH₂OH, NaOAc, EtOH;
b) PhSO₂Cl, NaOH, H₂O, acetone;
c) m-chloroperbenzoic acid, CH₂Cl₂;
d) Me₃O⁺BF₄⁻, CH₂Cl₂;
e) NH₄Cl, MeOH.
Scheme 3:
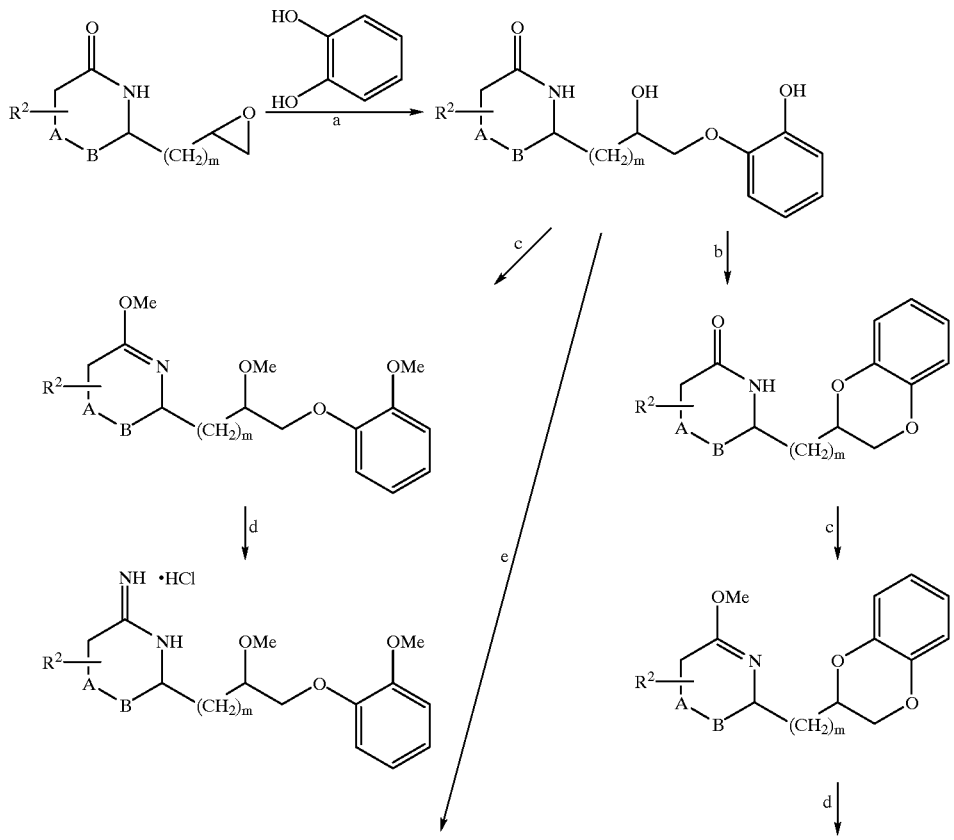

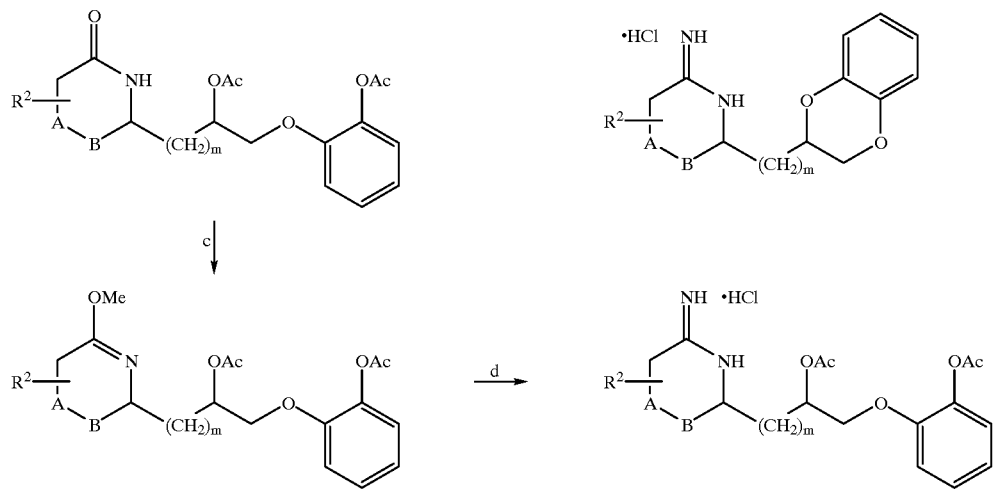
a) NaH, DMF;
b) Ph₃P, diethylazodicarboxylate (DEAD), THF;
c) Me₃O⁺BF₄⁻, CH₂Cl₂;
d) NH₄Cl, MeOH;
e) acetic anhydride, pyridine.
Scheme 4:
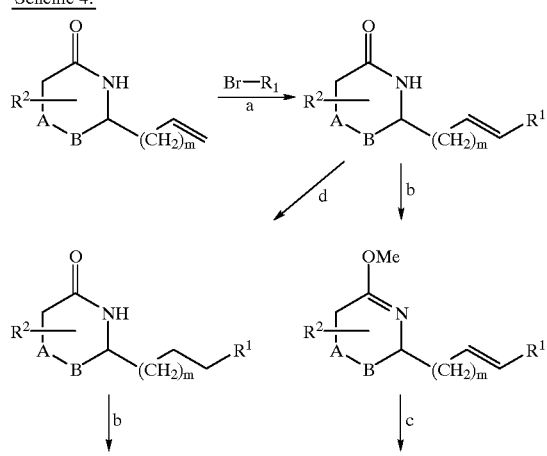
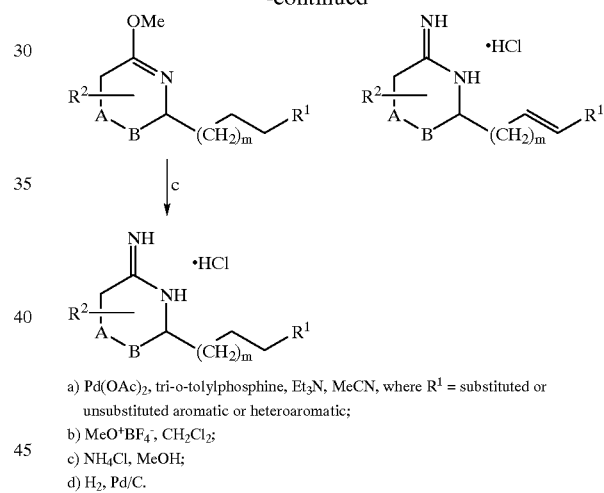
a) Pd(OAc)₂, tri-o-tolylphosphine, Et₃N, MeCN, where R¹ = substituted or unsubstituted aromatic or heteroaromatic;
b) MeO⁺BF₄⁻, CH₂Cl₂;
c) NH₄Cl, MeOH;
d) H₂, Pd/C.
Scheme 5:
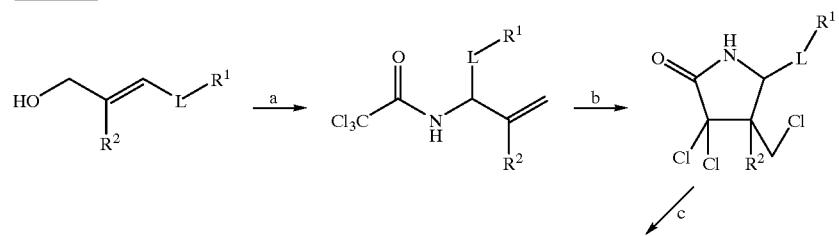

-continued
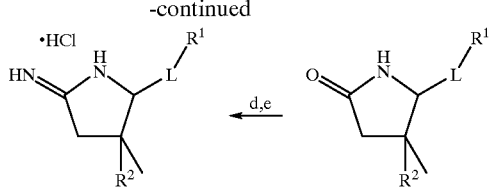
a) Cl$_3$CN, NaH, xylene, D;
b) Ru catalyst;
c) Bu$_3$SNH;
d) Me$_3$O$^+$BF$_4^-$, CH$_2$Cl$_2$;
e) NH$_4$Cl, MeOH.
Scheme 6:
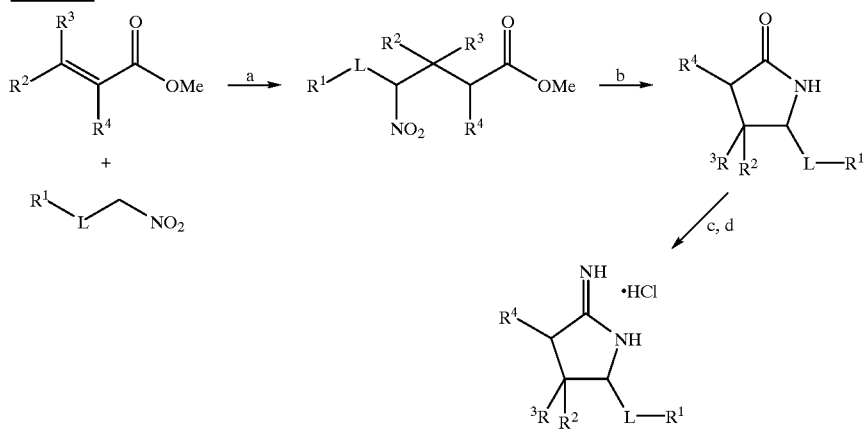
a) Base;
b) H$_2$/RaNi, 55° C.;
c) Me$_3$O$^+$BF$_4^-$, CH$_2$Cl$_2$;
d) NH$_4$Cl, MeOH
Scheme 7:
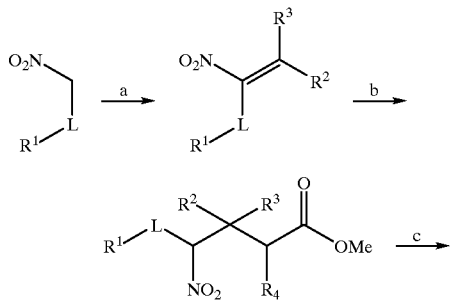
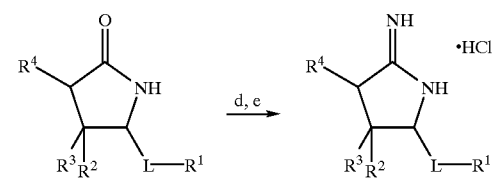
a) R$^2$COR$^3$;
b) Base, R$^4$CH$_2$CO$_2$Me;
c) H$_2$/RaNi, 55° C.;
d) Me$_3$O$^+$BF$_4^-$;
e) NH$_4$Cl Scheme 8:
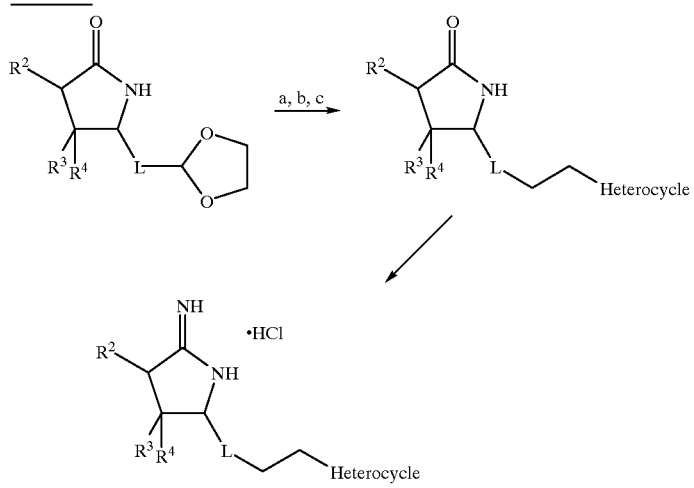
a) HCl;
b) Zn/BrCH$_2$Heterocycle;
c) Et$_3$SiH;
d) Me$_3$O$^+$BF$_4^-$;
e) NH$_4$Cl, MeOH
Scheme 9:
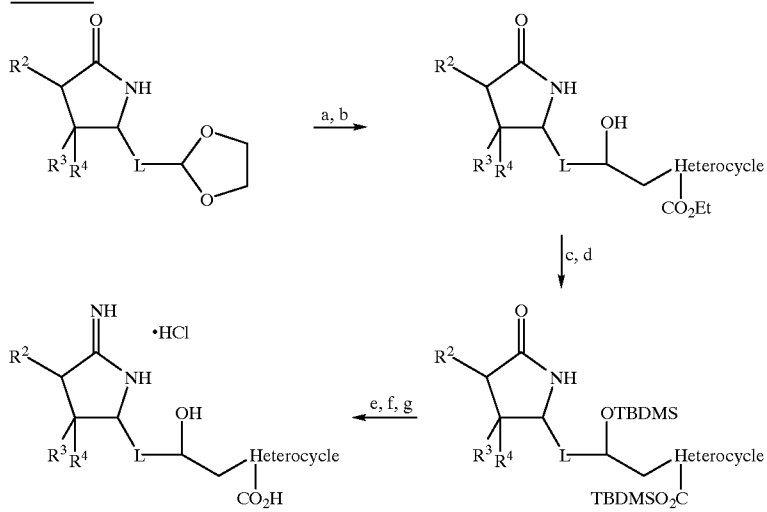
a) HCl;
b) Zn/BrCH$_2$Heterocycle-CO$_2$Et;
c) NaOH, MeOH;
d) t-butyldimethylsilyl chloride (TBDMSCl);
e) Me$_3$O$^+$BF$_4^-$, CH$_2$Cl$_2$;
f) NH$_4$Cl, MeOH;
g) HCl.

Scheme 10:
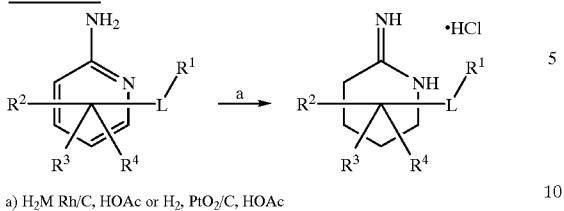
a) H₂M Rh/C, HOAc or H₂, PtO₂/C, HOAc
Scheme 11:
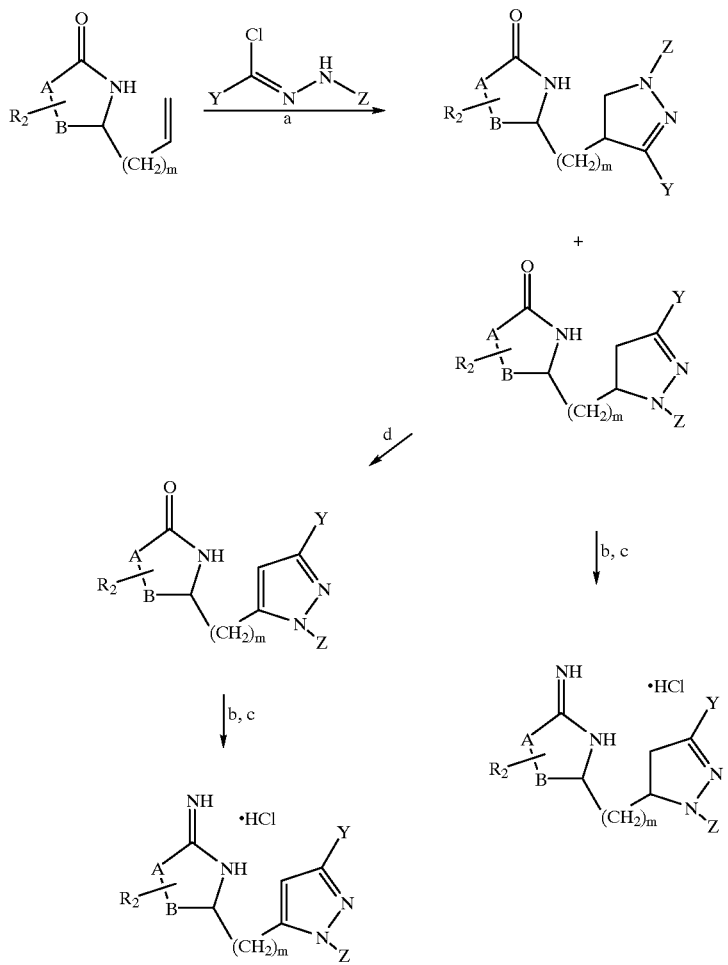
Y = Aryl, CF₃, alkoxycarbonyl
Z = 5-membered ring heterocycle (containing 1-4 N, and/or O, and/or S), phenyl or pyridyl substituted with 1-3 groups defined such as: CO₂H, alkoxycarbonyl, SO₂NH₂, SO₃H, alkylsulfonamides, and nitro.
a) Et₃N, toluene;
b) Me₃O⁺BF₄⁻, CH₂Cl₂;
c) NH₄Cl, CH₃OH;
d) DDQ, Benzene.

Scheme 12:
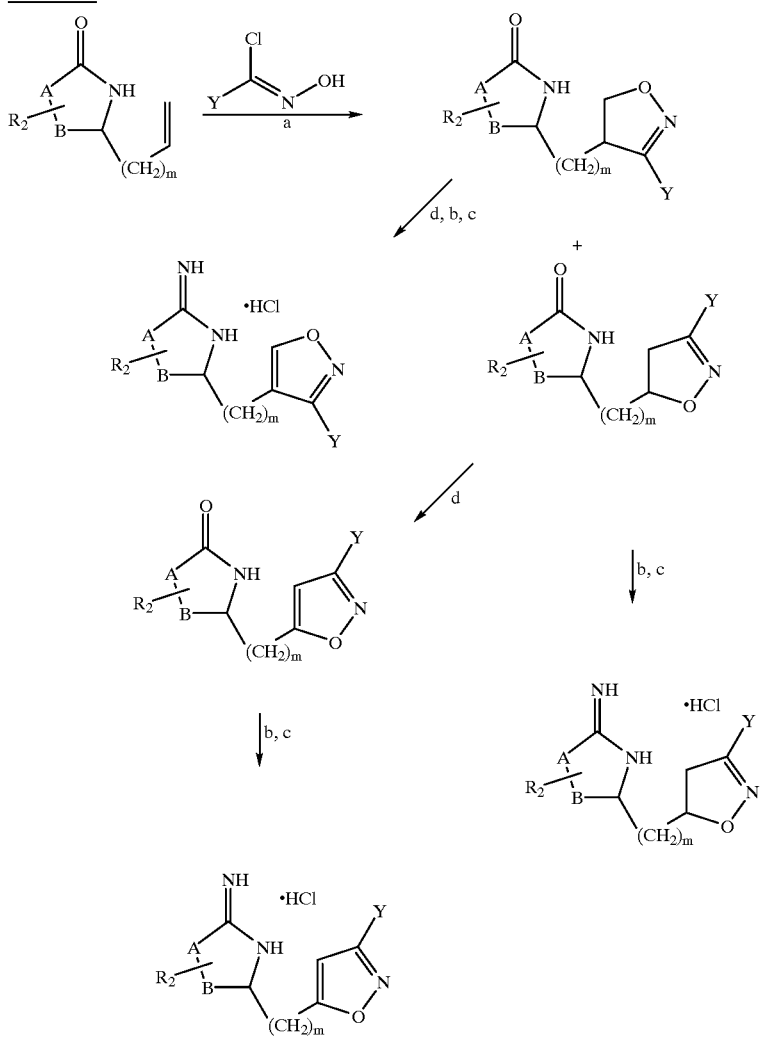
Y = Aryl, CF$_3$, alkoxycarbonyl
a) Et$_3$N, diethyl ether (or toluene);
b) Me$_3$O$^+$BF$_4^-$, CH$_2$Cl$_2$;
c) NH$_4$Cl, CH$_3$OH;
d) MnO$_2$, Benzene/dioxane.
Scheme 13:
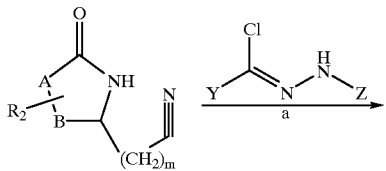

-continued
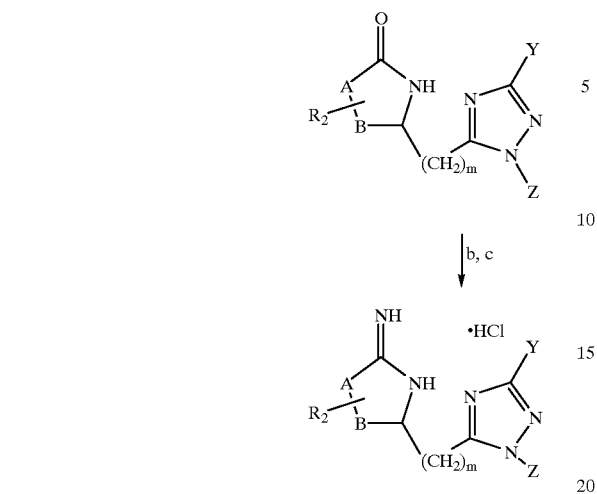
Y = Aryl, CF$_3$, alkoxycarbonyl
Z = 5-membered ring heterocycle (containing 1-4 N, and/or O, and/or S), phenyl or pyridyl substituted with 1-3 groups defined such as: CO$_2$H, alkoxycarbonyl, SO$_2$NH$_2$, SO$_3$H, alkylsulfonamides, nitro.
a) Et$_3$N, toluene;
b) Me$_3$O$^+$BF$_4^-$, CH$_2$Cl$_2$;
c) NH$_4$Cl, CH$_3$OH.
Scheme 14:
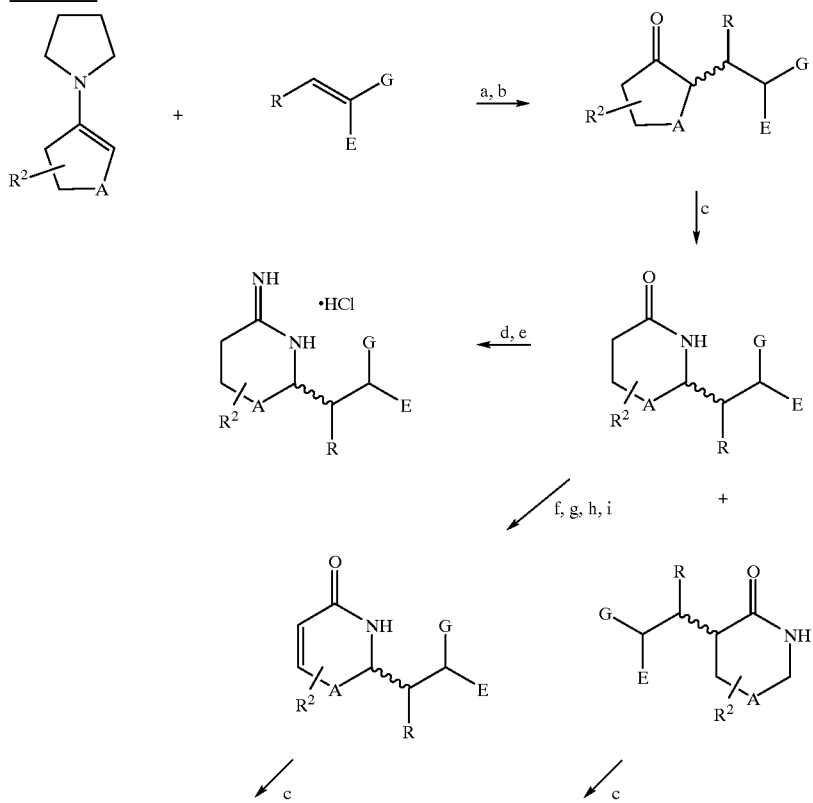

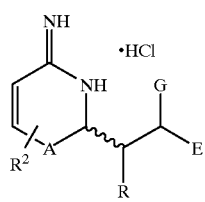 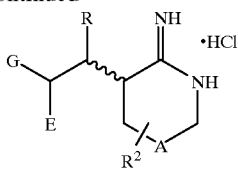

-continued

R = Hydrogen, amino, alkyl, alkenyl, alkynyl, carboxyl, ester, phenyl, halogen, alkoxy, heterocyclic, carbocyclic radicals wherein all said radicals may optionally substituted;
E = Cyano, carboxyl, ester, nitro, heterocylic;
G = Hydrogen, alkyl, haloalkyl, carboxyalkyl, carboxyl, ester;
R and G can form a carbocyclic ring containing 4-7 carbon atoms.
a) DMF, reflux, 24 h; add $H_2O$, reflux, 1h;
b) NLiOH/$CH_3OH$;
c) $H_2N$—O—$SO_3H$, $HCO_2H$, reflux, 3h;
d) $Me_3O^+BF_4^-$, $CH_2Cl_2$;
e) $NH_4Cl$, $CH_3OH$;
f) (t-butylOCO)$_2$O, DMAP, THF;
g) Li hexamethyldisilazide, THF, PhSeCl;
h) 30% $H_2O_2$, THF;
i) 4N HCl, HOAc.

Scheme 15:

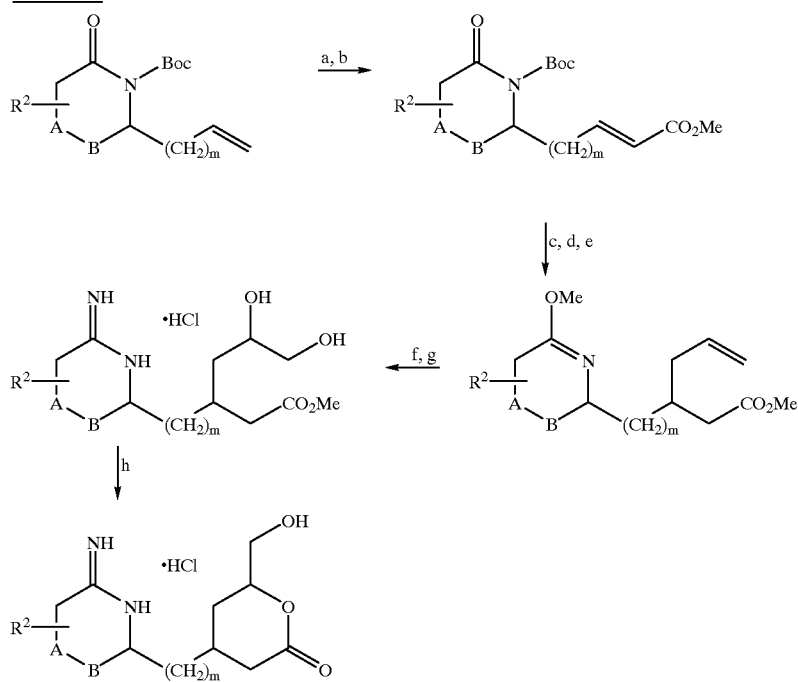

a) $O_3$/Ph$_3$P;
b) Ph$_3$P=CH—$CO_2CH_3$;
c) (allyl)$_2$CuLi
d) $CF_3CO_2H$;
e) $Me_3O^+BF_4^-$, $CH_2Cl_2$;
f) $OsO_4$, NMO;
g) $NH_4Cl$, MeOH;
h) dilute acid, warm Scheme 16:
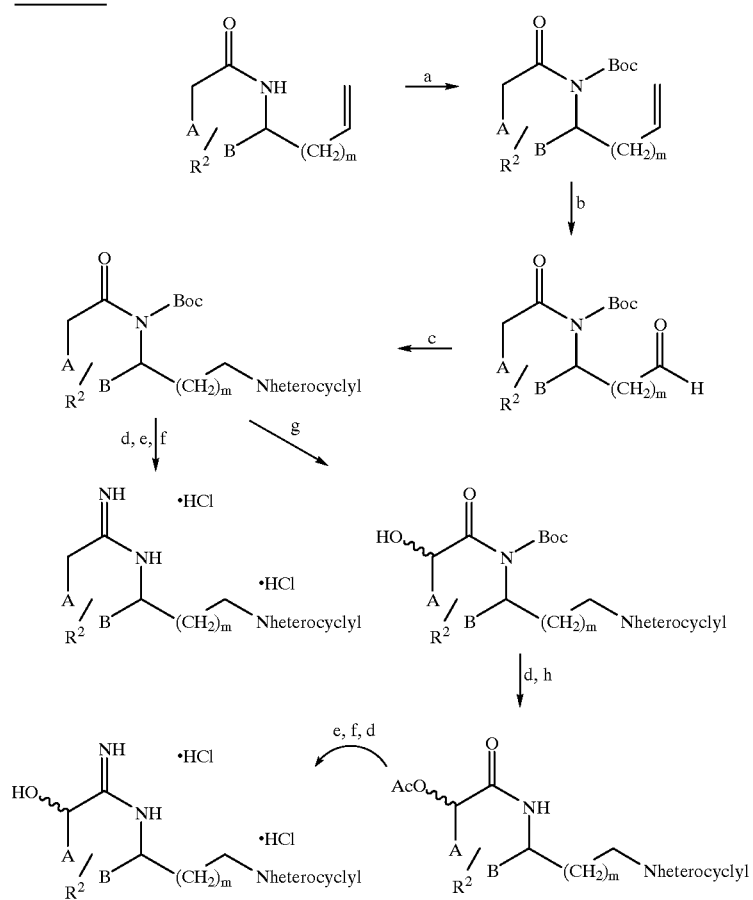
a) di-t-butyl dicarbonate, DMAP, THF;
b) O$_3$;
c) HNheterocyclyl = heterocyclyl containing NH as part of ring, H$_2$, Pd catalyst;
d) HCl, MeOH;
e) Et$_3$O$^+$ BF$_4^-$, CH$_2$Cl$_2$;
f) NH$_4$Cl, MeOH;
g) organo Li base, TMS$_2$O$_2$;
h) Ac$_2$O, pyridine
Scheme 17
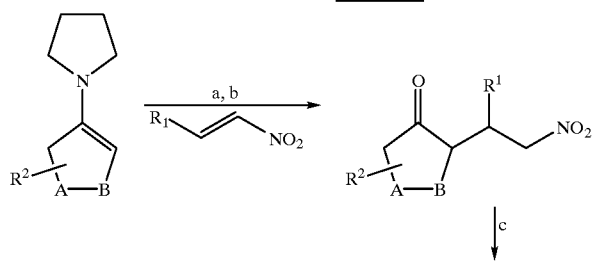

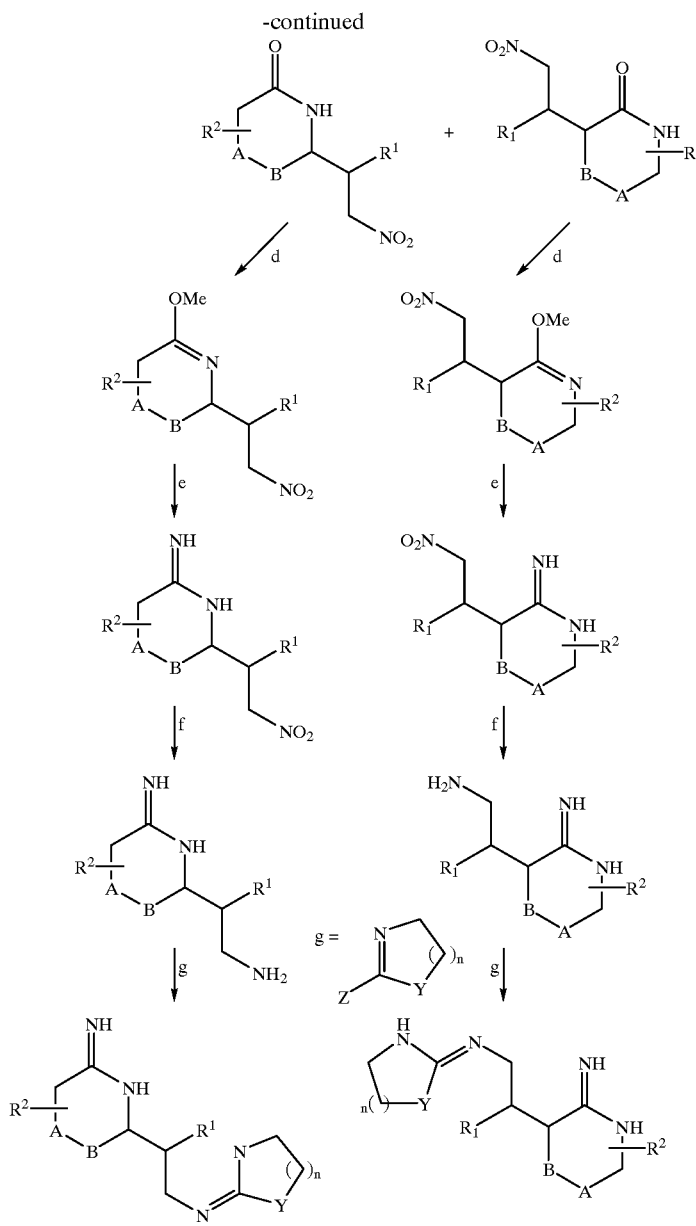
a) 1,4-dioxane;
b) $H_3O^+$;
c) Beckmann Rearrangement;
d) $Me_3O^+BF_4^-$;
e) $NH_3$;
f) catalytic hydrogenation;
g) see structure (Z = leaving group; Y = $CH_2$, N, O, S) wherein "*n*"has a value within 1–4.

Scheme 18
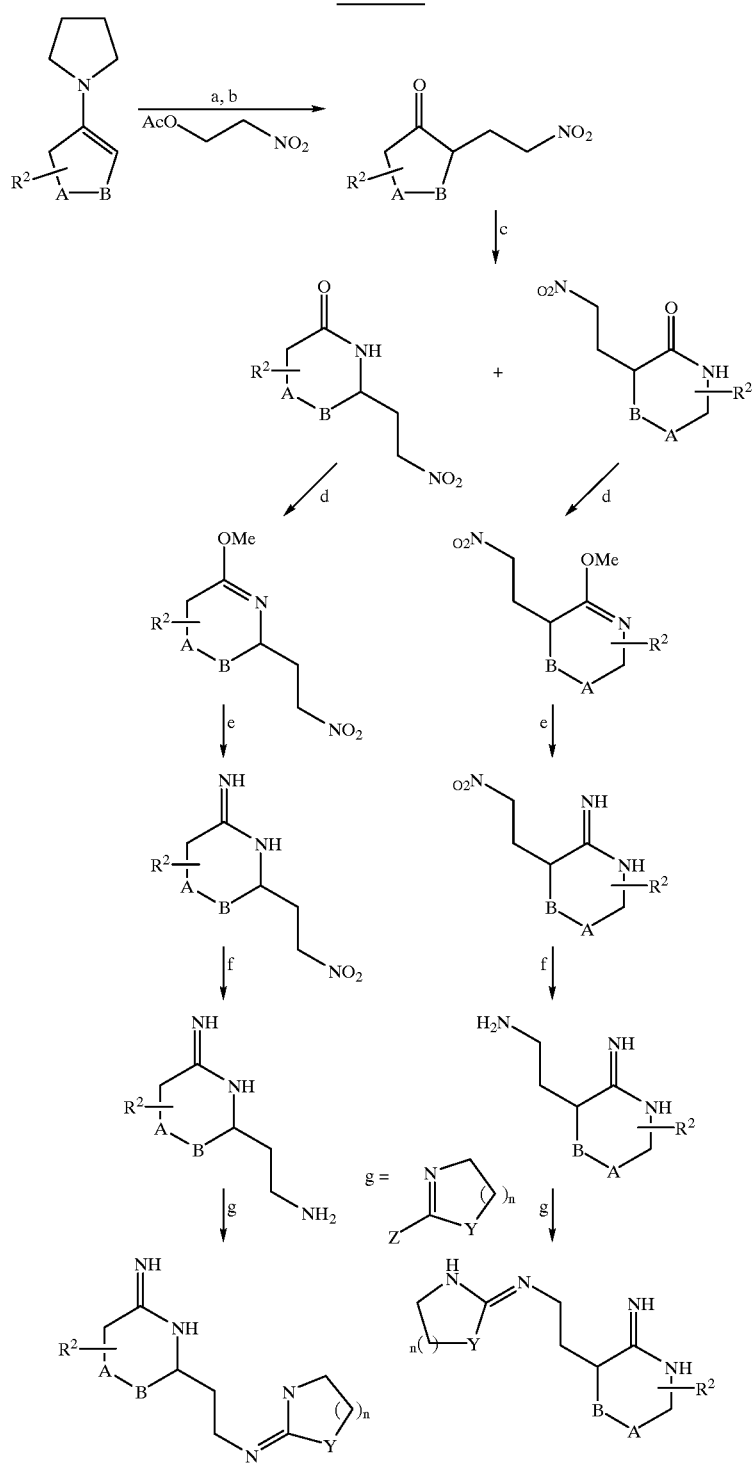
a) 1,4-dioxane;
b) $H_3O^+$;
c) Beckmann Rearrangement;
d) $Me_3O^+BF_4^-$;
e) $NH_3$;
f) catalytic hydrogenation;
g) see structure (Z = leaving group; Y = $CH_2$, N, O, S) wherein "*n*" has a value within 1–4.

Scheme 19
(from Scheme 17)

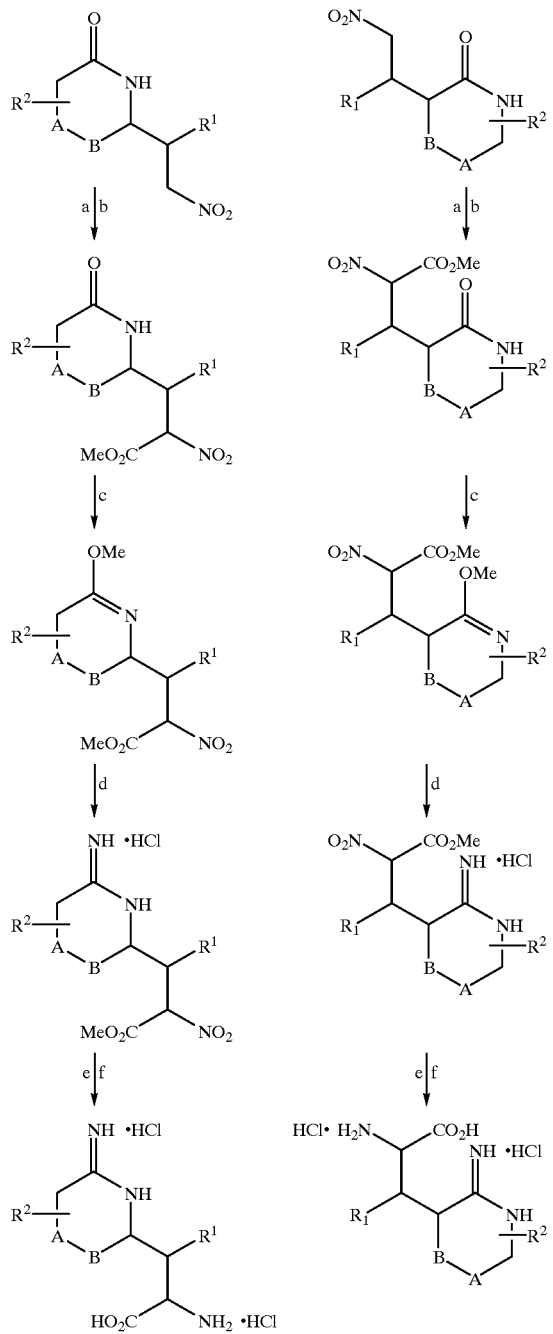

a) TBDMSCl, Et$_3$N;
b) LiHMDS, ClCO$_2$Me;
c) Me$_3$O$^+$BF$_4^-$;
d) NH$_4$Cl, MeOH;
e) catalytic hydrogenation;
f) H$_3$O$^+$.

Without further elaboration, it is believed that one skilled in the art can, using the preceding description, utilize the present invention to its fullest extent. Therefore the following preferred specific embodiments are to be construed as merely illustrative and not limitative of the remainder of the disclosure in any way whatsoever.

All experiments were performed under either dry nitrogen or argon. All solvents and reagents were used without further purification unless otherwise noted. The routine work-up of the reactions involved the addition of the reaction mixture to a mixture of either neutral, or acidic, or basic aqueous solutions and organic solvent. The aqueous layer was extracted n times (x) with the indicated organic solvent. The combined organic extracts were washed n times (x) with the indicated aqueous solutions, dried over anhydrous Na$_2$SO$_4$, filtered, concentrated in vacuo, and purified as indicated. Separations by column chromatography were achieved with conditions described by Still. (Still, W. C.; Kahn, M.; Mitra, A. Rapid Chromatograhic Technique for Preparative Separation with Moderate Resolution. *J. Org. Chem.*, 1978, 43, 2923–2925.) The hydrochloride salts were made from 1N HCl, HCl in ethanol (EtOH), 2 N in MeOH, or 6 N HCl in dioxane chain layer chromatograms were run on 0.25 mm EM precoated olates of silica gel 60 F254. High performance liquid chromatograms (HPLC) were obtained from C-8 or C-18 reverse phase columns which were obtained from several vendors. Analytical samples were dried in an Abderhalden apparatus at either 56° C. or 78° C. $^1$H NMR spectra were obtained from either General Electric QE-300 or Varian VXR 400 MHz spectrometer with tetramethylsilane as an internal standard. $^{13}$C NMR were obtained from a Varian spectrometer at 125.8 MHz with tetramethylsilane as an internal standard.

EXAMPLE 1

2-(phenylmethyl)cyclohexanone, oxime

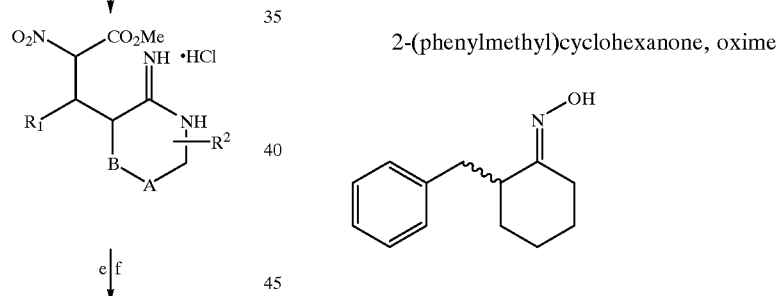

A sample of 2-benzylcyclohexanone (Aldrich, 9.3 g, 49.7 mmol) was combined with hydroxylamine hydrochloride (NH$_2$OH. HCl, 4.8 g, 69.6 mmol) and sodium acetate (NaOAc, 7.3 g, 89.5 mmol) in a mixture of ethanol (EtOH, 90 mL) and water (90 mL). This mixture was refluxed for 15 h under a nitrogen atmosphere. After the reaction was cooled to room temperature, all solvent was removed under reduced pressure. The residue was partitioned between ethyl acetate (EtOAc) and water and the organic phase was washed with 1×75 mL of saturated NaCl (brine), dried over Na$_2$SO$_4$, and stripped of all solvent under reduced pressure. This provided 9.7 g (97%) of the title compound as a cream colored solid. This material showed a retention time of 17.3 min (100% purity by peak area integration) on a Shimadzu GC-14A gas chromatograph (GC) with a 0.25 mm×25 M methyl, 5% phenylsilicone column. Under identical conditions, the starting ketone had a retention time of 14.9 min. The NMR and IR spectra of the product were consistent with the assigned structure.

EXAMPLE 2 hexahydro-7-(phenylmethyl)-2H-azepin-2-one, mixture with hexahydro-3-(phenylmethyl)-2H-azepin-2-one

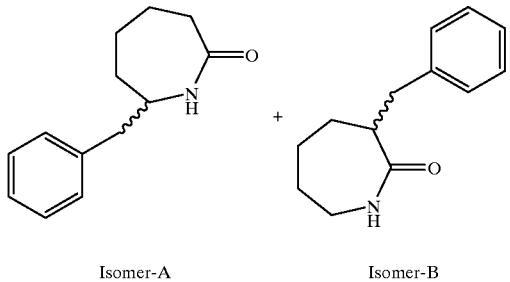

Isomer-A        Isomer-B

A 2.7 g (13.5 mmol) sample of the title material of Example 1 was added to a dropping funnel containing 2.4 mL of 80% $H_2SO_4$. After using a stirring rod to obtain a turbid solution, this mixture was added dropwise (30 min) to 1 mL of 80% $H_2SO_4$ stirred magnetically and maintained at 120° C. with an external oil bath. Within 5 minutes of the start of addition an exotherm was noted and the temperature of the reaction rose to 150° C. before cooling again to 120° C. Ten minutes after the addition was complete, the flask was removed from the bath and allowed to cool to room temperature. The product mixture was diluted with water (20 mL) and brought to pH 6 with concentrated $NH_4OH$. This solution was further diluted with 75 mL of water and extracted with 2×35 mL of $CH_2Cl_2$. The combined organic phase was washed with 1×35 mL of brine, dried ($Na_2SO_4$), filtered, and stripped of all solvent under reduced pressure. The crude solid (980 mg, 36%) was separated into its title Isomer-A and Isomer-B components by column chromatography under conditions identical to that described in Example 1, the Isomer-A and Isomer-B components had GC retention times of 20.7 and 17.2 minutes respectively. The NMR and IR spectra of the products were consistent with their assigned structures.

The Isomer-A material (1.1 g) was chromatographed on a Chiralpak AD column eluting with 3% isopropanol (IPA)/hexane to yield 275 mg (50%) of the (+)Isomer-A enantiomer and 254 mg (46%) of the (−)Isomer-A enantiomer. The NMR and IR spectrum of these two compounds were identical in all respects to that of racemic Isomer-A.

(+) Isomer-A enantiomer:
$[a]_D$ (1.0, $CHCl_3$) = +16.4 ± 3.9
Elemental analysis: $C_{13}H_{17}NO$ (MW = 203.28)

|  | C | H | N |
|---|---|---|---|
| Calculated: | 76.81 | 8.43 | 6.89 |
| Found: | 76.55 | 8.69 | 6.63 |

(−) Isomer-A enantiomer:
$[a]_D$ (1.0, $CHCl_3$) = −13.5 ± 2.7
Elemental analysis: $C_{13}H_{17}NO$ (MW = 203.28)

|  | C | H | N |
|---|---|---|---|
| Calculated: | 76.81 | 8.43 | 6.89 |
| Found: | 76.53 | 8.50 | 6.61 |

EXAMPLE 3

4,5,6,7-tetrahydro-2-methoxy-7-(phenylmethyl)-2H-azepine

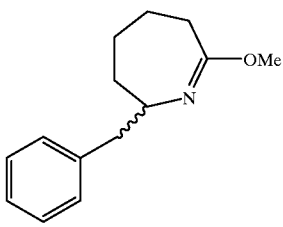

To a magnetically stirred slurry of trimethyloxonium tetrafluoroborate (Lancaster, 0.30 g, 2.0 mmol) and 3A molecular sieves (2 g) in $CH_2Cl_2$ (15 mL) under argon (Ar) was added the Isomer-A product of Example 2 (0.31 g, 1.5 mmol). This mixture was stirred at room temperature for 3 days before it was diluted with 10 mL of $CH_2Cl_2$ and partitioned between 40 mL of saturated $KHCO_3$ and 50 mL of EtOAc. The organic phase was separated, dried over $Na_2SO_4$, filtered, and stripped of all solvent under reduced pressure to provide the crude title product as a pale yellow oil. This material was chromatographed on Merck silica gel using conditions described by W. T. Still *J. Org. Chem.* 1978, 43, 2923–2925 eluting with EtOAc/n-hexane (1:1). The title pale yellow liquid product (308 mg, 93%) had a GC retention time of 15.5 min (100%) under the conditions of Example 1 and NMR and IR spectra consistent with the indicated product.

EXAMPLE 4

4,5,6,7-tetrahydro-2-methoxy-3-(phenylmethyl)-2H-azepine

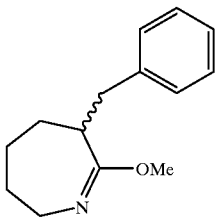

The Isomer-B product of Example 2 is reacted with trimethyloxonium tetrafluoroborate by the method of Example 3 to produce she title material.

EXAMPLE 5 hexahydro-7-(phenylmethyl)-2H-azepin-2-imine, monohydrochloride

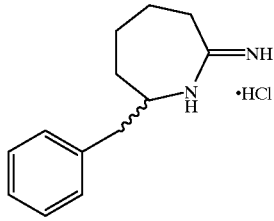

The title product of Example 3 (0.30 g, 1.4 mmol) and 0.06 g (1.1 mmol) of ammonium chloride (NH$_4$Cl) were refluxed in 13 mL of methanol (MeOH) under a nitrogen atmosphere for 19 h. After cooling the reaction to room temperature, it was filtered, stripped of all solvent under reduced pressure, and partitioned between 15 mL of water and 7 mL of CH$_2$Cl$_2$. The organic and aqueous phases were separated and the aqueous phase was washed with a 25 mL portion of EtOAc before it was lyophilized to provide 0.24 g (92%) of the white solid title material.

HRMS (EI) calcd for C$_{13}$H$_{18}$N$_2$ m/e 202.147, found m/e 202.147. $^1$H NMR(CD$_3$OD): d 7.20–7.35 (m, 5H), 3.96 (m, 1H), 2.99 (dd, 1H, j=14.8 Hz), 2.89 (dd, 1H, J=14.8 Hz), 2.82 (m, 1H), 2.64 (m, 1H) 2.05–1.86 (m, 3H) , 1.71–1.36 (m, 3H).

| Elemental analysis: C$_{13}$H$_{18}$N$_2$.HCl.0.15 H$_2$O (MW = 241.46) | | | | |
|---|---|---|---|---|
| | C | H | N | Cl |
| Calculated: | 64.67 | 8.06 | 11.60 | 14.68 |
| Found: | 64.86 | 8.45 | 11.54 | 14.60 |

EXAMPLE 6 hexahydro-3-(phenylmethyl)-2H-azepin-2-imine, monohydrochloride

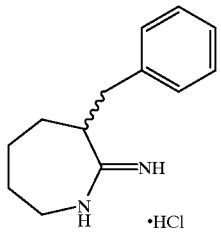

The title product of Example 4 in MeOH is reacted with ammonium chloride by the method of Example 5 to generate the title material.

EXAMPLE 7

7-(cyclohexylmethyl)hexahydro-2H-azepin-2-one

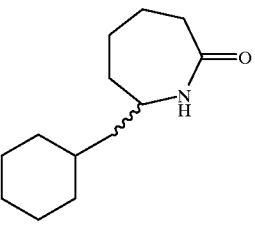

The Isomer-A title product of Example 2 (0.80 g, 3.9 mmol) dissolved in MeOH was placed in a standard Parr hydrogenation shaker flask along with 5% Rh/C. The reaction mixture was shaken under an H$_2$ pressure of 60 csi at 60° C. for 22 hr. All solvent was then removed under reduced pressure. The residue was then dissolved in CH$_2$Cl$_2$ and this solution was filtered and stripped of all solvent to yield 975 mg of the title material. The colorless semi-solid title product had a GC retention time of 15.5 min (100%) under the conditions of Example 1 and NMR and IR spectra consistent with the title product.

EXAMPLE 8

2-(cyclohexylmethyl)-3,4,5,6-tetrahydro-7-methoxy-2H-azepine

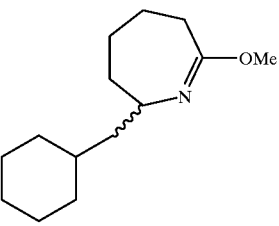

The title product of Example 7 (0.87 g, 4.2 mmol) was reacted with trimethyloxonium tetrafluoroborate (0.80 g, 5.4 mmol) by the method of Example 3 to yield 0.76 g (82%) of the title material. The pale yellow oil title product had a GC retention time of 14.9 min (100%) under the conditions of Example 1 and NMR and IR spectra consistent with the title product.

EXAMPLE 9

7-(cyclohexylmethyl)hexahydro-2H-azepin-2-imine, monohydrochloride

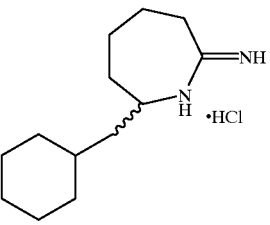

The product of Example B (0.76 g, 3.4 mmol) in 20 ml, of MeOH was reacted with ammonium chloride (144 mg, 2.7 mmol) by the method of Example 5 to yield 258 mg (30.4%) so the title material.

HRMS (EI) calcd for $C_{13}H_{24}N_2$ m/e 208.194, found m/e 208.105. $^1$H NMR(CD$_3$OD): d 3.70 (m, 1H), 2.82 (m, 1H), 2.6: (S, 1H), 2.06–1.93 (m, 2H), 1.86–1.62 (m, 7H), 1.62.–1.13 (m, 8H).

| Elemental analysis: $C_{13}H_{24}N_2$.HCl.0.33 H$_2$O (MW = 250.81) | | | | |
| --- | --- | --- | --- | --- |
| | C | H | N | Cl |
| Calculated: | 62.27 | 10.31 | 11.17 | 14.14 |
| Found: | 62.23 | 10.09 | 10.83 | 13.52 |

EXAMPLE 10

3-(cyclohexylmethyl)hexahydro-2H-azepin-2-one, monohydrochloride

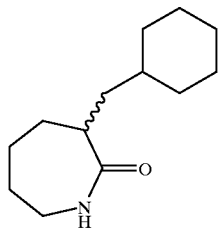

The Isomer-B title product of Example 2 is converted to the title material by the method of Example 7.

EXAMPLE 11

6-(cyclohexylmethyl)-3,4,5,6-tetrahydro-7-methoxy-2H-azepine

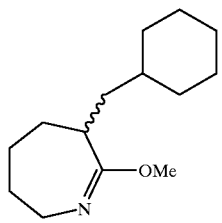

The product of Example 10 is reacted with trimethyloxonium tetrafluoroborate by the method of Example 3 to produce the title material.

EXAMPLE 12

3-(cyclohexylmethyl)hexahydro-2H-azepin-2-imine, monohydrochloride

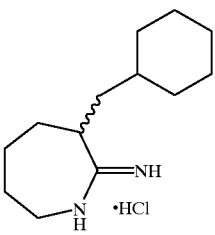

The title product of Example 11 in MeOH is reacted with ammonium chloride by the method of Example 5 to generate the title material.

EXAMPLE 13

(+)-3,4,5,6-tetrahydro-7-methoxy-2-(phenylmethyl)-2H-azepine

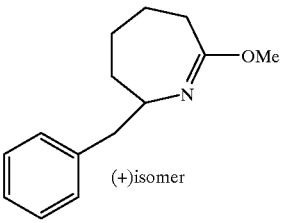

The (+)Isomer-A enantiomer product of Example 2 (0.24 g, 1.2 mmol) was reacted with trimethyloxonium tetrafluoroborate (0.23 g, 1.6 mmol) by the method of Example 3 to yield 0.25 g (95%) of the title material. The pale yellow oil title product had a GC retention time of 15.4 min (100%) under the conditions of Example 1 and NMR and IR spectra were identical to the title products of Examples 3 and 15.

EXAMPLE 14

(+)-hexahydro-7-(phenylmethyl)-2H-azepin-2-imine, monohydrochloride

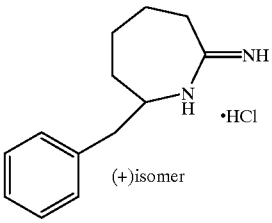

The product of Example 13 (0.25 g, 1 mmol) in 19 mL of MeOH was reacted with ammonium chloride (50 mg, 0.93 mmol) by the method of Example 5 to yield 200 mg (88%) of the title material. The NMR and IR spectra of the title compound were identical to that of the title products of Examples 5 and 15.

HRMS (EI) calcd for $C_{13}H_{18}N_2$ m/e 202.147, found m/e 202.147.

$[\alpha]_D$ (0.095, CHCl$_{33}$)=+35.6±2.8

Elemental analysis: C₁₃H₂₄N₂·0.95 HCl·0.45 H₂O (MW = 245.04)

|  | C | H | N | Cl |
|---|---|---|---|---|
| Calculated: | 63.72 | 8.17 | 11.43 | 13.74 |
| Found: | 64.05 | 8.70 | 11.15 | 13.91 |

EXAMPLE 15

(−)-3,4,5,6-tetrahydro-7-methoxy-2-(phenylmethyl)-2H-azepine

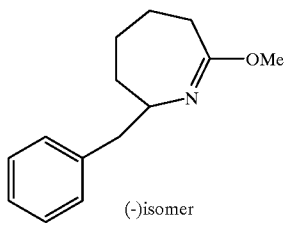

(-)isomer

The (−)Isomer-A enantiomer product of Example 2 (0.23 g, 1.1 mmol) was reacted with trimethyloxonium tetrafluoroborate (0.21 g, 1.4 mmol) by the method of Example 3 to yield 0.21 g (88%) of the title material. The pale yellow oil title product had a GC retention time of 15.4 min (100%) under the conditions of Example 1 and NMR and IR spectra were identical to the title products of Examples 3 and 13.

EXAMPLE 16

(−)-hexahydro-7-(phenylmethyl)-2H-azepin-2-imine, monohydrochloride

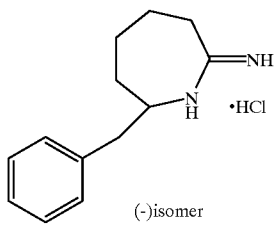

(-)isomer

The product of Example 15 (0.21 g, 1.0 mmol) in 18 mL of MeOH was reacted with ammonium chloride (43 mg, 0.80 mmol) by the method of Example 5 to yield 173 mg (89%) of the title material. The NMR and IR spectra of the title compound were identical to that of the title products of Examples 5 and 14.

HRMS (EI) calc. for C₁₃H₁₈N₂ m/e 202.147, found m/e 202.147.

[α]$_D$ (0.149, CHCl₃₃)=−35.6±2.8

Elemental analysis: C₁₃H₂₄N₂·HCl·0.2 H₂O (MW = 242.36)

|  | C | H | N | Cl |
|---|---|---|---|---|
| Calculated: | 64.43 | 8.07 | 11.56 | 14.63 |
| Found: | 64.43 | 8.31 | 11.15 | 14.88 |

EXAMPLE 17

2-(2-propenyl)cyclohexanone, oxime

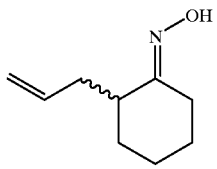

A sample of 2-allylcyclohexanone (Frinton, 2.0 g, 14.5 mmol) was converted to the title compound by the method of Example 1 using 1.5 g (21.7 mmol) of hydroxylamine hydrochloride and 2.0 g (24.6 mmol) of NaOAc in a mixture of 25 mL of EtOH and 25 mL of water. The procedure produced 2.6 g of the crude title compound.

EXAMPLE 18 hexahydro-3-(2-propenyl)-2H-azepin-2-one, mixture with hexahydro-7-(2-propenyl)-2H-azepin-2-one

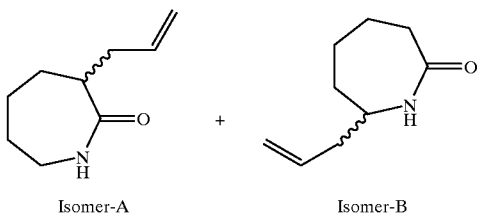

Isomer-A          Isomer-B

The title product of Example 17 (2.0 g, 13.0 mmol) in 15 mL of acetone containing 1N NaOH (14.3 mL, 52.4 mmol) was reacted with benzene sulfonylchloride (2.3 g, 13.1 mmol) by the method described in Example 67. The crude reaction mixture was separated into its Isomer-A and Isomer-B components by silica gel chromatography.

EXAMPLE 19 hexahydro-7-[(oxiran-2-yl)methyl]-2H-azepin-2-one

The title product isomer B of Example 18 (2.99 g, 19.5 mmol) in 150 mL of CH₂Cl₂ was refluxed with m-chloroperbenzoic acid (MCPBA, 5.05 g, 29.3 mmol) for 3 hr. After stirring at room temperature overnight, an additional 1.0 g (5.8 mmol) of MCPBA was added and the reaction reheated to reflux for an additional 6 hr. The solvent was removed and the residue was dissolved in EtOAc (150 mL). After this solution was washed 3×50 mL of saturated NaHCO₃ and dried (Na₂SO₄), all solvent was removed to provided the crude desired product. Purification via flash column chromatography using 100% EtOAc and deactivated silica gel yielded 2.25 g (68%) of the title compound.

EXAMPLE 20

3,4,5,6-tetrahydro-7-methoxy-2-[(oxiran-2-yl) methyl-yl-2H-azepine

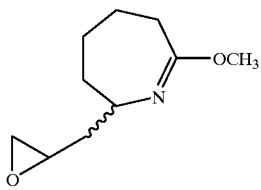

The product of Example 19 (2.0 g, 13 mmol) was reacted with trimethyloxonium tetrafluoroborate (2.49 g, 16.8 mmol) in CH$_2$Cl$_2$ (30 mL) by the method of Example 3 to produce 1.8 g (83%) of the title material following chromatography.

EXAMPLE 21 hexahydro-7-[(oxiran-2-yl)methyl]-2H-azepin-2-imine, monohydrochloride

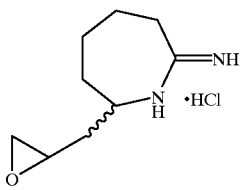

The product of Example 20 in MeOH was reacted with ammonium chloride by the method of Example 5 to yield the title material.

EXAMPLE 22 hexahydro-7-[(2-hydroxy-3-(2-hydroxyphenoxy) propyl]-2H-azepin-2-one

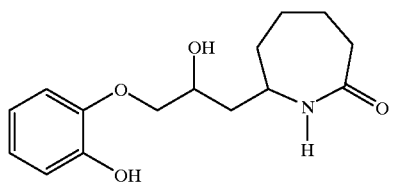

Sodium hydride (52.4% in mineral oil, 66.5 mmol, 3.05 g) is washed with hexane in a 500 mL flask. The hexane-mineral oil is decanted, and DMF (35 mL) is added. A dropping funnel is fitted onto the flask, with nitrogen flow maintained through the reaction system. 1,2-Dihydroxybenzene (63.6 mmol, 7.0 g) dissolved in DMF (150 mL) is added CAREFULLY dropwise to the stirring mixture. When the addition is complete, the mixture is allowed to stir at room temperature for one hour. The title compound of Example 19 (58 mmol) is dissolved in DMF (100 mL) and added quickly to the reaction mixture. The stirring mixture is immersed in a 75° C. oil bath, and allowed to react for 24 h. The mixture is removed from the oil bath, allowed to come to room temperature, and poured into 150 mL 0.5M KHSO$_4$ solution. This mixture is diluted with water to 500 mL, and extracted thrice with 150 mL portions of CH$_2$Cl$_2$. The organic fractions are combined, dried (MgSO$_4$), filtered, and stripped at reduced pressure. The residue is purified by silica column chromatography to give the title compound.

EXAMPLE 23

7-[(1,4-benzodioxan-2-yl)methyl]hexahydro-2H-azepin-2-one

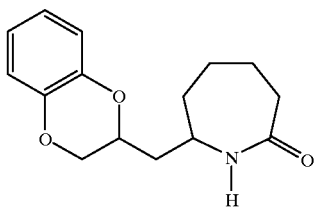

A 1000 mL three-necked round bottom flask fitted with a magnetic stirrer, thermometer, dropping funnel, and Y-tube (nitrogen inlet, drying tube outlet) is charged with the title compound from Example 22 (21.6 mmol), triphenylphosphine (5.67 g, 21.6 mmol), and THF (300 mL). The temperature is reduced to 2° C. (ice bath), and diethyl azodicarboxylate (DEAD, 3.77 g, 3.4 mL, 21.6 mmol) in 50 ML THF is added dropwise, keeping the reaction temperature at or below 4° C. After the addition is completed, the reaction is stirred a farther 45 min in the ice bath; the cold bath is removed and the mixture is allowed to stir at room temperature overnight. The reaction mixture is then stripped in vacuo to a residue which is applied to a silica gel column for purification with hexane/ethyl acetate eluents giving the title compound.

EXAMPLE 24

2-[(1,4-benzodioxan-2-yl)methyl]-3,4,5,6-tetrahydro-7-methoxy-2H-azepine

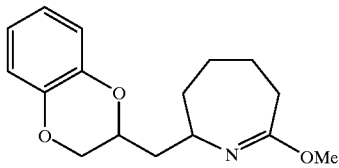

The title compound of Example 23 is treated by the method described in Example 3 to yield the present title compound.

EXAMPLE 25

7-[(1,4-benzodioxan-2-yl)methyl]hexahydro-2H-azepin-2-imine, monohydrochloride

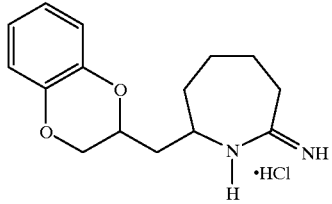

The title compound of Example 24 is treated by the method described in Example 5 to yield the present title compound.

EXAMPLE 26

3,4,5,6-tetrahydro-7-methoxy-2-[2-methoxy-3-(2-methoxyphenoxy)propyl]-2H-azepine

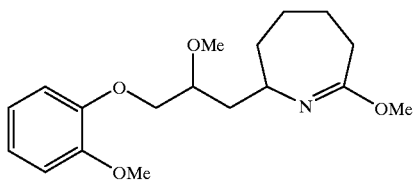

The title compound of Example 22 is treated by the method described in Example 3 to yield the present title compound.

EXAMPLE 27 hexahydro-7-[2-methoxy-3-(2-methoxyphenoxy)propyl]-2H-azepin-2-imine, monohydrochloride

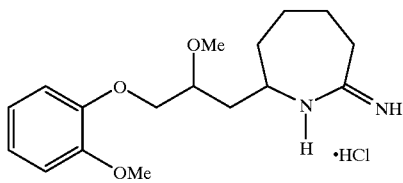

The title compound of Example 26 is treated by the method described in Example 5 to yield the present title compound.

EXAMPLE 28

7-[2-acetyloxy-3-(2-acetyloxyphenoxy)propyl]hexahydro-2H-azepin-2-one

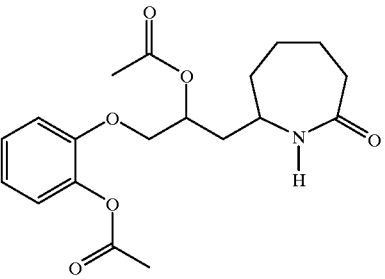

The title compound of Example 22 (20 mmol) is dissolved in 100 mL $CH_2Cl_2$ and cooled to −5° C. (ice-methanol bath). The solution is Protected from moisture and 10 mL dry pyridine is added. A solution of 50 mmol acetic anhydride in 20 mL $CH_2Cl_2$ is slowly added, keeping the reaction temperature at or below 0° C. The mixture is allowed to stir an additional 2 hr, and is then stripped in vacuo to a residue. This residue is partitioned between 0.1 M $KHSO_4$ and ether. The aqueous phase is washed with ether, the organic phases are combined, dried ($MgSO_4$), filtered and stripped in vacuo to give the title compound.

EXAMPLE 29 a-[(2-acetyloxyphenoxy)methyl]-3,4,5,6-tetrahydro-7-methoxy-2H-azepine-2-ethanol acetate (ester)

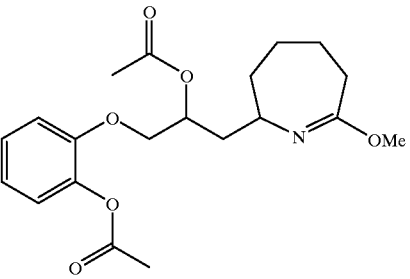

The title compound of Example 28 is treated by the method described in Example 3 to yield the present title compound.

EXAMPLE 30 hexahydro-a-[(2-hydroxyphenoxy)methyl]-7-imino-1H-azepine-2-ethanol, monohydrochloride

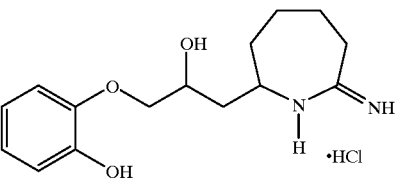

The title compound of Example 29 is treated by the method described in Example 5 to yield the partially acetylated present title compound. The acetyl groups are removed with refluxing (1 hr) 0.5 N HCl, followed by in vacuo concentration to one third volume. The resulting aqueous solution is lyophilized to give title compound.

EXAMPLE 31 a-[(2-acetyloxyphenoxy)methyl]hexahydro-7-imino-1H-azepine-2-ethanol acetate(ester), monohydrochloride

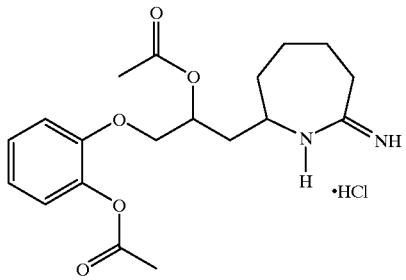

The dried title compound of Example 30 is treated with a three-fold excess of acetyl chloride in $CH_2Cl_2$, followed by stripping in vacuo. The resulting residue is dissolved in water and lyophilized to give the title compound.

EXAMPLE 32 hexahydro-7-(3-phenyl-2-propenyl)-2H-azepin-2-one

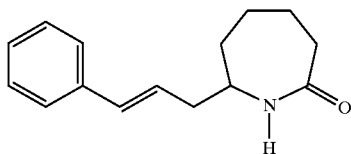

A mixture of palladium acetate (Johnson Matthey, 65 mg, 0.29 mmol), tri-o-tolylphosphine (Aldrich, 176 mg, 0.6 mmol), bromobenzene (Aldrich, 2.50 g, 16.0 mmol), and triethylamine (Aldrich, 1.62 g, 16 mmol) was refluxed under nitrogen for 30 minutes. After cooling this mixture to room temperature, the isomer B of the title material of Example 18 (2.2 g, 14.5 mmol) in 6 mL of acetonitrile was added to the reaction mixture. The reaction was refluxed for 24 hrs., cooled to room temperature, and stripped of all solvent under reduced pressure. The residue was partitioned between saturated $NaHCO_3$ and EtOAc and the organic was dried ($Na_2SC_4$), filtered and concentrated to the crude product. This material was chromatographed (HPLC) on silica gel eluting with acetone/hexane (1:1) to give 1.06 g (32%) of the title material.

| Elemental analysis: $C_{15}H_{19}NO$ (MW = 229.32) | | | |
|---|---|---|---|
| | C | H | N |
| Calculated: | 78.57 | 8.35 | 6.11 |
| Found: | 78.14 | 8.31 | 5.89 |

EXAMPLE 33

3,4,5,6-tetrahydro-7-methoxy-2-(3-phenyl-2-propenyl)-2H-azepine

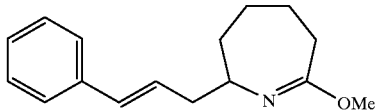

The title material of Example 32 (0.50 g, 2.2 mmol) in $CH_2Cl_2$ (15 mL) and in the presence of 3A molecular sieves (1.0 g) was reacted with trimethyloxonium tetrafluoroborate (0.39 g, 2.6 mmol) by the method of Example 3 to produce 0.53 g (99%) of the title material.

EXAMPLE 34 hexahydro-7-(3-phenyl-2-propenyl)-2H-azepin-2-imine, monohydrochloride

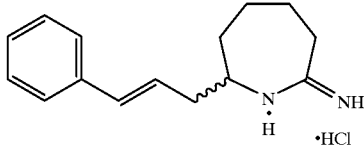

The product of Example 33 (0.50 g, 2.05 mmol) in 18 mL of MeOH was reacted with ammonium chloride (144 mg, 2.7 mmol) by the method of Example 5 to yield 258 mg (30%) of the title material.

HRMS (EI) calcd for $C_{15}H_{20}N_2$ m/e 228.163, found m/e 228.163. $^1$H NMR($CD_3OD$): d 7.40–7.17 (m, 5H), 6.59 (d, 1H, J=16 Hz), 6.26 (dt, 1H, J=16, 7 Hz), 3.80 (m, 1H), 2.80 (td, 1H, J=15, 2 Hz), 2.55 (m, 2H), 2.64 (dd, 1H, J=15, 6 Hz), 2.03–1.92 (m, 3H), 1.70 (m, 1H), 1.55–1.38 (m, 2H).

| Elemental analysis: $C_{15}H_{20}N_2 \cdot HCl \cdot 0.8\ H_2O \cdot 0.05\ NH_4Cl$ (MW = 281.88) | | | | |
|---|---|---|---|---|
| | C | H | N | Cl |
| Calculated: | 63.91 | 8.15 | 10.19 | 13.21 |
| Found: | 63.86 | 8.10 | 9.97 | 13.42 |

EXAMPLE 35 hexahydro-7-(3-phenylpropyl)-2H-azepin-2-one

The title material of Example 32 (0.46 g, 2.0 mmol) in MeOH and 4% Pd on carbon (0.10 g) were combined in a standard Parr apparatus (125 mL bottle). The hydrogenation was carried out at room temperature under a $H_2$ pressure of 5 psi for 1 hr. All solvent was then removed under reduced pressure to yield 0.50 (09%) of the title material as a white semi-solid.

| Elemental analysis: $C_{15}H_{21}NO$ (MW = 231.33) | | | |
|---|---|---|---|
| | C | H | N |
| Calculated: | 77.28 | 9.17 | 6.01 |
| Found: | 77.15 | 8.97 | 5.89 |

EXAMPLE 36

3,4,5,6-tetrahydro-7-methoxy-2-(3-phenylpropyl)-2H-azepine

The title material of Example 35 (0.47 g, 2.0 mmol) in $CH_2Cl_2$ (10 mL) and in the presence of 3A molecular sieves (1.0 g) was reacted with trimethyloxonium tetrafluoroborate (0.35 g, 2.4 mmol) by the method of Example 3 to produce 0.42 g (87%) of the title material as a pale yellow oil.

EXAMPLE 37 hexahydro-7-(3-phenylpropyl)-2H-azepin-2-imine, monohydrochloride

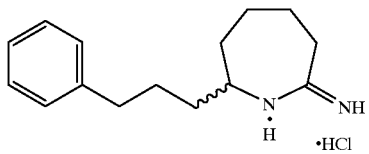

The product of Example 36 (0.41 g, 1.65 mmol) in 18 mL of EtOH was reacted with ammonium chloride (75 mg, 1.4 mmol) by the method of Example 5 to yield 195 mg (63%) of the title material.

HRMS (EI) calcd for $C_{15}H_{22}N_2$ m/e 230.178, found m/e 230.178. $^1$H NMR($CD_3OD$): d 7.28–7.13 (m, 5H), 3.57 (m, 1H), 2.73 (ddd, 1H, J=15,12, 2 Hz), 2.67 (t, 2H, J=8 Hz), 2.57 (dd, 1H, J=15, 7 Hz), 1.96 (m, 2H), 1.85–1.57 (m, 6H), 1.47 (m, 1H), 1.35 (m, 1H).

| Elemental analysis: $C_{15}H_{22}N_2$.HCl.0.25 $H_2O$ (MW = 271.32) | | | | |
|---|---|---|---|---|
| | C | H | N | Cl |
| Calculated: | 66.40 | 8.73 | 10.32 | 13.07 |
| Found: | 66.31 | 8.91 | 10.10 | 13.06 |

EXAMPLE 38

2-[(tetrahydro-2-furanyl)methyl]cyclohexanone

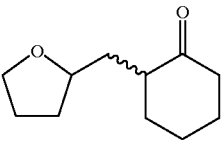

2-carboethoxycyclohexanone (1 mmol), finely powdered potassium carbonate (2 mmol), 2-bromomethyltetrahydrofuran (1.5 mmol), and tetrabutylammonium iodide (10 mg/mmol) are combined in dry DMF (1.25 mL/mmol) and stirred under $N_2$ at 55 to 60° C. for 16 to 18 hours. The room temperature reaction mixture is poured into water and extracted with $Et_2O$ and EtOAc. The combined organics are washed with brine, dried, and stripped of all solvent under reduced pressure to provide 2-tetrahydrofuranylmethyl-2-carboethoxycyclohexanone. This material is combined with lithium chloride (5 mmol), water (1.05 mmol) and dimethyl sulfoxide (5 mL/mmol) and the mixture refluxed for approximately 4 hrs. The mixture is poured into water and extracted with $Et_2O$ and EtOAc. The combined organics are washed with brine, dried, and stripped of all solvent under reduced pressure to generate the title material.

EXAMPLE 39

2-[(tetrahydro-2-furanyl)methyl]cyclohexanone, oxime

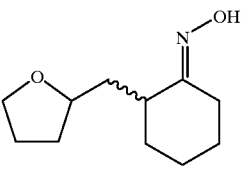

The product of Example 38 is reacted with hydroxylamine hydrochloride and NaOAc in a mixture of EtOH and water, by the method of Example 1 to produce the tattle material.

EXAMPLE 40 hexahydro-7-[(tetrahydro-2-furanyl)methyl]-2H-azepin-2-one, mixture with hexahydro-3-[(2-tetrahydrofuranyl)methyl-2H-azepin-2-one

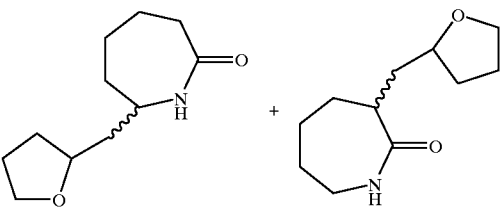

Isomer-A          Isomer-B

The product of Example 39 is reacted with 80% $H_2SO_4$, by the method of Example 2 to produce the title materials.

EXAMPLE 41

3,4,5,6-tetrahydro-7-methoxy-2-[(tetrahydro-2-furanyl)methyl]-2H-azepine

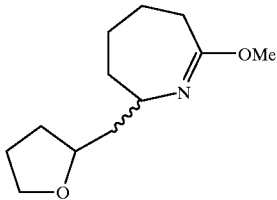

The Isomer-A product of Example 40 is reacted with trimethyloxonium tetrafluoroborate by the method of Example 3 to produce the title material.

EXAMPLE 42

3,4,5,6-tetrahydro-7-methoxy-6-[(tetrahydro-2-furanyl)methyl]-2H-azepine

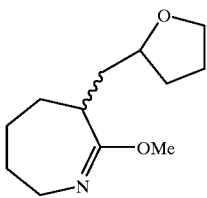

The Isomer-B product of Example 40 is reacted with trimethyloxonium tetrafluoroborate by the method of Example 3 to produce the title material.

EXAMPLE 43 hexahydro-7-[(tetrahydro-2-furanyl)methyl]-2H-azepin-2-imine, monohydrochloride

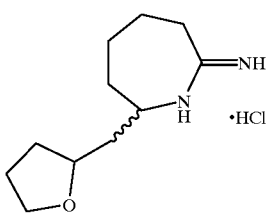

The title product of Example 4; in MeOH is reacted with ammonium chloride by the method of Example 5 to generate the title material.

EXAMPLE 44 hexahydro-3-[(tetrahydro-2-furanyl)methyl]-2H-azepin-2-imine, monohydrochloride

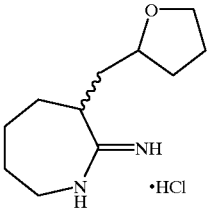

The title product of Example 42 in MeOH is reacted with ammonium chloride by the method of Example 5 to generate the title material.

EXAMPLE 45

2-[(2-furanyl)methyl]cyclohexanone

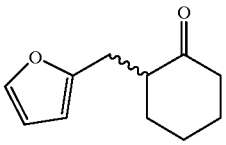

2-carboethoxycyclohexanone, finely powdered potassium carbonate, 2-bromomethyl furan, and tetrabutylammonium iodide are reacted by the method of Example 38 to generate the title material.

EXAMPLE 46

2-[(2-furanyl)methyl]cyclohexanone, oxime

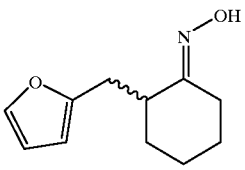

The product of Example 45 is reacted with hydroxylamine hydrochloride and NaOAc in a mixture of EtOH and water, by the method of Example 1 to produce the title material.

EXAMPLE 47

7-[(2-furanyl)methyl]hexahydro-2H-azepin-2-one, mixture with 3-[(2-furanyl)methyl]hexahydro-2H-azepin-2-one

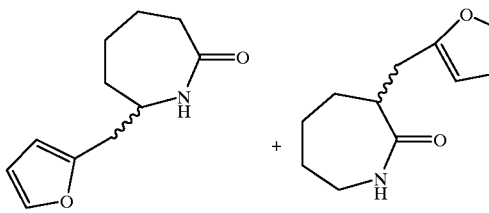

Isomer-A      Isomer-B

The product of Example 46 is reacted with 80% $H_2SC_4$, by the method of Example 2 to produce the title materials.

EXAMPLE 48

2-[(2-furanyl)methyl]-3,4,5,6-tetrahydro-7-methoxy-2H-azepine

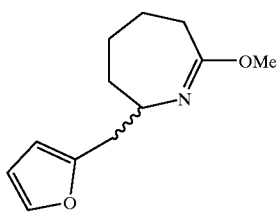

The Isomer-A product of Example 47 is reacted with trimethyloxonium tetrafluoroborate by the method of Example 3 to produce the title material.

EXAMPLE 49

6-[(2-furanyl)methyl]-3,4,5,6-tetrahydro-7-methoxy-2H-azepine

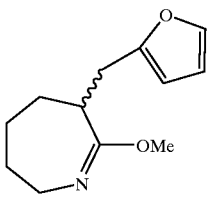

The Isomer-B product of Example 47 is reacted with trimethyloxonium tetrafluoroborate by the method of Example 3 to produce the title material.

EXAMPLE 50

7-[(2-furanyl)methyl]hexahydro-2H-azepin-2-imine, monohydrochloride

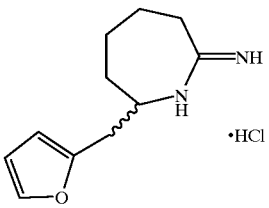

The title product of Example 48 in MeOH is reacted with ammonium chloride by the method of Example 5 to generate the title material.

EXAMPLE 51

3-[(2-furanyl)methyl]hexahydro-2H-azepin-2-1-mine, monohydrochloride

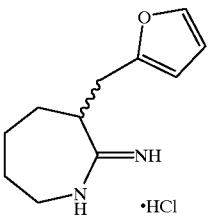

The title product of Example 49 In MeOH is reacted with ammonium chloride by the method of Example 5 to generate the title material.

EXAMPLE 52

2-((2-thienyl)methyl]cyclohexanone

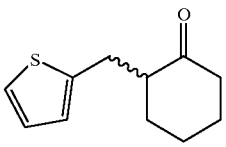

2-carboethoxycyclohexanone, finely powdered potassium carbonate, 2-bromomethyl thiophene, and tetrabutylammonium iodide are reacted by the method of Example 38 to generate the title material.

EXAMPLE 53

2-[(2-thienyl)methyl]cyclohexanone, oxime

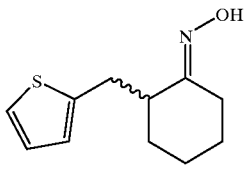

The product of Example 52 is reacted with hydroxylamine hydrochloride and NaOAc in a mixture of EtOH and water, by the method of Example 1 to produce the title material.

EXAMPLE 54 hexahydro-7-[(2-thienyl)methyl]-2H-azepin-2-one, mixture with hexahydro-3,-F(2-thienyl)methyl]-2H-azepin-2-one

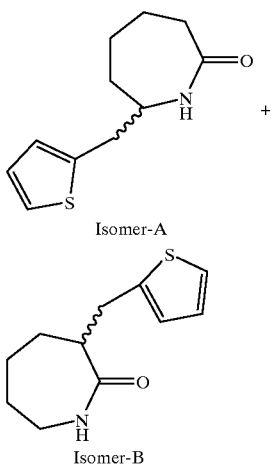

The product of Example 53 is reacted with 80% $H_2SO_4$, by the method of Example 2 to produce the title materials.

EXAMPLE 55

3,4,5,6-tetrahydro-7-methoxy-2-[(2-thienyl)methyl]-2H-azepine

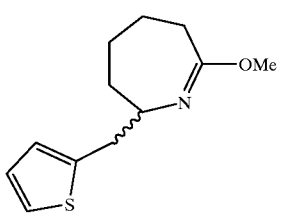

The Isomer-A product of Example 54 is reacted with trimethyloxonium tetrafluoroborate by the method of Example 3 to produce the title material.

EXAMPLE 56

3,4,5,6-tetrahydro-7-methoxy-6-[(2-thienyl)methyl]-2H-azepine

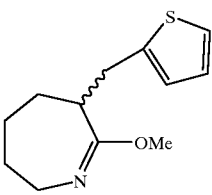

The Isomer-B product of Example 54 is reacted with trimethyloxonium tetrafluoroborate by the method of Example 3 to produce the title material.

EXAMPLE 57 hexahydro-7-[(2-thienyl)methyl]-2H-azepin-2-imine, monohydrochloride

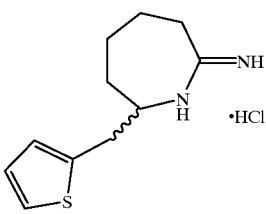

The title product of Example 55 in MeOH is reacted with ammonium chloride by the method of Example 5 to generate the title material.

EXAMPLE 58 hexahydro-3-[(2-thienyl)methyl]-2H-azepin-2-imine, monohydrochloride

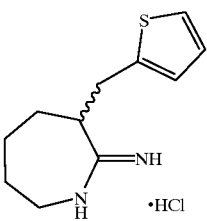

The title product of Example 56 in MeOH is reacted with ammonium chloride by the method of Example 5 to generate the title material.

EXAMPLE 59

4-phenyl-2-buten-1-ol

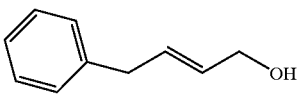

To a –10° C. solution of phenylmagnesium bromide, 3M in ether (68 mL) was added a solution of cupric acetate (5.6 g) and butadiene monoxide (6.43 mL) in THF (200 mL) over 40 min while maintaining the reaction temperature below −5° C. The reaction was stirred at −10° C. for 1 h, room temperature for 16 h, refluxed for 15 min then cooled to room temperature. Aqueous HCl (10%, 100 mL) was added and the mixture extracted with ethyl acetate. The organic solution was washed with aqueous HCl (10%), NaHCO$_3$ (saturated) and brine (saturated), dried (MgSO$_4$) and concentrated to yield a blue liquid. The residue was chromatographed to yield the title compound (6.3 g, 30%).

| Elemental analysis: C$_{10}$H$_{12}$O (MW = 146.21) | | |
|---|---|---|
|  | C | H |
| Calculated: | 82.15 | 8.27 |
| Found: | 82.18 | 8.61 |

EXAMPLE 60

2,2,2-trichloro-N-[1-(phenylmethyl)-2-propenyl] acetamide

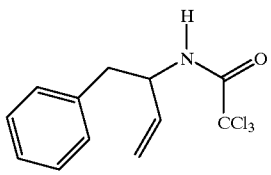

A solution of the product of Example 53 (5.15 g) 4n ether (20 mL) was added to a suspension of NaH (0.1 equivalent) in ether (40 mL). The solution was cooled to −15° and treated with trichloroacetonitrile (3.6 mL) over 30 min, the solution was stirred at room temperature for 1 h, treated with a solution of pentane (100 mL) and methanol (0.4 mL), filtered and concentrated. The residue was then dissolved in xylene (500 mL) and refluxed for 12 h. Concentration of the reaction mixture followed by chromatography afforded the title material (6.9 g, 69%).

| Elemental analysis: C$_{12}$H$_{12}$NOCl$_3$ (MW = 292.59) | | |
|---|---|---|
|  | C | H | N |
| Calculated: | 49.26 | 4.13 | 4.79 |
| Found: | 48.88 | 4.07 | 4.76 |

EXAMPLE 61 trans-3,3-dichloro-4-(chloromethyl)-5-(phenylmethyl)pyrrolidin-2-one

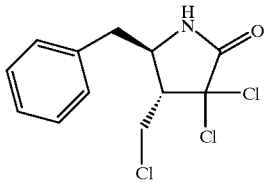

A solution of the product of Example 60 (2.7 g, 9.3 mmol) in xylene (100 mL) was reacted with bis-triphenylphosphine-ruthenium dichloride (300 mg) and refluxed for 8 h. Concentration of the reaction mixture followed by chromatography afforded the title material (1.5 g, 55%).

EXAMPLE 62 trans-4-methyl-5-(phenylmethyl)pyrrolidin-2-one

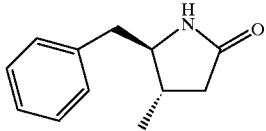

A solution of the product of Example 61 (1.3 g), tributyltin hydride (3.85 g) and AIBN (16 mg) in toluene (50 mL) was refluxed for 4 hours. The reaction mixture was treated with a solution of KF (20%, 40 mL) and ethyl acetate (100 mL), filtered, concentrated and chromatographed to yield the title material (270 mg).

| Elemental analysis: C$_{12}$H$_{15}$NO.0.1 CH$_3$CO$_2$C$_2$H$_5$ (MW = 198.06) | | | |
|---|---|---|---|
|  | C | H | N |
| Calculated: | 75.19 | 8.04 | 7.07 |
| Found: | 74.84 | 7.92 | 7.15 |

EXAMPLE 63 trans-3,4-dihydro-5-methoxy-3-methyl-2-(phenylmethyl)-2H-pyrrole

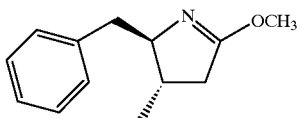

A solution of the product of Example 62 (400 mg, 2.0 mmol) in methylene chloride (25 mL) was treated with trimethyloxonium tetrafluoroborate (361 mg, 2.4 mmol) by the method of Example 3 to produce the title material (300 mg, 40%).

EXAMPLE 64

(±) (trans) 4-methyl-5-(phenylmethyl)pyrrolidin-2-imine, monohydrochloride

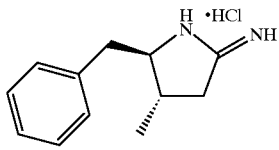

A solution of the title product of Example 63 (300 mg, 1.4 mmol) in MeOH (20 mL) was reacted with ammonium chloride (77 mg, 1.6 mmol) by the method of Example 5 followed by chromatography to generate the title material (240 mg, 75%).

MS (CI) for C$_{12}$H$_{17}$N$_2$ (MW=188): m+189 (100%).

Purity by analytical HPLC 97%.

EXAMPLE 65

2-(2-propenyl)cycloheptanone

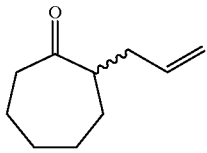

To a mechanically stirred mixture of potassium t-butoxide (Aldrich, 67.0 g, 0.6 mol) in benzene (600 mL) cooled to 0° C. under a nitrogen atmosphere was added cycloheptanone (Aldrich, 56.1 g, 0.5 mol) dropwise over 15 minutes. Ten minutes after the addition was complete, allyl bromide (Aldrich, 61.6 g, 0.51 mol) was added dropwise over 20 minutes. The reaction was warmed to room temperature, refluxed or 7 hrs., stirred at room temperature for 18 hrs., and diluted with 0.5 N $KHSO_4$ (300 mL). This mixture was further diluted with $Et_2O$ (600 mL), 3.5 N $KHSO_4$ (200 mL) and $H_2O$ (200 mL) before the organic was separated, washed with $H_2O$ (200 mL) and brine (200 mL), dried ($Na_2SO_4$), filtered, and stripped of all solvent under reduced pressure. The crude product (76.1 g) was distilled to yield 24.4 g (32%) of the title material (bp=104–108° C., 25 mm of Hg).

Elemental analysis: $C_{10}H_{16}O$ (MW = 152.24)

|  | C | H |
|---|---|---|
| Calculated: | 78.90 | 10.59 |
| Found: | 78.96 | 10.36 |

EXAMPLE 66

2-(2-propenyl)cycloheptanone, oxime

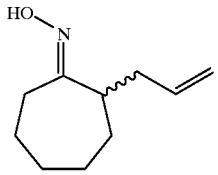

The title material of Example 65 (15.0 g, 98.5 mmol) was converted to the title compound by the method o Example 1 using 10.3 g (98.5 mmol) of hydroxylamine hydrochloride and 14.5 g (180.0 mmol) of NaOAc in a mixture of 90 mL EtOH and 60 mL of water. The procedure produced 16.4 g (97%) of the title compound.

Elemental analysis: $C_{10}H_{17}NO.0.25\ H_2O$ (MW = 171.75)

|  | C | H | N |
|---|---|---|---|
| Calculated: | 69.93 | 10.27 | 8.16 |
| Found: | 69.67 | 10.08 | 8.03 |

EXAMPLE 67 octahydro-8-(2-propenyl)azocin-2-one, mixture with octahydro-3-(2-propenyl)azocin-2-one

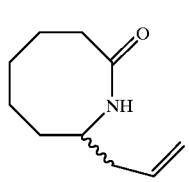 + 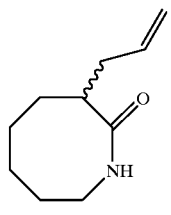

Isomer-A                Isomer-B

To the title product of Example 66 (16.2 g, 96.9 mmol) in 115 mL of acetone containing 1N NaOH (110 mL, 110 mmol) cooled to 0° C. was added benzenesulfonyl chloride (17.6 g, 100 mmol) dropwise over 10 minutes. The reaction mixture was warmed to room temperature and stirred over night. After removing the acetone under reduced pressure, the residue was diluted with EtOAc (300 mL) and water (75 me). The aqueous layer (pH=1) was separated and the organic layer was washed with 2×100 mL of 5% $KHCO_3$ and 2×75 mL of brine, dried over $Na_2SO_4$, filtered, and stripped of all solvent under reduced pressure. The crude residue (15.6 g) was separated into its Isomer-A (5.6 g, 34%) and Isomer-B (4.8 g, 29%) components by silica gel chromatography.

Isomer A:
Elemental analysis: $C_{10}H_{17}NO.0.125\ H_2O$ (MW = 169.50)

|  | C | H | N |
|---|---|---|---|
| Calculated: | 70.86 | 10.26 | 8.26 |
| Found: | 70.68 | 10.22 | 8.19 |

Isomer B:
Elemental analysis: $C_{10}H_{17}NO.0.25\ H_2O$ (MW = 171.75)

|  | C | H | N |
|---|---|---|---|
| Calculated: | 69.93 | 10.27 | 8.16 |
| Found: | 70.15 | 10.19 | 8.06 |

EXAMPLE 68 octahydro-8-(3-phenyl-2-propenyl)azocin-2-one

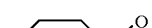

The Isomer A of the title material of Example 67 in acetonitrile is coupled to bromobenzene in the presence palladium acetate, tri-o-tolylphosphine, and triethylamine by the method of Example 32 to provide the title material.

EXAMPLE 69

2,3,4,5,6,7-hexahydro-8-methoxy-2-(3-phenyl-2-propenyl)azocine

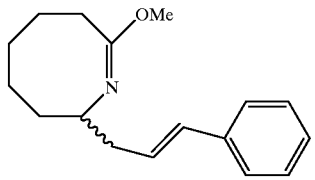

The product of Example 68 is reacted with trimethyloxonium tetrafluoroborate in CH$_2$Cl$_2$ by the method of Example 3 to produce the title material.

EXAMPLE 70 octahydro-8-(3-phenyl-2-propenyl)azocin-2-imine, monohydrochloride

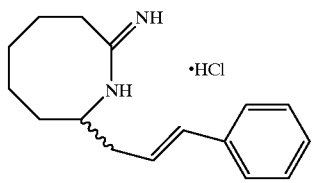

The title product of Example 69 in MeOH is reacted with ammonium chloride by the method of Example 5 to generate the title material.

EXAMPLE 71 octahydro-8-(3-phenylpropyl)azocin-2-one

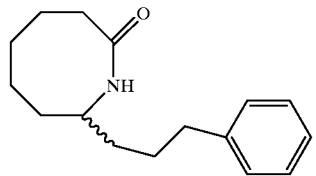

The title material of Example 68 in MeOH is hydrogenated over Pd on carbon in a standard Parr apparatus by the method of Example 35 to generate the title product.

EXAMPLE 72

2,3,4,5, 6,7-hexahydro-8-methoxy-2-(3-phenylpropyl)azocine

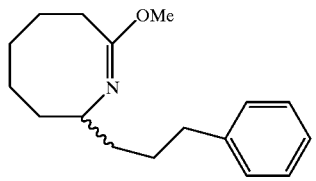

The product of Example 71 is reacted with trimethyloxonium tetrafluoroborate in CH$_2$Cl$_2$ by the method of Example 3 to produce the title material.

EXAMPLE 73 octahydro-8-(3-phenylpropyl)azocin-2-imine, monohydrochloride

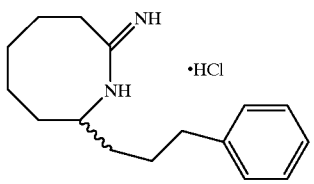

The title product of Example 72 in MeOH is reacted with ammonium chloride by the method of Example 5 to generate the title material.

EXAMPLE 74 ethyl 1,4-dioxaspiro[4.5]decane-6-carboxylate

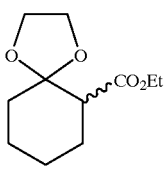

To ethyl 2-cyclohexanonecarboxylate (Aldrich, 169.5 g, 1.0 mol) and ethylene glycol (Sigma, 166.7 g, 2,7 mol) in benzene (1.5 L) was added pyridinium tosylate (50.2 g, 0.2 mol). The reaction was refluxed under a nitrogen atmosphere and the water generated was removed using a Dean-Stark trap. After cooling the reaction to room temperature, half of the benzene was removed under reduced pressure and the residue was washed with 25% aqueous NaHCO$_3$, stripped of all solvent, dissolved in CH$_2$Cl$_2$, dried (Na$_2$SO$_4$), filtered, and again stripped of all solvent under reduced pressure to provide 213 g of the title material.

EXAMPLE 75

1,4-dioxaspiro[4.5]decane-6-carboxaldehyde

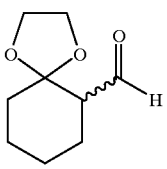

To the product of Example 74 (10.0 g, 46.7 mmol) in 150 mL of toluene cooled to –78° C. was added dropwise under argon (Ar) 93.5 mL (93.5 mmol) of diisobutylaluminum hydride (DIBAL) in toluene over a 15 min. period. After stirring this reaction for 45 min., MeOH (40 mL) was added dropwise followed by 200 mL of a saturated solution of Rochelle salts (potassium sodium tartrate tetrahydrate). The reaction was warmed to room temperature, stirred for one hour, and the organic layer was separated The aqueous layer was washed with EtOAc and the organic layer was stripped of all toluene. The residue and the EtOAc extract were combined, diluted with EtOAc, washed with water, dried (MgSO$_4$), filtered and stripped of all solvent to yield the crude desired produce. This material was chromatographed through silica gel eluting with a 1:1 mixture of EtOAc and hexane to yield 6.4 g of the title material as a colorless oil.

EXAMPLE 76

2-ethenylcyclohexanone

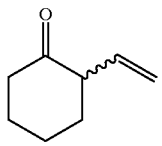

To a cold suspension of methylphosphonium bromide in $Et_2O$ under Ar is added an $Et_2O$ solution of potassium hexamethyldisilylazide (KHMDS). After stirring this mixture for one hr, the title material of Example 75, dissolved in $Et_2O$, is added dropwise to the stirred reaction mixture. The reaction is allowed to stir cold, warm to room temperature and to stir at room temperature. After quenching the reaction with water, it is extracted with $Et_2O$, dried, stripped of solvent under reduced pressure to yield the crude product. The title material is isolated from the crude product by silica gel chromatography. Alternatively, the title material is synthesized by the method described by S. Kim and S. Lee, *Tetrahedron Letters*, 1991, 32, 6575–6578.

EXAMPLE 77

2-ethenylcyclohexanone, oxime

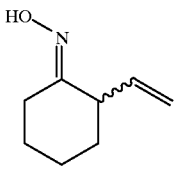

The product of Example 76 is reacted with hydroxylamine hydrochloride and NaOAc in a mixture of EtOH and water, by the method of Example 1 to produce the title material.

EXAMPLE 78

7-ethenylhexahydro-2H-azepin-2-one, mixture with 3-ethenylhexahydro-2H-azepin-2-one

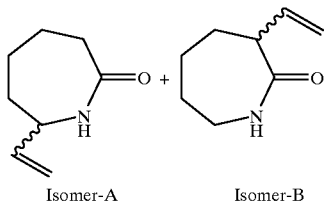

Isomer-A    Isomer-B

The title product of Example 77 in acetone containing 1N NaOH is reacted with benzenesulfonyl chloride by the method described in Example 67 to generate the Isomer-A and Isomer-B title materials.

EXAMPLE 79 methyl 2-[2-(hexahydro-7-oxo-1H-azepin-2-yl) ethenyl]benzoate

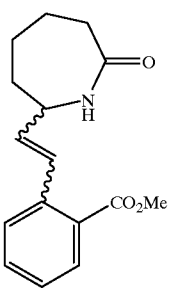

The Isomer A of the title material of Example 78 acetonitrile is coupled to methyl 2-bromobenzoate (Aldrich) in the presence palladium acetate, tri-o-tolylphosphine, and triethylamine by the method or Example 32 to provide the title material as either or both the Z and E isomers.

EXAMPLE 80 methyl 2-[2-(3,4,5,6-tetrahydro-7-methoxy-2H-azepin-2-yl)ethenyl]benzoate

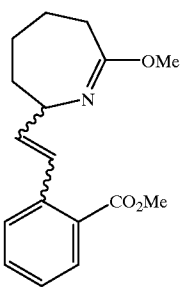

The product of Example 79 is reacted with trimethyloxonium tetrafluoroborate in $CH_2Cl_2$ by the method of Example 3 to produce the title material.

EXAMPLE 81 methyl 2-[2-(hexahydro-7-imino-1H-azepin-2-yl) ethenyl]benzoate, monohydrochloride

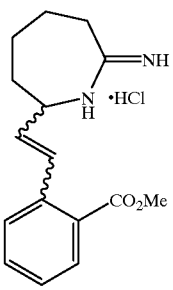

The title product of Example 80 in MeOH is reacted with ammonium chloride by the method of Example 5 to generate the title material.

EXAMPLE 82 methyl 2-[2-(hexahydro-7-oxo-1H-azepin-2-yl)ethyl]benzoate

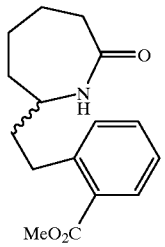

The title material of Example 79 in MeOH is hydrogenated over Pd on carbon in a standard Parr apparatus by the method of Example 35 to generate the title product.

EXAMPLE 83 methyl 2-[2-(3,4,5,6-tetrahydro-7-methoxy-2H-azepin-2-yl)ethyl]benzoate

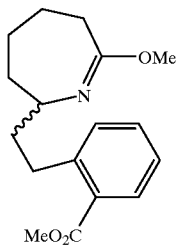

The product of Example 82 is reacted with trimethyloxonium tetrafluoroborate in CH$_2$Cl$_2$ by the method of Example 3 to produce the title material.

EXAMPLE 84 methyl 2-[2-(hexahydro-7-imino-1H-azepin-2-yl)ethyl]benzoate, monohydrochloride

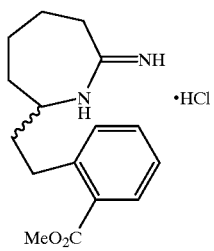

The title product of Example 83 in MeOH is reacted with ammonium chloride by the method of Example 5 to generate the title material.

EXAMPLE 85 methyl 2-[2-(hexahydro-2-oxo-1H-azepin-3-yl)ethenyl]benzoate

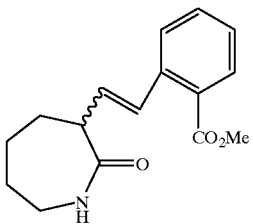

The Isomer B of the title material of Example 78 in acetonitrile is coupled to methyl 2-bromobenzoate (Aldrich) In the presence palladium acetate, tri-o-tolylphosphine, and triethylamine by the method of Example 32 to provide the title material as either or both the Z and E isomers.

EXAMPLE 86 methyl 2-[2-(3,4,5,6-tetrahydro-7-methoxy-2H-azepin-6-yl)ethenyl]benzoate

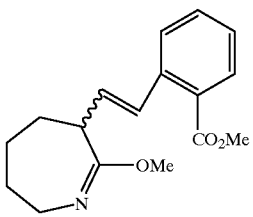

The product of Example 85 is reacted with trimethyloxonium tetrafluoroborate in CH$_2$Cl$_2$ by the method of Example 3 to produce the title material.

EXAMPLE 87 methyl 2-[2-(hexahydro-2-imino-1H-azepin-3-yl)ethenyl]benzoate, monohydrochloride

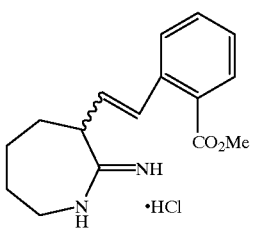

The title product of Example 86 in MeOH is reacted with ammonium chloride by the method of Example 5 to generate the title material.

EXAMPLE 88 methyl 2-[2-(hexahydro-2-oxo-1H-azepin-3-yl)ethyl]benzoate

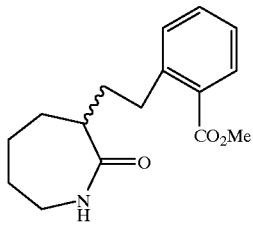

The title material of Example 85 in MeOH is hydrogenated over Pd on carbon in a standard Parr apparatus by the method of Example 35 to generate the title product.

EXAMPLE 89 methyl 2-[2-(3,4,5,6-tetrahydro-7-methoxy-2H-azepin-6-yl)ethyl]benzoate

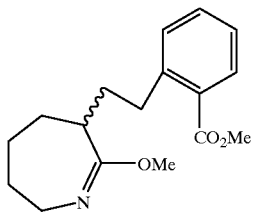

The product of Example 88 is reacted with trimethyloxonium tetrafluoroborate in CH$_2$Cl$_2$ by the method of Example 3 to produce the title material.

EXAMPLE 90 methyl 2-[2-(hexahydro-2-imino-1H-azepin-3-yl)ethyl]benzoate, monohydrochloride

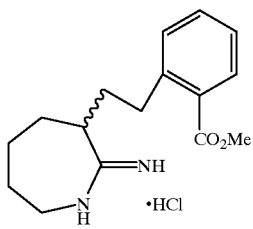

The title product of Example 89 in MeOH is reacted with ammonium chloride by the method of Example 5 to generate the title material.

EXAMPLE 91 methyl 3-[2-(hexahydro-7-oxo-1H-azepin-2-yl)ethenyl]benzeneacetate

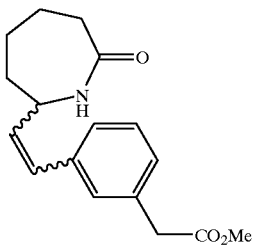

The Isomer A of the title material of Example 78 in acetonitrile is coupled to methyl 3-bromobenzeneacetate (Aldrich) in the presence palladium acetate, tri-o-tolylphosphine, and triethylamine by the method of Example 32 to provide the title material as either or both the Z and E isomers.

EXAMPLE 92 methyl 2-[2-(3,4,5,6-tetrahydro-7-methoxy-2H-azepin-6-yl)ethenyl]benzeneacetate

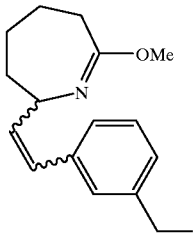

The product of Example 91 is reacted with trimethyloxonium tetrafluoroborate in CH$_2$Cl$_2$ by the method of Example 3 to produce the title material.

EXAMPLE 93 methyl 3-[2-(hexahydro-7-imino-1H-azepin-2-yl)ethenyl]benzeneacetate, monohydrochloride

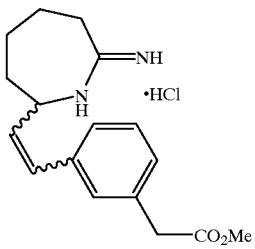

The title product of Example 92 in MeOH is reacted with ammonium chloride by the method of Example 5 to generate the title material.

EXAMPLE 94

6-(phenylmethyl)piperidin-2-imine, monohydrochloride

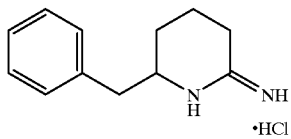

2-benzylpyridine (Aldrich, 2.5 g, 0.015 mole), sodium amide (780 mg, 0.02 mole) and N, N-dimethylaniline (25 mL) were refluxed overnight. Contents were allowed to cool and partitioned between ether ($Et_2O$) and water. The ether layer was dried ($MgSO_4$) and concentrated in vacuo leaving an oil. The oil was purified by chromatography. The purified material was dissolved in 1N HCl, lyophilized, and triturated with EtOAc to give 2-amino-6-benzylpyridine as a white solid. This 2-amino-6-benzylpyridine (470 mg), 5% rhodium/carbon (250 mg), and glacial acetic acid (30 mL) were shaken at 55 psi hydrogen on a Parr hydrogenation apparatus overnight. More catalyst (300 mg) was added and contents were again shaken at 55 psi hydrogen overnight. Contents were filtered and the filtrate was concentrated in vacuo leaving a viscous oil (500 mg). The product was purified by C-18 reverse phase chromatography to give a white solid. The solid was dissolved in 1 N HCl, lyophilized, and recrystallized from EtOH/EtOAc to give the desired as a white solid. The analysis of the product was found to be consistent with the proposed structure.

MH+=189.

$^1$H NMR ($CDCl_3$): d 9.85 (s, 1H); 8.95 (s, 1H); 8.62 (s, 1H); 7.40–7.10 (m, 5H); 3.80–3.60 (m, 1H); 3.20–3.00 (m, 1H); 2.90–2.70 (m, 2H); 2.65–2.45 (S, 1H) ; 2.42–2.25 (m, 2H); 1.92 (m, 2H); 1.75 (m, 1H); 1.50–1.35 (m, 1H).

EXAMPLE 95

6-(cyclohexylmethyl)piperidin-2-imine, monohydrochloride

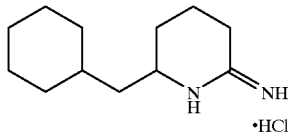

The 2-amino-6-benzylpyridine was reduced as in Example 94, except platinum oxide was used as the catalyst. The product was obtained as an oil which was dissolved in 1 N HCl and lyophilized to give a white solid. The solid was recrystallized from EtOAc to give the desired title compound as white crystals. The analysis of the product was found to be consistent with the proposed structure.

MH+=195.

$^1$H NMR (CDCl3): d 9.60 (s, 1H); 8.90 (s, 1H); 8.70 (s, 1H); 3.60–3.40 (m, 1H); 2.90–2.70 (m, 1H); 2.70–2.50 (m, 1H); 2.10–1.80 (m, 2H); 1.80–1.00 (m, 13H); 1.00–0.80 (m, 2H)

EXAMPLE 96

6-(3-phenyl-2-propenyl)piperidin-2-one

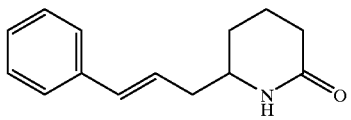

6-Allyl valerolactam is reacted with bromobenzene by the method of Example 32 to generate the title compound.

EXAMPLE 97

2,3,4,5-tetrahydro-6-methoxy-2-(3-phenyl-2-propenyl)pyridine

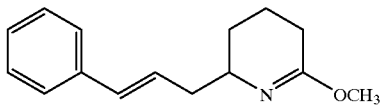

The product of Example 96 is reacted with trimethyloxonium tetrafluoroborate by the method of Example 3 to generate the title compound.

EXAMPLE 98

6-(3-phenyl-2-propenyl)piperidin-2-imine, monohydrochloride

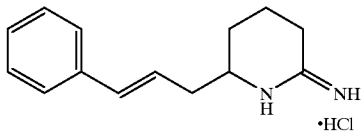

The product of Example 97 is reacted with ammonium chloride by the method of Example 5 to generate tee compound.

EXAMPLE 99

6-(3-phenylpropyl)piperidin-2-one

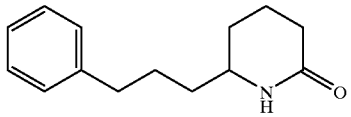

The product of Example 96 is hydrogenated by the method of Example 35 to generate the title compound.

EXAMPLE 100

2,3,4,5-tetrahydro-6-methoxy-2-(3-phenylpropyl) pyridine

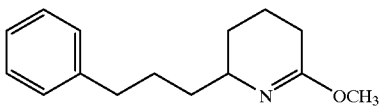

The product of Example 99 is reacted with trimethyloxonium tetrafluoroborate by the method of Example 3 to generate the title compound.

EXAMPLE 101

6-(3-phenylpropyl)piperidin-2-imine, monohydrochloride

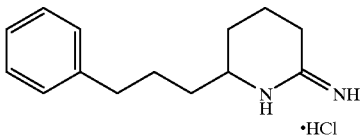

The product of Example 100 is reacted with ammonium chloride by the method of Example 5 to generate the title compound.

EXAMPLE 102 methyl 1-[2-(1,3-dioxolan-2-yl)ethyl]-2-oxocyclohexanecarboxylate

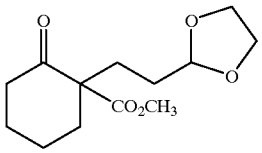

A solution of 2-carbomethoxycyclohexanone (2.0 g, 12.8 mmoles) in 50 mL of DMF was reacted at 70° C. for 15 h with 2-(2-bromoethyl)-1,3-dioxolane (4.6 g, 25 moles) and potassium carbonate (4.8 g, 34.8 mmoles). The reaction mixture was diluted to 500 mL with water and extracted with ethyl ether/ethyl acetate. The organic extracts were dried over sodium sulfate, and the solvent was evaporated to generate the title compound as an oil.

FAB-MS: m/z263 (M+Li).

EXAMPLE 103

2-[2-(1,3-dioxolan-2-yl)ethyl]cyclohexanone

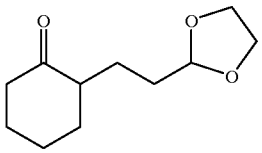

The product of Example 102 was reacted with sod ,m cyanide (0.69 g, 14.1 mmoles) in 25 mL of DMSO at 160° C. for 12 hrs. The reaction mixture was then diluted to 700 mL with water and extracted with ethyl acetate/hexane (1:1). The solvent removed from the extracts to provide the title compound as oil.

FAB-MS: m/z205.7 (M+Li).

EXAMPLE 104

2-[2-(1,3-dioxolan-2-yl)ethyl]cyclohexanone, oxime

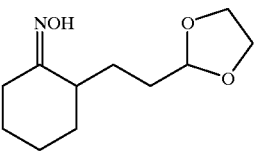

The product of Example 103 was reacted with hydroxylamine hydrochloride (1.25 g, 18 mmoles) and sodium acetatetrihydrate (2.9 g, 21 mmoles) in 30 mL ethanol/water (2:1) for 4 hrs under gentle reflux. The solvent was evaporated and the solid dissolved in ethyl acetate, washed with sat. sodium chloride, dried over sodium sulfate, and the solvent stripped off to leave the title compound as an oil.

FAB-MS: m/z214.1 (M+H).

EXAMPLE 105

7-[2-(1,3-dioxolan-2-yl)ethyl]hexahydro-2H-azepin-2-one

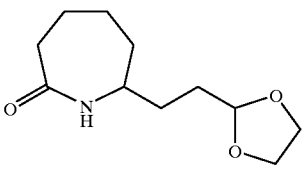

The product of Example 104 is reacted with benzenesulfonyl chloride and sodium hydroxide In acetone/water by the method of Example 67 to generate the title compound.

EXAMPLE 106

2-[2-(1,3-dioxolan-2-yl)ethyl]-3,4,5,6-tetrahydro-7-methoxy-2H-azepine

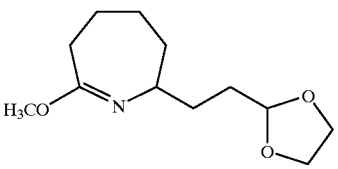

The product of Example 105 is reacted with trimethyloxonium tetrafluoroborate by the method of Example 3 to generate the title compound.

EXAMPLE 107

7-[2-(1,3-dioxolan-2-yl)ethyl]hexahydro-2H-azepin-2-imine, monohydrochloride

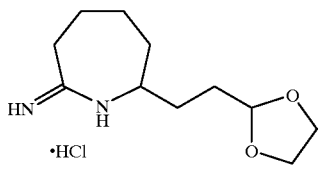

The product of Example 106 is reacted with ammonium chloride by the method of Example 5 to generate the t compound.

EXAMPLE 108 methyl 1-[2-(1,3-dioxan-2-yl)ethyl]-2-oxocyclohexanecarboxylate

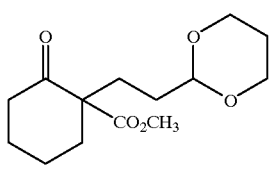

A solution of 2-carbomethoxycyclohexanone in DMF is reacted with 2-(2-bromoethyl)-1,3-dioxane and potassium carbonate by the method of Example 102 to generate the title compound.

EXAMPLE 109

2-[2-(1,3-dioxan-2-yl)ethyl]cyclohexanone

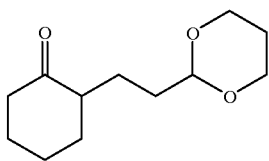

The product of Example 108 is reacted with sodium cyanide in DMSO at 160° C. by the method of Example 103 to generate the title compound.

EXAMPLE 110

2-[2-(1,3-dioxan-2-yl)ethyl]cyclohexanone, oxime

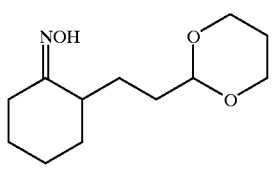

The product of Example 109 is reacted with hydroxyamine hydrochloride and sodium acetate in ethanol/water by the method of Example 1 to generate the title compound.

EXAMPLE 111

7-[2-(1,3-dioxan-2-yl)ethyl]hexahydro-2H-azepin-2-one

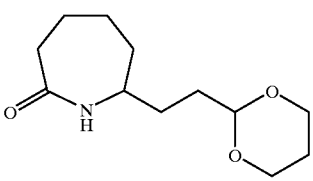

The product of Example 110 is reacted with benzenesulfonyl chloride and sodium hydroxide in acetone/water by the method of Example 67 to generate the title compound.

EXAMPLE 112

2-[2-(1,3-dioxan-2-yl)ethyl]-3,4,5,6-tetrahydro-7-methoxy-2H-azepine

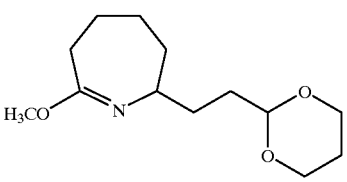

The product of Example 111 is reacted with trimethyloxonnum tetrafluoroborate by the method of Example 3 to generate the title compound.

EXAMPLE 113

7-[2-(1,3-dioxan-2-yl)ethyl]hexahydro-2H-azepin-2-imine, monohydrochloride

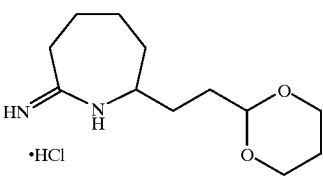

The product of Example 112 is reacted with ammonium chloride by the method of Example 5 to generate the title compound.

EXAMPLE 114

7-[[4,5-dihydro-3-(trifluoromethyl)isoxazol-5-yl-]methyl]hexahydro-2H-azepin-2-one, mixture with 7-[[4,5-dihydro-3-(trifluoromethyl)isoxazol-4-yl]methyl]hexahydro-2H-azepin-2-one

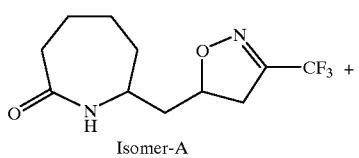

Isomer-A

-continued

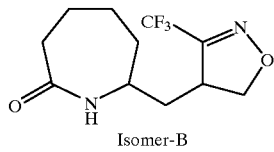
Isomer-B

The title product isomer B of Example 18 (7-allyl caprolactam) is reacted with trifluoromethyloximoyl chloride and triethylamine in toluene by the method of R. Huisgen, *Ang. Chem. Int. Ed.* 1963, 2(10), 562, generate a mixture of the two title compounds. The title Isomer-A and isomer-B materials are separated by HLPC.

EXAMPLE 115

2-[[4,5-dihydro-3-(trifluoromethyl)isoxazol-5-yl]methyl]-3,4,5,6-tetrahydro-7-methoxy-2H-azepine

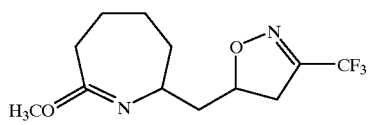

The title Isomer-A of Example 114 is reacted with trimethyloxonium tetrafluoroborate by the method of Example 3 to generate the title compound.

EXAMPLE 116

7-[[4,5-dihydro-3-(trifluoromethyl)isoxazol-5-yl]methyl]hexahydro-2H-azepin-2-imine, monohydrochloride

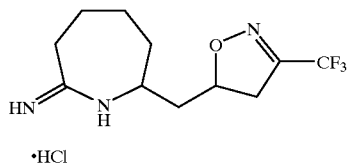

The product of Example 115 is reacted with ammonium chloride by the method of Example 5 to generate the title compound.

EXAMPLE 117

2-[[4,5-dihydro-3-(trifluoromethyl)isoxazol-4-yl]methyl]-3,4,5,6-tetrahydro-7-methoxy-2H-azepine

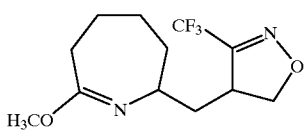

The title Isomer-B of Example 114 is reacted with trimethyloxonium tetrafluoroborate by the method of Example 3 to generate the title compound.

EXAMPLE 118

7-[[4,5-dihydro-3-(trifluoromethyl)isoxazol-4-yl]methyl]hexahydro-2H-azepin-2-imine, monohydrochloride

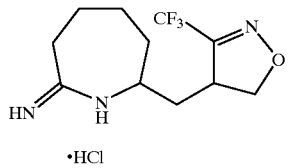

The title product of Example 117 is reacted with ammonium chloride by the method of Example 5 to generate the title compound.

EXAMPLE 119 hexahydro-7-[[3-(trifluoromethyl)isoxazol-5-yl]methyl]-2H-azepin-2-one

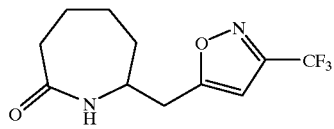

The title Isomer-A of Example 114 is reacted with manganese dioxide in benzene/dioxane by the method of A. Barco, *Synth. Commun.* 1978, 8, 219, to generate the title compound.

EXAMPLE 120

3,4,5,6-tetrahydro-7-methoxy-2-[[3-(trifluoromethyl)isoxazol-5-yl]methyl]-2H-azepine

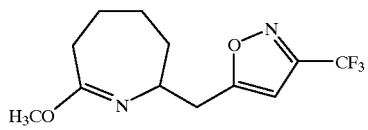

The title product of Example 119 is reacted with trimethyloxonium tetrafluoroborate by the method of Example 3 to generate the title compound.

EXAMPLE 121 hexahydro-7-[[3-(trifluoromethyl) isoxazol-5-yl]methyl]-2H-azepin-2-imine, monohydrochloride

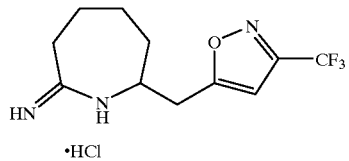

The title product of Example 120 is reacted with ammonium chloride by the method of Example 5 to generate the title compound.

EXAMPLE 122 hexahydro-7-[[3-(trifluoromethyl)isoxazol-4-yl]
methyl]3-2H-azepin-2-one

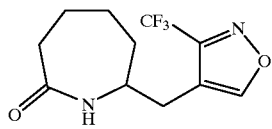

The title Isomer-B of Example 114 is reacted with manganese dioxide in benzene/dioxane by the method of A. Barco, *Synth. Commun.* 1978, 8, 219, to generate the title compound.

EXAMPLE 123

3,4,5,6-tetrahydro-7-methoxy-2-[[3-(trifluoromethyl)
isoxazol-4-yl]methyl)-2H-azepine

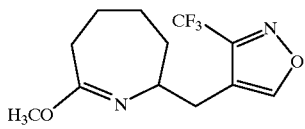

The title product of Example 122 is reacted with trimethyloxonium tetrafluoroborate by the method of Example 3 to generate the title compound.

EXAMPLE 124 hexahydro-7-[(3-(trifluoromethyl)isoxazol-4-yl]
methyl]-2H-azepin-2-imine, monohydrochloride

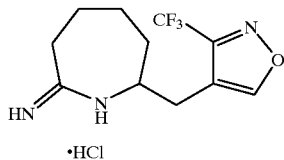

The title product of Example 123 is reacted with ammonium chloride by the method of Example 5 to generate the title compound.

EXAMPLE 125

7-[(4,5-dihydro-3-phenylisoxazol-4-yl)methyl]
hexahydro-2H-azepin-2-one, mixture with 7-[(4,5-
dihydro-3-phenylisoxazol-5-yl)methyl]hexahydro-
2H-azepin-2-one

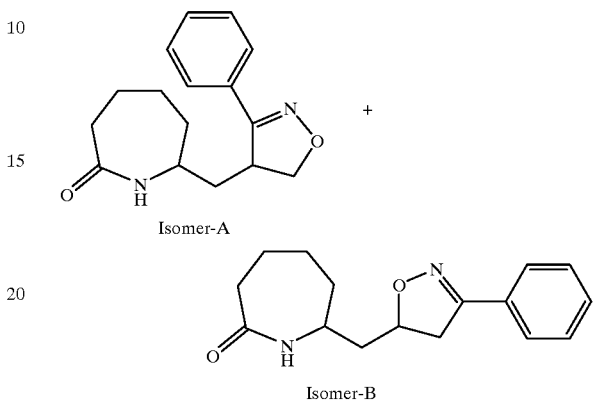

The title product Isomer B of Example 18 (7-Allyl caprolactam) s reacted with benzaldehydeoximinoxy chloride and triethylamine in toluene by the method of R. Huisgen, *Ang. Chem. Int. Ed.* 1963, 2(10), 562: To a solution of 2 g (0.013 mol) of benzaldehyde oximioyl chloride and 2 g (0.006 mol) of 7-allylcaprolactam in 30 mL of ethyl ether was added 1.3 g (0.013 mol) of triethylamine dropwise. This mixture was stirred at 25° C. for 18 hours. The mixture was then diluted with ethyl acetate, washed with dilute HCl, dried (MgSO$_4$), leered and concentrated to afford an off-white semi-solid. Trituration with ethyl ether and filtration afforded 1.1 g of an off-white solid. Column chromatography (ethyl acetate) afforded a mixture of the title compounds as a white solid, mp=118–128° C., M+H=273. The title Isomer-A and Isomer-B materials are separated by EPIC.

EXAMPLE 126 hexahydro-7-[(3-phenylisoxazol-4-yl)methyl]-2H-
azepin-2-one

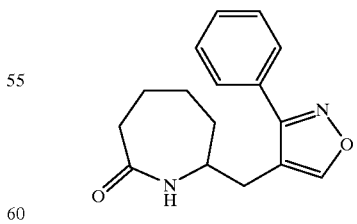

The title Isomer-A material of Example 125 is reacted with manganese dioxide in benzene/dioxane by the method of A. Barco, *Synth. Commun.* 1978, 8, 219, to generate the title compound.

EXAMPLE 127

3,4,5,6-tetrahydro-7-methoxy-2-[(3-phenylisoxazol-4-yl)methyl]-2H-azepine

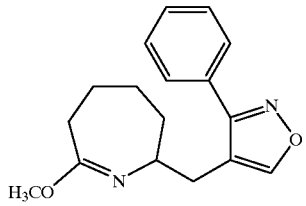

The title product of Example 126 is reacted with trimethyloxonium tetrafluoroborate by the method of Example 3 to generate the title compound.

EXAMPLE 128 hexahydro-7-[(3-phenylisoxazol-4-yl)methyl]-2H-azepin-2-imine, monohydrochloride

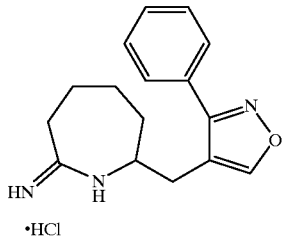

The title product of Example 127 is reacted with ammonium chloride by the method of Example 5 to generate the title compound.

EXAMPLE 129 hexahydro-7-[(3-(phenylisoxazol-5-yl)methyl]-2H-azepin-2-one

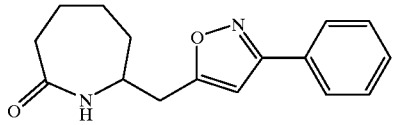

The title Isomer-B material of Example 125 is reacted with manganese dioxide in benzene/dioxane by the method of A. Barco, *Synth. Commun.* 1978, 8, 219, to generate the title compound.

EXAMPLE 130

3,4,5,6-tetrahydro-7-methoxy-2-[(3-phenylisoxazol-5-yl)methyl]-2H-azepine

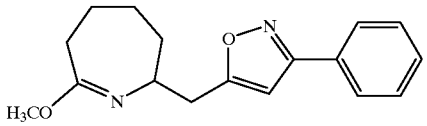

The product of Example 129 is reacted with trimethyloxonium tetrafluoroborate by the method of Example 3 to generate the title compound.

EXAMPLE 131 hexahydro-7-[(3-phenylisoxazol-5-yl)methyl]-2H-azepin-2-imine, monohydrochloride

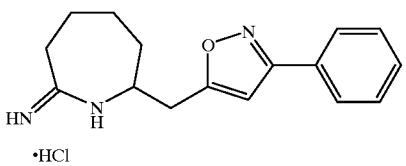

The product of Example 130 is reacted with ammonium chloride by the method of example 5 to generate the title compound.

EXAMPLE 132

7-[[4,5-dihydro-1-phenyl-3-(trifluoromethyl)-2H-pyrazol-5-yl]methyl]hexahydro-1H-azepin-2-one, mixture with 7-[[4,5-dihydro-1-phenyl-3-(trifluoromethyl)-2H-pyrazol-4-yl]methyl]hexahydro-1H-azepin-2-one

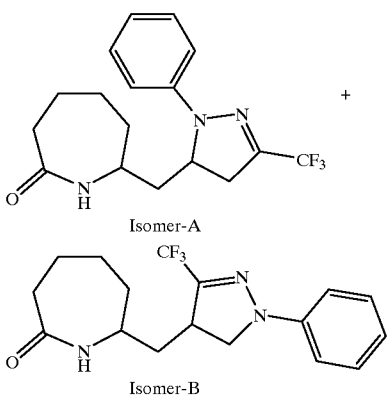

The title product Isomer B of Example 18 (7-Allyl caprolactam) is reacted with trifluoroacetaldehydebenzenehydrazonoyl chloride and triethylamine in toluene by the method of R. Huisgen, *Ang. Chem. Int. Ed.* 1963, 2(10), 562, to generate a mixture of the two title compounds. The title Isomer-A and Isomer-B materials are separated by HPLC.

EXAMPLE 133

2-[[4,5-dihydro-1-phenyl-3-(trifluoromethyl)-1H-pyrazol-5-yl]methyl)-3,4,5,6-tetrahydro-7-methoxy-2H-azepine

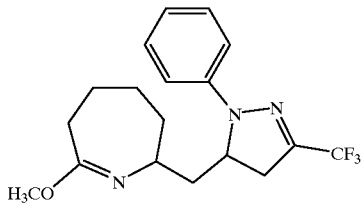

The title isomer-A material of Example 132 is reacted with trimethyloxonium tetrafluoroborate by the method of Example 3 to generate the title compound.

EXAMPLE 134

7-[[4,5-dihydro-1-phenyl-3-(trifluoromethyl)-1H-pyrazol-5-yl]methyl]-hexahydro-2H-azepin-2-imine, monohydrochloride

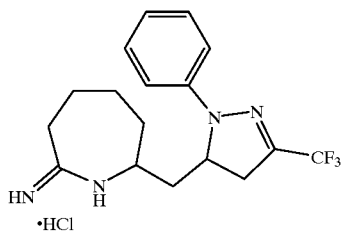

The title product of Example 133 is reacted with ammonium chloride by the method of Example 5 to generate the title compound.

EXAMPLE 135

2-[[4,5-dihydro-1-phenyl-3-(trifluoromethyl)-1H-pyrazol-4-yl]methyl]-3,4,5,6-tetrahydro-7-methoxy-2H-azepine

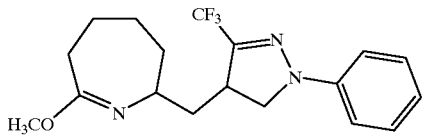

The title isomer-B material of Example 132 is reacted with trimethyloxonium tetrafluoroborate by the method of Example 3 to generate the title compound.

EXAMPLE 136

7-[[4,5-dihydro-1-phenyl-3-(trifluoromethyl)-1H-pyrazol-4-yl]methyl)hexahydro-2H-azepin-2-imine, monohydrochloride

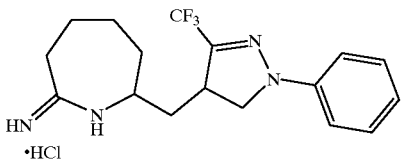

The title product of Example 135 is reacted with ammonium chloride by the method of Example 5 to generate the title compound.

EXAMPLE 137 hexahydro-7-[[1-phenyl-3-(trifluoromethyl)-1H-pyrazol-5-yl]methyl]-2H-azepin-2-one

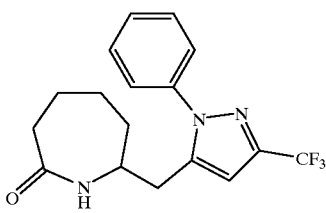

The title Isomer-A material of Example 132 is reacted with DDQ in benzene by the method of E. W. Bousquet, *J. Org. Chem.* 1975, 40, 2208, to generate the title compound.

EXAMPLE 138

3,4,5,6-tetrahydro-7-methoxy-2-[[1-phenyl-3-(trifluoromethyl)-1H-pyrazol-5-yl]methyl]-2H-azepine

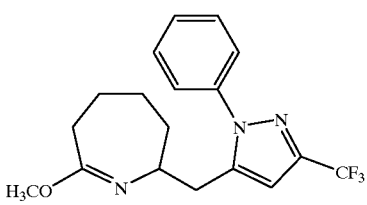

The title material of Example 137 is reacted with trimethyloxonium tetrafluoroborate by the method of Example 3 to generate the title compound.

EXAMPLE 139 hexahydro-7-[[1-*phenyl*-3-(trifluoromethyl)-1H-pyrazol-5-yl]methyl]-2H-azepin-2-imine, monohydrochloride

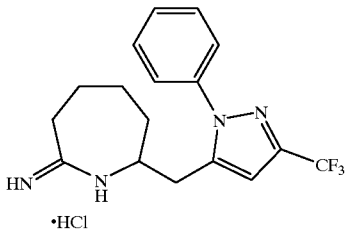

The title material of Example 138 is reacted with ammonium chloride by the method of Example 5 to generate the title compound.

EXAMPLE 140 hexahydro-7-[[1-phenyl-3-(trifluoromethyl)-1H-pyrazol-4-yl]methyl]-2H-azepin-2-one

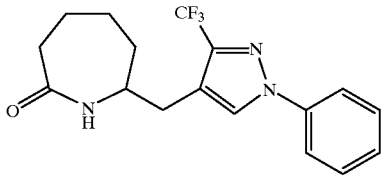

The title Isomer-B material of Example 132 is reacted with DDQ in benzene by the method of E. W. Bousquet, *J. Org. Chem.* 1975, 40, 2208, to generate the title compound.

EXAMPLE 141

3,4,5,6-tetrahydro-7-methoxy-2-[[1-phenyl-3-(trifluoromethyl)-1H-pyrazol-4-yl]methyl]-2H-azepine

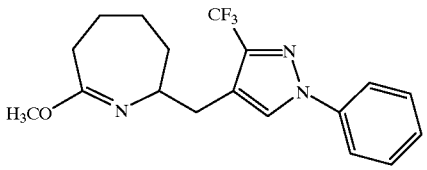

The title material of Example 140 is reacted with trimethyloxonium tetrafluoroborate by the method of Example 3 to generate the title compound.

EXAMPLE 142 hexahydro-7-[[1-phenyl-3-(trifluoromethyl)-1H-pyrazol-4-yl]methyl]-2H-azepin-2-imine, monohydrochloride

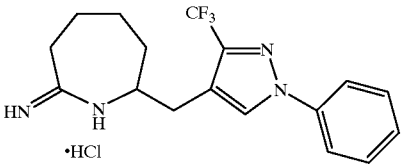

The title material of Example 141 is reacted with ammonium chloride by the method of Example 5 to generate the title compound.

EXAMPLE 143

7-[(4,5-dihydro-1,3-diphenyl-1H-pyrazol-4-yl]methyl] hexahydro-2H-azepin-2-one, mixture with 7-[(4,5-dihydro-1,3-diphenyl-1H-pyrazol-5-yl)methyl]hexahydro-2H-azepin-2-one

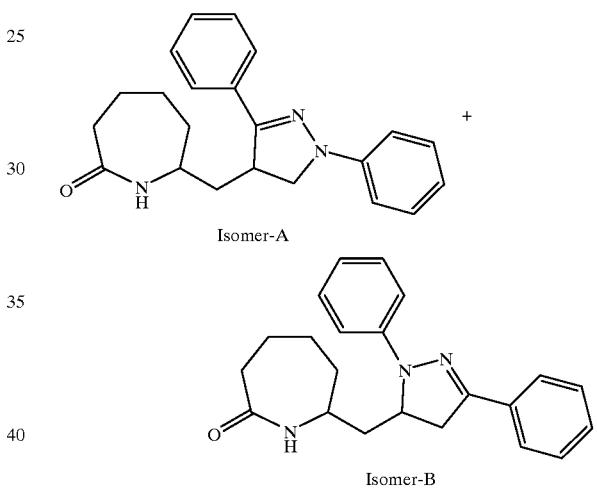

The title product Isomer B of Example 18 (7-Allyl caprolactam) is reacted with benzaldehyde, benzenehydrazonoyl chloride, and triethylamine in toluene by the method of R. Huisgen, *Ang. Chem. Int. Ed.* 1963, 2(10), 562, to generate a mixture of the two title compounds. The title Isomer-A and Isomer-B materials are separated by HPLC.

EXAMPLE 144

2-[(4,5-dihydro-1,3-diphenyl-1H-pyrazol-4-yl)methyl]3,4,5,6-tetrahydro-7-methoxy-2H-azepine

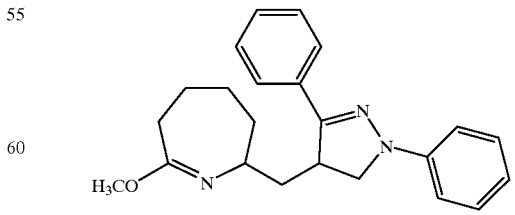

The title Isomer-A material of Example 143 is reacted with trimethyloxonium tetrafluoroborate by the method of Example 3 to generate the title compound.

EXAMPLE 145

7-[(4,5-dihydro-1,3-diphenyl-1H-pyrazol-4-yl)methyl]hexahydro-2H-azepin-2-imine, monohydrochloride

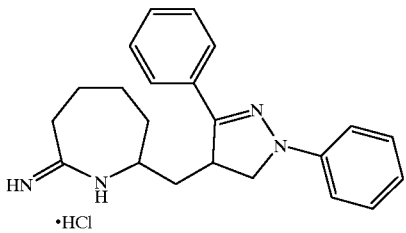

The title material of Example 144 is reacted with ammonium chloride by the method of Example 5 to generate the title compound.

EXAMPLE 146

7-[(1,3-diphenyl-1H-pyrazol-5-yl)methyl]hexahydro-2H-azepin-2-one

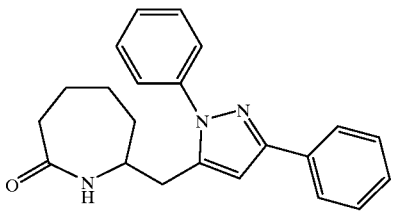

The title Isomer-B material of Example 143 is reacted with DDQ in benzene by the method of E. W. Bousquet, *J. Org. Chem.* 1975, 40, 2208, to generate the title compound.

EXAMPLE 147

2-[(1,3-diphenyl-1H-pyrazol-5-yl)methyl]-3,4,5,6-tetrahydro-7-methoxy-2H-azepine

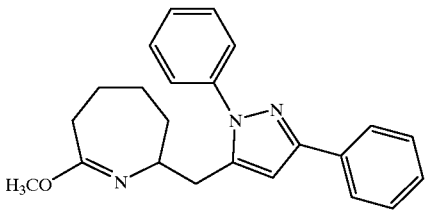

The title product of Example 146 is reacted with trimethyloxonium tetrafluoroborate by the method of Example 3 to generate the title compound.

EXAMPLE 148

7-[(1,3-diphenyl-1H-pyrazol-5-yl)methyl]hexahydro-2H-azepin-2-imine, monohydrochloride

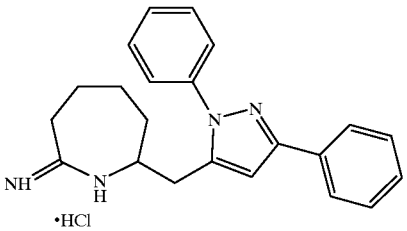

The title material of Example 147 is reacted with ammonium chloride by the method of Example 5 to generate the title compound.

EXAMPLE 149

2-oxocyclohexaneacetonitrile

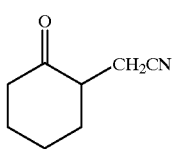

Cyclohexanone is reacted with bromoacetonitrile by the method of Example 65 to generate the title compound.

EXAMPLE 150

2-(hydroxyimino)cyclohexaneacetonitrile

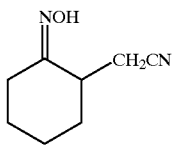

The product of Example 149 is reacted with hydroxylamine hydrochloride and sodium acetate in ethanol/water by the method of Example 1 to generate the title compound.

EXAMPLE 151 hexahydro-7-oxo-1H-azepine-2-acetonitrile

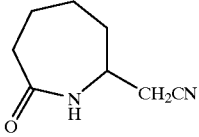

The product of Example 150 is reacted with benzenesulfonyl chloride and sodium hydroxide in acetone/water by the method of Example 67 to generate the title compound.

EXAMPLE 152 hexahydro-7-[[1-phenyl-3-(trifluoromethyl)-1H-1,2,
4-triazol-5-yl]methyl]-2H-azepin-2-one

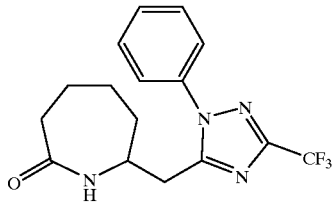

The product of Example 151 is reacted with trifluoroacetaldehyde, benzenehydrazonoyl chloride, and triethylamine in toluene by the method of R. Huisgen, *Ang. Chem. Int. Ed.* 1963, 2(10), 562, to generate the title compound.

EXAMPLE 153

3,4,5,6-tetrahydro-7-methoxy-2-[[-phenyl-3-
(trifluoromethyl)-1H-1,2,4-triazol-5-yl]methyl]-2H-
azepine

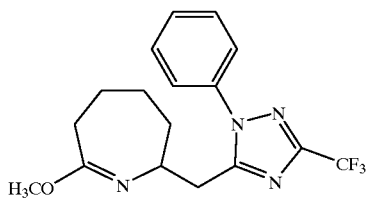

The product of Example 152 is reacted with trimethyloxonium tetrafluoroborate by the method of Example 3 to generate the title compound.

EXAMPLE 154 hexahydro-7-[[1-phenyl-3-(trifluoromethyl)-1H-1,2,
4-triazol-5-yl]methyl]-2H-azepin-2-imine,
monohydrochloride

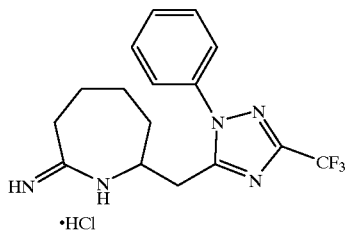

The product of Example 153 is reacted with ammonium chloride by the method of Example 5 to generate the title compound.

EXAMPLE 155 hexahydro-7-[2-(2-nitrophenyl)ethenyl]-2H-azepin-
2-one

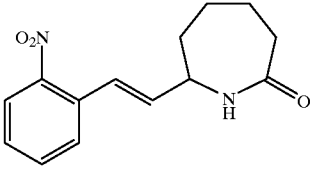

The Isomer A title material of Example 78 in acetonitrile is coupled to 1-bromo-2-nitrobenzene (Aldrich) in the presence palladium acetate, tri-o-tolylphosphine, and triethylamine by the method of Example 32 to provide the title material as either or both the Z and E isomers.

EXAMPLE 156

3,4,5,6-tetrahydro-7-methoxy-2-[2-(2-nitrophenyl)
ethenyl]-2H-azepine

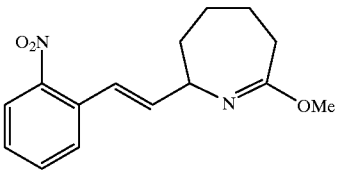

The product of Example 155 is reacted with trimethyloxonium tetrafluoroborate in CH$_2$Cl$_2$ by the method of Example 3 to produce the title material.

EXAMPLE 157 hexahydro-7-[2-(2-nitro-phenyl)ethenyl]-2H-azepin-
2-imine, monohydrochloride

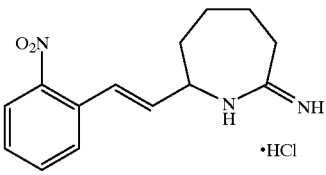

The product of Example 156 is reacted with ammonium, chloride by the method of Example 5 to generate the title compound.

EXAMPLE 158

2-[2-(hexahydro-7-imino-2H-azepin-2-yl)ethyl]benzenamine, dihydrochloride

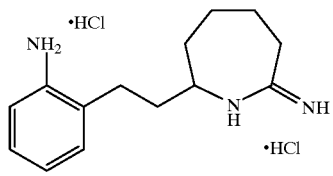

The title material of Example 157 in MeOH is hydrogenated over Pd on carbon in a standard Parr apparatus by the method of Example 35 reducing both the nitro and double bond functions to generate the title product.

EXAMPLE 159 methyl 2-[3-(hexahydro-7-oxo-1H-azepin-2-yl)-1-propenyl]-5-nitrobenzoate

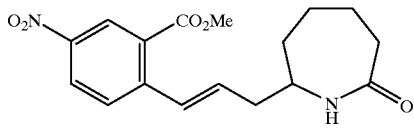

The Isomer B title material of Example 18 in acetonitrile is coupled to methyl-2-bromo-5-nitrobenzoate (Aldrich) in the presence of palladium acetate, tri-o-tolylphosphine, and triethylamine by the method of Example 32 to provide the title material as either or both the Z and E isomers.

EXAMPLE 160 methyl 5-nitro-2-[3-(3,4,5,6-tetrahydro-7-methoxy-2H-azepin-2-yl)-1-propenyl]benzoate

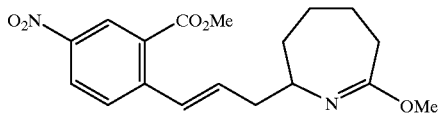

The product of Example 159 is reacted with trimethyloxonium tetrafluoroborate in $CH_2Cl_2$ by the method of Example 3 to produce the title material.

EXAMPLE 161 methyl 2-[3-(hexahydro-7-imino-1H-azepin-2-yl)-1-propenyl]-5-nitrobenzoate, monohydrochloride

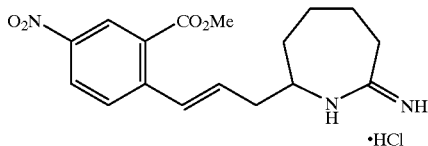

The product of Example 160 is reacted with ammonium chloride by the method of Example 5 to generate the title compound.

EXAMPLE 162 methyl 5-amino-2-[3-(hexahydro-7-imino-1H-azepin-2-yl)-1-propenyl]benzoate, dihydrochloride

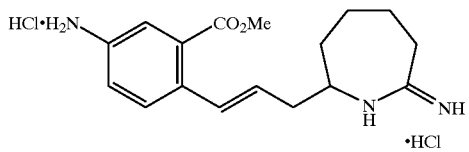

The title material of Example 161 in MeOH is hydrogenated over Pd on carbon in a standard Parr apparatus selectively reducing the nitro function to generate the title product.

EXAMPLE 163 hexahydro-7-[2-(3-methoxyphenyl)ethenyl]-2H-azepin-2-one

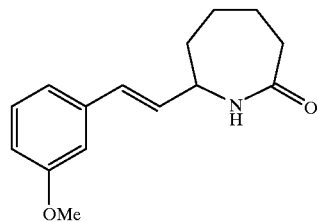

The Isomer A title material of Example 78 in acetonitrile is coupled to 3-bromo-anisole (Aldrich) in the presence palladium acetate, tri-o-tolylphosphine, and triethylamine by the method of Example 32 to provide the title material as either or both the Z and E isomers.

EXAMPLE 164

3,4,5,6-tetrahydro-7-methoxy-2-[2-(3-methoxyphenyl)ethenyl]-2H-azepine

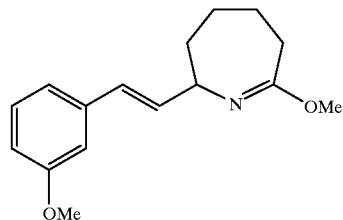

The product of Example 163 is reacted with trimethyloxonium tetrafluoroborate in $CH_2Cl_2$ by the method of Example 3 to produce the title material.

EXAMPLE 165 hexahydro-7-[2-(3-methoxyphenyl)ethenyl]-2H-azepin-2-imine, monohydrochloride

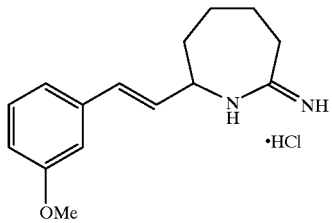

The product of Example 164 is reacted with ammonium chloride by the method of Example 5 to generate the title compound.

EXAMPLE 166 hexahydro-7-(2-(3-methoxyphenyl)ethyl]-2H-azepin-2-one

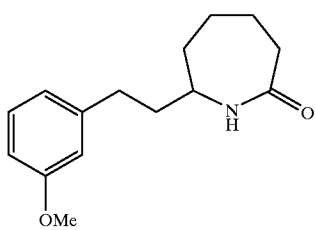

The title material of Example 163 in MeOH is hydrogenated over Pd on carbon in a standard Parr apparatus by the method of Example 35 to generate the title product.

EXAMPLE 167

3,4,5,6-tetrahydro-7-methoxy-2-[2-(3-methoxyphenyl)ethyl]-2H-azepine

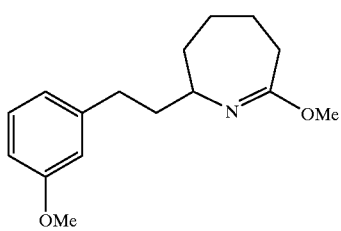

The product of Example 166 is reacted with trimethyloxonium tetrafluoroborate in CH$_2$Cl$_2$ by the method of Example 3 to produce the title material.

EXAMPLE 168 hexahydro-7-[2-(3-methoxyphenyl)ethyl]-2H-azepin-2-imine, monohydrochloride

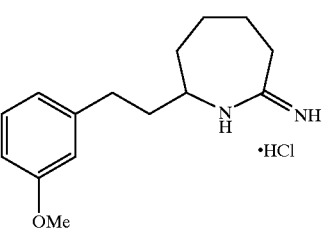

The product of Example 167 is reacted with ammonium chloride by the method of Example 5 to generate the compound.

EXAMPLE 169

7-[2-(3-furanyl)ethenyl]hexahydro-2H-azepin-2-one

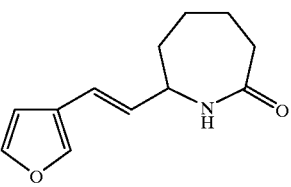

The Isomer A title material of Example 78 in acetonitrile is coupled to 3-bromo-furan (Aldrich) in the presence palladium acetate, tri-o-tolylphosphine, and triethylamine by the method of Example 32 to provide the title material as either or both the Z and E isomers.

EXAMPLE 170

7-[2-(3-furanyl)ethyl]hexahydro-2H-azepin-2-one

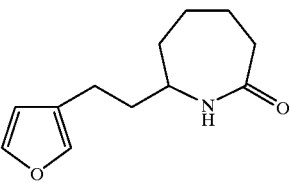

The title material of Example 163 In MeOH is hydrogenated over Pd on carbon in a standard Parr apparatus by the method of Example 35 to generate the title product

EXAMPLE 171

3,4,5,6-tetrahydro-2-[2-(3-furanyl)ethyl]-7-methoxy-2H-azepine

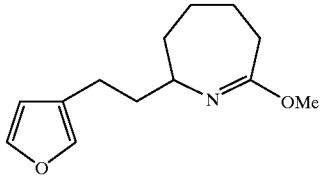

The product of Example 170 is reacted with trimethyloxonium tetrafluoroborate in CH$_2$Cl$_2$ by the method of Example 3 to produce the title material.

EXAMPLE 172

7-[2-(3-furanyl)ethyl]hexahydro-2H-azepin-2-imine, monohydrochloride

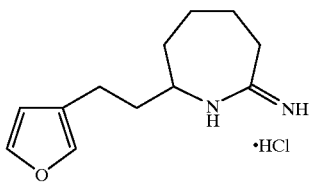

The product of Example 171 is reacted with ammonium chloride by the method of Example 5 to generate the title compound.

EXAMPLE 173 hexahydro-7-[2-(2-thienyl)ethenyl]-2H-azepin-2-one

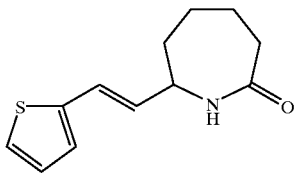

The Isomer A title material of Example 78 in acetonitrile is coupled to 2-bromothiophene (Aldrich) in the presence palladium acetate, tri-o-tolylphosphine, and triethylamine by the method of Example 32 to provide the title material as either or both the Z and E isomers.

EXAMPLE 174

3,4,5,6-tetrahydro-7-methoxy-2-[2-(2-thienyl)ethyl]-2H-azepine

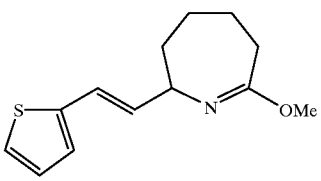

The product of Example 173 is reacted with trimethyloxonium tetrafluoroborate in CH$_2$Cl$_2$ by the method of Example 3 to produce the title material.

EXAMPLE 175 hexahydro-7-[2-(2-thienyl)ethenyl]-2H-azepin-2-imine, monohydrochloride

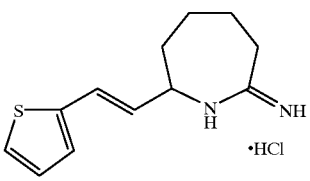

The product of Example 175 is reacted with ammonium chloride by the method of Example 5 to generate the title compound.

EXAMPLE 176 hexahydro-7-[2-(2-thienyl)ethyl]-2H-azepin-2-imine, monohydrochloride

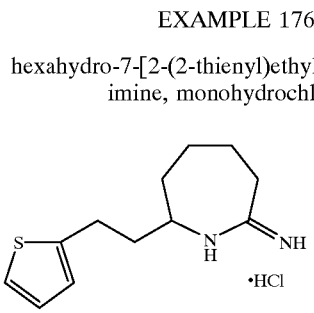

The title material of Example 175 in EtOH is hydrogenated over 10% Pd on carbon catalyst in a standard Parr apparatus by the method of Example 35 to generate the title product.

EXAMPLE 177 methyl 5-[3-(hexahydro-7-oxo-1H-azepin-2-yl)-1-propenyl]furan-2-carboxylate

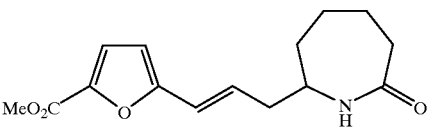

The Isomer B title material of Example 18 in acetonitrile is coupled to methyl 5-bromo-furanate, prepared from 5-bromofuroic acid (Aldrich) and thionyl chloride in methanol, in the presence of palladium acetate, tri-o-tolylphosphine, and triethylamine by the method of Example 32 to provide the title material as either or both the Z and E isomers.

EXAMPLE 178 methyl 5-[3-(3,4,5,6-tetrahydro-7-methoxy-2H-azepin-2-yl)-1-propenyl]furan-2-carboxylate

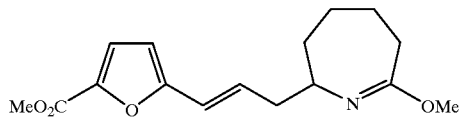

The product of Example 177 is reacted with trimethyloxonium tetrafluoroborate in CH$_2$Cl$_2$ by the method of Example 3 to produce the title material.

EXAMPLE 179 methyl 5-[3-(hexahydro-7-imino-1H-azepin-2-yl)-1-propenyl]furan-2-carboxylate, monohydrochloride

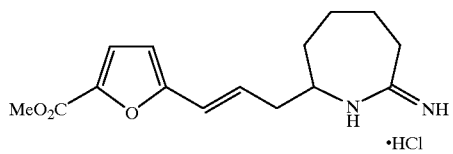

The product of Example 178 is reacted with ammonium chloride by the method of Example 5 to generate the title compound.

EXAMPLE 180 methyl 5-[3-(hexahydro-7-imino-1H-azepin-2-yl)propyl]furan-2-carboxylate, monohydrochloride

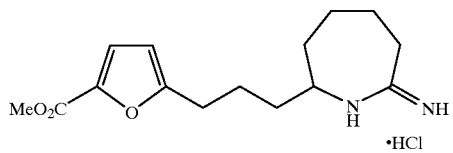

The title material of Example 179 in EtOH is hydrogenated over 10% Pd on carbon catalyst in a standard Parr apparatus by the method of Example 35 to generate the title product.

EXAMPLE 181 hexahydro-7-[2-(2-thiazolyl)ethenyl]-2H-azepin-2-one

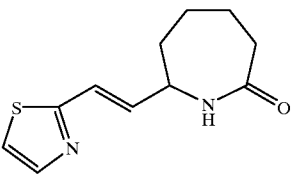

The Isomer A title material of Example 78 in acetonitrile is coupled to 2-bromothiazole (Aldrich) in the presence of palladium acetate, tri-o-tolylphosphine, and triethylamine by the method of Example 32 to provide the title material as either or both the Z and E isomers.

EXAMPLE 182

3,4,5,6-tetrahydro-7-methoxy-2-[2-(2-thiazolyl)ethenyl]-2H-azepine

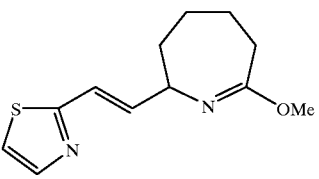

The product of Example 181 is reacted with one equivalent of trimethyloxonium tetrafluoroborate in CH$_2$Cl$_2$ by the method of Example 3 to produce a mixture of the title material and the N-methylated thiazolium salt which is isomerized on heating to the title material.

EXAMPLE 183 hexahydro-7-[2-(2-thiazolyl)ethenyl]-2H-azepin-2-imine, monohydrochloride

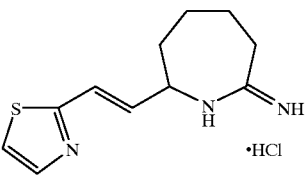

The product of Example 182 is reacted with ammonium chloride by the method of Example 5 to generate the title compound.

EXAMPLE 184 hexahydro-7-[2-(2-thiazolyl)ethyl]-2H-azepin-2-imine, monohydrochloride

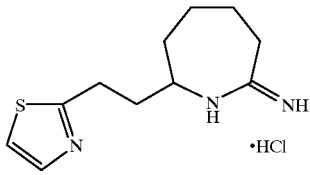

The title material Of Example 183 in EtOH is hydrogenated over 10% Pd on carbon catalyst in a standard Parr apparatus by the method of Example 35 to generate the title product.

EXAMPLE 185

1,1-dimethylethyl hexahydro-2-oxo-7-(phenylmethyl)-1H-azepine-1-carboxylate

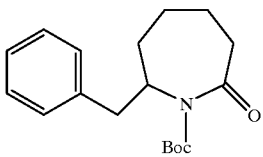

To the Isomer-A title product of Example 2 in dry THF maintained under an Ar atmosphere is added dimethylaminopyridine (DMAP). di-t-butyl dicarbonate in THF is then added and the reaction mixture is brought to reflux. After cooling the reaction to room temperature, all solvent is removed under reduced pressure and the title material is isolated by HPLC.

EXAMPLE 186

1.1-dimethylethyl hexahydro-2-oxo-7(phenylmethyl)-3-(phenylseleno)-1H-azepine-1-carboxylate

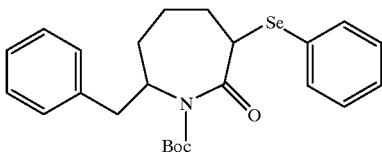

To a stirring solution of the product of Example 185 in THF at −78° C. is added lithium hexamethyidisilazide also in THF. After stirring the solution at −78° C., benzeneselenyl chloride is added. The reaction is stirred cold, warmed to room temperature and stirred at this temperature. The mixture is then diluted with Et$_2$O, partitioned between water and brine, and the title product isolated from the organic layer by HPLC.

EXAMPLE 187

1,5,6,7-tetrahydro-7-(phenylmethyl)-2H-azepin-2-one

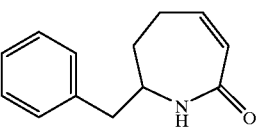

187 A) The product of Example 186 in THF is treated with 30% hydrogen peroxide (H$_2$O$_2$). All solvent is removed under reduced pressure and the unsaturated product, 1,1-dimethylethyl 1,5,6,7-tetrahydro-2-oxo-7-(phenylmethyl)-2H-azepine-1-carboxylate, is purified by HPLC methods.

187) The Boc protected product of this Example part A is dissolved in acetic acid and treated with a 4N solution of HCl in dioxane. All solvent is removed under reduced pressure and the title material purified by HPLC methods.

EXAMPLE 188

3,4-dihydro-7-methoxy-2-(phenylmethyl)-2H-azepine

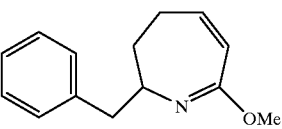

The product of Example 187 is reacted with one equivalent of trimethyloxonium tetrafluoroborate in CH$_2$Cl$_2$ by the method of Example 3 to produce the title material.

EXAMPLE 189

1,5,6,7-tetrahydro-7-(phenylmethyl)-2H-azepin-2-imine, monohydrochloride

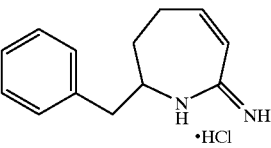

The product of Example 188 is reacted with ammonium chloride by the method of Example 5 to generate the title compound.

EXAMPLE 190

2-[(4,5-dihydro-3-phenylisoxazolyl-5-yl)methyl]-3,4,5,6-tetrahydro-7-methoxy-2H-azepine

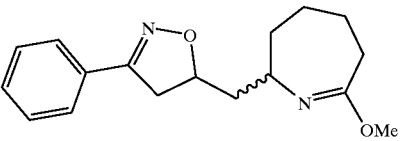

To a magnetically stirred slurry of trimethyloxonium tetrafluoroborate (Sigma, 0.13 g, 0.9 mmol) and CH$_2$Cl$_2$ (10 mL) under nitrogen (N₂) was added the isomer-B product of Example 125 (0.22 g, 0.81 mmol). This mixture was stirred at room temperature for 18 hours before it was diluted with 30 mL of EtOAc and partitioned between the organic layer and 40 mL of saturated NaHCO₃. The organic phase was separated, dried over MgSO₄, filtered, and stripped of all solvent under reduced pressure to provide 0.17 g (73%) of the crude title produce as a pale yellow oil. This material was used as is in subsequent Example 191.

EXAMPLE 191

7-[(4,5-dihydro-3-phenylisoxazolyl-5-yl)methyl] hexahydro-2H-azepine-2-imine, monotrifluoroacetic acid salt

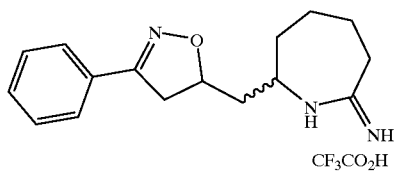

CF₃CO₂H

The title product of Example 190 (0.17 g, 0.6 mmol) and 0.035 g (0.65 mmol) of NH₄Cl were refluxed in 10 m of MeOH under a N₂ atmosphere for 18 h. After cooling the reaction to room temperature, it was filtered and partitioned between 15 mL of water and 7 mL of EtOAc. The organic and aqueous phases were separated and the aqueous phase was extracted with a 15 mL portion of EtOAc before it was lyophilized to provide 0.13 g (71%) of an orange solid material. Chromatography of 0.1 g on a preparatory C-18 column eluting with acetonitrile/water afforded after lyophilization from trifluoroacetic acid (TFA)/ water 0.04 g of the title compound as an off-white solid material.

$^1$H NMR(D₂O): d 7.6 (d, 2H), 7.4 (m, 3H), 4.85 (m, 1H), 3.75 (m, 1H), 3.6 (dd, 1H), 3.15 (dd, 1H) 2.65 (m, H), 2.5 (m, 1H), 2.0–1.3 (m, 8H). M+H=272.

EXAMPLE 192

The following functionalized aromatic methyl halides and equivalents are reacted with cyclohexanone by the process described in Example 65. The resulting 2-[(substituted aromatic)methyl]cyclohexanone is treated with hydroxylamine as described in Example 1 to yield the corresponding oxime, which is then treated as described in Example 2 to give a mixture of 3- and 7-substituted caprolactams. They are separated as also described in Example 2, and then individually treated as described in Example 3 to yield the corresponding imino ether. This imino ether is treated with ammonium chloride in methanol as described in Example 5 to give the desired product amidines:

| STARTING HALIDE | CORRESPONDING PRODUCT |
|---|---|
| α-bromo-2,6-dichlorotoluene | 7-[(2,6-dichlorophenyl)methyl]-hexahydro-2H-azepin-2-imine |
| α-bromo-4-fluorotoluene | 7-[(4-fluorophenyl)methyl]hexahydro-2H-azepin-2-imine |
| α-bromo-2,4-difluorotoluene | 7-[(2,4-difluorophenyl)methyl]-hexahydro-2H-azepin-2-imine |
| α-bromo-2,3,4,5,6- | 7-[(2,3,4,5- |
| pentafluoro-toluene | pentafluorophenyl)-methyl]hexahydro-2H-azepin-2-imine |
| α-bromo-4-trifluoromethyl-toluene | hexahydro-7-[[4-(trifluoromethyl)phenyl]methyl]-2H-azepin-2-imine |
| α-bromo-3-trifluoromethyl-toluene | hexahydro-7-[[3-(trifluoromethyl)phenyl]methyl]-2H-azepin-2-imine |
| 2-(bromomethyl)biphenyl | 7-[(2-biphenylyl)methyl]hexahydro-2H-azepin-2-imine |
| α-bromo-2-nitrotoluene | hexahydro-7-[(2-nitrophenyl)-methyl]-2H-azepin-2-imine |
| α-bromo-4-nitrotoluene | hexahydro-7-[(4-nitrophenyl)-methyl]-2H-azepin-2-imine |
| α-bromo-4-carboxymethyl-toluene | 4-[(hexahydro-7-imino-2H-azepin-2-yl)methyl]benzene-acetic acid |
| 2-chloro-5-(chloromethyl)thiophene | 7-[(5-chlorothien-2-yl)methyl]-hexahydro-2H-azepin-2-imine |
| 4-(chloromethyl)-3,5-dimethylisoxazole | 7-[(3,5-dimethylisoxazol-4-yl)methyl]hexahydro-2H-azepin-2-imine |

EXAMPLE 193

2-[(tetrahydro-2H-pyran-2-yl)methyl]cyclohexanol

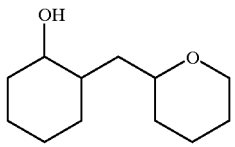

To a stirring THF solution of the Grignard reagent (formed from 2-(bromomethyl)tetrahydro-2H-pyran, 16a and powdered magnesium, 20 milligram-atoms) and cooled to −30° C., CuI is added as a bolus. After approx. 10 min., a solution of cyclohexene oxide (10 mmol) is added slowly, maintaining the reaction temperature below −25° C. until the addition is complete. The mixture is then stirred at 0° C. for 2 hours and checked by TLC and/or GC. The reaction is quenched by pouring into concentrated NH₄Cl solution (if starting material remains, the reaction may be warmed to r.t. and followed by TLC or GC until no additional starting material is observed). Also, the addition of some concentrated NH₄OH solution combined with vigorous stirring may be used to remove suspended CuI from the mixture. This mixture is then extracted with 2 portions of ether or 1:1 EA-hexane. The combined extracts are then washed with brine and dried (MgSO₄). The product may be sufficiently pure at this point for use in the next reaction. Otherwise, it may be purified by distillation or flash chromatography.

EXAMPLE 194

2-[(tetrahydro-2H-pyran-2-yl)methyl]cyclohexanone

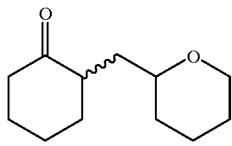

Neat, dry DMSO (4 equivalents) is added slowly to a CH$_2$Cl$_2$ solution of the oxalyl chloride (1.25 equivalents) cooled to −70° C. under N$_2$. After stirring for about 15 min., the product of Example 193 (1 equivalent) in CH$_2$Cl$_2$ is added slowly. Neat triethylamine (4 equivalents) is then added and the mixture is warmed to 0° C. After 30 min., the mixture is poured into stirred ice-water and neutralized with dilute HCl. The mixture is then separated and the aqueous layer extracted with CH$_2$Cl$_2$. The organic extracts are then combined, washed with dilute brine, dried (MgSO$_4$) and stripped of all solvent under reduced pressure. The crude title compound is purified by column chromatography.

EXAMPLE 195 hexahydro-7-[(tetrahydro-2H-pyran-2-yl)methyl]-1H-azepin-2-imine monohydrochloride

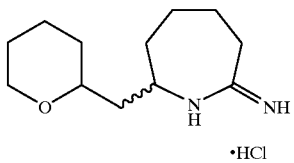

·HCl

The product of Example 194 is converted to the corresponding oxime by the methods taught in Example 39, and then to the corresponding mixture of lactams as taught in Example 67. The mixture of lactams is separated as also described in Example 67. The resulting 3-substituted caprolactam is reserved for use as described in Example 196 (vide infra), and the 7-substituted caprolactam is treated with trimethyloxonium tetrafluoroborate as described in Example 3 to give the corresponding imino ether. This imino ether is treated with NH$_4$Cl in methanol as described in Example 5 to give the title compound.

EXAMPLE 196 hexahydro-3-[(tetrahydro-2H-pyran-2-yl)methyl]-1-2H-azepin-2-imine

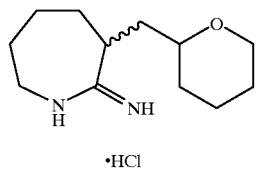

·HCl

The 3-[(2-tetrahydropyanyl)methyl]caprolactam isolated in Example 195 is treated as described in Example 3 to give the corresponding imino ether, and then with NH$_4$Cl in methanol as described in Example 5 to give the title compound.

EXAMPLE 197

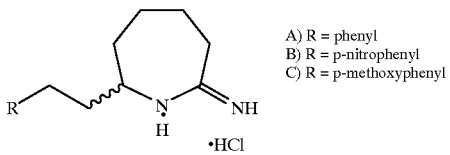

A) R = phenyl
B) R = p-nitrophenyl
C) R = p-methoxyphenyl

·HCl

The aromatic ethyl halides listed below as STARTING HALIDE are reacted with cyclohexene oxide by the process described in Example 193. The resulting 2-(aromatic-ethyl) cyclohexanols are then oxidized to the respective 2-(aromatic-ethyl) cyclohexanones by the method of Example 194. The 2-(aromatic-ethyl) cyclohexanones are treated with hydroxylamine as taught in Example 1 to yield the corresponding oxime, which is then treated as described in Example 2 to give a mixture of 3- and 7-substituted caprolactams. This mixture is separated also as described in Example 2, and then individually treated as taught in Example 3 to yield the corresponding imino ether. The imino ethers are treated with ammonium chloride in methanol as described in Example 5 to give the desired product amidines described below:

| | STARTING HALIDE | CORRESPONDING PRODUCT |
|---|---|---|
| A) | (2-bromoethyl)benzene | hexahydro-7-(2-phenylethyl)-1H-azepin-2-imine, monohydrochloride |
| B) | (2-bromoethyl)-4-nitrobenzene | hexahydro-7-[2-(4-nitrophenyl)et 1H-azepin-2-imine-monohydrochloride |
| C) | (2-bromoethyl)-4-methoxybenzene | hexahydro-7-[2-(4-methoxyphenyl)ethyl]-1H-azepin-2-imine, monohydrochloride |

EXAMPLE 198

7-[3-[5-(1,3-dioxolan-2-yl)thien-2-yl)-2-propenyl] hexahydro-2H-azepin-2-imine, monohydrochloride

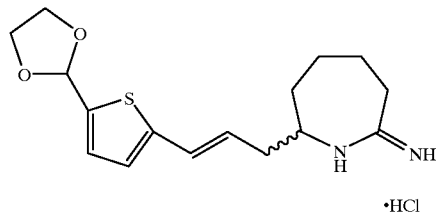

·HCl

Example 198 A) The Isomer B title material of Example 18 in acetonitrile is coupled to 2-(5-bromo-2-thienyl) dioxolane in the presence palladium acetate, tri-o-tolylphosphine, and triethylamine by the method of Example 32 to provide 7-[3-[5-(1,3-dioxolan-2-yl)thien-2-yl]-2-propenyl]hexahydro-1H-azepin-2-one as primarily the E isomer.

Example 198 B) The product of part A above is reacted with trimethyloxonium tetrafluoroborate by the method of Example 67 to yield imino ether, 2-[3-[5-(1,3-dioxolan-2-yl) thien-2-yl]propyl]-3,4,5,6-tetrahydro-7-methoxy-2H-azepine.

Example 198) the crude product of part B above is reacted with ammonium chloride in methanol by the method of Example 5 to give the title material after reverse phase chromatographic purification.

EXAMPLE 199

5-[3-(hexahydro-7-imino-1H-azepin-2-yl)-1-propenyl]thiophene-2-carboxamide, monohydrochloride

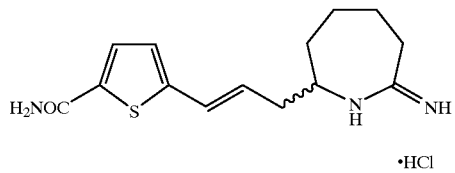

Example 199 A) A sample of the product of part A, Example 198, 7-[3-[5-(I,3-dioxolan-2-yl)thien-2-yl]-2-propenyl]hexahydro-1H-azepin-2-one, is treated with dilute HCl to generate aldehyde, 5-[3-(hexahydro-7-oxo-1H-azepin-2-yl)-1-propenyl]thiophene-2-carboxaldehyde.

Example 199 B) The product of this Example, part A above, is oxidized to 5-[3-(hexahydro-7-oxo-1H-azepin-2-yl)-1-propenyl]thiophene-2-carboxylic acid using potassium permanganate solubilized in benzene with dicyclohexyl-18-crown-6 by the method described by D. J. Sam et al *J. Am. Chem. Soc.* 1972, 94, 4024.

Example 199 C) To a cold solution of thionyl chloride in methanol is added the product of this Example, part B above. The product methyl ester, methyl 5-[3-(hexahydro-7-oxo-1H-azepin-2-yl)-1-propenyl]thiophene-2-carboxylate, is isolated after quenching the reaction with KHCO$_3$, extracting with EtOAc, and purifying by column chromatography.

Example 199 D) The product of this Example, part C above, is reacted with trimethyloxonium tetrafluoroborate by the method of Example 67 to yield imino ether, methyl 5-[3-(3,4,5,6-tetrahydro-7-methoxy-2H-azepin-2-yl)-1-propenyl]thiophene-2-carboxylate.

Example 199 E) The crude product of this Example, part D above, is reacted with ammonium chloride in methanol by the method of Example 5 to give the amidine, methyl 5-[3-(hexahydro-7-imino-1H-azepin-2-yl)-1-propenyl] thiophene-2-carboxylate, monohydrochloride.

Example 199 F) The product of this Example, part E above, is hydrolyzed to its free acid, 5-[3-(hexahydro-7-imino-1H-azepin-2-yl)-1-propenyl]thiophene-2-carboxylic acid, monohydrochloride using HCl.

Example 199) The product of this Example, part F above, is reacted with isobutylchloroformate in the presence of N-methylmorpholine followed by ammonium chloride to provide the title product after reverse phase chromatographic purification.

EXAMPLE 200 methyl 2-[3-(hexahydro-7-imino-1H-azepin-2-yl)-1-propenyl]-5-methoxybenzoate, monohydrochloride

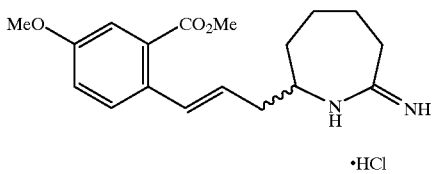

Example 200 A) The Isomer B title material of Example 18 in acetonitrile is coupled to methyl 2-bromo-5-methoxybenzoate in the presence of palladium acetate, tri-o-tolylphosphine, and triethylamine by the method of Example 32 to provide methyl 2-[3-(hexahydro-7-oxo-1H-azepin-2-yl)-1-propenyl]-5-methoxybenzoate as primarily its E isomer.

Example 200 B) The produce of this Example, part A above, is reacted with trimethyloxonium tetrafluoroborate by the method of Example 67 to yield imino ether, nethyl 2-[3-(3,4,5,6-tetrahydro-7-methoxy-2H-azepin-2-yl)-propenyl]-5-methoxybenzoate.

Example 200) The crude product of this Example, part B above, is reacted with ammonium chloride in methanol by the method of Example 5 to give the title material after reverse phase chromatographic purification.

EXAMPLE 201

β-(2-oxocyclohexyl)-4-methylbenzenepropanoic acid

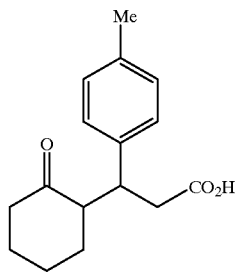

1-pyrrolidino-1-cyclohexene is refluxed with methyl a-(2-oxocyclohexyl)benzenepropanoate in dimethylformamide (DMF) for 24 hours and refluxing is continued for another hour after the addition of water. DMF is removed under reduced pressure and the residue is diluted with water and extracted three times with EtOAc. The combined EtOAc extracts are washed with 1N HCl and then with brine. The organic phase is dried over MgSO$_4$ and evaporated to give crude methyl b-(2-cxocyclohexyl)-4-methylbenzenepropanoate. This material is treated with 1 N LiOH/methanol to give the title material.

EXAMPLE 202

Isomer A: hexahydro-b-(4-methylphenyl)-7-oxo-1H-azepine-2-propanoic acid

Isomer B: hexahydro-b-(4-methylphenyl)-2-oxo-1H-azepine-3-propanoic acid

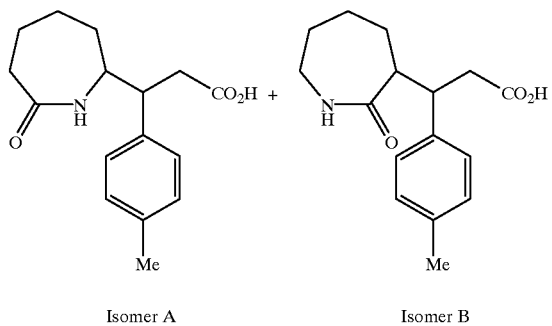

Isomer A   Isomer B

The title material of Example 201 in formic acid is added to a solution of hydroxylamine-O-sulfonic acid in formic acid over a 5 min. period with stirring under $N_2$. The mixture is heated under reflux for 3 hours and then cooled to room temperature. The reaction is quenched with cold water and the solution is neutralized with 6N NaOH. It is then extracted three times with $CH_2Cl_2$. The combined organic layers are dried over $MgSO_4$ and the solvent is removed on a rotary evaporator. The desired products are purified and isolated by HPLC to give both the 3- and 7-substituted title products.

EXAMPLE 203

Isomer A: methyl hexahydro-7-imino-b-(4-methylphenyl)-1H-azepine-2-propanoate, monohydrochloride Isomer B: methyl hexahydro-2-imino-b-(4-methylphenyl)-1H-azepine-3-propanoate, monohydrochloride

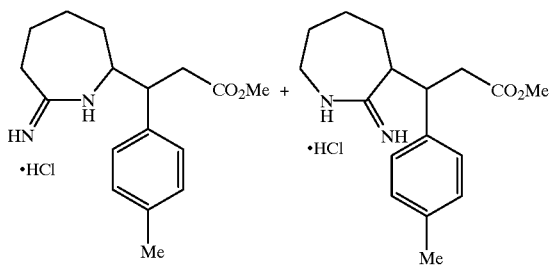

Each of the title caprolactams of Example 202 is independently treated as described in Example 3 to yield the corresponding imino ethers. The imino ethers are then treated with ammonium chloride in methanol as described in Example 5 to give the desired amidines.

EXAMPLE 204

The following activated vinyl derivatives are reacted with 1-pyrrolidino-1-cyclohexene following the method described in Example 201. The resulting 2-substituted cyclohexanone is treated with a solution of hydroxylamine-O-sulfonic acid in formic acid as described in Example 202 to give a mixture of 3- and 7-substituted caprolactams. These lactams are treated as described in Example 3 to yield the corresponding imino ether. This imino ether is treated with ammonium chloride in methanol as described in Example 5 to give the desired amidine products illustrated below.

Example 204 A) methyl 3-[4-(trifluoromethyl)phenyl]propenoate methyl hexahydro-7-imino-b-[4-(trifluoromethyl)phenyl]-1H-azepine-2-propanoate, monohydrochloride

A)

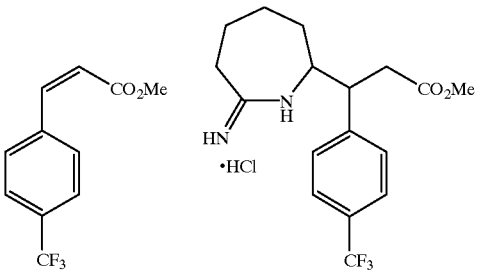

Example 204 B) (2-nitroethenyl)benzene hexahydro-7-(2-nitro-1-phenylethyl)-2H-azepin-2-imine, monohydrochloride

B)

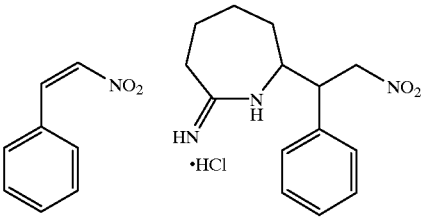

Example 204 C) 3-(2-furanyl)propoenenitrile b-(2-furanyl)hexahydro-7-imino-1H-azepine-2-propoenenitrile, monohydrochloride

C)

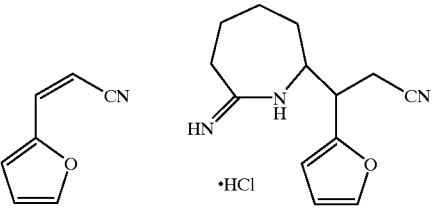

Example 204 D) methyl 3-(2-furanyl)propenoate

107 methyl β-(2-furanyl)hexahydro-7-imino-1H-azepine-2-propanoate, monohydrochloride

D)

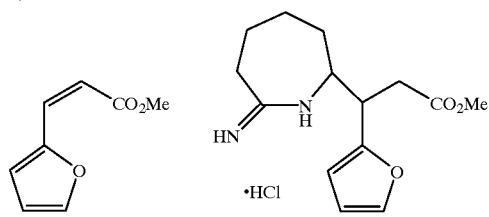

Example 204 E) (ethenylsulfonyl)benzene hexahydro-7-[2-(phenylsulfonyl)ethyl]-2H-azepin-2-imine, monohydrochloride

E)

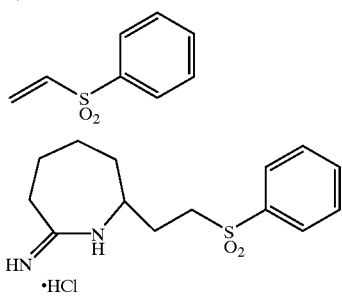

EXAMPLE 205 hexahydro-7-imino-β-phenyl-1H-azepine-2-ethanamine, bis(trifluoroacetate) salt

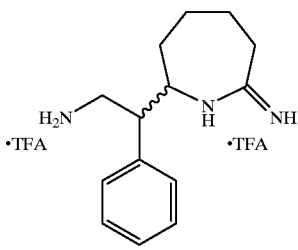

The product of Example 253 (350 mg; 1.3 mmol) was reduced via catalytic hydrogenation to afford 230 mg (75% yield) of the title product as a white solid.

Mass spectral analysis for $C_{14}H_{21}N_3$: M+H=232

$^1$H NMR ($D_2O$): δ 7.40–7.20 (m,5H); 3.90–3.80 (m,1H); 3.50–3.35 (m,1H); 3.30–3.05 (m,2H); 2.80–2.40 (m,2H); 1.80–1.00 (m,6H)

108

EXAMPLE 206

N-[2-(hexahydro-7-imino-1H-azepin-2-yl)-2-phenylethyl]methanesulfonamide, monohydrochloride

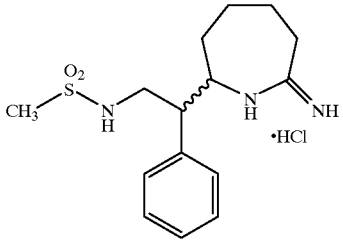

Example 206 A) The nitro function of the 7-substituted lactam generated in Example 204, reaction 3, hexahydro-7-(2-nitro-1-phenylethyl)-1H-azepin-2-one, is reduced to an amine, 7-(2-amino-1-phenylethyl) hexahydro-1-azepin-2-one, monohydrochloride, by the method of Example 205.

Example 206 B) The product of this Example, part A is treated with an equivalent of methanesulfonyl chloride in the presence of triethylamine to yield its sulfonamide derivative, N-[2-(hexahydro-7-oxo-1H-azepin-2-yl)-2-phenyl]methanesulfonamide.

Example 206 C) The sulfonamide material of this Example, part B, is treated with trimethyloxonium tetrafluoroborate (1.5 equivalents) in $CH_2Cl_2$ following the method of Example 3 to give the iminoether intermediate, N-[2-phenyl-2-(3,4,5,6-tetrahydro-7-methoxy-2H-azepin-2-yl)ethyl]methanesulfonamide.

Example 206) The crude product of this Example, part C, is then treated with ammonium chloride in methanol following the method of Example 5 to give the title compound.

EXAMPLE 207

γ-(2-furanyl)hexahydro-7-imino-1H-azepine-2-propanamine, dihydrochloride

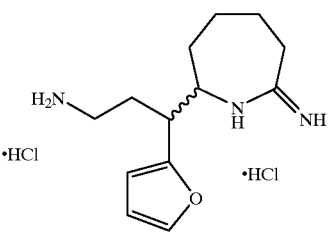

The product of Example 204, reaction C, b-(2-furanyl)hexahydro-7-imino-1H-azepine-2-propoenenitrile, monohydrochloride, is reduced with $H_2$ in a standard Parr hydrogenation apparatus using a Pd catalyst on a carbon support by the method described by J. A. Secrist et al *J. Org. Chem.* 1972, 47, 335.

EXAMPLE 208

N-[3-(2-furanyl)-3-(hexahydro-7-imino-1H-azepin-2-yl)propyl]methanesulfonamide, monohydrochloride

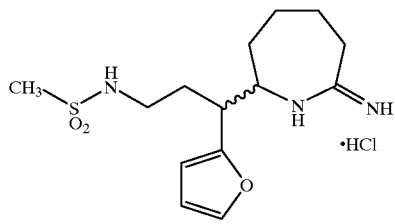

Example 208 A) The cyano function of the 7-substituted lactam generated in Example 204, reaction C, b-(2-furanyl) hexahydro-7-oxo-1H-azepinepropanenitrile, is reduced to its amine, g-(2-furanyl)hexahydro-7-oxo-1H-azepinepropanamine, monohydrochloride, by the method of Example 207.

Example 208 B) The product of this Example, part A is treated with an equivalent of methanesulfonylchloride in the presence of triethylamine to yield its sulfonamide derivative, N-[3-(2-furanyl)-3-(hexahydro-7-oxo-1H-azepin-1-yl) propyl]methanesulfonamide.

Example 208 C) The sulfonamide material of this Example, part B, is treated with trimethyloxonium tetrafluoroborate (1.5 equivalents) in CH$_2$Cl$_2$ following the method of Example 3 to give the iminoether intermediate, N-[3-(2-furanyl)-3-(hexahydro-7-oxo-1H-azepin-1-yl)propyl] methanesulfonamide.

Example 208) The crude product of this Example, part C, is then treated with ammonium chloride in methanol following the method of Example 5 to give the title compound.

EXAMPLE 209

1,1-dimethylethyl hexahydro-2-(4-methoxy-4-oxo-2-butenyl)-7-oxo-1H-azepine-1-carboxylate

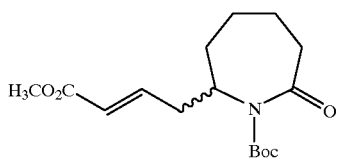

Example 209 A) The title material of Example 18, isomer B, is converted to its Boc derivative, 1,1-dimethylethyl hexahydro-2-oxo-7-(2-propenyl)-1H-azepine-1-carboxylate, by the method of Example 185.

Example 209 B) The Boc allyl lactam of this Example, part A above, is dissolved in CH$_2$Cl$_2$, cooled to below −70° C., treated with ozone until a persistent blue color is observed. After sparging with oxygen to remove excess ozone, triphenylphosphine (1.5 equivalents) is added and the mixture stirred at 0° C. for 30 minutes and then at room temperature overnight. The mixture is concentrated and the residue is triturated with several volumes of pentane to remove the phosphorous salts, filtered and stripped to give a crude aldehyde, 1,1-dimethylethyl hexahydro-2-(2-oxoethyl)-7-oxo-1H-azepine-1-carboxylate, which is used without further purification in Part C below.

Example 209) The crude aldehyde of this Example, part B above, is dissolved in toluene and treated with 1.2 equivalents of methyl (triphenylphosphoranylidene)acetate. The mixture is refluxed for four hours. After cooling, the mixture is concentrated and the residue is triturated with several volumes of pentane to remove the phosphorous salts. The extracts are filtered and stripped of all solvent. The crude residue is then purified by column chromatography to give the title product.

EXAMPLE 210 methyl 1-[(1,1-dimethylethoxy)carbonyl]hexahydro-7-oxo-β-(2-propenyl)-1H-azepine-2-butanoate

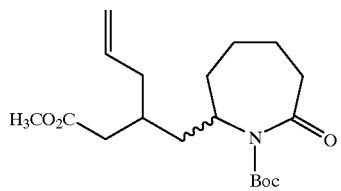

Four equivalents of allyl lithium are added to a stirring suspension of 2 equivalents copper (I) iodide in THF at −50° C. under argon. After the mixtures becomes homogeneous (approx. 20 minutes.), a solution of the title ester of Example 209 (1 equivalent) in THF is added to the cold mixture and stirred below −50° C. for approx. 30 minutes. The mixture is poured into saturated ammonium chloride solution and stirred vigorously for 15 minutes. The mixture is then partitioned between ether and water and the organic layer is washed with water and brine before it is dried (Na$_2$SO$_4$). The mixture is then filtered and stripped of all solvent. The title material is then purified by column chromatography.

EXAMPLE 211 methyl 7-ethoxy-3,4,5,6-tetrahydro-β-(2-propenyl)-2H-azepine-2-butanoate

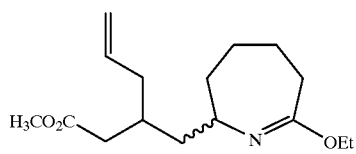

Example 211 A) The Boc group is removed from title compound of Example 210 by the method of Example 199, part A, to generate methyl hexahydro-7-oxo-b-(2-propenyl)-1H-azepine-2-butanoate.

Example 211) This crude product of Example 211, part A, is then treated with triethyloxonium tetrafluoroborate (1.5 equivalents) in CH$_2$Cl$_2$ following the method of Example 3 to give the title compound.

EXAMPLE 212 methyl-β-(2,3-dihydroxypropyl)hexahydro-7-imino-1H-azepine-2-butanoate, monohydrochloride

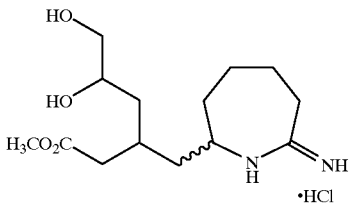

Example 212 A) The title product of Example 211 dissolved in a 1:1 mixture of acetone and water and treated with osmium tetraoxide (2.5 equivalent %) and 4-methylmorpholine oxide (2 equivalents) at room temperature is allowed to stir overnight. The mixture is then carefully neutralized with dilute HCl, concentrated on a rotary evaporator, and extracted with 3 portions of EtOAc. The combined organic extracts are then dried ($Na_2SO_4$), stripped and purified by column chromatography on silica gel to yield methyl b-(2,3-dihydroxypropyl)-7-ethoxy-3,4,5,6-tetrahydro-2H-azepine-2-butanoate.

Example 212) The product of Example 211 part A is treated with ammonium chloride in methanol following the method of Example 5 to give the title compound.

EXAMPLE 213

4-[(hexahydro-7-imino-1H-azepin-2-yl)methyl]-3,4,5,6-tetrahydro-6-hydroxymethyl-2H-pyran-2-one, monohydrochloride

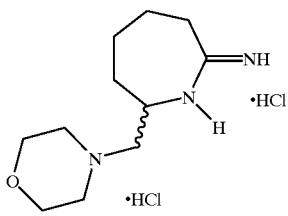

The amidine diol title product of Example 212 is dissolved in 0.5N HCl and warmed to 50° C. for 3 hours. The excess water and acid are then removed by lyophilization to give the title compound.

EXAMPLE 214 hexahydro-7-[(4-morpholinyl)methyl]-2H-azepin-2-imine, dihydrochloride

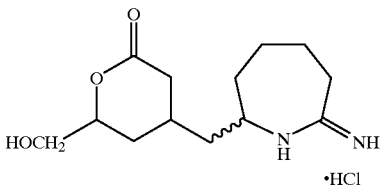

Example 214 A) The title product of Example 78, isomer-A, is converted to its Boc derivative, 1,1-dimethylethyl 2-ethenylhexahydro-7-oxo-1H-azepine-1-carboxylate, by the method of Example 185.

Example 214 B) Treatment of the product of this Example, part A above, with ozone as described in example 209, part B, generates aldehyde product, 1,1-dimethylethyl 2-formylhexahydro-7-oxo-1H-azepine-1-carboxylate.

Example 214 C) The product of this Example, part 3 above, in THF is reacted with morpholine in the presence $H_2$ and a metal catalyst to yield, 1,1-dimethylethyl hexahydro-2-[(4-morpholinyl)methyl]-7-oxo-1H-azepine-1-carboxylate.

Example 214 D) The Boc group is removed from the product of this Example, part C above by the method of Example 199, part A, to generate hexahydro-7-[(4-morpholinyl)methyl]-1H-azepin-2-one.

Example 214 E) This product of this Example, part D above is then treated with triethyloxonium tetrafluoroborate (1.1 equivalents) in $CH_2Cl_2$ following the method of Example 3 to give 7-ethoxy-3,4,5,6-tetrahydro-2-[(4-morpholinyl)methyl]-2H-azepine.

Example 214) The crude product of this Example, part E above, is then reacted with ammonium chloride in methanol following the method of Example 5 and then with dilute HCl to produce the title compound.

EXAMPLE 215 hexahydro-2-imino-7-[(4-morpholinyl)methyl]-1H-azepin-3-ol, dihydrochloride

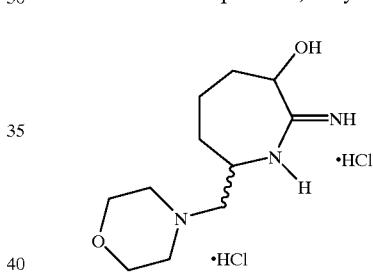

Example 215 A) The product of Example 214, part A, 1,1-dimethylethyl 2-ethenylhexahydro-7-oxo-1H-azepine-1-carboxylate, is treated with an organo lithium base at low temperature to generate the enolate which is subsequently reacted with bis(trimethylsilyl)peroxide by the methods of F. A. Davis et al *Tettrahodron Lett.* 1988, 29, 4269 and L. Camici et al *Tettrahodron Lett.* 1988, 29, 4197 to yield 1,1-dimethylethyl hexahydro-3-hydroxy-7-[(4-morpholinyl)methyl]-2-oxo-1H-azepine-1-carboxylate.

Example 215 B) Removal of the Boc protecting group by treatment of the product of this Example, part A above with dilute HCl gives the lactam hexahydro-3-hydroxy-7-[(4-morpholinyl)methyl]-1H-azepin-2-one.

Example 215 C) The product of Example 215, part B is treated with acetic anhydride in the presence of pyridine to generate 3-acetyloxyhexahydro-7-[(4-morpholinyl)methyl]-1H-azepin-2-one.

Example 215 D) The product of this Example, part C above is then treated with trimethyloxonium tetrafluoroborate (1.5 equivalents) in $CH_2Cl_2$ by the method of Example 3 to give 3,4,5,6-tetrahydro-7-methoxy-2-[(4-morpholinyl)methyl]-2H-azepin-3-ol acetate.

Example 215) The crude product of this Example, part D above, is then reacted with ammonium chloride in methanol following the method of Example 5 and then with dilute HCl to produce the title compound.

EXAMPLE 216

5-[(hexahydro-7-imino-1H-azepin-2-yl)methyl]4,5-dihydroisoxazol-3-amine, dihydrochloride

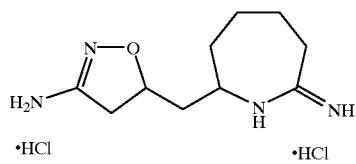

216 A) The title product isomer B of Example 13 (7-allyl caprolactam) is reacted with ethyl chlorooximinoyl acetate in toluene by the method of P. Caldirola, et. al., Heterocycles 1985, 23(10), 2479, to generate ethyl 5-[(hexahydro-7-oxo-1H-azepin-2-yl)methyl]-4,5-dihydroisoxazole-3-carboxylate.

216 B) The crude product of this Example, part A above, is hydrolyzed in aqueous HCl to generate 5-[(hexahydro-7-oxo-1H-azepin-2-yl)methyl]-4,5-dihydroisoxazole-3-carboxylic acid.

216 C) The crude product of this Example, part B above, is reacted with diphenylphosphoryl azide and triethylamine in benzene to generate 7-[(3-amino-4,5-dihydroisoxazol-5-yl)methyl]hexahydro-1H-azepin-2-one, monohydrochloride.

216 D) The crude product of this Example, part C above, is reacted with di-tert-butyldicarbonate in aqueous sodium hydroxide to generate 1,1-dimethylethyl [5-[(hexahydro-7-oxo-1H-azepin-2-yl)methyl]-4,5-dihydroisoxazol-3-yl]carbamate.

216 E) The crude product of this Example, part D above, is reacted with trimethyloxonium tetrafluoroborate by the method of Example 3 to generate the iminoether. The iminoether is reacted with ammonium chloride by the method of Example 5 to generate 1,1-dimethylethyl [5-[(hexahydro-7-imino-1H-azepin-2-yl)methyl]-4,5-dihydroisoxazol-3-yl]carbamate.

216) The crude product of this Example, part E above, is reacted with HCl/dioxane to generate the title compound.

EXAMPLE 217

5-[(hexahydro-7-imino-1H-azepin-2-yl)methyl]-1-methylpyrazolidin-3-one, dihydrochloride

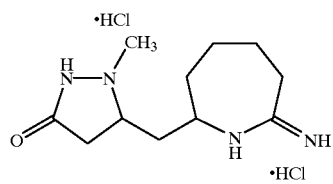

217 A) 1-morpholinocyclohexene is reacted with ethyl 4-bromocrotonate in 1,4-dioxane. The reaction mixture is diluted with water to generate ethyl 4-(2-oxocyclohexyl)-2-butenoate.

217 B) The crude product of this Example, part A above, is reacted with hydroxylamine-O-sulfonic acid to generate ethyl 4-(hexahydro-7-oxo-1H-azepin-2yl)-2-butenoate.

217 C) The crude product of this Example, part B above, is reacted with methylhydrazine to generate 7-[(4,5-dihydro-3-hydroxy-1-methyl-1H-pyrazol-5-yl)methyl]hexahydro-1H-azepin-2-one.

217 D) The crude product of this Example, part C above, is reacted with acetic anhydride to generate 7-[[3-(acetyloxy)-4,5-dihydro-1-methyl-1H-pyrazol-5-yl]methyl]hexahydro-1H-azepin-2-one.

217 E) The crude product of this Example, part D above, is reacted with trimethyloxonium tetrafluoroborate by the method of Example 3 to generate the iminoether. The iminoether is reacted with ammonium chloride by the method of Example 5 to generate 5-[(hexahydro-7-imino-1H-azepin-2-yl)methyl]-4,5-dihydro-1-methyl-1H-pyrazol-3-ol acetate, monohydrochloride.

217 F) The crude product of this Example, part E above, is heated in 2N HCl to generate the title compound.

EXAMPLE 218

5-[(hexahydro-7-imino-1H-azepin-2-yl)methyl]-1,2-dihydro-3H-pyrazol-3-one, dihydrochloride

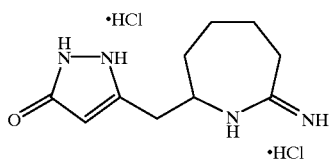

218 A) The title compound of Example 217, part B, is reacted with hydrazine to generate 7-[(4,5-dihydro-3-hydroxy-1H-pyrazol-5-yl)methyl]hexahydro-1H-azepin-2-one.

218 B) The crude product of this Example, part A above, is reacted with acetic anhydride to generate 7-[(3-acetyloxy-4,5-dihydro-1H-pyrazol-5-yl)methyl]hexahydro-1H-azepin-2-one.

218 C) The crude product of this Example, part 3 above, is reacted with DDQ by the method of E. W. Bousquet, *J. Org. Chem.* 1975, 40, 2208 to generate 7-[(3-acetyloxy-1H-pyrazol-5-yl)methyl]hexahydro-1H-azepin-2-one.

218 D) The crude product of this Example, part C above, is reacted with trimethyloxonium tetrafluoroborate by the method of Example 3 to generate the iminoether. The iminoether is reacted with ammonium chloride by the method of Example 5 to generate 7-[(3-acetyloxy-1H-pyrazol-5-yl)methyl]hexahydro-1H-azepin-2-imine, monohydrochloride.

218) The crude product of this Example, part D above, is heated in 2N HCl to generate the title compound.

EXAMPLE 219 AND EXAMPLE 64

Isomer A: (±) (cis) 4-methyl-5-(phenylmethyl)pyrrolidin-2-imine, monohydrochloride Isomer B: (±) (trans) 4-methyl-5-(phenylmethyl)pyrrolidin-2-amine, monohydrochloride

115

Example 219

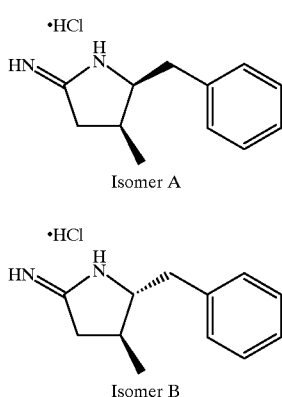

Isomer A

Example 64

Isomer B

Example 219 A) trans-b-Nitrostyrene (63.0 g, 0.42 mole) was reacted with benzaldehyde (53.4 g, 0.5 mole) and 1,2-diaminobenzene (54.4 g, 0.5 mole) according to the procedure of Chikashita et. al. (*Synth. Commun.* 1985, 15 (6), 527) to yield (2-nitroethyl)benzene (60.0 g, 95%) as a yellow oil.

Example 219 B) Methyl crotonate (6.4 g, 64 mmol) was mixed with the product of Example 219 A (9.7 g, 64 mmol), potassium carbonate (8.9 g, 64 mmol) and Aliquat 336 (20 drops). The mixture was sonicated at room temperature. When the reaction, monitored by G.C., was complete, the mixture was acidified with HCl (1N) and the aqueous phase extracted with ether. The organic phase was dried ($Na_2SO_4$), filtered and stripped of solvent under reduced pressure to provide the crude product oil. Purification by chromatography on silica gel yielded methyl b-methyl-g-nitrobenzenepentanoate (14.7 g, 91%).

Example 219 C) The product material from Example 219 B (5.0 g, 20 mmol) in absolute MeOH was hydrogenated over RaNi at 55° C. and 60 psi or 24 h. The reaction product was purified by column chromatography to yield 4-methyl-5-(phenylmethyl)pyrrolidin-2-one (2.4 g, 62%) as a mixture of diasteromers.

Example 219 D) The products of Example 219 C (1.35 g, 7.0 mmol) were treated with trimethyloxonium tetrafluoroborate (1.26 g, 8.6 mmol) in $CH_2Cl_2$ (DCM, 20 mL) by the method of Example 3, to yield 3,4-dihydro-5-methoxy-3-methyl-2-(phenylmethyl)-2H-pyrrole (1.0 g, 67%) as a mixture of diastereomers.

Example 219 and Example 64) A solution of the product of Example 219 D (1.0 g, 4.7 mmol) in MeOH (30 mL) was reacted with ammonium chloride (200 mg, 3.8 mmol) by the method of Example 5 followed by chromatography on reverse phase HPLC to generate the cis and trans title materials 219 (300 mg) and 64 (220 mg). The sample of trans isomer obtained by this method was identical to that obtained the method of Example 64.

DSC: 142.1° C.

| Elemental analysis: $C_{12}H_{16}N_2$.1.09 HCl (MW = 228.01) | | | | |
|---|---|---|---|---|
| | C | H | N | Cl |
| Calculated: | 63.21 | 7.55 | 12.29 | 16.95 |
| Found: | 63.53 | 7.56 | 12.11 | 17.29 |

116

EXAMPLES 220

Isomer A: (+) (cis) 5-(phenylmethyl)-4-(trifluoromethyl)pyrrolidin-2-imine, monohydrochloride Isomer B: (+) (trans) 5-(phenylmethyl)-4-(trifluoromethyl)pyrrolidin-2-imine, monohydrochloride

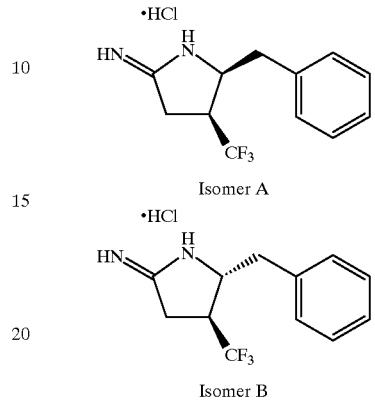

Isomer A

Isomer B

Example 220 A) Ethyl 4,4,4-trifluoromethyl crotonate (5.5 g, 33 mmol) and the product of Example 219 A (5.0 g, 33 mmol) were reacted with potassium carbonate (4.6 g, 33 mmol) and Aliquat 336 (10 drops), by the method of Example 219 B. Purification by chromatography on silica gel yielded the product ethyl g-nitro-b-(trifluoromethyl)benzenepentanoate (4.4 g, 42%).

| Elemental analysis: $C_{14}H_{16}NO_4F_3$ (MW = 359.28) | | | |
|---|---|---|---|
| | C | H | N |
| Calculated: | 52.67 | 5.05 | 4.39 |
| Found: | 52.81 | 5.40 | 4.31 |

Example 220 B) The material 220 A (4.3 g, 13.5 mmol) in absolute MeOH was hydrogenated over RaNi at 55° C. and 60 psi for 16 h. The reaction product was purified by column chromatography to yield 5-(phenylmethyl)-4-trifluoromethyl)pyrrolidin-2-one (2.3 g, 71%) as a mixture of diasteromers.

Example 220 C) The product material from Example 220 B (0.74 g, 3 mmol) was treated with trimethyloxonium tetrafluoroborate (0.54 g, 3.7 mmol) in DCM (20 mL) by the method of Example 3, to yield 3,4-dihydro-5-methoxy-2-(phenylmethyl)-3-(trifluoromethyl)-2H-pyrrole (0.58 g, 76%) as a mixture of diastereomers.

Example 220) A solution of the product of Example 220 C (0.6 g, 2.3 mmol) in MeOH (20 mL) was reacted with ammonium chloride (134 mg, 2.3 mmol) by the method of Example 5 followed by chromatography on reverse phase HPLC to generate the cis and trans title materials 220 Isomer A (240 mg) and 220 Isomer B (250 mg).

Example 220 Isomer A:
Elemental analysis: $C_{12}H_{13}N_2F_3$.1 HCl.1.1 $NH_4Cl$.0.67 $H_2O$ (MW = 349.62)

| | C | H | N | Cl |
|---|---|---|---|---|
| Calculated: | 41.23 | 5.69 | 12.42 | 21.30 |
| Found: | 41.01 | 5.34 | 12.65 | 21.67 |

117
-continued

Example 220 Isomer B:
Elemental analysis: $C_{12}H_{13}N_2F_3 \cdot 1$ HCl$\cdot 0.1$ AcOH (MW = 284.71)

|  | C | H | N |
|---|---|---|---|
| Calculated: | 51.47 | 5.10 | 9.84 |
| Found: | 51.87 | 5.20 | 9.59 |

EXAMPLE 221

4,4-dimethyl-5-(phenylmethyl)pyrrolidin-2-imine, monohydrochloride

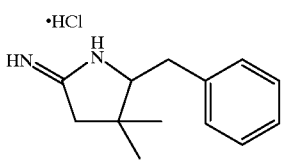

Example 221 A) Ethyl dimethyl acrylate (10.75 g, 84 mmol) was mixed with the product of Example 219 A (12.68 g, 84 mmol), in tetra-n-butylammonium fluoride in THF (84 mL, 1 M) and heated at 40° C. When the reaction, monitored by G.C., was complete, the mixture was treated with brine (satd.) and the aqueous phase extracted with ether. Purification by chromatography on silica gel yielded the product ethyl b,b-dimethyl-g-nitrobenzenepentanoate (9.04 g, 34%).

Elemental analysis: $C_{15}H_{21}NO_4$ (MW = 279.34)

|  | C | H | N |
|---|---|---|---|
| Calculated: | 64.50 | 7.58 | 5.01 |
| Found: | 64.60 | 7.96 | 4.96 |

Example 221 B) The product material from Example 221 A (3.5 g, 12.5 mmol) in absolute MeOH was hydrogenated over RaNi at 55° C. and 60 psi for 6 h. The reaction product was purified by column chromatography to yield 4,4-dimethyl-5-(phenylmethyl)pyrrolidin-2-one (2.41 g, 95%).

Example 221 C) The product material from Example 221 B (1.04 g, 5.1 mmol) was treated with trimethyloxonium tetrafluoroborate (0.91 g, 6.2 mmol) in DCM (25 mL) by the method of example 3, to yield 3,4-dihydro-5-methoxy-3,3-dimethyl-2-(phenylmethyl)-2H-pyrrole (0.83 g, 75%).

Example 221) A solution of the product of Example 221 C (0.8 g, 3.5 mmol) in MeOH (60 mL) was reacted with ammonium chloride (187 mg, 3.5 mmol) by the method of Example 5 followed by chromatography on reverse phase HPLC to generate the title material (570 mg, 68 %).

Elemental analysis: $C_{13}H_{18}N_2 \cdot 1.0$ HCl (MW = 238.76)

|  | C | H | N | Cl |
|---|---|---|---|---|
| Calculated: | 65.40 | 8.02 | 11.73 | 14.85 |
| Found: | 65.04 | 7.78 | 11.85 | 14.75 |

118

EXAMPLE 222

5-(phenylmethyl)pyrrolidin-2-imine, monohydrochloride

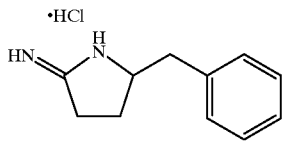

Example 222 A) Methyl acrylate (2.8 g, 33 mmol) was mixed with the product of Example 219 A (5.0 g, 33 mmol), potassium carbonate (4.6 g, 33 mmol) and Aliquat 336 (10 drops), by the method of Example 219 B. Purification by chromatography on silica gel yielded 4.0 g (55%) of methyl g-nitrobenzenepenzanoate.

Elemental analysis: $C_{12}H_{16}NO_4 \cdot 0.05$ hexane (MW = 242.57)

|  | C | H | N |
|---|---|---|---|
| Calculated: | 61.16 | 6.55 | 5.80 |
| Found: | 61.54 | 6.52 | 6.16 |

Example 222 B) The product material from Example 222 A (4.0 g, 18 mmol) was hydrogenated over Pd/C (4%) at 55° C. and 5 psi for 40 h. The reaction product was purified by column chromatography to yield 5-(phenylmethyl)pyrrolidin-2-one (0.6 g, 29%).

Example 222 C) The product material of Example 222 B (0.5 g, 3.1 mmol) was treated with trimethyloxonium tetrafluoroborate (0.55 g, 3.7 mmol) in DCM (25 mL) by the method of Example 3, to yield 3,4-dihydro-5-methoxy-2-(phenylmethyl)-2H-pyrrole (0.5 g, 78%).

Example 222) A solution of the title product of Example 222 C (0.5 g, 2.4 mmol) in MeOH (20 mL) was reacted with ammonium chloride (0.14 g, 2.7 mmol) by the method of Example 5. The crude product residue after removal of solvent was subjected to reverse phase HPLC to generate the title material (0.31 g, 55%).

Elemental analysis: $C_{11}H_{14}N_2 \cdot 1$ HCl$\cdot 0.35$ NH$_4$Cl$\cdot 0.25$ H$_2$O (MW = 233.93)

|  | C | H | N | Cl |
|---|---|---|---|---|
| Calculated: | 56.48 | 7.28 | 14.07 | 20.46 |
| Found: | 56.43 | 7.48 | 14.38 | 20.83 |

EXAMPLES 223

Isomer A: (±) (cis) 5-[(1,3-dioxolan-2-yl)methyl]-4-(trifluoromethyl)pyrrolidin-2-imine, monohydrochloride Isomer B: (±) (trans) 5-[(1,3-dioxolan-2-yl)methyl]-4-(trifluoromethyl)pyrrolidin-2-imine, monohydrochloride

119

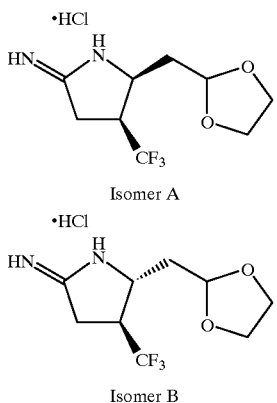

Isomer A

Isomer B

Example 223 A) Ethyl 4,4,4-trifluoromethyl crotonate (10 mmol) and 2-(2-nitroethyl)-1,3-dioxolane (12 mmol) are reacted with potassium carbonate (5 mmol) and Aliquat 336 (3 drops), by the method of Example 219 B. Purification by chromatography on silica gel yields ethyl g-nitro-b-(trifluoromethyl)-1,3-dioxolane-2-pentanoate.

Example 223 B) The product material from Example 223 A in MeOH is hydrogenated over RaNi at 55° C. and 60 psi for 6 h. The reaction product is purified by column chromatography to yield 5-[(1,3-dioxolan-2-yl)methyl]-4-(trifluoromethyl)pyrrolidin-2-one as a mixture of diastereomers.

Example 223 C) The product material from Example 223 B is treated with trimethyloxonium tetrafluoroborate in DCM by the method of Example 3 to yield 2-[(1,3-dioxolan-2-yl)methyl]-3,4-dihydro-5-methoxy-3-(trifluoromethyl)-2H-pyrrole as a mixture of diastereomers.

Example 223) A solution of the title products of Example 223 C in MeOH are reacted with ammonium chloride by the method of Example 5 followed by chromatography on reverse phase HPLC to generate the cis and trans title materials 223 Isomer A and 223 Isomer B.

EXAMPLES 224

Isomer A: (±) (trans) 2-[2-hydroxy-3-[5-imino-3-(trifluoromethyl)pyrrolidin-2-yl]propyl]oxazole-4-carboxylic acid, monohydrochloride Isomer B: (±) (cis) 2-[2-hydroxy-3-[5-imino-3-(trifluoromethyl)pyrrolidin-2-yl]propyl]oxazole-4-carboxylic acid, monohydrochloride

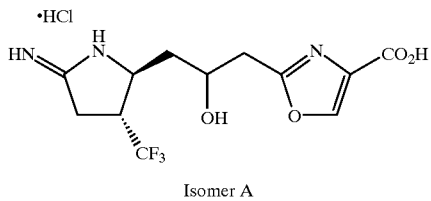

Isomer A

120

-continued

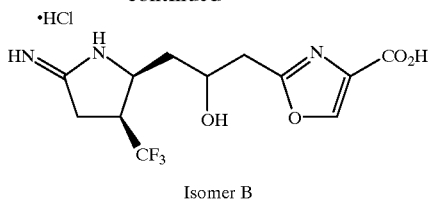

Isomer B

Example 224 A) The product of Example 223 B in MeOH is treated with HCl (1N) to yield 5-oxo-3-(trifluoromethyl) pyrrolidine-2-acetaldehyde which is used directly in the next step.

Example 224 B) As described by Helquist et al. in *J. Org. Chem.*, 1992, 57, 4799–4802, to a stirring suspension of Zn (7.5 mg-atm) and the product of 224 A (5.5 mmol) in 10 mL of THF at 0° C. is added dropwise ethyl 2-bromomethyioxazole-4-carboxylate (U.S. Pat. No. 5,395, 932) (5.0 mmol) in 10 mL of THF. After stirring for 2 h, the reaction is quenched with saturated $NH_4Cl$ and extracted with $Et_2O$. The organic phase is dried over $MgSO_4$, concentrated under vacuum, and purified by column chromatography to give ethyl 2-[2-hydroxy-3-[5-oxo-3-(trifluoromethyl)pyrrolidin-2-yl]propyl]oxazole-4-carboxylate.

Example 224 C) To a stirring solution of 224 B (5 mmol) in 10 mL of MeOH is added 10 mL of 1N NaOH. After 2 h, the reaction mixture is adjusted to pH 3 with 1M $KHSO_4$ The reaction mixture is extracted 3×50 mL of EtOAc. The combined organic layers are dried over $Na_2SO_4$ anhydrous, filtered, and stripped to give 2-[2-hydroxy-3-[5-oxo-3-(trifluoromethyl)pyrrolidin-2-yl]propyl]oxazole-4-carboxylic acid.

Example 224 D) To a stirring solution of the product of Example 224 C (5 mmol) and imidazole (6 mmol) in 10 mL of DMF is added t-butyldimethylsilyl chloride (12 mmol). After 16 h, the solvent is removed under high vacuum and the residue is purified by column chromatography to provide (1,1-dimethylethyl)dimethylsilyl 2-[2-[(1,1-dimethylethyl) dimethylsilyloxy]-3-[5-oxo-3-(trifluoromethyl)pyrrolidin-2-yl)propyl]oxazole-4-carboxylate.

Example 224 E) The product of Example 224 C is treated with trimethyloxonium tetrafluoroborate in DCM by the method of Example 3 to yield (1,1-dimethylethyl) dimethylsilyl 2-[3-[3,4-dihydro-5-methoxy-3-(trifluoromethyl)-2H-pyrrole-2-yl]-2-[(1,1-dimethylethyl) dimethylsiloxy]propyl]oxazole-4-carboxylate as a mixture of diastereomers.

Example 224) A solution of the title products of Example 224 D in MeOH are reacted with ammonium chloride by the method of Example 5. The material is dissolved in HCl (2N) and refluxed for 2 h. The crude product residue after removal of solvent was subjected to reverse phase HPLC to generate both the cis and trans title materials 224 Isomer A and 224 Isomer B.

EXAMPLE 225

Isomer A: (±) ethyl (trans) 2-[3-[5-imino-3-(trifluoromethyl)pyrrolidin-2-yl]propyl]oxazole-4-carboxylate, monohydrochloride Isomer B: (±) ethyl (cis) 2-[3-(5-imino-3-(trifluoromethyl)pyrrolidin-2-yl]propyl]oxazole-4-carboxylate, monohydrochloride

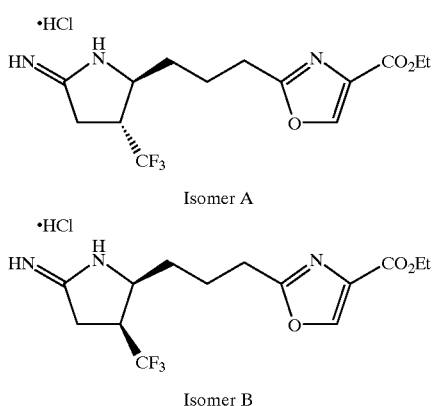

Isomer A

Isomer B

Example 225A) To a stirring solution of the product of Example 224 B (5 mmol) in 10 mL of 10% TFA/DCM is added Et₃SiH (7.5 mmol). After stirring for 30 min, the solvent is removed under vacuum and the residue is purified by column chromatography to provide ethyl 2-[3-[5-oxo-3-(trifluoromethyl)pyrrolidin-2-yl]propyl]oxazole-4-carboxylate.

Example 225 B) The product material from Example 225 A is treated with trimethyloxonium tetrafluoroborate in DCM by the method of Example 3, to yield ethyl 2-[3-[3,4-dihydro-5-methoxy-3-(trifluoromethyl)-2H-pyrrol-2-yl]propyl]oxazole-4-carboxylate as a mixture of diastereomers.

Example 225) A solution of the product of Example 225 B in MeOH is reacted with ammonium chloride by the method of Example 5. The crude product residue after removal of solvent was subjected to reverse phase HPLC to generate both the cis and trans title materials 225 Isomer A and 225 Isomer B.

EXAMPLE 226

Isomer A: (±) (trans) 2-[3-[5-imino-3-(trifluoromethyl)pyrrolidin-2-yl]propyl]oxazole-4-carboxylic acid, monohydrochloride Isomer B: (±) (cis) 2-[3-[5-imino-3-(trifluoromethyl)pyrrolidin-2-yl]propyl]oxazole-4-carboxylic acid, monohydrochloride

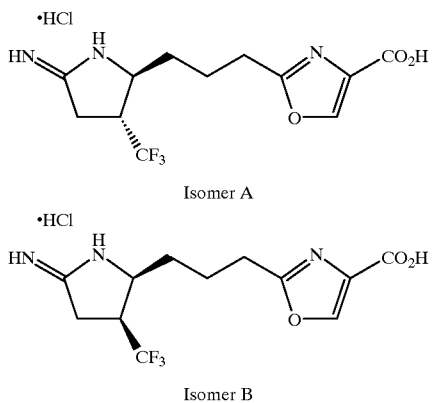

Isomer A

Isomer B

A solution of the crude title product mixture of Example 225 in HCl (2N) is reacted by the method of Example 224 E. The crude product residue after removal of solvent was subjected to reverse phase HPLC to generate the title material to generate both the cis and trans title materials 226 Isomer A and 226 Isomer B.

EXAMPLES 227

Isomer A: (±) (cis) 5-[(4-methoxyphenyl)methyl]-3-methylpyrrolidin-2-imine, monohydrochloride Isomer B: (±) (trans) 5-[(4-methoxyphenyl)methyl]-3-methylpyrrolidin-2-imine, monohydrochloride

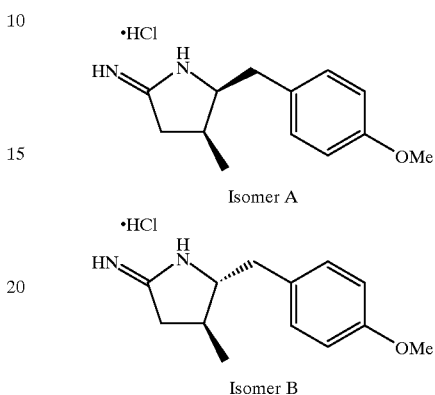

Isomer A

Isomer B

Example 227 A) 4-Methoxy-β-nitrostyrene (25.0 g, 0.15 mole) was reacted with benzaldehyde (19.1 g, 0.18 mole) and 1,2-diaminobenzene (19.8 g, 0.18 mole) according to the procedure of Chikashita et. al. (*Synth. Commun.* 1985, 15 (6), 527) to yield methoxy-4-(2-nitroethyl) benzene (25.0 g, 93%) as a yellow oil.

Example 227 B) Methyl crotonate (6.1 g, 61 mmol) was mixed with the product of Example 227 A (10 g, 61 mmol), potassium carbonate (8.4 g, 61 mmol) and Aliquat 336 (10 drops). The mixture was sonicated at room temperature. When the reaction, monitored by G.C., was complete the mixture was acidified with HCl (1N) and the aqueous phase extracted with ether. Purification by chromatography on silica gel gave methyl 4-methoxy-b-methyl-g-nitrobenzenepentanoate (6.7 g, 39%).

Example 227 C) The product of Example 227 B (6.7 g, 24 mmol) in MeOH was hydrogenated over RaNi at 55° C. and 60 psi for 16 h. The reaction product was purified by column chromatography to yield 5-[(4-methoxyphenyl)methyl]-4-methylpyrrolidin-2-one (3.3 g, 67%) as a mixture of diasteromers.

Example 227 D) The product from Example 227 C (1.4 g, 6.6 mmol) was treated with trimethyloxonium tetrafluoroborate (1.2 g, 7.5 mmol) in DCM by the method of Example 3, to yield 3,4-dihydro-5-methoxy-2-[(4-methoxyphenyl)methyl]-3-methyl-2H-pyrrole (1.4 g, 95%) as a mixture of diastereomers.

Example 227) A solution of the title product of Example 227 D in MeOH is reacted with ammonium chloride by the method of Example 5. The crude product residue after removal of solvent was subjected to reverse phase HPLC to generate the cis and trans title materials 227 Isomer A and 227 Isomer B.

EXAMPLE 228 hexahydro-3-[[(methoxyphenyl)methyl]thio]-2H-azepin-2-imine, trifluoroacetate salt

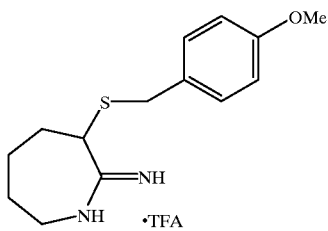

Example 228 A) To a solution of 10 g (0.088 mol) of caprolactam in 200 mL of anhydrous THF was added 38.2 g (0.177 mol) of Boc-anhydride and 0.2 g DMAP. This mixture was stirred at reflux for 4 days, allowed to cool to 25° C., diluted with EtOAc, washed with aqueous sodium bicarbonate, dried (MgSO$_4$), filtered and concentrated to afford the N-Boc-caprolactam as a yellow oil. Chromatography (silica gel, ethyl acetate/hexanes) afforded 14 g of the Boc-protected caprolactam as a pale yellow oil.

Example 228 B) To a solution of 1 g (0.0047 mol) of this Boc-caprolactam product of Example 228 A in 10 mL of anhydrous THF at −78° C. was added 0.005 mol of LiHMDS. After stirring for 30 minutes, 1.2 g (0.005 mol) of hexachloroethane in 5 ml of anhydrous THF was added. The mixture was allowed to warm to 0° C. and was quenched with dilute HCl. The mixture was extracted with EtOAc and the organic layer was washed with 5% HCl, dried (MgSO$_4$), filtered and concentrated to afford a yellow oil. The residue oil was dissolved in 40 mL of 1,4-dioxane (satd. with anhydrous HCl), stirred for 40 minutes, concentrated to afford 0.9 g of 3-chlorocaprolactam as an off-white solid.

Example 228 C) A solution of 0.45 g (0.003 mol) of the 3-chlorocaprolactam product of Example 228 B in 5 mL of methylene chloride was treated with 0.5 g (0.0033 mol) of Me$_3$O$^+$BF$_4^-$. This mixture was stirred for 18 hours at 25° C. The solution was diluted with EtOAc before the organic fraction was washed with aqueous sodium bicarbonate, dried (MgSO$_4$), filtered and concentrated to afford 0.3 g of the iminoether as a yellow oil. This iminoether was dissolved in 5 mL of methanol and 0.1 g (0.0019 mol) of ammonium chloride was added. The mixture was stirred at 60° C. for 3 days. The solvent was removed in vacuo and the residue, dissolved in water, was washed with EtOAc. Chromatography (C-18, acetonitrile/water) followed by lyophilization afforded 2-imino, 3-chlorohexamethyleneimine as a white solid.

Example 228) To a solution of 4-methoxybenzylmercaptan in 50 mL of anhydrous THF was added 0.55 g (0.0135 mol) of sodium hydride. After stirring at 25° C. for fifteen minutes, 1.6 g (0.006 mol) of the 2-imino, 3-chlorohexamethyleneimine product of Example 228 C was added. This mixture was stirred at reflux for 6 hours and then at 25° C. for 3 days. The reaction mixture was diluted with dilute HCl and concentrated to afford a sticky off-white solid. The residue was dissolved in water, washed with EtOAc, and chromatographed (C-18, acetonitrile/water) top afforded 1.6 g of the title product as a yellow oil.

Mass spectral analysis for $C_{13}H_{18}N_2S_1$: M$^+$H=265.

$^1$H NMR (D$_2$O): δ 1.2–2.0(m, 6H), 3.2 (m, 1H), 3.5 (m, 1H), 3.65 (bs, 5H), 3.7 (d, 2H), 6.8 (d, 2H), 7.15 (d, 2H).

EXAMPLE 229

2-[2-(2-iminohexahydro-1H-azepin-3-yl)ethyl-1-methylpyridinium chloride, monohydrochloride

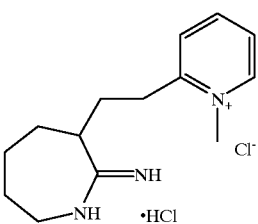

The title material was prepared by the method of Example 291 using hexahydro-3-[2-(2-pyridyl)ethyl]-1H-azepin-2-one material prepared in Example 290).

Mass spectral analysis for $C_{14}H_{22}N_3$: M$^+$H=232.

$^1$H NMR (D$_2$O): δ 8.60 (d, J=7 Hz, 1H); 8.35 (z, J=7 Hz, 1H); 7.85 (d, J=7 Hz, 1H); 7.75 (t, J=7 Hz, 1H); 4.2 (s, 3H); 3.42–3.30 (m, 2H); 3.22–3.00 (m, 2H); 3.00–2.80 (m, 1H); 2.30–2.00 (m, 2H); 1.90–1.50 (m, 6H).

EXAMPLE 230 hexahydro-3-[2-(1-methylpiperidin-2-yl)ethyl)-2H-azepin-2-imine, dihydrochloride

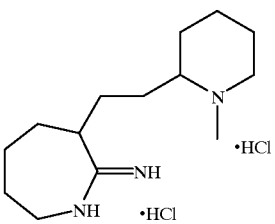

The title material was prepared by the method of Example 292 from the product of Example 229.

Mass spectral analysis for $C_{14}H_{27}N_3$: M$^+$H=238.

$^1$H NMR (D$_2$O): δ 3.40–3.20 (m, 3H); 3.20–2.05 (m, 3H); 2–80–2.60 (m, 4H); 1.90–1.20 (m, 15H).

EXAMPLE 231 ethyl 5-[(hexahydro-2-imino-1H-azepin-3-yl)methyl]-4,5-dihydroisoxazole-3-carboxylate, trifluoroacetate salt

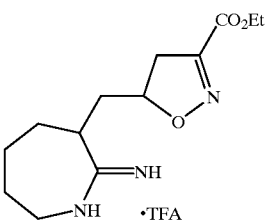

Example 231 A) The Isomer A title product of Example 18 (3-allylcaprolactam, 5 g, 0.033 mol) was reacted with 10 g (0.066 mol) of ethyl chlorooximidoacetate in 500 mL of toluene. This mixture was stirred at reflux for 18 hours. The reaction mixture was allowed to cool and then concentrated to afford a brown oil. Chromatography of this oil (silica gel, EtOAc) afforded 7 g of 3-[[4,5-dihydro-3-(ethoxycarbonyl) isoxazol-5-yl]methyl]hexahydro-1H-azepin-2-one as a yellow oil.

Mass spectral analysis for $C_{13}H_{20}N_2O_4$: $M^+H=269$.

Example 231) To a magnetically stirred slurry of 3 g (0.021 mol) of $Me_3O^+BR_4^-$ and 60 mL of $CH_2Cl_2$ under nitrogen ($N_2$) was added 5 g (0.019 mol) of the 3-[[4,5-dihydro-3-(ethoxycarbonyl)isoxazol-5-yl]methyl] hexahydro-1H-azepin-2-one product of Example 231 A. This mixture was stirred at room temperature for 18 hours before it was diluted with 30 mL of EtOAc and partitioned between the organic layer and 40 mL of saturated $NaHCO_3$. The organic phase was separated, dried ($MgSO_4$), filtered, and concentrated under reduced pressure to provide 5.3 g of the iminoether as a red oil. This iminoether and 1.1 g (0.021 mol) of ammonium chloride ($NH_4Cl$) were refluxed in 25 mL of methanol (MeOH) under a nitrogen atmosphere for 18 hours. After cooling the react on to room temperature, it was concentrated to give a dark reissue which was filtered and partitioned between water and EtOAc. The organic and aqueous phases were separated and the aqueous phase was washed with a 15 mL portion of EtOAc. Chromatography of the aqueous layer (C-18, acetonitrile/water) afforded 2.5 g of the title product as a red oil.

Mass spectral analysis for $C_{13}H_{21}N_3O_3$: $M^+H=268$ $^1H$ NMR ($D_2O$): δ 1.2 (t, 3H), 1.4–2.2 (m, 8H), 2.9 (m, 2H), 3.35 (m, 3H), 4.2 (q, 2H), 4.9 (m, 1H).

EXAMPLE 232 cyclohexyl hexahydro-7-iminoazepine-2-carboxylate, monohydrochloride

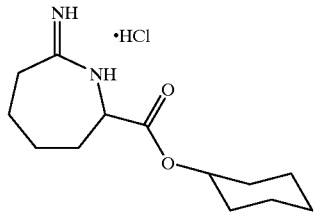

A solution of 0.1 g of the 2-imino, 3-carbomethoxyhexamethyleneimine product of Example 233d in 5 mL of cyclohexanol was treated with 5 drops of acetyl chloride and stirred at reflux for eighteen hours. After cooling the reaction to room temperature, it was concentrated in vacuo to afford a sticky oil. Lyophilization afforded the title compound as an off-white solid.

Mass spectral analysis for $C_{13}H_{22}N_2O_2$: $M^+H=239$.

$^1H$ NMR ($D_2O$): δ 1.1–1.85 (m, 15H), 2.05 (m, 1H), 2.55 (m, 2H), 4.35 (dd, 1H), 4.75 (h, 1H).

EXAMPLE 233 phenylmethyl hexahydro-7-iminoazepine-2-carboxylate, monohydrochloride

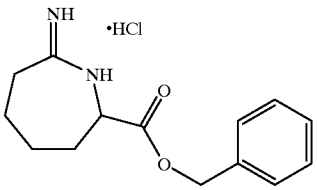

Example 233 A) Anhydrous HCl was bubbled into a mixture of 25 g (0.14 mol) of 2-aminopimellic acid in 500 mL of methanol until the solid was dissolved. After standing for 18 hours, the reaction was concentrated to afford 33.5 g (100% yield) of the bis-methyl ester salt as a white solid.

Example 233 B) The HCl salt product of Example 233 A was neutralized by the addition of a small amount of water containing 1 equivalent of sodium bicarbonate. This solution was extracted with EtOAc, dried ($MgSO_4$), filtered and concentrated to afford 22 g of the free base.

Example 233 C) A solution of 17 g (0.084 mol) of the free base product of Example 233 B in 900 mL of p-cymene was stirred at reflux for two days. The solvent was removed in vacuo and the residue recrystallized from cyclohexane to afford 12.2 g (85% yield) of 7-(methoxycarbonyl) caprolactam as an off-white solid.

Example 233 D) A solution of 0.3 g (0.0018 mol) of the lactam product of Example 233 C in 10 mL of methylene chloride was treated with 0.3 g (0.002 mol) of $Me_3O^+BF_4^-$. This mixture was stirred for 18 hours at 25° C. The solution was diluted with EtOAc, washed with aqueous sodium bicarbonate, dried ($MgSO_4$), filtered and concentrated to afford 0.25 g of the iminoether as a yellow oil. The iminoether was dissolved in 10 mL of methanol and 0.08 g (0.0014 mol) of ammonium chloride was added to the solution. This mixture was stirred at 60° C. for 6 hours. The solvent was removed in vacuo and the residue dissolved in water was washed with EtOAc, and lyophilized to afford 2-imino, 3-carbomethoxyhexamethyleneimide as an off-white foam.

Example 233) A solution of 0.1 g of the 2-imino, 3-carbomethoxyhexamethyleneimine product of Example 233 D in 5 mL of benzyl alcohol was treated with 5 drops of acetyl chloride and stirred at reflux for eighteen hours. Removed heat and concentrated in vacuo to afford a sticky oil. Lyophilization afforded the title compound as an off-white solid.

$^1H$ NMR ($D_2O$): δ 1.2–1.95 (m, 5H), 2.05 (m, 1H), 2.5 (m, 2H), 4.4 (dd, 1H), 5.2 (q, 2H), 7.3 (s, 5H).

Mass spectral analysis for $C_{14}H_{18}N_2O_2$: $M^+H=247$

EXAMPLE 234 hexahydro-7-[3-(phenylmethoxy)propyl]-2H-azepin-2-imine, trifluoroacetate salt

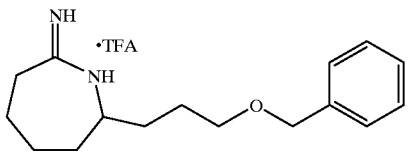

Example 234 A) To a mechanically stirred mixture of KOt-Bu (10.1 g, 104 mmol) in benzene (100 mL) cooled to 0° C. under nitrogen was added cyclohexanone (7.4 g, 83 mmol) dropwise over 20 min. Ten minutes after the addition was complete, benzyl 3-bromo-propyl ether (20 g, 87 mmol) was added over a twenty minute period. The reaction mixture was warmed to room temperature, refluxed for seven hours, stirred at room temperature or eighteen hours, and diluted with 0.5N potassium hydrogen sulfate (200 mL). The reaction mixture was further diluted with Et$_2$O, 0.5N potassium hydrogen sulfate, and water, until two phases formed. The organic phase was washed with water, brine, dried over sodium sulfate, filtered, and the solvent removed under reduced pressure to give 19.2 g of the 2-(3-benzyloxypropyl)-cyclohexan-1-one.

Mass spectral analysis for $C_{16}H_{22}O_2$: M$^+$H=247.

$^1$H NMR (CDCl$_3$): δ 0.8–2.5 (m, 13H), 3.40–3.45 (m, 2H), 4.5 (s, 2H), 7.2–7.4 (m, 5H).

Example 234 B) To the product from Example 234 A (4.9 g, 20 mmol) in 40 mL EtOH and 30 mL water was added hydroxylamine hydrochloride (2.1 g, 30 mmol) and sodium acetate (3.3 g, 40 mmol). The mixture was refluxed for 4 hours, followed by stirring for 18 hours at room temperature. The EtOH was evaporated in vacuo and the solution was diluted with 100 mL water and extracted with EtOAc. The organic phase was washed with brine, dried over MgSO$_4$ and concentrated in vacuo, yielding 5.7 g of the 2-(3-benzyloxypropyl)-cyclohexanone oxime as an oil.

Example 234 C) The 2-(3-benzyloxypropyl)-cyclohexanone oxime product of Example 234 B was dissolved in 20 mL acetone and was reacted with benzenesulfonyl chloride (3.5 g, 20 mmol) at 0° C. in the presence of 20 mL 1N NaOH. The mixture was stirred for 18 h at room temperature and the acetone was evaporated, diluted with 100 mL water, and extracted with EtOAc. The organic phase was washed with brine and concentrated in vacuo to yield 4.3 g of a mixture of the 3 and 7 isomers of benzyloxypropylcaprolactam. The crude material was purified by HPLC chromatography on silica gel using 30% acetone in hexane to obtain 1.3 g of the 7-(benzyloxypropyl)caprolactam as oil.

Mass spectral analysis for $C_{16}H_{23}N_1O_2$: M$^+$H=262.

Example 234 D) To the product from Example 234 C (1.3 g, 5.0 mmol) dissolved in 25 mL CH$_2$Cl$_2$ was added Me$_3$O$^+$BF$_4^-$ (0.8 g, 1.1 equiv.), and the mixture stirred for 16 hours. The solvent was removed under reduced pressure and the resulting oil was dissolved in 50 mL MeOH. This solution was saturated with ammonia gas at 0° C. for 20 minutes. The flask was stoppered and the reaction was stirred at room temperature for 16 hours. The reaction was concentrated by evaporation and the residue was subjected by reverse phase HPLC (C-18), to give 0.87 g of the title product as a white powder.

Mass spectral analysis for $C_{16}H_{24}N_2O$: M$^+$H=261.

$^1$H NMR (CDCl$_3$): δ 1.37–1.55 (m, 3H), 1.65–1.83 (m, 5H), 1.90–2.04 (m, 2H), 2.40–2.63 (m, 2H), 3.34–3.43 (m, 1H), 3.43–3.52 (m, 2H), 4.49 (s, 2H), 7.26–7.34 (m, 5H).

EXAMPLE 235

N-[2-(hexahydro-7-imino-1H-azepin-2-yl)ethyl] benzenimidamide, bis(trifluoroacetate)salt

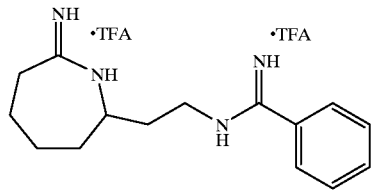

Example 235 A) A sample of 2-nitroethanol (10 g, 110 mmol) was added over a period of 30 minutes to a mixture of sodium acetate (2.5 g) and acetic anhydride (13 g, 127 mmol) cooled in an ice bath and maintained under a N$_2$ atmosphere. After 1 hour of stirring, the ice bath was removed and the mixture was stirred for 12 hours at room temperature. The reaction was diluted with 200 mL of water and extracted with 3×100 mL of EtOAc. The combined extracts were washed with brine, dried (MgSO$_4$) and concentrated of all solvent in vacuo to afford the 2-nitro ethylacetate as a clear oil.

Example 235 B) The 2-nitro ethylacetate product of Example 235 A (13.3 g, 100 mmol) was dissolved in 15 mL acetonitrile (AcN) which was added to a solution of morpholino cyclohexene (18.4 g, 110 mmol) in 30 mL of AcN at −20° C. under N$_2$. After the addition was complete, stirring was continued for 16 hours at room temperature. After 40 mL of 1N HCl was added to the solution, stirring was continued for 4 more hours. The mixture was diluted with 100 mL water and extracted with 3×100 mL EtOAc. The combined organic phase was washed with brine, dried (MgSO$_4$) and evaporated in vacuo to yield 14.5 g 2-(2-nitro ethyl)cyclohexanone as dark oil (85% yield).

Mass spectral analysis for $C_8H_{13}NO_3$: M$^+$H=172 and M$^+$Li=178.

Example 235 C) The 2-(2-nitroethyl)cyclohexanone product of Example 235 B (3.42 g, 20 mmol) in 25 mL formic acid was refluxed for 30 minutes in the presence of H$_2$N—OSO$_3$H (2.48 g, 22 mmol). The formic acid was removed in vacuo. The residual oil was dissolved in a mixture of water (40 mL) and AcN (10 mL) and the isomers were separated on preparative HPLC using AcN/H$_2$O (0.05% TFA) gradient (10–25% AcN in 30 minutes) to yield 7-(2-nitroethyl) caprolactam: 1.95 g (52% yield) and 3-(2 nitroethyl) caprolactam: 0.55 g (15% yield).

Mass spectral analysis for $C_8H_{14}N_2O_3$: M$^+$H=187.

Example 235 D) The 7-(2-nitroethyl)caprolactam product of Example 235 C (2 g, 10.7 mmol) was dissolved in 30 mL CH$_2$Cl$_2$ and reacted with Me$_3$O$^+$BF$_4^-$ (2.2 g, 15 mmol) for 16 hours. The solvent was evaporated and the residue was dissolved in 30 mL MeOH. This solution was saturated with NH$_3$ at 0° C. or 15 minutes and the mixture was stirred for 12 hours at room temperature. All solvent was removed in vacuo and the product was isolated on preparative HPLC using AcN/H$_2$O (0.05% TFA) gradient (0–25% AcN in 30 minutes) affording 1.85 g (93% yield) of 2-imino, 7-(nitroethyl)hexamethyleneimine as a white solid.

Mass spectral analysis for $C_8H_{15}N_3O_2$: $M^+H=186$.

$^1$H NMR ($D_2O$): δ 4.60–4.45 (t, J=7 Hz, 2H); 3.70–3.55 (m, 1H); 2.70–2.40 (m, 2H); 2.30–2.15 (m, 2H); 1.90–1.25 (m, 6H).

Example 235 E) The product of Example 235 D (420 mg, 2.2 mmol) was dissolved in 30 mL EtOH (1% HCl) and hydrogenated at 55 psi for 12 hours in the presence of 0.5 g Pd/carbon. After the catalyst was filtered off and all solvent was removed in vacuo, the residue was purified on preparative HPLC using $H_2O$ as solvent, yielding 210 mg (62% yield) of 2-imino, 7-(aminoethyl)hexamethyleneimine as a clear glassy material.

Mass spectral analysis for $C_8H_{17}N_3$: $M^+H=156$.

$^1$H NMR ($D_2O$): δ 3.70–3.55 (m, 1H); 3.05 2.90 (m, 2H); 2.70–2.40 (m, 2H); 2.00–1.25 (m, 8H).

Example 235) The product of Example 235 E (383 mg; 1 mmol) was reacted with methylbenzimidate (343 mg; 2 mmol) in 5 mL DMF in the presence of DIPEA (0.35 mL; 2 mmol). Purification afforded 160 mg (33% yield) of the title product as a white solid.

Mass spectral analysis for $C_{15}H_{22}N_4$: $M^+H=259$.

$^1$H NMR ($D_2O$): δ 7.65–7.40 (m, 5H); 3.70–3.60 (m, 1H); 3.50–3.40 (m, 2H); 2.70–2.40 (m, 2H); 2.05–1.30 (m, 8H).

EXAMPLE 236

N-[2-(hexahydro-7-imino-1H-azepin-2-yl)ethyl)]-3,4,5,6-tetrahydro-2H-azepin-7-amine, bis(trifluoroacetate)salt

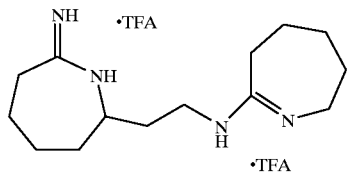

The product of Example 235 E (383 mg; 1 mmol) was reacted with 1-aza-2-methoxy-1-cycloheptene (254 mg; 1 mmol) in 5 mL of MeOH for 16 hours at room temperature. The MeOH was evaporated and the residue was purified on preparative HPLC using $AcN/H_2O$ gradient (0–30% AcN in 30 minutes), affording 470 mg (98% yield) of the title product as an oil.

Mass spectral analysis for $C_{14}H_{26}N_4$: $M^+H=251$.

EXAMPLE 237

N-[2-(hexahydro-7-imino-1H-azepin-2-yl)ethyl]-2,3,4,5-tetrahydropyridin-6-amine, bis(trifluoroacetate) salt

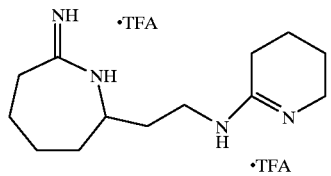

The product of Example 235 E (328 mg; 0.85 mmol) was refluxed with 1-aza-2-methyl-thio-1-cyclohexene hydroiodide (211 mg; 1 mmol) in 20 mL MeOH in the presence of DIPEA (0.35 mL; 2 mmol) for 1 hour. The mixture was diluted with 50 mL of $H_2O$ and purified as described in Example 235 affording 260 mg (88% yield) of the title product as a hygroscopic material.

Mass spectral analysis for $C_{13}H_{24}N_4$: $M^+H=237$.

EXAMPLE 238

N-[2-(hexahydro-7-imino-1H-azepin-2-yl)ethyl]-3,4-dihydro-2H-pyrrol-5-amine, bis(trifluoroacetate)salt

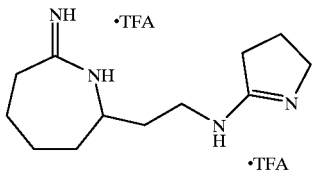

The product of Example 235 E (383 mg; 1 mmol) was reacted with 2-methoxypyrrolidine (198 mg; 2 mmol) in 20 mL MeOH for 16 hours and the product was isolated as described in Example 235 to afford 310 mg (69% yield) of the title product as a white solid.

Mass spectral analysis for $C_{12}H_{22}N_4$: $M^+H=223$.

EXAMPLE 239

N-[2-(hexahydro-7-imino-1H-azepin-2-yl)ethyl] benzenesulfonamide, trifluoroacetate salt

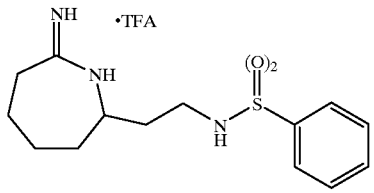

To the product of Example 235 E (0.11 g, 0.6 mmol) in 5 mL DMF was added benzenesulfonyl-chloride (0.12 g, 1.1 equiv), and the reaction mixture was maintained at neutral pH by the dropwise addition of N-methylmorpholine. The reaction was quenched after 30 minutes by the addition of 1 mL water. The solvent was removed under reduced pressure and title product was isolated by reverse phase HPLC (C-18) to give 0.046 g of the title material as a white powder.

Mass spectral analysis for $C_{14}H_{21}N_3O_2S$: $M^+H=296$.

$^1$H NMR ($D_2O$): δ 1.13–1.52 (m, 3H), 1.53–1.69 (m, 3H), 1.73–1.77 (m, 2H), 2.30–2.46 (m, 2H), 2.82–2.99 (m, 2H), 3.37–4.51 (m, 1H), 7.48–7.61 (m, 3H), 7.74–7.78 (m, 2H).

EXAMPLE 240

N-(2-(hexahydro-7-imino-1H-azepin-2-yl)ethyl] benzenemethanesulfonamide, trifluoroacetate salt

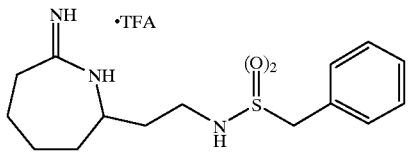

To the product of Example 235 E (0.27 g, 0.7 mmol) in 5 mL DMF was added α-toluenesulfonyl chloride (0.15 g, 1.1 equiv), and the resulting solution was adjusted to pH 7 with 20 drops of N-methylmorpholine and stirred for 3 hours. The solvent was removed under reduced pressure and the crude residue subjected to reverse phase HPLC (C-18) to give 0.015 g of the title product as a glassy solid.

Mass spectral analysis for $C_{15}H_{23}N_3O_2S$: $M^+H=310$.

$^1H$ NMR (DMSO-$d_6$): δ 1.29–1.92 (m, 8H), 2.55–2.67 (m, 2H), 2.95–3.04 (m, 2H), 3.56–3.64 (m, 1H), 4.34 (s, 2H), 7.13–7.20 (m, 1H), 7.33–7.39 (m, 5H).

EXAMPLE 241

N-[2-(hexahydro-7-imino-1H-azepin-2-yl)ethyl] morpholin-4-amine, bis(trifluoroacetate)salt

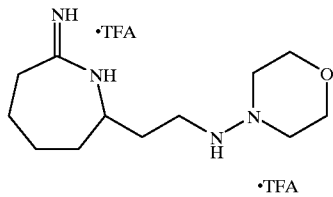

Example 241 A) To a mechanically stirred mixture of KOt-Bu (87 g, 0.9 mol) in benzene (700 mL) cooled to 0° C. under an $N_2$ atmosphere was added cyclohexanone (67 g, 0.75 mol) dropwise over 15 minutes. Ten minutes after the addition was complete, bromoethyl methylether (90 g, 0.78 mol) was added dropwise over 20 minutes. The reaction mixture was warmed to room temperature, refluxed for 7 hours, stirred at room temperature for 18 hours, and diluted with 0.5N potassium hydrogen sulfate (300 mL). The mixture was further diluted with $Et_2O$ (600 mL), 0.5N potassium hydrogen sulfate (200 mL), and water (200 mL) before the organic phase was separated. The organic layer was washed with water (200 mL) and brine (200 mL), dried ($Na_2SO_4$), filtered, and concentrated under reduced pressure. The crude product was distilled to afford 41 g (25% yield) of 2-(2-methoxyethyl)cyclohexanone.

Mass spectral analysis for $C_9H_{16}O_2$: $M^+H=157$.

$^1H$ NMR (CDCl$_3$): δ 3.35 (m, 2H), 3.25 (S, 3H), 2.45 (m, 1H), 2.20–2.35 (m, 2H), 1.30–2.15 (m, 8H).

Example 241 B) The title material of Example 241 A (10 g, 64 mmol) was combined with hydroxylamine hydrochloride (8.9 g, 128 mmol) and sodium acetate (13 g, 160 mmol) in a mixture of EtOH and water. This mixture was refluxed for 4 hours under an $N_2$ atmosphere. After the reaction was cooled to room temperature and stirred for an additional 18 hours, solvent was removed under reduced pressure. The residue was partitioned between EtOAc and water and the organic phase was washed with 100 mL of saturated sodium chloride, dried over sodium sulfate and concentrated of all solvent under reduced pressure. This provided 10.2 g (94% yield) of 2-(2-methoxyethyl)cyclohexanone oxime.

Mass spectral analysis for $C_9H_{17}N_1O_2$: $M^+H=172$.

Example 241 C) To a 250 mL round-bottomed flask was added (10 g, 71 mmol) of the oxime product of Example 241 B, 60 mL of acetone and 78 mL of 1N NaOH. This mixture was cooled to 0° C. and benzenesulfonyl chloride (10.5 g, 74 mmol) was added dropwise. The mixture was stirred at 25° C. for 18 hours. The reaction mixture was poured into water and this mixture was extracted with EtOAc. The organic layer was washed with brine, dried (MgSO$_4$), filtered, and concentrated to afford 4 g of yellow oily residue. The oily residue was separated by HPLC on silica gel with a mixture of hexanes and acetone (8/3, v/v) to yield 7-(2-methoxyethyl)caprolactam.

Mass spectral analysis for $C_9H_{17}N_1O_2$: $M^+H=171$.

$^1H$ NMR (D$_2$O): δ 3.38–3.50 (m, 3H), 3.20 (s, 3H), 2.42–2.52 (m, 1H), 2.10–2.20 (m, 1H), 1.18–1.82 (m, 8H).

Example 241 D) To a magnetically stirred slurry of Me$_3$O$^+$BF$_4^-$ in methylene chloride under nitrogen atmosphere was added the 7-(2-methoxylethyl)caprolactam product of Example 241 C. This mixture was stirred at room temperature for 3 days. The solvent was concentrated and ice-cold ammonia-saturated methanol was added and stirred for 12 hours. The reaction was concentrated and the residue was dissolved in water. The pH of this aqueous solution was adjusted to pH 3 and the 2-imino, 7-methoxyethylhexamethyleneimine product was purified on C-18 reversed phase HPLC.

Mass spectral analysis for $C_9H_{18}N_2O_1$: $M^+H=171$.

$^1H$ NMR (D$_2$O): δ 1.30–1.82 (m, 8H), 2.35–2.67 (m, 2H), 3.18 (s, 3H), 3.42 (t, 3H), 3.52 (m, 1H).

Example 241 E) The 2-imino, 7-methoxyethylhexamethyleneimine product of Example 241 D (1.8 g, 6.6 mmol) was dissolved in acetic acid (80 mL). Hydrobromic acid (48%, 8.9 M, 7 mL) was added and the reaction mixture was refluxed for 12 hours under an $N_2$ atmosphere. After removal of all solvent under reduced pressure, the residue was dissolved in water and purified by C-18 reversed phase HPLC to provide 1.0 g (70% yield) of 2-imino, 7-bromoethylhexamethyleneimine.

Mass spectral analysis for $C_8H_{15}Br_1N_2$: $M^+H=219$.

$^1H$ NMR (CDCl$_3$): 3.68–3.75 (m, 1H), 3.36–3.56 (m, 2H), 2.60–2.65 (m, 2H), 2.42–2.35 (m 8H).

Example 241) The product of Example 241 E (200 mg, 0.60 mmol) and N-aminomorpholine (300 mg, 3 mmol) were dissolved in 1 ml of N,N-dimethylformamide (DMF) and incubated at 25° C. for 7 days. The solvent was removed by rotary evaporation under reduced pressure. The residue was dissolved in 1 ml of water and the pH was adjusted to pH 3.0. The solution was purified by C-18 reverse phase chromatography to give the title product (40 mg).

Mass spectral analysis for $C_{12}H_{24}N_4O_1$: $M^+H=241$.

$^1H$ NMR (D$_2$O): δ 3.70–3.76 (t, 4H), 3.55–3.66 (m, 1H), 3.10–3.20 (t, 2H), 3.-2-3.08 (m, 4H), 2.40–2.65 (m, 2H), 1.30–1.90 (m, 8H).

EXAMPLE 242

N-[2-(hexahydro-7-imino-1H-azepin-2-yl)ethyl] pyridin-2-methanamine, tris(trifluoroacetate)salt

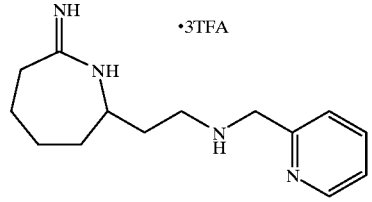

The product of Example 235 E (383 mg; 1 mmol) was reacted with 2-pyridinealdehyde in 10 mL DMF (containing 0.1 mL AcOH) in the presence of NaCNBH$_3$ for 16 hours at room temperature. The DMF was evaporated in vacuo and the residue was purified on preparative HPLC using AcN/ H$_2$O gradient (0–30% AcN in 30 minutes) affording 170 mg (55% yield) of the title product as an oil.

Mass spectral analysis for $C_{15}H_{22}N_4$: $M^+H$=247.

EXAMPLE 243

N-[2-(hexahydro-7-imino-1H-azepin-2-yl)ethyl]pyridin-3-methanamine, tris(trifluoroacetate)salt

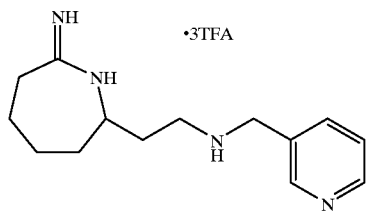

A sample of 3-pyridinealdehyde (107 mg; 1 mmol) was reacted with the product of Example 235 E as described in Example 242 to afford 175 mg (30% yield) of the title product as an oil.

Mass spectral analysis for $C_{15}H_{22}N_4$: $M^+H$=247.

EXAMPLE 244

N-[2-(hexahydro-7-imino-1H-azepin-2-yl)ethyl]pyridin-4-methanamine, tris(trifluoroacetate)salt

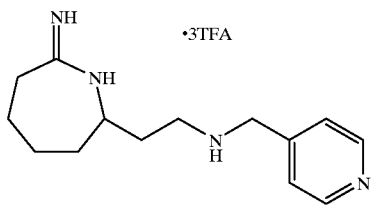

A sample of 4-pyridinealdehyde (107 mg; 1 mmol) was reacted with the product of Example 235 E by the method of Example 242 to afford 210 mg (36% yield) of the title product as an oil.

Mass spectral analysis for $C_{15}H_{22}N_4$: $M^+H$=247.

EXAMPLE 245

1-[2-(hexahydro-7-imino-1H-azepin-2-yl)ethyl]-1H-imidazole, bis(trifluoroacetate)salt

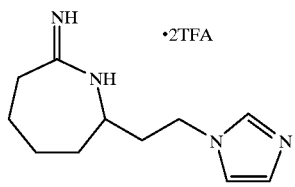

The product of Example 241 E (240 mg, 0.72 mmol) and imidazole (700 mg, 10.2 mmol) were dissolved in 0.5 ml of N,N-dimethylformamide (DMF) and incubated at –50° C. for 1 day. The solvent was removed by rotary evaporation under reduced pressure. The residue was dissolved in 1 ml of water and the pH was adjusted to pH 3.0. The solution was purified by C-18 reverse phase chromatography to give the title product (200 mg).

Mass spectral analysis for $C_{11}H_{18}N_4$: $M^+H$=207.

$^1$H NMR (D$_2$O): δ 8.62 (s, 1H), 7.60 (s, 1H), 7.55 (s, 1H), 4.20–4.25 (t, 1H), 3.20–3.40 (m, 2H), 2.40–2.65 (m, 2H), 1.30–2.20 (m, 8H).

EXAMPLE 246

1-[2-(hexahydro-7-imino-1H-azepin-2-yl)ethyl]-1H-1,2,4-triazole, bis(trifluoroacetate)salt

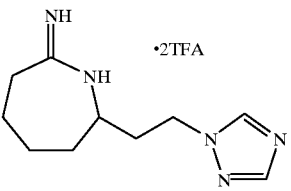

The product of Example 241 E and 1,2,4-triazole were reacted by the method of Example 245 to provide 65 mg of the title product.

Mass spectral analysis for $C_{10}H_{17}N_5$: $M^+H$=208.

$^1$H NMR (D$_2$O): δ 9.02 (s, 1H), 8.30 (s, 1H), 4.25–4.40(t, 2H0, 3.90–3.94 (t, 1H), 3.40–3.60 (m, 2H), 1.10–2.60 (m, 8H).

EXAMPLE 247

4-[2-(hexahydro-7-imino-1H-azepin-2-yl)ethyl]-4H-1,2,4-triazole, bis(trifluoroacetate)salt

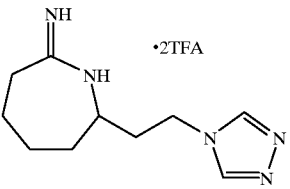

The product of Example 241 E and 1,2,4-triazole were reacted by the method of Example 245 to provide 32 mg of the title product.

Mass spectral analysis for $C_{10}H_{17}N_5$: $M^+H$=208

$^1$H NMR (D$_2$O): δ 9.02 (s, 2H), 4.20–4.26 (t, 2H), 3.50–3.62 (m, 2H), 3.00–3.05 (m, 1H), 1.20–2.60 (m, 8H).

EXAMPLE 248

1-[2-(hexahydro-7-imino-1H-azepin-2-yl)ethyl])-1H-tetrazole, trifluoroacetate salt

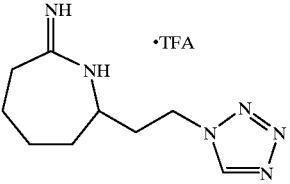

The product of Example 241 E and 1H-tetrazole were reacted by the method of Example 245 to provide 50 mg of the title product.

Mass spectral analysis for $C_9H_{16}N_6$: $M^+H$=209.

$^1$H NMR (D$_2$O): δ 8.60 (s, 1H), 4.72–4.80 (m, 3H), 3.40–3.47 (m, 2H), 1.20–2.60 (m, 8H).

EXAMPLE 249 methyl 1-[2-(hexahydro-7-imino-1H-azepin-2-yl)ethyl]pyrrolidine-2-carboxylate, bis(trifluoroacetate) salt

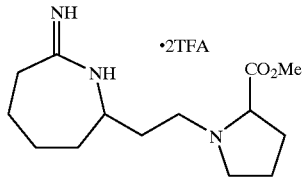

The product of Example 241 E and L-proline methyl ester hydrochloride were reacted by the method of Example 245 to provide 30 mg of the title product.

Mass spectral analysis for $C_{14}H_{25}N_3O_2$: $M^+H=268$.

$^1$H NMR ($D_2O$): δ 4.22–4.32 (t, 1H), 3.70 (s, 3H), 3.50–3.60 (m, 2H), 2.96–3.05 (m, 2H), 2.40–2.62(m, 2H), 1.15–2.05 (m, 12H).

EXAMPLE 250

4-[2-(hexahydro-7-imino-1H-azepin-2-yl)ethyl]morpholine, bis(trifluoroacetate)salt

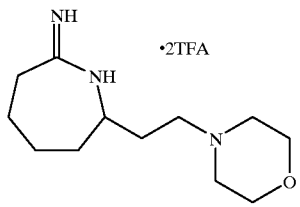

The product of Example 241 E and morpholine were reacted by the method of Example 245 to provide 12 mg of the title product.

Mass spectral analysis for $C_{12}H_{23}N_3O_1$: $M^+H=226$.

$^1$H NMR ($D_2O$): δ 3.95–4.02 (m, 2H), 3.52–3.72 (m, 3H), 3.35–3.45 (m, 2H), 3.00–3.19 (4H), 2.40–2.65(mu, 2H), 1.30–2.05 (m, 8H).

EXAMPLE 251

1-[2-(hexahydro-7-imino-1H-azepin-2-yl)ethyl]piperazine, bis(trifluoroacetate)salt

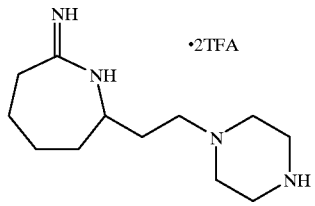

The product of Example 241 E and piperazine were reacted by the method of Example 245 to provide 370 mg of the title product.

Mass spectral analysis for $C_{12}H_{24}N_4$: $M^+H=225$.

$^1$H NMR ($D_2O$): δ 3.55–3.65 (m, 1H), 3.45–3.54 (m, 8H), 3.22–3.30 (t, 2H), 2.40–2.65(m, 2H), 1.30–2.10 (m, 8H).

EXAMPLE 252

1-[2-(hexahydro-7-imino-1H-azepin-2-yl)ethyl]-4-methylpiperazine, tris(trifluoroacetate)salt

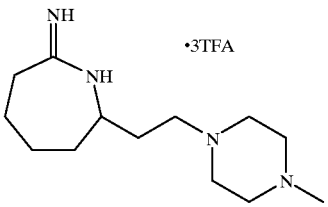

The product of Example 241 E and 1-methylpiperazine were reacted by the method of Example 245 to provide 60 mg of the title product.

Mass spectral analysis for $C_{13}H_{26}N_4$: $M^+H=239$.

EXAMPLE 253 hexahydro-7-(2-nitro-1-phenyl)-2H-azepin-2-imine, trifluoroacetate salt

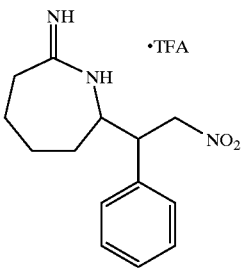

Example 253 A) A sample of 2-nitrostyrene (2 g; 13.4 mmol) in 5 mL AcN was cooled to −10° C. and 1-morpholinocyclohexene was added to the solution under $N_2$. The temperature was raised to 25° C. over a 1 hour period and the solvent was then removed in vacuo. The residue was dissolved in 15 mL MeOH and 5 mL of 1N HCl were added to the solution and it was refluxed gently for 15 minutes. The product precipitated, filtered and dried, yielding 1.6 g (54% yield) of 2-(2-Nitro-1-phenylethyl)cyclohexanone as a white solid.

Mass spectral analysis for $C_{14}H_{17}N_1O_3$: $M^+H=248$ and $M^+Li=254$.

Example 253 B) The 2-(2-Nitro-1-phenylethyl)cyclohexanone product of Example 253 A (2.47 g; 10 mmol) underwent a Beckmann Rearrangement when allowed to react with $H_2N$—$OSO_3H$ (1.24 g; 11 mmol) in 20 mL formic acid. Purification yielded 2.1 g (80% yield) 7-[(2-Nitro-1-phenyl)ethyl]caprolactam as a white solid.

Mass spectral analysis for $C_{14}H_{18}N_2O_3$: $M^+H=263$.

Example 253) The 7-[(2-Nitro-1-phenyl)ethyl] caprolactam product of Example 253 B was converted to the amidine via the method of Example 228 C to afford 0.85 g (78% yield) of the title compound as a white solid.

Mass spectral analysis for $C_{14}H_{19}N_3O_2$: $M^+H=262$.

$^1$H NMR ($D_2O$): δ 7.40–7.20 (m, 5H); 5.00–4.70 (m, 2H); 3.95–3.85 (m, 1H); 2.80–2.45 (m, 2H); 1.85–1.05 (m, 6H).

EXAMPLE 254

N-[2-(hexahydro-7-imino-1H-azepin-2-yl)-2-phenylethyl]guanidine, bis(trifluoroacetate)salt

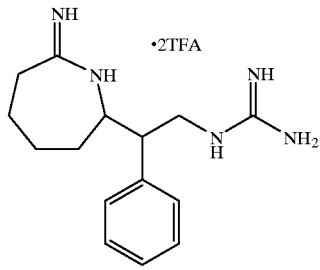

The product of Example 205 (459 mg; 1 mmol) was reacted with formamidine sulfonic acid (124 mg; 1 mmol) in 15 mL MeOH in the presence of N,N-diisopropylethylamine (DIPEA) (0.38 mL, 2 mmol) for 18 hours. The MeOH solvent was evaporated and the residue purified on preparative HPLC using AcN/H$_2$O gradient (0–30% AcN in 30 minutes), affording 380 mg (75% yield) of the title product as a white solid.

Mass spectral analysis for $C_{15}H_{23}N_5$: M$^+$H=274.

EXAMPLE 255 hexahydro-N-(hexahydro-1H-azepin-2-ylidene)-7-imino-β-phenyl-1H-azepine-2-ethanamine, bis(trifluoroacetate)salt

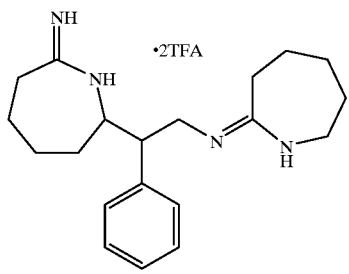

The product of Example 205 was allowed to react with 1-aza-2-methoxy-1-cycloheptene by the method of Example 236 to afford 320 mg (58% yield) of the title product as a white solid material.

Mass spectral analysis for $C_{20}H_{30}N_4$: M$^+$H=327.

$^1$H NMR (D$_2$O): 7.40–7.10 (m, 5H); 3.95–3.85 (t, J=7 Hz, 1H); 3.60–3.35 (m, 2H); 3.20–3.00 (m, 3H); 2.80–2.60 (m, 1H); 2.55–2.40 (m, 1H); 2.35–2.10 (m, 2H); 1.85–1.00 (m, 12H).

EXAMPLE 256 hexahydro-7-(2-nitro-1-phenylpropyl)-2H-azepin-2-imine, trifluoroacetate salt

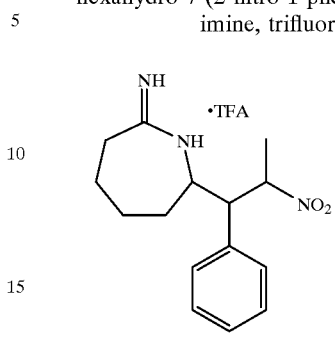

A sample of 2-methyl-2-nitrostyrene was reacted with 1-morpholinocyclohexene by the method of Example 253 A and the resulting intermediate was converted by the subsequent procedures of Example 253 to 600 mg (68% yield) of the title product as a white solid.

Mass spectral analysis for $C_{15}H_{21}N_3O_2$: M$^+$H=276.

$^1$H NMR (D$_2$O): δ 7.40–7.05 (m, 5H); 4.22–4.10, 4.00–3.90, 3.80–3.70, 3.50–3.30 (m, 2H); 2.80–2.45 (m, 2H); 1.90–1.10 (m, 9H).

EXAMPLE 257 hexahydro-7-imino-α-methyl-β-phenyl-1H-azepine-2-ethanamine, bis(trifluoroacetate)salt

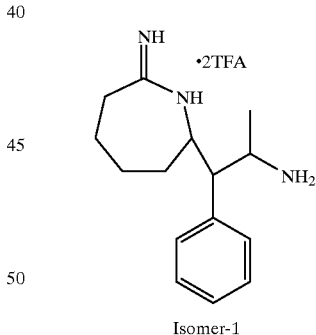

Isomer-1

The product of Example 256 (600 mg; 2.2 mmol) was reduced via catalytic hydrogenation in 25 mL EtOH. The crude product was purified as described in Example 205 to afford two diastereomers. The first eluting peak #1 afforded 135 mg (31% yield) of the title Isomer-1 as a white solid.

Mass spectral analysis for $C_{15}H_{23}N_3$: M$^+$H=246.

$^1$H NMR (D$_2$O): δ 7.40–7.17 (m, 5H); 4.10–4.00 (m, 1H); 3.85–3.70 (m, 1H); 3.07–2.96 (m, 1H); 2.80–2.65 (m, 1H); 2.50–2.35 (m, 1H); 1.90–1.70 (m, 3H); 1.60–1.00 (m, 6H).

EXAMPLE 258 hexahydro-7-imino-α-methyl-β-phenyl-1H-azepine-2-ethanamine, bis(trifluoroacetate)salt

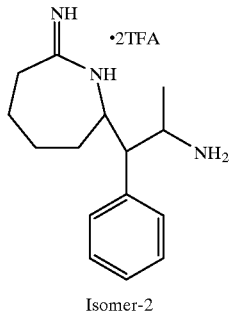

Isomer-2

The product of Example 256 (600 mg; 2.2 mmol) was reduced via catalytic hydrogenation in 25 mL EtOH. The crude product was purified as described in Example 257 to afford two diastereomers. The second eluting peak #2 afforded 120 mg (22% yield) of the title Isomer-2 as a white solid.

Mass spectral analysis for $C_{15}H_{23}N_3$: $M^+H=246$.

$^1H$ NMR ($D_2O$): δ 7.40–7.15 (m, 5H); 4.10–4.00 (m, 1H); 3.85–3.70 (m, 1H); 3.30–3.20 (m, 1H); 2.85–2.70 (m, 1H); 2.60–2.45 (m, 1H); 1.90–1.55 (m, 2H); 1.50–1.30 (m, 3H); 1.30–1.05 (m, 4H).

EXAMPLE 259 hexahydro-7-imino-α-methyl-β-cyclohexyl-1H-azepine-2-ethanamine, bis(trifluoroacetate)salt

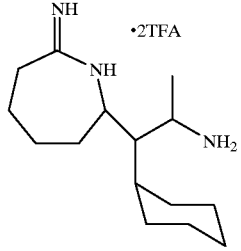

The product of Example 253 (240 mg; 0.88 mmol) was hydrogenated in 20 mL EtOH (5% HCl) for two days in the presence of 300 mg $PtO_2$. Work up and purification afforded 110 mg (53% yield) of the title product as a white solid.

Mass spectral analysis for $C_{14}H_{27}N_3$: $M^+H$ 238.

EXAMPLE 260

7-[1-(1,3-benzodioxol-5-yl)-2-nitropropyl]hexahydro-2H-azepin-2-imine, trifluoroacetate salt

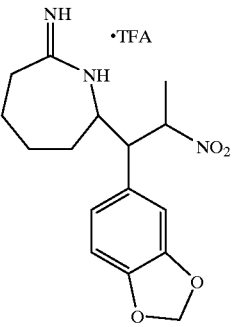

A sample of 3,4-dioxomethylene-1-nitrostyrene (3.86 g; 20 mmol) was reacted with 1-morpholino-1-cyclohexene in 25 mL AcN by the method of Example 253 A and the resulting intermediate was converted by the subsequent procedures of Example 253 to 1.25 g (74% yield) of the title product as a white solid.

Mass spectral analysis for $C_{15}H_{19}N_3O_4$: $M^+H=306$.

$^1H$ NMR ($D_2O$): 6.80–6.65 (m, 3H); 5.85 (s, 2H); 4.95–4.70 (m, 2H); 3.90–3.80 (M, 1H); 3.70–3.60 (m, 1H); 2.70–2.45 (m, 2H); 1.80–1.10 (m, 6H).

EXAMPLE 261

β-(1,3-benzodioxol-5-yl)hexahydro-7-imino-α-methyl-1H-azepine-2-ethanamine, bis(trifluoroacetate)salt

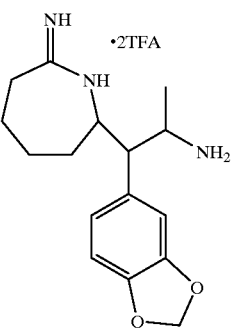

The product of Example 260 (600 mg; 1.43 mmol) was reduced and purified as described in Example 205. Purification of the crude product afforded 420 mg (58% yield) of the title material as a white solid.

Mass spectral analysis for $C_{15}H_{21}N_3O_2$: $M^+H=276$.

$^1H$ NMR ($D_2O$): δ 6.85–0.70 (m, 3H); 5.90 (s,2H); 3.82–3.70 (m, 1H); 3.42–3.30 (m, 1H); 3.20–3.00 (m, 2H); 2.80–2.43 (m, 2H); 1.85–1.05 (m, 6H).

EXAMPLE 262 hexahydro-7-[2-nitro-1-(2-thienyl)ethyl]-2H-azepine, trifluoroacetate salt

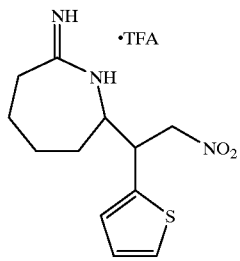

A sample of 2-(2-nitrovinyl)thiophene (3.1 g; 20 mmol) was reacted with 1-morpholino-1-cyclohexene in 20 mL AcN by the method of Example 253 A and the resulting intermediate was converted by the subsequent procedures of Example 253 to 1.1 g (47% yield) of the title product as a white solid.

Mass spectral analysis for $C_{12}H_{17}N_3O_2S$: $M^+H=268$.

$^1$H NMR (CDCl$_3$): δ 10.00 (br, 1H); 9.85 (br, 1H); 8.45 (br, 1H); 7.35–6.95 (m, 3H); 5.20–5.00 (m, 1H); 4.90–4.75 (m, 1H); 4.30–4.10 (m, 1H); 3.70–3.50 (m, 1H); 2.70–2.50 (m, 1H); 2.40–2.25 (m, 1H); 2.10–1.90 (m, 2H); 1.85–1.25 (m, 4H).

EXAMPLE 263 hexahydro-7-imino-β-(2-thienyl)-1H-azepine-2-ethanamine, bis(trifluoroacetate)salt

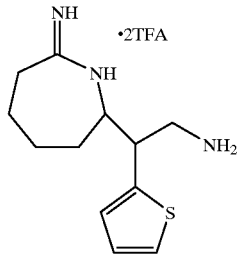

The product of Example 262 (600 mg; 1.57 mmol) was reduced and purified as described in Example 205 to afford 390 mg (73% yield) of the title product as a white solid.

Mass spectral analysis for $C_{12}H_{19}N_3S$: $M^+H=238$.

$^1$H NMR (D$_2$O): δ 7.45–7.32 (m, 1H); 7.10–7.05 (m, 1H); 7.05–6.95 (m, 1H); 3.95–3.40 (m, 4H); 2.70–2.20 (m, 2H); 2.00–1.20 m, 6H).

EXAMPLE 264 hexahydro-7-imino-β-(3-thienyl)-1H-azepine-2-ethanamine, bis(trifluoroacetate)salt

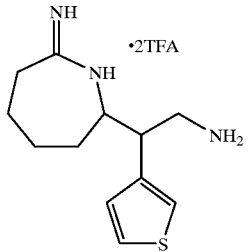

A sample of 3-(2-nitrovinyl)thiophene (3.1 g; 20 mmol) was reacted with 1-morpholino-1-cyclohexene in 10 mL AcN by the method of Example 253 A and the resulting intermediate was converted by the subsequent procedures of Example 253 and Examples 205 to afford 380 mg (78% yield) of the title product as a white solid.

Mass spectral analysis for $C_{12}H_{19}N_3S$: $M^+H=238$.

$^1$H NMR (D$_2$O): 7.50–7.40 (m, 1H); 7.40–7.30 (m, 1H); 7.05–7.00 (m, 1H); 3.90–3.75 (m, 1H); 3.60–3.50 (m, 3H); 2.75–2.40 (m, 2H); 1.850–1.60 (m, 2H); 1.60–1.30 (m, 3H); 1.30–1.05 (m, 1H).

EXAMPLE 265 hexahydro-7-imino-β-(2-furanyl)-1H-azepine-2-ethanamine, bis(trifluoroacetate)salt

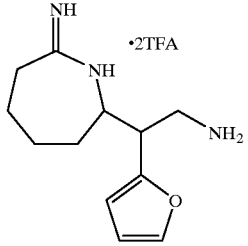

2-(2-nitrovinyl)furan (1.39 g; 10 mmol) was reacted with 1-morpholino-1-cyclohexene in 25 mL AcN by the method of Example 253 A and the resulting intermediate was converted by the subsequent procedures of Example 253 and Examples 205 to 140 mg (48% yield) of the title product as a white solid.

Mass spectral analysis for $C_{12}H_{19}N_3O_1$: $M^+H=222$.

$^1$H NMR (D$_2$O): δ 7.42 (s, 1H); 6.45–6.30 (m, 2H); 3.90–3.80 (m, 1H); 3.40–3.22 (m, 3H); 2.70–2.40 (m, 2H); 1.90–1.70 (m, 2H); 1.60–1.10 (m, 4H).

EXAMPLE 266 hexahydro-N-(hexahydro-1H-azepin-2-ylidene)-7-imino-β-(2-thienyl)-1H-azepine-2-ethanamine, bis(trifluoroacetate)salt

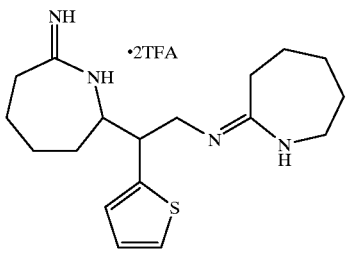

The product of Example 263 (23 mg; 0.5 mmol) was reacted with 1-aza-2-methoxy-1-cycloheptene (127 mg; 0.5 mmol) and the product was isolated as described in Example 236 to afford 225 mg (80% yield) of the title product as a white solid.

Mass spectral analysis for $C_{18}H_{28}N_4S$: $M^+H=333$.

$^1$H NMR ($D_2O$): 7.35–7.25 (m, 1H); 7.00–6.90 (m, 2H); 4.25–3.75 (m, 2H); 3.60–3.40 (m, 1H); 3.35–3.15 (m, 2H); 2.80–2.60 (m, 1H); 2.60–2.05 (m, 4H); 1.90–1.10 (m, 12H).

EXAMPLE 267 hexahydro-7-imino-N-(2-pyrrolidinylidene)-β-(2-thienyl)-1H-azepine-2-ethanamine, bis(trifluoroacetate)salt

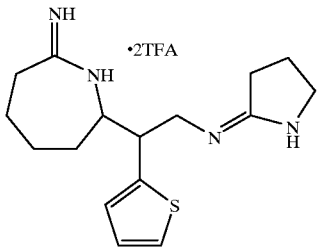

The product of Example 263 (100 mg; 0.21 mmol) was reacted with 2-methoxy-pyrrolidine (99 mg; 1 mmol) as described in Example 236 to afford 80 mg (71% yield) of the title product as a white solid.

Mass spectral analysis for $C_{16}H_{24}N_4S$: $M^+H=305$.

EXAMPLE 268 hexahydro-7-[1-(1H-indol-3-yl)-2-nitroethyl]-2H-azepin-2-imine, trifluoroacetate salt

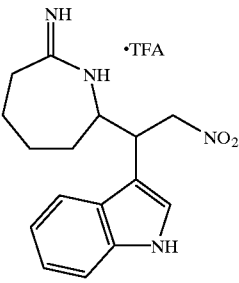

3-(2-nitrovinyl)indole (500 mg; 2.6 mmol) was reacted with 1-morpholino-1-cyclohexene (0.5 g; 3 mmol) in 5 mL AcN by the method of Example 253 A and the resulting intermediate was converted by the subsequent procedures of Example 253 to afford 255 mg (65% yield) of the title product as a light yellow solid.

Mass spectral analysis for $C_{16}H_{20}N_4O_2$: $M^+H=301$.

$^1$H NMR ($D_2O$): δ 7.60 (d, J=8 Hz, 1H); 7.40 (d, J=8 Hz, 1H); 7.22 (s, 1H); 7.18–7.00 (m, 2H); 5.00–4.80 (m, 2H); 4.08–3.90 (m, 2H); 2.70–2.40 (m, 2H); 1.80–1.15 (m, 6H).

EXAMPLE 269 hexahydro-7-imino-β-(1H-indol-3-yl)-1H-azepine-2-ethanamine, bis(trifluoroacetate)salt

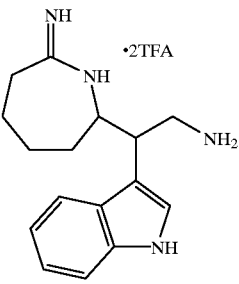

A sample of Example 208 (255 mg; 0.62 mmol) was reduced and purified as described in Example 205. Purification afforded 120 mg (52% yield) of the title product as a white solid.

Mass spectral analysis for $C_{16}H_{22}N_4$: $M^+H=271$.

$^1$H NMR ($D_2O$): δ 7.60 (d, J=8 Hz, 1H); 7.45 (d, J=8 Hz, 1H); 7.33 (s, 1H); 7.22–7.00 (m, 2H); 4.10–3.95 (m, 1H); 3.60–3.30 (m, 2H); 3.20–3.00 (m, 1H); 2.80–2.35 (m, 2H); 2.00–1.00 (m, 6H).

EXAMPLE 270 hexahydro-7-[(2-nitrophenyl)methyl]-2H-azepin-2-imine, monohydrochloride

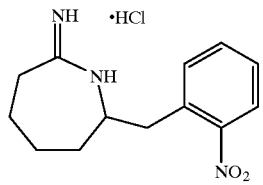

Example 270 A) Commercially available (Shanghai Institute of Organic Chemistry) 7-(2-nitrobenzyl) caprolactam (0.50 g, 2.01 mmol) was dissolved in $CH_2Cl_2$ (25 mL, 0.1 M solution) and treated with triethyloxonium tetrafluoroborate (0.57 g, 3.02 mmol) by the method of Example 3 to give 0.68 g of the crude ethyl iminoether product.

Example 270) The product of Example 270 A was dissolved in methanol (25 mL, 0.1 M solution) and treated with ammonium chloride (0.20 g, 3.73 mmol) by the method of Example 4 to give 0.36 g title material.

Elemental analysis: $C_{13}H_{17}N_3O_2$.1.05 HCl.0.50 $H_2O$ (MW = 294.59).

|  | C | H | N | Cl |
|---|---|---|---|---|
| Calculated: | 53.00 | 6.52 | 14.26 | 12.64 |
| Found: | 53.22 | 6.45 | 13.94 | 12.61 |

EXAMPLE 271

2-[(hexahydro-7-imino-1H-azepin-2-yl)methyl]benzenamine, dihydrochloride

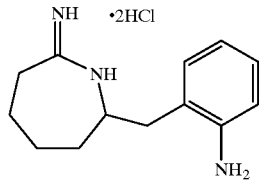

The product of Example 270 (0.150 g, 0.59 mmol) was dissolved in ethanol and treated with 5% Palladium on Carbon under 5 psi of Hydrogen to give the title product (141 mg, 0.46 mmol).

Elemental analysis: $C_{13}H_{19}N_3$.2.00 HCl.1.00 $H_2O$ (MW = 308.25).

|  | C | H | N | Cl |
|---|---|---|---|---|
| Calculated: | 50.65 | 7.52 | 13.63 | 23.00 |
| Found: | 50.99 | 7.47 | 13.44 | 22.90 |

EXAMPLE 272

2-[(hexahydro-7-imino-1H-azepin-2-yl)methyl]cyclohexanamine, dihydrochloride

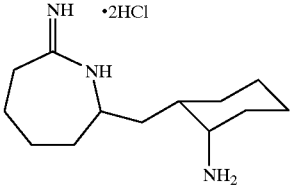

The product of Example 270 (0.262 g, 0.9 mmol) was dissolved in ethanol, treated with 5% Rhodium on Carbon under 60 psi of Hydrogen and warmed to 60° C. to give the title product (66 mg, 0.22 mmol).

Elemental analysis: $C_{13}H_{25}N_3$.2.00 HCl.1.00 $H_2O$ (MW = 308.25).

|  | C | H | N | Cl |
|---|---|---|---|---|
| Calculated: | 46.28 | 8.64 | 12.12 | 24.16 |
| Found: | 46.25 | 8.24 | 12.30 | 24.25 |

EXAMPLE 273 hexahydro-7-[(4-nitrophenyl)methyl]-2H-azepin-2-imine, monohydrochloride

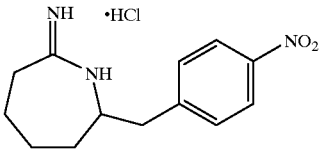

Example 273 A) Commercially available (Shanghai Institute of Organic Chemistry) 7-(p-nitrobenzyl)caprolactam (1.1 g, 4.6 mmol) dissolved in 50 mL of $CH_2Cl_2$ was treated with $Me_3O^+BF_4^-$ (0.7 g, 4.6 mmol) by the method of Example 3 to give 850 mg of its imino ether.

Example 273) The imino ether product of Example 273 A (0.83 g, 3.2 mmol) in 50 mL of MeOH was reacted with $NH_4Cl$ (0.15 g, 2.9 mmol) by the method of Example 4 to give 0.77 g (87%) of the title material.

HRMS (EI) calcd for $C_{13}H_{17}N_3O_2$ m/e 247.132, found m/e 247.132

Elemental analysis: $C_{13}H_{17}N_3O_2$.1.2 HCl.0.9 $H_2O$ (MW = 307.26).

|  | C | H | N | Cl |
|---|---|---|---|---|
| Calculated: | 50.82 | 6.56 | 13.68 | 13.85 |
| Found: | 50.54 | 6.33 | 13.85 | 14.14 |

EXAMPLE 274

4-[(hexahydro-7-imino-1H-azepin-2-yl)methyl]benzenamine, dihydrochloride

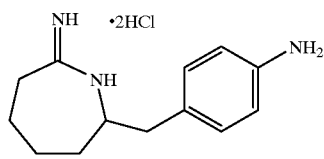

The product from Example 273 (0.55 g, 1.8 mmol) in 30 mL of EtOH was reduced with 5% Palladium on carbon under 5 psi of hydrogen. Solvent removal in vacuo followed by lyophilization in water gave 0.46 g (97%) of the title material.

HRMS (EI) calcd for $C_{13}H_{19}N_3$ m/e 217.158, found m/e 217.158

Elemental analysis: $C_{13}H_{19}N_3 \cdot 1.1$ HCl$\cdot 0.4$ H$_2$O (MW = 266.45).

|  | C | H | N | Cl |
|---|---|---|---|---|
| Calculated: | 58.60 | 7.93 | 15.77 | 15.30 |
| Found: | 58.46 | 7.54 | 15.72 | 15.17 |

EXAMPLE 275 hexahydro-7-[[4-(trifluoromethyl)phenyl]methyl]-2H-azepin-2-imine, monohydrochloride

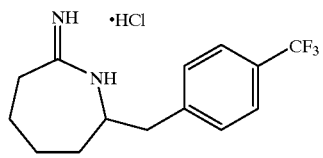

Example 275 A) Commercially available (Shanghai institute of Organic Chemistry) 7-(p-trifluoromethylbenzyl) caprolactam (0.9 g, 3.4 mmol) dissolved in 50 mL of CH$_2$Cl$_2$ was treated with Me$_3$O$^+$BF$_4^-$ (0.5 g, 3.4 mmol) by the method of Example 3 to give 835 mg of its imino ether.

Example 275) The imino ether product of Example 27, A (0.78 g, 2.7 mmol) in 50 mL of MeOH was reacted with NH$_4$Cl (0.13 g, 2.5 mmol) by the method of Example 4 to give 0.45 g (56%) of the title material.

HRMS (EI) calcd for $C_{14}H_{17}N_2F_3$ m/e 270.139, found m/e 270.137

Elemental analysis: $C_{14}H_{17}N_2F_3 \cdot 1.0$ HCl$\cdot 0.75$ H$_2$O (MW = 320.27).

|  | C | H | N | Cl |
|---|---|---|---|---|
| Calculated: | 52.50 | 6.14 | 8.75 | 11.56 |
| Found: | 52.31 | 6.18 | 8.71 | 11.36 |

EXAMPLE 276

7-[(4-fluorophenyl)methyl]hexahydro-2H-azepin-2-imine, monohydrochloride

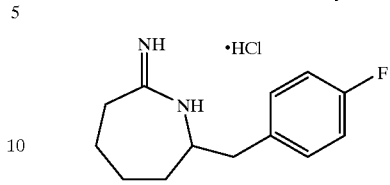

Example 276 A) Commercially available (Shanghai institute of Organic Chemistry) 7-(p-fluorobenzyl) caprolactam (1.3 g, 6.0 mmol) dissolved in 50 mL of CH$_2$Cl$_2$ was treated with Me$_3$O$^+$BF$_4^-$ (1.2 g, 7.8 mmol) by the method of Example 3 to give 1.3 g of its imino ether.

Example 276) The imino ether product of Example 276 A (1.2 g, 5.1 mmol) in 25 mL of MeOH was reacted with NH$_4$Cl (0.26 g, 4.9 mmol) by the method of Example 4 to give 1.1 g of the title material.

Elemental analysis: $C_{13}H_{17}N_2F \cdot 1.0$ HCl$\cdot 0.75$ H$_2$O (MW = 270.26).

|  | C | H | N | Cl |
|---|---|---|---|---|
| Calculated: | 57.77 | 7.27 | 10.37 | 13.12 |
| Found: | 57.80 | 7.39 | 10.34 | 13.43 |

EXAMPLE 277 hexahydro-7-[[3-(trifluoromethyl)phenyl]methyl]-2H-azepin-2-imine, monohydrochloride

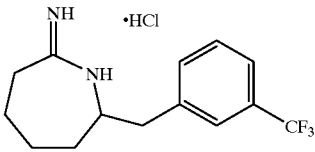

Example 277A) Commercially available 7-(3-trifluoromethylphenylmethyl) caprolactam (Shanghai Institute of Organic Chemistry, 1.12 g, 3.5 mmol) was treated with trimethyloxonium tetrafluoroborate (1.11 g, 5.3 mmol) in CH$_2$Cl$_2$ (10 mL) by the method of Example 3, to yield its iminoether derivative (1.23 g) as a thick oil.

Example 277) A solution of the imino ether product of Example 277A (1.20 g, 3.5 mmol) in MeOH (12 mL) was reacted with ammonium chloride (0.17 g, 3.1 mmol) by the method of Example 5. The residue after removal of solvent was subjected to lyophilization in water to generate the title material (1.27 g).

Elemental analysis: $C_{14}H_{17}N_2F_3 \cdot 1$ HCl$\cdot 0.55$ H$_2$O (MW = 316.36)

|  | C | H | N | Cl |
|---|---|---|---|---|
| Calculated: | 53.10 | 6.08 | 8.85 | 11.20 |
| Found: | 53.18 | 6.00 | 8.46 | 11.33 |

EXAMPLE 278

7-[(2,4-difluorophenyl)methyl]hexahydro-2H-azepin-2-imine, monohydrochloride

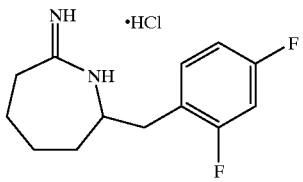

Example 278 A) 7-(2'-4'-difluorobenzyl)caprolactam (Shanghai Institute of Organic Chemistry, 1.24 g, 5.2 mmol) was dissolved in $CH_2Cl_2$ (25 mL) under an argon atmosphere. To this was added trimethyloxonium tetrafluoroborate ($Me_3O^+BF_4^-$) and the reaction was carried out by the method of Example 3. The residue was purified by flash column chromatography (80% hexane/acetone) to generate 950 mg (72%) of clean imino ether.

Example 278 B) The imino ether product of Example 278 A (910 mg, 3.6 mmol) and $NH_4Cl$ in MeOH (10 mL) were reacted by the method of Example 5. After removing all solvent in vacuo, the residue was dissolved in $H_2O$ (40 mL) and washed once with EtOAc (20 mL). The aqueous layer was then lyophilized twice from water to give the title compound.

Elemental analysis: $C_{13}H_{16}N_2F_2.1$ HCl.0.5 $H_2O$ (MW = 283.75).

|  | C | H | N |
|---|---|---|---|
| Calculated: | 55.03 | 6.39 | 9.87 |
| Found: | 55.08 | 6.57 | 9.66 |

EXAMPLE 279

7-[(2,6-dichlorophenyl)methyl]hexahydro-2H-azepin-2-imine, monohydrochloride

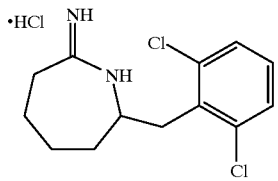

Example 279 A) Commercially available (Shanghai Institute of Organic Chemistry) 7-(2,6-dichlorobenzyl) caprolactam (0.50 g, 1.84 mmol) was dissolved in $CH_2Cl_2$ (25 mL, 0.1 M solution) and treated with triethyloxonium tetrafluoroborate (0.52 g, 2.76 mmol) by the method of Example 3 to give 0.56 g of the crude ethyl iminoether product.

Example 279 B) The ethyl iminoether product of Example 279 A was dissolved in methanol (25 mL, 0.1 M solution) and treated with ammonium chloride (0.150 g, 2.79 mmol) by the method of Example 4 to give 0.58 g of the title material.

Elemental analysis: $C_{13}H_{16}N_2Cl_2.0.9$ HCl.0.75 $H_2O$ (MW = 317.52).

|  | C | H | N | Cl |
|---|---|---|---|---|
| Calculated: | 49.18 | 5.84 | 8.82 | 32.38 |
| Found: | 49.47 | 5.64 | 8.57 | 32.32 |

EXAMPLE 280 hexahydro-7-[3-(2-thienyl)-2-propenyl)-2H-azepin-2-imine, monohydrochloride

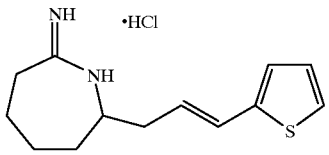

Example 280 A) Palladium acetate (0.063 g, 0.23 mmol) and tri-o-tolylphosphine (0.170 g, 0.56 mmol) were combined in a 250 mL round bottom flask under nitrogen.

To this was added triethylamine (1.62 g, 16 mmol) and 2-bromothiophene (2.55 g, 15.6 mmol). After this mixture was stirred for 5 min., the Isomer B title product of Example 18 (7-allylcaprolactam, 2.17 g, 14.2 mmol) was added along with 5 mL of Acetonitrile. The reaction mixture was refluxed for 2 h. before 10 mL of acetonitrile was added and the mixture was refluxed overnight. The cooled mixture was partition between 75 mL of saturated $NaHCO_3$ and 100 mL of EtOAc and then chromatographed to produce 1.7 g (67 mmol) of product.

Example 280 B) The product of Example 280 A (1.0 g, 4.26 mmol) was dissolved in 50 mL of $CH_2Cl_2$ and treated with trimethyloxonium tetrafluoroborate (0.82 g, 5.5 mmol) by the method of Example 3. This produced 1.11 g of the methyl imino ether.

Example 280) The methyl imino ether product of Example 280 B (0.88 g, 3.53 mmol) was treated with ammonium chloride (0.17 g, 3.18 mmol) and methanol (50 mL, 0.05 M solution) by the method of Example 4 to produce 0.68 g (71%) of title product.

Elemental analysis: $C_{13}H_{18}N_2S.1.1$ HCl.0.4 $H_2O.0.3$ $NH_4Cl$ (MW = 297.72).

|  | C | H | N | Cl |
|---|---|---|---|---|
| Calculated: | 52.45 | 7.14 | 10.82 | 16.67 |
| Found: | 52.21 | 7.02 | 11.10 | 16.40 |

EXAMPLE 281 methyl α-[[(3,4-dihydro-2H-pyrrol-5-yl)amino]methyl]hexahydro-7-imino-1H-azepine-2-acetate, bis(trifluoroacetate)salt

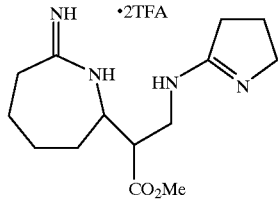

Example 281 A) Methyl, 2-iodo-3-nitropropionate (prepared as in Org. Synth. VI, 799 (1988)) is allowed to react with the morpholine enamine of cyclohexanone to afford after mild hydrolysis, 2-[1-methoxycarbonyl-2-nitroethyl]cyclohexanone.

Example 281 B) The 2-[1-methoxycarbonyl-2-nitroethyl] cyclohexanone product of Example 281 A is converted via a Beckmann Rearrangement to a substituted caprolactam. Isolation and purification affords the 7-[1-methoxycarbonyl-2-nitroethyl]caprolactam.

Example 281 C) The 7-[1-methoxycarbonyl-2-nitroethyl] caprolactam product of Example 281 B is converted to the corresponding amidine via the method of Example 228c to afford 7-[1-methoxycarbonyl-2-nitroethyl]homoiminopiperidine.

Example 281 D) The 7-[1-methoxycarbonyl-2-nitroethyl) homoiminopiperidine product of Example 281 C is reduced via catalytic hydrogenation as in the method of Example 205 to afford 7-[1-methoxycarbonyl-2-aminoethyl)homoiminopiperidine.

Example 281) The 7-[1-methoxycarbonyl-2-aminoethyl] homoiminopiperidine product of Example 281 D is allowed to react with 2-methoxypyrrolidine by the method of example 236 to afford the title product.

EXAMPLE 282

4,5-dihydro-5-[(hexahydro-7-imino-1H-azepin-2-yl)methyl]isoxazole-3-carboxylic acid, monohydrochloride

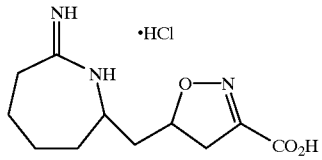

A solution of 0.2 g (0.00048 mol) of the product of Example 283 in 18.5 mL of water, 25 mL of acetone and 7.5 mL of conc. HCl was heated at reflux for 44 hours. After all solvent was removed in vacuo, the residue was dissolved in water and lyophilized to afford the title product as a yellow foam.

$^1$H NMR (D$_2$O): δ 1.25–2.0 (m, 8H), 2.4–2.7 (m, 2H), 2.85 (m, 1H), 3.3 (m, 1H), 3.7 (m, 1H), 4.9 (m, 1H).

Mass spectral analysis for $C_{11}H_{17}N_3O_3$: M$^+$H=240.

EXAMPLE 283 ethyl 4,5-dihydro-5-[(hexahydro-7-imino-1H-azepin-2-yl)methyl]isoxazole-3-carboxylate, trifluoroacetate salt

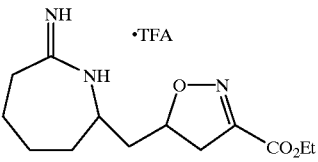

Example 283 A) The Isomer B title product of Example 18 (7-allyl caprolactam, 7 g, 0.046 mol) was reacted with 13.9 g (0.092 mol) of ethyl chlorooximidoacetate in 700 mL of toluene. This mixture was stirred at reflux for 18 hours. The reaction mixture was allowed to cool and then concentrated to afford 13 g of a brown oil. Chromatography (silica gel, EtOAc) afforded 10.5 g of 7-[[4,5-dihydro-3-(ethoxycarbonyl)isoxazol-5-yl]methyl]hexahydro-1H-azepin-2-one as an off-white solid.

Mass spectral analysis for $C_{13}H_{20}N_2O_4$: M$^+$H=269

Example 283) To a magnetically stirred slurry of 1.16 g (0.0078 mol) of Me$_3$O$^+$BF$_4^-$ and 20 mL of CH$_2$Cl$_2$ under nitrogen (N$_2$) was added 2 g (0.0075 mol) of the 7-[[4,5-dihydro-3-(ethoxycarbonyl)isoxazol-5-yl]methyl]hexahydro-1H-azepin-2-one product of Example 283 A. This mixture was stirred at room temperature for 18 hours before it was diluted with 30 mL of EtOAc and partitioned between the organic layer and 40 mL of saturated NaHCO$_3$. The organic phase was separated, dried (MgSO$_4$), filtered, and concentrated under reduced pressure to provide 1.0 g of the iminoether as a yellow oil. The iminoether (1.6 g, 0.0057 mol) and 0.3 g (0.0057 mol) of ammonium chloride (NH$_4$Cl) were refluxed in 25 mL of methanol (MeOH) under a nitrogen atmosphere for 22 hours. After cooling the reaction to room temperature, it was filtered and partitioned between 25 mL of water and 7 mL of EtOAc. The aqueous phase was washed with a 15 mL portion of EtOAc before lyophilization to provide 1.3 g of a dark foam. Chromatographic purification of this material on a preparatory C-18 column eluting with acetonitrile/water afforded after lyophilization, 1.1 g of the title compound as a dark oil.

Mass spectral analysis for $C_{13}H_{21}N_3O_3$: M$^+$H=268.

Further chromatographic separations (C-18, acetonitrile/water) were successful in separating two diastereomers.

(slow eluting diastereomer)

$^1$H NMR (D$_2$O): δ 1.15 (t, 3H), 1.25–2.0 (m, 8H), 2.4–2.7 (m, 2H), 2.85 (m, 1H), 3.3 (m, 1H), 3.7 (m, 1H), 4.2 (q, 2H), 4.9 (m, 1H).

(fast eluting diastereomer)

$^1$H NMR (D$_2$O): δ 1.15 (t, 3H), 1.25–2.0 (m, 8H), 2.4–2.7 (m, 2H), 2.85 (m, 1H), 3.3 (m, 1H), 3.7 (m, 1H), 4.2 (q, 2H), 4.95 (m, 1H).

EXAMPLE 284

4,5-dihydro-5-[(hexahydro-7-imino-1H-azepin-2-yl)methyl]isoxazole-3-carboxamide, trifluoroacetate salt

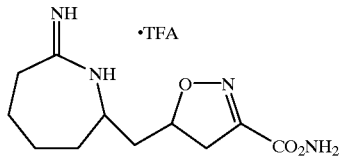

A solution of 0.1 g (0.00024 mol) of the product of Example 283 in 10 mL of methanol (saturated with anhydrous ammonia) was capped and heated at 60° C. for 18 hours. After all solvent was removed in vacuo, the residue was dissolved in water and lyophilized to afford the title product as a yellow foam.

$^1$H NMR (D$_2$O): δ 1.25–2.0 (m, 8H), 2.4–2.7 (m, 2H), 2.85 (m, 1H), 3.3 (m, 1H), 3.7 (m, 1H), 4.9 (m, 1H).

Mass spectral analysis for $C_{11}H_{18}N_4O_1$: M$^+$H=239.

EXAMPLE 285

3-amino-5-[(hexahydro-7-imino-1H-azepine-2-yl)methyl]-tetrahydrofuran-2-one, bis(trifluoroacetate) salt

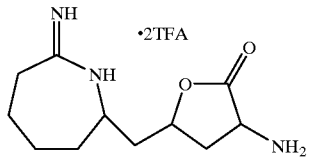

To a solution of 0.1 g (0.00024 mol) of the product of Example 283 (prior to diastereomer separation) in 10 mL of methanol was added 0.02 g palladium/carbon (10%). This mixture was pressurized under 50 psi H$_2$ and stirred for 3 days at 25° C. Filtration and concentrated gave a colorless oil. Chromatography (C-18, acetonitrile/water) afforded 30 mg of the title compound as a white solid.

$^1$H NMR (D$_2$O): δ 1.2–2.1(m, 9H), 2.45 (m, 1H), 2.6 (m, 1H), 32.8 (m, 1H), 3.75 (m, 2H), 4.4 (m, 1H).

Mass spectral analysis for $C_{11}H_{19}N_3O_2$: M$^+$H=226.

EXAMPLE 286

7-[2-(2,2-dimethyldioxolan-4-yl)ethyl]hexahydro-2H-azepin-2-imine, monohydrochloride

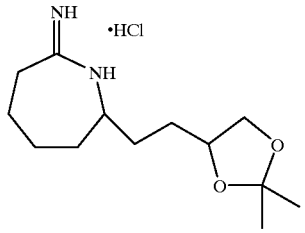

Example 286 A) Sodium hydride, 60% in mineral oil (8,3 g, 200 mmol) was washed with 2 portions of hexane and then dried under an N$_2$ flow. This material was suspended in DMF and ethyl 2-cyclohexanonecarboxylate (34.1 g, 200 mmol) was added slowly under N$_2$ with cooling with a 25° C. water bath. After complete addition, the mixture was stirred at 25° C. for ~1 hour and 4-bromo-1-butene (35.1 g, 260 mmol) and tetrabutylammonium iodide (2.0 g) were added. The stirring mixture was heated to 50° C. for 13 hours (overnight). The reaction was then cooled to room temperature. The entire mixture was poured into water, neutralized with dilute HCl, and extracted with two portions of 1:1 ether-hexane. The combined organics were then washed with two portions of water and saturated brine, dried over MgSO$_4$, filtered and stripped giving 41.8 g of an impure mixture of products. Purification of the product by chromatography (silica gel, : 5% methyl t-butyl ether / 90% hexane) gave 28.4 g of 2-(1-butenyl)-2-carboethoxycyclohexanone.

Example 286 B) The product of Example 286 A (11.2 g, 50 mmol), lithium chloride (10.6 g, 250 mmol), water (0.99 g, 55 mmol), and DMSO (250 mL) were combined under N$_2$ and refluxed for 2 hours. The reaction was then cooled to 25° C. The reaction mixture was poured into water and extracted with two portions of 1:1 ether - hexane. The organic phases were combined and washed with two portions water followed by saturated brine and then dried over MgSO$_4$. After filtering and stripping, the product was purified by fractional distillation at 1.5 mm Hg. (The product boils at 65 to 70° C. at 1 to 2 mm Hg.), giving 5.5 g of 2-(1-butenyl) cyclohexanone.

Example 286 C) The 2-(1-butenyl)cyclohexanone product of Example 286 B (7.70 g, 51 mmol) was converted to its oxime by the method of Example 1 using 5.3 g (76 mmol) of hydroxylamine hydrochloride and 7.0 g (85 mmol) of NaOAc in a mixture of 70 mL of ethanol and 70 mL of water. The procedure produced 8.48 g of the 2-(1-butenyl) cyclohexanone, oxime as a white solid.

Example 286 D) The product of Example 286 C (4.2 g, 25 mmol) was converted to the title compound mixture of two regioisomers by the method of Example 18 using 4.6 g (26 mmol) of benzene sulfonylchloride. The crude product mixture was triturated with Et$_2$O to give 1.8 g of 7-(1-butenyl)-hexahydro-1H-azepin-2-one (Isomer A). The filtrate was concentrated to provide a mixture of isomers but predominantly Isomer A. This mixture is separated into its Isomer-A and Isomer-B (3-(1-butenyl)-hexahydro-1H-azepin-2-one) components by chromatography.

Example 286 E) The Isomer-A title product of Example 286 D (15.2 g, 91 mmol) was reacted with di-t-butyl dicarbonate (25.8 g, 118 mmol) and DMAP (1.55 g, 12.6 mmol) in 350 mL THF to give 20.9 g (86%) of the N-BOC derivative by the method of Example 285.

Example 286 F) The product from Example 286 E (3.46 g, 13 mmol) was dissolved in a 1:1 mixture of acetone and water and treated with osmium tetraoxide (3.0 mL, 2.5 equivalent %) and 4-methylmorpholine oxide (3.1 g, 26.4 mmol) by the method of Example 212 A. The combined organic extracts were then dried (Na$_2$SO$_4$), stripped and purified by column chromatography on silica gel to yield (2.98 g, 76%) of (3,4-dihydroxybutyl)-hexahydro-1H-azepin-2-one.

Example 286 G) The product from Example 286 F (2.18 g) was treated with 2 mL trifluoroacetic acid in 20 mL CH$_2$Cl$_2$ for 30 min., and stripped in vacuo. Then, 25 mL toluene was added along with 12 mL 2,2-dimethoxypropane and 100 mg p-toluenesulfonic acid and brought to reflux for 4 hours. The mixture was cooled and partitioned between ether and dilute aqueous sodium bicarbonate. The organic layer was the washed with brine, dried (sodium sulfate), stripped and purified by column chromatography on silica gel to yield (0.98 g) of (3,4-dihydroxyacetonylbutyl)-hexahydro-1H-azepin-2-one.

Example 286 H) The product from Example 286 G (0.44 g, 1.3 mmol) was reacted with trimethyloxonium tetrafluoroborate (0.27 g, 1.8 mmol) by the method of Example 3 to yield 0.46 g (100%) of its methyl imino ether derivative.

Example 286) The product of Example 286 H (0.31 g, 0.87 mmol) in 3 mL of MeOH was reacted with ammonium chloride (43 mg, 0.8 mmol) by the method of Example 5 to yield 0.38 g of hexahydro-7-(1,2-acetonylbutyl)-1H-azepin-2-imine, monohydrochloride.

$^1$H NMR (CD3OD): 4.2–4.0 (m, 2H), 3.65 (m, 1H), 3.55 (t, 1H) 2.85–2.55 (m, 2H), 2.1–1.5 (m, 10H), 1.4 –1.3 (d, 6H).

EXAMPLE 287 hexahydro-7-[2-(4-pyridinyl)ethyl]-2H-azepin-2-imine, monohydrochloride

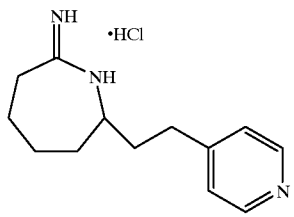

The title compound was prepared from 4-vinylpyridine and cyclohexanone by the methods described in Example 290.

Mass spectral analysis for $C_{13}H_{19}N_3$: M$^+$H=218.

$^1$H NMR (D$_2$O): δ 8.52 (d, J=7 Hz, 2H); 7.80 (d, J=7 Hz, 2H); 3.60–3.45 (m, 1H); 3.00–2.80 (m, 2H); 2.68–2.38 (m, 2H); 2.00–1.63 (m, 5H); 1.60–1.20 (m, 3H).

EXAMPLE 288

4-[2-(hexahydro-7-imino-1H-azepin-2-yl)ethyl] pyridinium-1-oxide, bis(trifluoroacetate)salt

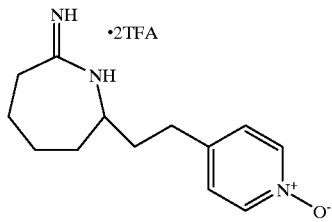

To the product of Example 287 (500 mg, 1.7 mmol) dissolved in a pH 5 phosphate buffer (50 mL) and ethanol (50 mL) was added oxone (2.1 g, 3.5 mmol). The reaction contents were stirred for 3 days and lyophilized. The residue was purified by C-18 reverse phase chromatography eluting with a CH$_3$CN/H$_2$O (0.05% TFA) gradient to give the title material as a white solid (350 mg, 60% yield).

Mass spectral analysis for $C_{13}H_{19}N_3O$: M$^+$H=234.

$^1$H NMR (D$_2$O): δ 8.20 (d, J=7 Hz, 2H); 7.45 (d, J=7 Hz, 2H); 3.50–3.40 (m, 1H); 2.80–2.60 (m, 2H); 2.60–2.35 (m, 2H); 2.00–1.60 (m, 5H); 1.60–1.20 (m, 3H).

EXAMPLE 289

4-[2-(hexahydro-7-imino-1H-azepin-2-yl)ethyl]-1-methylpyridinium chloride, monohydrochloride salt

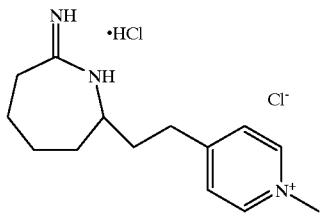

Hexahydro-7-[2-(4-pyridyl) ethyl]-1H-azepin-2-one was prepared as described in Example 290 by the condensation of 4-vinylpyridine with cyclohexanone. The title material was prepared from this hexahydro-7-[2-(4-pyridyl) ethyl]-1H-azepin-2-one as described in Example 291.

Mass spectral analysis for $C_{14}H_{22}N_3$: M$^+$H=232.

$^1$H NMR (D$_2$O): δ 8.48 (d, J=7 Hz, 2H); 7.75 (d, J=7 Hz, 2H); 4.20 (s, 3H); 3.60–3.40 (m, 1H); 3.00–2.30 (m, 2H); 2.065–2.40 (m, 2H); 2.00–1.65 (m, 5H); 1.60–1.20 (m, 3H).

EXAMPLE 290 hexahydro-7-[2-(2-pyridinyl)ethyl]-2H-azepin-2-imine, monohydrochloride

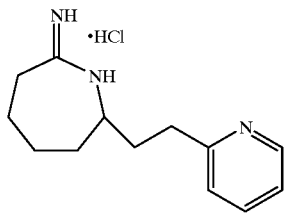

Example 290 A) A sample of 1-Pyrrolidino-1-cyclohexene (7.1 mL, 44 mmol) and 2-vinylpyridine (4.3 mL, 40 mmol) were refluxed overnight in diglyme (100 mL). Water was then added and the mixture was stirred an additional 2 hours before extracting it with Et$_2$O. The ether layer was dried over MgSO$_4$ and concentrated in vacuo leaving an oil. The residue oil was distilled on a kugelrohr apparatus at 60–80° C. (0.1 mm) to give 2-(2-pyridyl) ethyl-2-cyclohexanone as a yellow oil (6.5 g).

Example 290 B) The 2-(2-Pyridyl) ethyl-2-cyclohexanone product of Example 290 A (6.6 g, 32 mmol) in formic acid (99%, 200 mL) was added dropwise to hydroxylamine-O-sulfonic acid (2.0 g, 36 mmol) in formic acid (200 mL). The exothermic reaction was stirred overnight and concentrated in vacuo. The residue was partitioned between CH$_2$Cl$_2$ and water. The aqueous layer was neutralized to pH 5.5 with 50% NaOH and extracted with CH$_2$Cl$_2$ which was dried over MgSO$_4$ and concentrated in vacuo leaving an oil (3.5 g) which solidified. The solid was recrystallized from EtOAc to give hexahydro-7-[2-(2-pyridyl) ethyl]-1H-azepin-2-one as a light amber solid (1.6 g). The filtrate contained a mixture of hexahydro-7-[2-(2-piperidyl) ethyl]-1H-azepin-2-one and hexahydro-3-[2-(2-pyridyl)ethyl]-1H-azepin-2-one. The isomers were separated by chromatography on silica gel eluting with 60% acetone/hexanes. The first component to elute was hexahydro-3-[2-(2-pyridyl) ethyl]-1H-azepin-2-one and the second to elute was hexahydro-7-[2-(2-pyridyl) ethyl]-1H-azepin-2-one.

Example 290) To the hexahydro-7-[2-(2-pyridyl) ethyl]-1H-azepin-2-one product component of Example 290 A (684 mg, 3 mmol) in CH$_3$ON (20 mL) was added dropwise phosphorous oxychloride (0.6 mL, 6 mmol). The contents were stirred overnight and then concentrated in vacuo. The residue was taken up in methanol (10 mL) and anhydrous ammonia was bubbled into the solution. The reaction was stoppered and stirred overnight. The reaction mixture was concentrated in vacuo and the residue dissolved in 1N HCl and lyophilized. The lyophilized material was purified by C$_{18}$ reverse phase chromatography eluting with a CH$_3$CN/H$_2$O (0.05% TFA) gradient to give a solid. This solid was dissolved in 1N HCl and lyophilized to provide the title material as a white solid (220 mg).

Mass spectral analysis for C$_{13}$H$_{19}$N$_3$: M$^+$H=218.

$^1$H NMR (D$_2$O): δ 8.50 (d, J=7 Hz, 1H); 8.40 (t, J=7 Hz, 1H); 7.85–7.75 (m, 2H); 3.60–3.50 (m, 1H); 3.10–3.00 (m, 2H); 2.70–2.40 (m, 2H); 2.10–1.70 (m, 5H); 1.60–1.25 (m, 3H).

EXAMPLE 291

2-[2-(hexahydro-7-imino-1H-azepin-2-yl)ethyl]-1-methylpyridinium chloride, bis(trifluoroacetate)salt

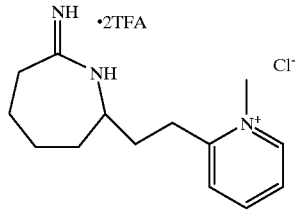

The Hexahydro-7-[2-(2-piperidyl) ethyl]-1H-azepin-2-one product component of Example 290 A (1.7 g, 8 mmol) was converted to the amidine via the method of Example 228c to afford a white solid. The solid was dissolved in 1N HCl and lyophilized to afford the title material as a white solid (1.1 g, 45% yield).

Mass spectral analysis for C$_{14}$H$_{22}$N$_3$: M$^+$H=232.

$^1$H NMR (D$_2$O): δ 8.60 (d, J=7 Hz, 1H); 8.32 (t, J=7 Hz, 1H); 7.82 (d, J=7 Hz, 1H); 7.77 (t, J=7 Hz, 1H); 4.20 (s, 3H); 3.75–3.60 (m, 1H); 3.20–3.00 (m, 2H); 2.75–2.40 (m, 2H); 2.15–1.95 (m, 2H); 1.95–1.75 (m, 3H); 1.70–1.30 (m, 3H).

EXAMPLE 292 hexahydro-7-[2-(1-methylpiperidin-2-yl)ethyl]-2H-azepin-2-imine, dihydrochloride

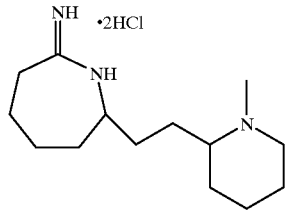

The product of Example 291 (300 mg, 1 mmol), platinum oxide (200 mg), H$_2$O (5 mL) and HOAc (30 mL) were shaken on a Parr hydrogenator at 55 psi of hydrogen overnight. Filtration and concentration in vacuo gave a colorless oil (490 mg). The oil was purified by C-18 reverse phase chromatography eluting with a CH$_3$CN/H$_2$O (0.05% TFA) gradient to give a white solid. The solid was dissolved in 1N HCl and lyophilized to afford the title material as a white solid (285 mg, 92% yield).

Mass spectral analysis for C$_{14}$H$_{27}$N$_3$: M$^+$H=238.

$^1$H NMR (D$_2$O): δ 3.55–3.40 (m, 1H); 3.40–3.25 (m, 1H); 3.15–2.80 (m, 2H); 2.70 (s, 3H); 2.65–2.35 (m, 2H); 2.00–1.20 (m, 16H).

EXAMPLE 293 hexahydro-7-[2-(2-piperidinyl)ethyl]-2H-azepin-2-imine, dihydrochloride

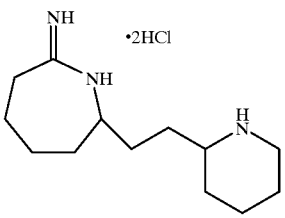

The product of Example 290 (138 mg, 0.5 mmol), platinum oxide (100 mg), conc HCl (0.5 mL) and ethanol (30 mL) were shaken on a Parr hydrogenator at 55 psi of hydrogen overnight. Filtration and concentration in vacuo gave a colorless oil. The oil was purified by C-18 reverse phase chromatography eluting with a CH$_3$CN/H$_2$O (0.05% TFA) gradient to give a white solid. The solid was dissolved in 1N HCl and lyophilized to afford the title product as a colorless foam (81 mg, 55% yield).

Mass spectral analysis for C$_{13}$H$_{25}$N$_3$: M$^+$H=224.

$^1$H NMR (D$_2$O): δ 3.60–3.40 (m, 1H); 3.35–3.20 (m, 1H); 3.05–2.92 (m, 1H); 2.90–2.75 (m, 1H); 2.70–2.50 (m, 1H); 2.50–2.40 (m, 1H); 2.00–1.00 (m, 16H).

EXAMPLE 294 hexahydro-7-[2-(4-piperidinyl)ethyl]-2H-azepin-2-imine, dihydrochloride

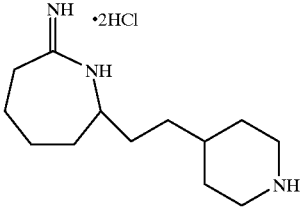

The title material was prepared by the method of Example 293 from the product of Example 287.

Mass spectral analysis for C$_{13}$H$_{25}$N$_3$: M$^+$H=224.

$^1$H NMR (D$_2$O): δ 3.45–3.35 (m, 1H); 3.30–3.15 (m, 2H); 2.85–2.70 (m, 2H); 2.60–2.30 (m, 2H); 1.90–1.10 (m, 15H).

EXAMPLE 295 hexahydro-7-[2-(4-piperidinyl)ethyl]-2H-azepin-2-imine, dihydrochloride

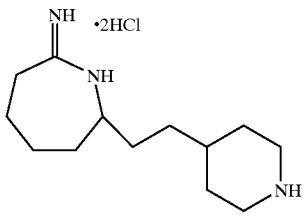

The title material was prepared by the procedure of Example 292 from the product of Example 289.

Mass spectral analysis for $C_{14}H_{27}N_3$: $M^+H=238$.

$^1$H NMR ($D_2O$): δ 3.50–3.25 (m, 3H); 2.90–2.70 (m, 2H); 2.67 (s, 3H); 2.65–2.32 (m, 2H); 1.90–1.60 (m, 5H); 1.60–1.10 (m, 10H).

EXAMPLE 296 hexahydro-7-[2-[1-(methylsulfonyl)piperidin-2-yl] ethyl]-2H-azepin-2-imine, trifluoroacetate salt

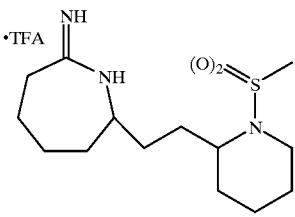

Example 296 A) A sample of the Hexahydro-7-[2-(2-pyridyl)ethyl]-1H-azepin-2-one product of Example 290b (2.4 g, 11 mmol), platinum oxide (500 mg) and glacial acetic acid (30 mL) were shaken on a Parr hydrogenator at 55 psi of hydrogen overnight. The contents were filtered and the filtrate was concentrated in vacuo. The residue was dissolved in water and adjusted to pH 9 with 2.5N NaOH. The aqueous solution was extracted with $CH_2Cl_2$ and the organic layer was dried over $MgSO_4$ and concentrated in vacuo leaving hexahydro-7-[2-(2-piperidyl)ethyl]-1H-azepin-2-one as a white solid (2.3 g).

Example 296 B) To the hexahydro-7-[2-(2-piperidyl) ethyl]-1H-azepin-2-one product of Example 296 A (2–3 g, 10 mmol) in anhydrous pyridine (8 mL) and $CH_2Cl_2$ (4 mL) was added dropwise methanesulfonyl chloride (0.74 mL) in $CH_2Cl_2$ (2 mL). The contents were stirred overnight, concentrated in vacuo and partitioned between $CH_2Cl_2$ and water. The $CH_2Cl_2$ layer was dried over $MgSO_4$ and concentrated in vacuo leaving an oil. The oil was purified by $C_{18}$ reverse phase chromatography eluding with a $CH_3CN/H_2O$ (0.05% TFA) gradient to give hexahydro-7-[2-(2-methylsulfonylpiperidyl)ethyl]-1H-azepin-2-one (1.5 g).

Example 296) The title product was prepared from the hexahydro-7-[2-(2-methylsulfonylpiperidyl)ethyl]-1H-azepin-2-one product of Example 296 B by the method described in Example 291.

Mass spectral analysis for $C_{14}H_{27}N_3O_2$: $M^+H=302$.

$^1$H NMR ($D_2O$): δ 3.85–3.70 (m, 1H); 3.60–3.40 (m, 2H); 3.05–2.90 (m, 1H); 2.95 (s, 3H); 2.70–2.35 (m, 2H); 1.90–1.20 (m 16H).

EXAMPLE 297

3-(hexahydro-7-imino-1H-azepin-2-yl)-1-(4-morpholinyl) propan-1-one, trifluoroacetate salt

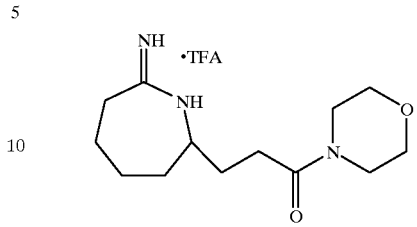

Example 297 A) A sample of Cyclohexanone-2-propionic acid was coupled with morpholine in the presence of TBTU (6.4 g; 20 mmol) and 3.5 mL (20 mmol) DIPEA in 25 mL DMF for 2 hours. The DMF was removed in vacuo and the product (4.4 g; 18.4 mmol) was isolated on preparative HPLC using $AcN/H_2O$ gradient (10–50% AcN in 30 minutes).

Example 297 B) The product of Example 297 A was converted to its lactam by the method of Example 253b to afford 1.3 g (28% yield) of the lactam as a white solid.

Example 297) This lactam product of Example 297 B was converted by the method of Example 228c to 810 mg (62% yield) of the title amidine product as a solid.

Mass spectral analysis for $C_{13}H_{23}N_3O_2$: $M^+H=254$.

EXAMPLE 298

6-(phenylmethyl)piperidin-2-imine, monohydrochloride

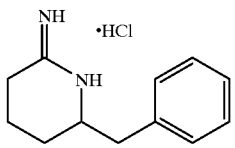

Example 298 A) A sample of 2-benzylpyridine (Aldrich, 2.5 g, 0.015 mole), sodium amide (780 mg, 0.02 mole) and N,N-dimethylaniline (25 mL) were refluxed overnight. The contents were allowed to cool and were partitioned between ether and water. The ether layer was dried ($MgSO_4$) and concentrated in vacuo leaving an oil. The oil was purified by chromatography. The purified material was dissolved in 1N HCl, lyophilized, and triturated with EtOAc to give 2-amino-6-benzylpyridine as a white solid.

Example 298) A sample of the 2-amino-6-benzylpyridine product of Example 298 A was reduced in acetic acid under hydrogen atmosphere utilizing 5% Rh/C catalyst to afford 2-imino-6-benzylpiperidine as an oil. The oil was purified by C-18 reverse phase chromatography to give a white solid. The solid was dissolved in 1N HCl, lyophilized, and recrystallized from EtOH/EtOAc to give the title product as a white solid.

Mass spectral analysis for $C_{12}H_{16}N_2$: $M^+H=189$.

$^1$H NMR ($CDCl_3$): δ 9.85 (s, 1H); 8.95 (s, 1H); 8.62 (s, 1H); 7.40–7.10 (m, 5H); 3.80–3.60 (m, 1H); 3.20–3.00 (m, 1H); 2.90–2.70 (m, 2H); 2.65–2.45 (m, 1H); 2.42–2.25 (m, 2H); 1.92 (m, 2H); 1.75 (m, 1H); 1.50–1.35 (m, 1H).

EXAMPLE 299

6-(cyclohexylmethyl)piperidin-2-imine, monohydrochloride

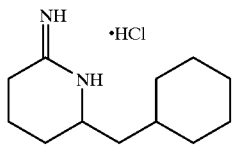

The 2-amino-6-benzylpyridine product of Example 298 A was reduced in acetic acid under hydrogen atmosphere utilizing platinum oxide catalyst to afford 2-imino-6-cyclohexylmethylpiperidine as an oil. The oil was dissolved in 1N HCl and lyophilized to give a white solid. The solid was recrystallized from EtOAc to give the title product as white crystals.

Mass spectral analysis for $C_{12}H_{22}N_2$: $M^+H=195$.

$^1$H NMR (CDCl$_3$): δ 9.60 (s, 1H); 8.90 (s, 1H); 8.70 (s, 1H); 3.60–3.40 (m, 1H); 2.90–2.70 (m, 1H); 2.70–2.50 (m, 1H); 2.10–1.80 (m, 2H); 1.80–1.00 (m, 13H); 1.00–0.80 (m, 2H).

EXAMPLE 300 trans-N-[3-(5-imino-3-methylpyrrolidin-2-yl)ethyl] phenylmethylamine, dihydrochloride

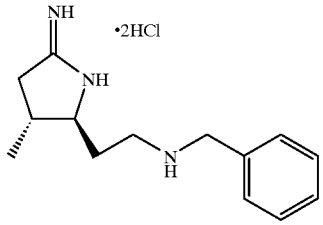

Example 300 A) cis and trans-5-[(1,3-dioxolan-2-yl) methyl]-4-(methyl)pyrrolidin-2-one was prepared in the manner described (R. Ohrlein, W. Schwab, R. Ehrler, V. Jager, *Synthesis* 1986, 535–538) starting with 1,1-dimethoxy-3-nitropropane and methyl crotonate.

Example 300 B) To a stirring solution of the product of Example 300A (1.0 g, 5.3 mmol) in 40 mL CHCl$_3$ was added 20 mL H$_2$O and 10 mL TFA. After stirring for 2 h, the reaction mixture was concentrated under reduced pressure. The residue was dissolved in EtOAc. The organic layer was washed with a minimum of saturated NaHCO$_3$, dried over MgSO$_4$, filtered, and concentrated under reduced pressure to recover 0.75 g of crude aldehyde.

Example 300 C and D) To a siding solution of product of Example 300 B (0.75 g, 5.3 mmol) and benzylamine (0.62 g, 5.8 mmol), in 20 mL MeOH was added NaBH$_3$CN (0.17 g, 2.7 mmol). The reaction was maintained at pH 4 by the addition of HOAc. After stirring for three days, the reaction mixture was concentrated under vacuum. To the residue was added 1N HCl and EtOAc. After separating the layers, the aqueous phase was neutralized with NaHCO$_3$ and extracted with EtOAc. After concentrating the organic phase, the residue was treated with 1N HCl and lyophilized. The resulting solid was purified by reverse phase column chromatography on a C-18 column. The cis (300 C) and trans (300 D) lactams were separated.

Example 300 E) The product of Example 300 D (0.28 g, 1.2 mmol) was treated with trimethyloxonium tetrafluoroborate (0.21 g, 1.4 mmol) in CH$_2$Cl$_2$ (DOM, 10 mL) by the method of Example 3, to yield 0.19 g.

Example 300) A solution of the product of Example 300 E (0.19 g, 0.78 mmol) in MeOH (10 mL) was reacted with ammonium chloride (0.05 g, 0.93 mmol) by the method of Example 5 followed by chromatography on reverse phase HPLC to generate the title material 300 (0.10 g).

| Elemental analysis: $C_{14}H_{21}N_3 \cdot 1.86$ HCl $\cdot 1$ H$_2$O (MW = 317.17) | | | | |
|---|---|---|---|---|
| | C | H | N | Cl |
| Calculated: | 53.02 | 7.90 | 13.25 | 20.79 |
| Found: | 52.67 | 7.87 | 12.90 | 20.44 |

EXAMPLE 301

N-[2-(hexahydro-7-imino-1H-azepin-2-yl)ethyl]-4,5-dihydro-1H-imidazol-2-amine, bis(trifluoroacetate) salt

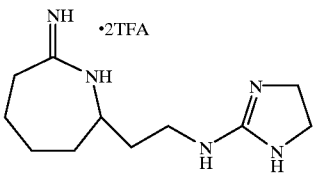

N-Boc-2-methylthio-2-imidazoline (0.46 g; 2 mmol) was combined with the 7-(2-aminoethyl)homoiminopiperidine product of Example 235 E (0.383 g; 1 mmol) in 20 mL MeOH and the mixture was stirred for 24 hours at room temperature. The solvent was removed in vacuo and the residue was redissolved in 20 mL CH$_2$Cl$_2$/TFA (1:1). After 30 minutes of stirring, the solvents were evaporated in vacuo and the title compound was isolated on preparative HPLC to afford 320 mg (71% yield) of the title product as a white solid.

Mass spectral analysis for $C_{11}H_{21}N_5$: $M^+H=224$.

$^1$H NMR (D$_2$O): δ 3.58 (m, 5H); 3.16 (m, 2H); 2.72–2.40 (m, 2H); 1.90–1.20 (m, 8H).

EXAMPLE 302

N-[2-(hexahydro-7-imino-1H-azepin-2-yl)ethyl]-1,4,5,6-tetrahydropyrimidin-2-amine, bis(trifluoroacetate)salt

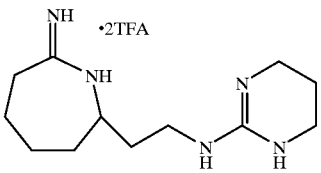

N-Boc-(3,4,5,6-tetrahydro)-2-methylthio-2-pyrimidine (0.46 g; 2 mmol) was reacted with the 7-(2-aminoethyl) homoiminopiperidine product of Example 235 E (0.383 g; 1 mmol) in 20 mL MeOH by the method of Example 301 to afford 280 mg (60% yield) of the title product as a white hygroscopic solid.

Mass spectral analysis for $C_{12}H_{23}N_5$: $M^+H=238$.

$^1H$ NMR ($D_2O$): δ 3.56 (m, 1H); 3.18 (m, 4H); 3.06 (m, 2H); 2.68–2.38 (m, 2H); 1.96–1.20 (m, 10H).

EXAMPLE 303

N-[2-(hexahydro-7-imino-1H-azepin-2-yl)ethyl]-3,4-dihydro-4-methyl-2H-pyrrol-5-amine, bis(trifluoroacetate)salt

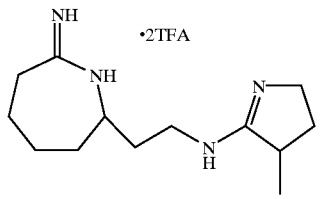

Example 303 A) A sample of 3-Methyl-2-pyrrolidinone (Aldrich, 5 g, 50 mmol) and Lawesson's Reagent (10 g, 25 mmol) were added to 120 ml of toluene and refluxed for 3 hours. After rotary evaporation, the residue was dissolved in methylene chloride and purified by silica gel column chromatography to afford 3-Methyl-2-pyrrolidinethione as a solid.

Mass spectral analysis for $C_5H_9N_1S_1$: $M^+H=116$.

Example 303 B) The 3-Methyl-2-pyrrolidinethione product of Example 303 A (1.7 g, 17 mmol) and methyl iodide (3.3 g, 20 mmol) were dissolved in acetone and stirred at 25° C. for 12 hours. After rotary evaporation, the residue was dissolved in EtOAc and extracted with water. The EtOAc fraction was dried over magnesium sulfate and filtered. The filtrate was evaporated and the residue was triturated with hexanes to afford 3-Methyl-2-methylthiopyrroline as a solid.

Mass spectral analysis for $C_6H11N_1S_1$: $M^+H=130$.

Example 303) The 7-(2-aminoethyl)homoiminopiperidine product of Example 235 E (0.6 g, 4.3 mmol) and the 3-methyl, 2-methylthio-pyrrolidine product of Example 303 B (0.3 g, 2.2 mmol ) were dissolved in acetonitrile (5 ml) and stirred under a nitrogen atmosphere for 12 hours. After rotary evaporation, the residue was dissolved in water and washed with $Et_2O$. The aqueous fraction was lyophilized and the residue was dissolved in 0.05% TFA and purified on C18-reversed phase HPLC.

Mass spectra analysis of $C_{13}H_{24}N_4$: $M^+H=237$.

$^1H$ NMR ($D_2O$): δ 1.10–1.20 (d, 3H), 1.30–2.65 (m, 13H), 2.90–3.70 (m, 5H).

EXAMPLE 304

N-[2-(hexahydro-7-imino-1H-azepin-2-yl)ethyl]-3,4-dihydro-2-methyl-2H-pyrrol-5-amine, bis(trifluoroacetate)salt

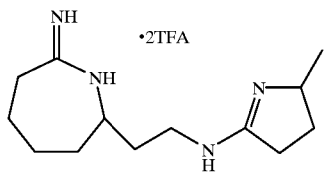

Example 304 A) A sample of 5-Methyl-2-pyrrolidinone (Aldrich, 5 g, 50 mmol) and Lawesson's Reagent (10 g, 25 mmol) were added to 120 ml of toluene and refluxed for 3 hours. After rotary evaporation, the residue was dissolved in methylene chloride and purified by silica gel column chromatography to afford 5-Methyl-2-pyrrolidinethione as a solid.

Mass spectral analysis for $C_5H_9N_1S_1$: $M^+H=116$.

Example 304 B) The 5-Methyl-2-pyrrolidinethione product of Example 304 A (1.7 g, 17 mmol) and methyl iodide (3.3 g, 20 mmol) were dissolved in acetone and stirred at 25° C. for 12 hours. After rotary evaporation, the residue was dissolved in EtOAc and washed with water. The EtOAc fraction was dried over magnesium sulfate and filtered. The filtrate was evaporated and the residue was triturated with hexanes to afford 5-methyl-2-methylthiopyrroline as a solid.

Mass spectral analysis for $C_6H_{11}N_1S_1$: $M^+H=130$.

Example 304) A sample of the 7-(2-aminoethyl)homoiminopiperidine product of Example 235e (0.6 g, 4.3 mmol) and the 5-methyl, 2-methylthiopyrroline product of Example 304 B (0.3 g, 2.2 mmol were dissolved in acetonitrile (5 ml) and stirred under nitrogen atmosphere for 12 hours. After rotary evaporation, the residue was dissolved in water and washed with $Et_2O$. The aqueous fraction was lyophilized and the residue was dissolved in 0.05% TFA and purified on C18-reversed phase HPLC to provide the title product.

Mass spectra analysis of $C_{13}H_{24}N_4$: $M^+H=237$.

$^1H$ NMR ($D_2O$): δ 1.05–1.10 (m, 3H), 1.14–2.85 (m, 13H), 3.08–4.03 (m, 5H).

EXAMPLE 305

(±) cis-5-imino-3-methyl-N-(phenylmethyl)pyrrolidine-2-ethanamine, dihydrochloride

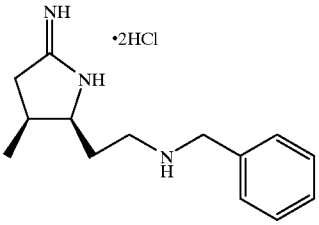

The title material is prepared in the same manner as described in Example 300 starting with the product of Example 300 C.

EXAMPLE 306

(±) trans-5-imino-N-(phenylmethyl)-3-(trifluoromethyl)pyrrolidine-2-ethanamine, dihydrochloride

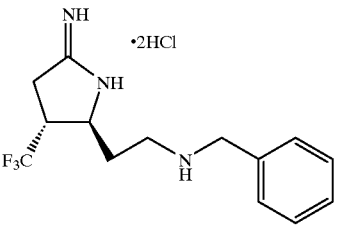

The title material is prepared in the same manner as described in Example 300 starting with Example 223 B.

EXAMPLE 307

(±) cis-5-imino-N-(phenylmethyl)-3-
(trifluoromethyl)pyrrolidine-2-ethanamine,
dihydrochloride

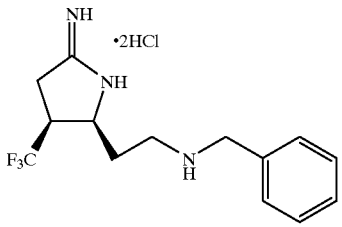

The title material is prepared in the same manner as described in Example 300 starting with Example 223 B.

EXAMPLE 308

(i) trans-5-imino-3-methyl-N-[(2-thienyl)methyl]
pyrrolidine-2-ethanamine, dihydrochloride

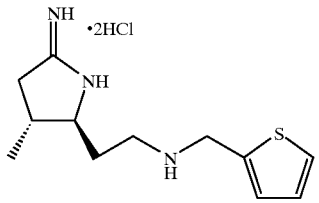

The title material is prepared in the same manner as described in Example 300 starting with Example 300 C.

EXAMPLE 309

(±) trans-5-imino-N-[(2-thienyl)methyl]-3-
(trifluoromethyl)-pyrrolidine-2-ethanamine,
dihydrochloride

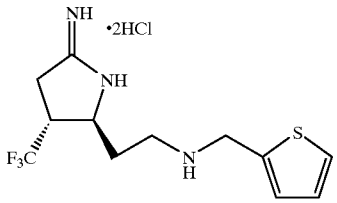

The title material is prepared in the same manner as described in Example 300 starting with Example 223 B.

EXAMPLE 310

(±) cis-5-imino-3-methyl-N-[(2-thienyl)methyl]
pyrrolidine-2-ethanamine, dihydrochloride

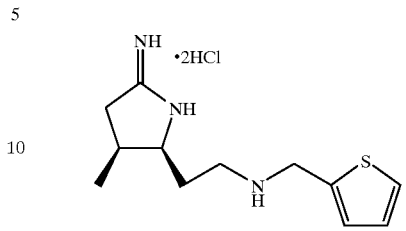

The title material is prepared in the same manner as described in Example 300 starting with Example 300 C.

EXAMPLE 311

(±) cis-5-imino-N-[(2-thienyl)methyl]-3-
(trifluoromethyl)-pyrrolidine-2-ethanamine,
dihydrochloride

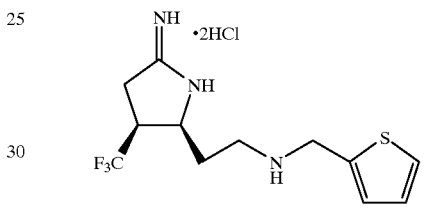

The title material is prepared in the same manner as described in Example 300 starting with Example 223 B.

EXAMPLE 312

(±) trans-5-imino-3-methyl-α-phenylpyrrolidine-2-
ethanamine, dihydrochloride

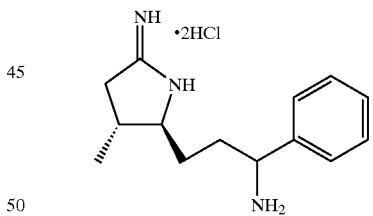

Example 312 A) To a stirring solution of phenylnitromethane and DBU in $CH_3CN$ is added the product of Example 300 B. After 16 h, the reaction is concentrated under vacuum. The residue is partitioned between brine and EtOAc. The organic layer is washed with brine, dried over $Na_2SO_4$, filtered and stripped to obtain the nitroolefin.

Example 312 B) The nitro amidine is prepared in the same manner as described in Examples 300 E and 300 from Example 312 A.

Example 312) A solution of the product of Example of 312 B is reduced under catalytic hydrogenation conditions using Pd black. The product is purified by reverse phase chromatography on a C-18 column using a gradient of $H_2O$ and $CH_3CN$ as the eluent.

EXAMPLE 313

(±) cis-5-imino-3-methyl-c-phenylpyrrolidine-2-ethanamine, dihydrochloride

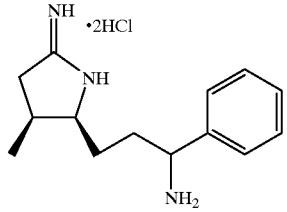

The title material is obtained from the reverse phase chromatography separation of Example 312.

EXAMPLE 314

(±) trans-5-imino-3-methyl-N-(phenylmethyl)pyrrolidine-2-propanamine, dihydrochloride

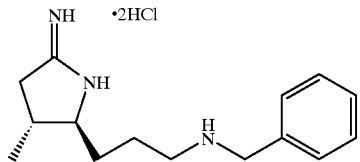

The title material is prepared in the same manner as described in Example 300 starting with cis and trans-5-[(1,3-dioxolan-2-yl)ethyl]-4-(methyl)pyrrolidin-2-one.

EXAMPLE 315

(±) cis-5-imino-3-methyl-N-(phenylmethyl)pyrrolidine-2-propanamine, dihydrochloride

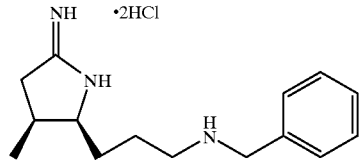

The title material is prepared in the same manner as described in Example 300 starting with cis and trans-5-[(1,3-dioxolan-2-yl)ethyl]-4-(methyl)pyrrolidin-2-one.

EXAMPLE 316

(±) trans-5-imino-a,3-dimethyl-N-(phenylmethyl)pyrrolidine-2-propanamine, dihydrochloride

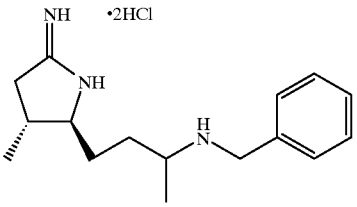

The title material is prepared in the same manner as described in Example 300 starting with cis and trans-5-[2-(1,3-dioxolan-2-yl)propyl]-4-(methyl)pyrrolidin-2-one.

EXAMPLE 317

(±) cis-5-imino-a,3-dimethyl-N-(phenylmethyl)pyrrolidine-2-propanamine, dihydrochloride

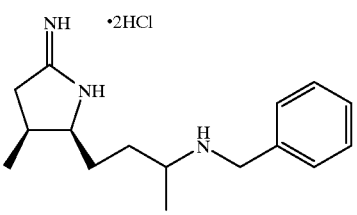

The title material is prepared in the same manner as described in Example 300 starting with cis and trans-5-[2-(1,3-dioxolan-2-yl)propyl]-4-(methyl)pyrrolidin-2-one.

EXAMPLE 318 hexahydro-7-imino-α-[[(3,4-dihydro-2H-pyrrol-5-yl)amino]methyl]-1H-azepine-2-acetamide, bis(trifluoroacetate)salt

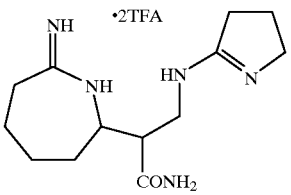

Example 318 A) The 7-[1-methoxycarbonyl-2-aminoethyl]homoiminopiperidine product of Example 281 D is allowed to react with an ethanolic ammonia solution to afford 7-[1-carboxamide-2-aminoethyl]homoiminopiperidine.

Example 318) The 7-(1-carboxamide-2-aminoethyl]homoiminopiperidine product of Example 318 A is allowed to react with 2-methoxypyrrolidine by the method of Example 236 to afford the title product.

EXAMPLE 319

β-cyclopropylhexahydro-7-imino-1H-azepine-2-ethanamine, bis(trifluoroacetate)salt

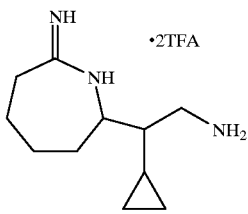

Example 319 A) To cyclopropyl carboxaldehyde in MeOH is added nitromethane and triethylamine. After stirring, the solvent is removed in vacuo and the residue is dissolved in $CH_2Cl_2$. The 2-nitro-1-cyclopropylethanol is isolated from the methylene chloride solution and added to a mixture of sodium acetate and acetic anhydride under $N_2$. After stirring, the mixture is diluted with water and extracted with EtOAc. The combined extracts are washed with brine, dried over $MgSO_4$ and the solvent is removed in vacuo. The 2-nitroethenylcyclopropane is used without further purification.

Example 319 B) Reaction of the 2-nitroethenyl cyclopropane product of Example 319 A with 1-morpholino-1-cyclohexene followed by mild hydrolysis affords 2-[1-cyclopropyl-2-nitroethyl]cyclohexanone.

Example 319 C) Beckmann Rearrangement of the 2-[1-cyclopropyl-2-nitroethyl)cyclohexanone product of Example 319 B affords 7-[1-cyclopropyl-2-nitroethyl] caprolactam.

Example 319 D) The 7-[1-cyclopropyl-2-nitroethyl] caprolactam product of Example 319 C is converted to the corresponding amidine via the method of Example 228 C to afford 7-[1-cyclopropyl-2-nitroethyl]homoiminopiperidine.

Example 319) The 7-[1-cyclopropyl-2-nitroethyl] homoiminopiperidine product of Example 319 D is dissolved in acetic acid and reduced via catalytic hydrogenation as described in the method of Example 205 to afford the title product.

EXAMPLE 320 hexahydro-7-imino-α-(1H-imidazol-5-yl)-1H-azepine-2-ethanamine, bis(trifluoroacetate)salt

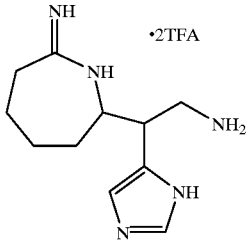

Example 320 A) To 2-imidazole carboxaldehyde in MeCH is added nitromethane and triethylamine. After stirring, the solvent is removed in vacuo and the residue is dissolved in $CH_2Cl_2$. The 2-nitro-1-(2-imidazole)ethanol is isolated from the methylene chloride solution and added to a mixture of sodium acetate and acetic anhydride under $N_2$. After stirring, the mixture is diluted with water and extracted with EtOAc. The combined extracts are washed with brine, dried over $MgSO_4$ and the solvent is removed in vacuo. The 4-(2-nitroethenyl)imidazole product is used without further purification.

Example 320 B) Reaction of the 4-(2-nitroethenyl) imidazole product of Example 320 A with 1-morpholino-1-cyclohexene followed by mild hydrolysis affords 2-[1-(4-imidazole)-2-nitroethyl]cyclohexanone.

Example 320 C) Beckmann Rearrangement of the 2-[1-(4-imidazole)-2-nitroethyl]cyclohexanone product of Example 320 B affords 7-[1-(4-imidazole)-2-nitroethyl] caprolactam.

Example 320 D) The 7-[1-(4-imidazole)-2-nitroethyl] caprolactam product of Example 320 C is converted to the corresponding amidine via the method of Example 228 C to afford 7-[1-(4-imidazole)-2-nitroethyl]homoiminopiperidine.

Example 320) The 7-[1-(4-imidazole)-2-nitroethyl] homoiminopiperidine product of Example 320 D is dissolved in acetic acid and reduced via catalytic hydrogenation by the method of Example 205 to afford the title product.

EXAMPLE 321

4-[(hexahydro-7-imino-1H-azepin-2-yl)methyl] cyclohexanamine, dihydrochloride

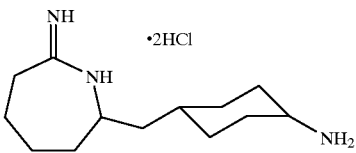

The product of Example 274 (0.31 g, 1.2 mmol) in 30 mL of EtOH was reduced with Rhodium on carbon under 60 psi of hydrogen at 60° C. Solvent removal in vacuo followed by lyophilization in water gave 0.3 g of the title material.

EXAMPLE 322

α-aminohexahydro-7-imino-β-phenyl-1H-azepine-2-propanoic acid, dihydrochloride

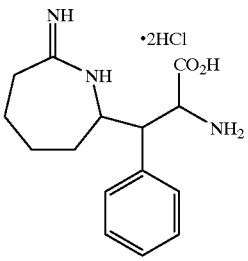

Example 322 A) The product of Example 253 (2.4 g, 9 mmol) in 50 mL of $CH_2Cl_2$ was reacted with $Et_3N$ (1.9 mL, 14 mmol) and TBDMSCl (1.5 g, 10 mmol) for 16 h at ambient temperature under $N_2$. The reaction mixture was then partitioned between water and $Ch_2Cl_2$. Drying ($Na_2SO_4$) the organic layer followed by solvent removal gave 3.3 g (98%) of the desired silylated lactam.

Example 322 B) The product of Example 322 A (2.3 g, 6.0 mmol) in 80 mL of anhydrous THF was reacted with LiHMDS (9.6 mL, 9.6 mmol) at −75° C. under $N_2$. Gradual warming (45 min) to −30° C. was followed by addition of methylchloroformate (1.0 g, 11 mmol) after which the reaction mixture was stirred for an hour between −30 to −20° C. Quenching with 20 mL of 4N HCl in dioxane was followed by extraction with water. Drying ($Na_2SO_4$) the organic layer, solvent removal and chromatographic purification (silica: 100% EA) gave 1.24 g (64%) of the desired 7-(2-carbomethoxy-2-nitro-1-phenylethyl)caprolactam.

| Elemental analysis: $C_{16}H_{20}N_2O_5$.0.8 $H_2O$ (MW = 334.75). | | | |
|---|---|---|---|
| | C | H | N |
| Calculated: | 57.41 | 6.50 | 8.37 |
| Found: | 57.34 | 6.11 | 8.01 |

Example 322 C) The product of Example 322 B (1.1 g, 3.6 mmol) dissolved in 50 mL of $CH_2Cl_2$ was treated with $Me_2O^+BF_4^-$ (0.6 g, 4.3 mmol) by the method of Example 3 to give 850 mgs of its imino ether.

Example 322 D) The product of Example 322 C (0.85 g, 2.5 mmol) in 50 mL of EtOH was refluxed with $NH_4Cl$ (0.13 g, 2.5 mmol) by the method of Example 4 to give its amidine hydrochloride.

Example 322 E) The crude product of Example 322 D in AcOH was treated with 20% palladium black under 5 psi hydrogen by the method of Example 205 to reduce the nitro group. The crude mixture was then stripped of solvent in vacuo, redissolved in 2N HCl and refluxed for 3 hours under $N_2$ in order to hydrolyze the ester group. Chromatographic purification gave the title material.

EXAMPLE 323

α-aminohexahydro-7-imino-β-(2-thienyl)-1H-azepine-2-propanoic acid, dihydrochloride

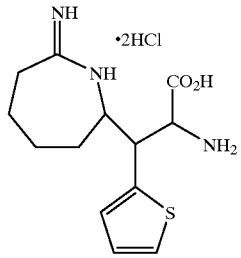

Example 323 A) The nitro lactam precursor to the title product of Example 262 is treated with TBDMSCl (1.1 eq) and $Et_3N$ (1.5 ea) by the method of Example 322 A to give the desired silylated lactam.

Example 323 B) The product of Example 323 A is converted to the desired 7-(2-carbomethoxy-2-nitro-1-thiophenylethyl)caprolactam following the method of Example 322 B.

Example 323 C) The product of Example 323 B in $CH_2Cl_2$ is treated with $Me_3O^+BF_4^-$ (1.0 eq) by the method of Example 3 to give its imino ether.

Example 323 D) The product of Example 323 C in EtOH is refluxed with $NH_4Cl$ (1.1 eq) by the method of Example 4 to give its amidine hydrochloride.

Example 323) The crude product of Example 323 D in ACOH is treated with 20% palladium black under 5 psi hydrogen by the method of Example 205 to reduce the nitro group. The crude mixture is then stripped of solvent in vacuo, redissolved in 2N HCl and refluxed for 3 hours under $N_2$ in order to hydrolyze the ester group. Chromatographic purification gives the title material.

EXAMPLE 324

α-(aminomethyl)hexahydro-7-imino-1H-azepine-2-acetonitrile, bis(trifluoroacetate)salt

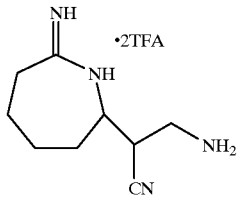

Example 324 A) A sample of the 7-[1-methoxycarbonyl-2-nitroethyl]caprolactam product of Example 281 C is allowed to react with ethanolic ammonia to afford 7-[1-carboxamide-2-nitroethyl]caprolactam.

Example 324 B) The 7-(1-carboxamide-2-nitroethyl] caprolactam product of Example 324 A is reduced via catalytic hydrogenation to afford 7-[1-carboxamide-2-aminoethyl]caprolactam.

Example 324 C) The 7-[1-carboxamide-2-aminoethyl] caprolactam product of Example 324 B is protected with an Fmoc protecting group on the primary amino group to afford 7-[1-carboxamide-2-(Fmoc-amino) ethyl]caprolactam.

Example 324 D) The 7-[1-carboxamide-2-(Fmoc-amino) ethyl]caprolactam product of Example 324 C is allowed to react with trifluoroacetic anhydride and pyridine to afford after mild hydrolysis, 7-[1-cyano-2-(Fmoc-amino)ethyl] caprolactam.

Example 324 E) The 7-[1-carboxamide-2-(Fmoc-amino) ethyl]caprolactam product of Example 324 D is converted to the corresponding amidine via the method of Example 228 C to afford 7-(1-cyano-2-(Fmoc-amino)ethyl] homoiminopiperidine.

Example 324 F) The Deprotection of 7-[1-cyano-2-(Fmoc-amino)ethyl]homoiminopiperidine product of Example 324 E with diethylamine affords 7-[1-cyano-2-aminoethyl)homoiminopiperidine.

Example 324) The 7-[1-cyano-2-aminoethyl] homoiminopiperidine product of Example 324 F is allowed to react with 2-methoxypyrrolidine by the method of Example 236 to afford the title product.

The following Examples are prepared via suitable modifications of applicable methods described within this application.

EXAMPLE 325

5-imino-3-methylene-N-(phenylmethyl)pyrrolidine-2S-ethanamine, dihydrochloride

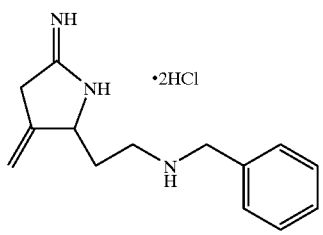

EXAMPLE 326

β-ethynylhexahydro-7-imino-N-(3,4-dihydro-2H-pyrrol-5-yl)-1H-azepine-2-ethanamine, bis(trifluoroacetate)salt

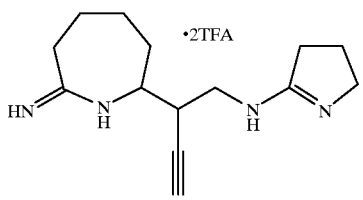

EXAMPLE 327 hexahydro-β-(1H-imidazol-1-yl)-7-imino-N-(3,4-dihydro-2H-pyrrol-5-yl)-1H-azepine-2-ethanamine, bis(trifluoroacetate)salt

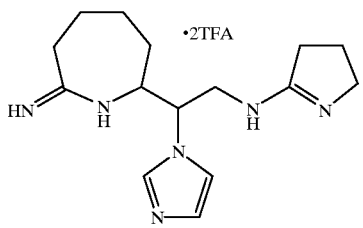

EXAMPLE 328

3-[[2-(hexahydro-7-imino-1H-azepin-2-yl)-2-(2-thienyl)ethyl]amino)alanine, trihydrochloride

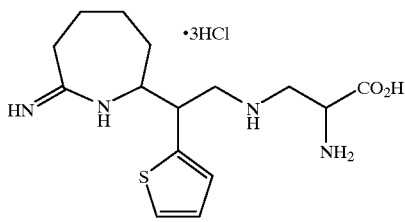

BIOLOGICAL DATA

The activity of the above listed compounds as NO synthase inhibitors has been determined in the following assays:

Citrulline Assay for Nitric Oxide Synthase

Nitric oxide synthase (NOS) activity was measured by monitoring the conversion of [$^3$H]-arginine to [$^3$H]-citrulline (Bredt and Snyder, *Proc. Natl. Acad. Sci. U.S.A.*, 87, 682–685, 1990 and Misko et al, *Eur. J. Pharm.*, 23, 119–125, 1993). Human inducible NOS (hiNOS), human endothelial constitutive NOS (hecNOS) and human neuronal constitutive NOS (hncNOS) were each cloned from RNA extracted from human tissue. The cDNA for human inducible NOS (hiNOS) was isolated from a λcDNA library made from RNA extracted from a colon sample from a patient with ulcerative colitis. The cDNA for human endothelial constitutive NOS (hecNOS) was isolated from a λcDNA library made from RNA extracted from human umbilical vein endothelial cells (HUVEC) and the cDNA for human neuronal constitutive NOS (hncNOS) was isolated from a λcDNA library made from RNA extracted from human cerebellum obtained from a cadaver. The recombinant enzymes were expressed in Sf9 insect cells using a baculovirus vector (Rodi et al, in *The Biology of Nitric Oxide, Pt. 4: Enzymology, Biochemistry and Immunology*; Moncada, S., Feelisch, M., Busse, R., Higgs, E., Eds.; Portland Press Ltd.: London, 1995; pp 447–450). Enzyme activity was isolated from soluble cell extracts and partially purified by DEAE-Sepharose chromatography. To measure NOS activity, 10 μL of enzyme was added to 40 μL of 50 mM Tris (pH 7.6) in the presence or absence of test compounds and the reaction initiated by the addition of 50 μL of a reaction mixture containing 50 mM Tris (pH 7.6), 2.0 mg/mL bovine serum albumin, 2.0 mM DTT, 4.0 mM CaCl$_2$, 20 μM FAD, 100 μM tetrahydrobiopterin, 0.4–2.0 mM NADPH and 60 μM L-arginine containing 0.9 μCi of L-[2,3-$^3$H]-arginine. The final concentration of L-arginine in the assay was 30 μM. For hecNOS, and hncNOS, calmodulin was included at a final concentration of 40–100 mM. Following incubation at 37° C. for 15 minutes, the reaction was terminated by addition of 300 μL of cold stop buffer containing 10 mM EGTA, 100 mM HEPES, pH 5.5 and 1 mM citrulline. [$^3$H]-Citrulline was separated by chromatography on Dowex 50W X-8 cation exchange resin and radioactivity determined with a liquid scintillation counter. Results are reported in Table I as the IC$_{50}$ values of compounds for hiNOS, hecNOS and hncNOS. Compounds giving less than 50% inhibition at 100 μM were reported as having IC$_{50}$ values of >100 μM and compounds giving greater than 50% inhibition at 100 μM were reported as having IC$_{50}$ values of <100 μM.

RAW cell nitrite assay

RAW 264.7 cells are plated to confluency on a 96-well tissue culture plate grown overnight (17 h) in the presence of LPS to induce NOS. A row of 3–6 wells were left untreated and served as controls for subtraction of nonspecific background. The media was removed from each well and the cells are washed twice with Krebs-Ringers-Hepes (25mM, pH 7.4) with 2 mg/ml glucose. The cells are then placed on ice and incubated with 50 μL of buffer containing L-arginine (30 μM) +/− inhibitors for 1 h. The assay is initiated by warming the plate to 37° C. in a water bath for 1–2 h. Production of nitrite by intracellular iNOS is linear with time. To terminate the cellular assay, the plate of cells is placed on ice and the nitrite-containing buffer removed and analyzed for nitrite (Misko et al, *Anal. Biochem.*, 214, 11–16, 1993). All values are the average of triplicate wells and are compared to a background-subtracted induced set of cells (100% value). IC$_{50}$ values of compounds with RAW cell mouse inducible NOS are reported in Table I.

The following examples were assayed with the following results.

TABLE I

Compounds giving less than 50% inhibition at 100 μM were reported as having $IC_{50}$ values of >100 μM and compounds giving greater than 50% inhibition at 100 μM were reported as having $IC_{50}$ values of <100 μM.

| Example Number | hiNOS | hecNOS | hncNOS | RAWcell |
|---|---|---|---|---|
| 5 | 6.2 | 792 | 15 | 66 |
| 9 | 9.7 | 575 | 74 | >100 |
| 14 | 62 | 651 | 30 | 170 |
| 16 | 3.6 | 599 | 14 | 1.8 |
| 21 | 4.3 | 147 | 7.8 | 58 |
| 34 | 8.1 | 183 | 24 | |
| 37 | 19 | 836 | 118 | 80 |
| 64 | 3 | 458 | 8.3 | 5.4 |
| 94 | 8.6 | 40 | 0.71 | 7.9 |
| 95 | 5.9 | 375 | 28 | |
| 191 | 9.3 | 1620 | 95 | 45 |
| 205 | <100 | >100 | >100 | |
| 219A | <100 | >100 | <100 | |
| 220A | <100 | >100 | <100 | |
| 220B | <100 | >100 | <100 | |
| 221 | >100 | >100 | >100 | |
| 222 | >100 | >100 | >100 | |
| 227 | <100 | >100 | <100 | |
| 228 | >100 | >100 | <100 | |
| 229 | >100 | >100 | >100 | |
| 230 | >100 | >100 | >100 | |
| 231 | >100 | >100 | >100 | |
| 232 | >100 | >100 | >100 | |
| 233 | >100 | >100 | >100 | |
| 234 | <100 | >100 | >100 | |
| 235 | <100 | >100 | <100 | |
| 236 | <100 | <100 | <100 | |
| 237 | <100 | <100 | <100 | |
| 238 | <100 | <100 | <100 | |
| 239 | <100 | >100 | <100 | |
| 240 | <100 | >100 | >100 | |
| 241 | <100 | >100 | <100 | |
| 242 | <100 | >100 | <100 | |
| 243 | <100 | >100 | <100 | |
| 244 | <100 | >100 | <100 | |
| 245 | <100 | >100 | <100 | |
| 246 | <100 | >100 | <100 | |
| 247 | <100 | <100 | <100 | |
| 248 | <100 | >100 | <100 | |
| 249 | <100 | >100 | <100 | |
| 250 | <100 | >100 | <100 | |
| 251 | <100 | >100 | >100 | |
| 252 | <100 | >100 | <100 | |
| 253 | >100 | >100 | >100 | |
| 254 | <100 | >100 | <100 | |
| 255 | <100 | >100 | <100 | |
| 256 | >100 | >100 | >100 | |
| 257 | >100 | >100 | >100 | |
| 258 | <100 | >100 | >100 | |
| 259 | <100 | >100 | >100 | |
| 260 | >100 | >100 | >100 | |
| 261 | <100 | >100 | <100 | |
| 262 | <100 | >100 | >100 | |
| 263 | <100 | >100 | <100 | |
| 264 | <100 | >100 | <100 | |
| 265 | <100 | <100 | <100 | |
| 266 | <100 | >100 | >100 | |
| 267 | <100 | >100 | <100 | |
| 268 | >100 | >100 | >100 | |
| 269 | <100 | >100 | >100 | |
| 270 | <100 | >100 | <100 | |
| 271 | <100 | >100 | <100 | |
| 272 | <100 | >100 | <100 | |
| 273 | <100 | >100 | <100 | |
| 274 | <100 | >100 | <100 | |
| 275 | >100 | >100 | <100 | |
| 276 | <100 | >100 | <100 | |
| 277 | <100 | >100 | <100 | |
| 278 | <100 | >100 | <100 | |
| 279 | <100 | >100 | <100 | |
| 280 | <100 | 100 | <100 | |
| 282 | <100 | <100 | <100 | |
| 283 | <100 | >100 | <100 | |
| 283A | <100 | >100 | <100 | |
| 283B | <100 | >100 | <100 | |
| 284 | <100 | <100 | <100 | |
| 285 | <100 | <100 | <100 | |
| 286 | <100 | >100 | <100 | |
| 287 | <100 | >100 | <100 | |
| 288 | <100 | >100 | >100 | |
| 289 | <100 | >100 | <100 | |
| 290 | <100 | >100 | >100 | |
| 291 | <100 | >100 | >100 | |
| 292 | <100 | >100 | <100 | |
| 293 | <100 | >100 | <100 | |
| 294 | <100 | <100 | <100 | |
| 295 | <100 | >100 | <100 | |
| 296 | >100 | >100 | >100 | |
| 297 | >100 | >100 | >100 | |
| 298 | <100 | <100 | <100 | |
| 299 | <100 | >100 | <100 | |
| 300 | <100 | >100 | <100 | |
| 301 | <100 | <100 | <100 | |
| 302 | <100 | >100 | <100 | |
| 303 | <100 | <100 | <100 | |
| 304 | <100 | >100 | <100 | |

In Vivo Assay

Rats were treated with an intraperitoneal injection of 10–12.5 mg/kg of endotoxin (LPS) to induce systemic expression of inducible nitric oxide synthase, resulting in markedly elevated plasma nitrite/nitrate levels. Compounds were administered orally 1 hour prior to LPS administration and plasma nitrite/nitrate levels were determined 5 hours following LPS administration. As shown in Table II, both compounds inhibited the LPS induced increase in plasma nitrite/nitrate levels demonstrating the ability to inhibit inducible nitric oxide synthase activity in vivo.

TABLE II

% inhibition of plasma nitrite/nitrate levels in LPS treated rats

| Example Number | % Inhibition (10 mg/kg, p.o.) |
|---|---|
| 64 | 35 |
| 5 | 37 |

From the foregoing description, one skilled in the art can easily ascertain the essential characteristics of this invention, and without departing from the spirit and scope thereof, can make various changes and modifications of the invention to adapt it to various usages and conditions.

What is claimed:

1. A compound having the formula:

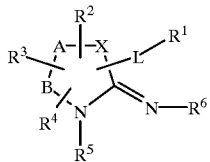

$R^1$ is selected from the group consisting of $C_3$–$C_{10}$-cycloalkyl, $C_4$–$C_{10}$-heterocyclyl, and aryl, which may optionally be substituted by one or more of the following: $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, $S(O)R^9$, $S(O)_2R^9$, halogen, nitro, amino, alkylamino, dialkylamino, aminoalkyl, dialkylaminoalkyl, arylamino, aminoaryl, alkylaminoaryl, acylamino, amidino, carboxyl, carboalkoxy, carboaryloxy, carboarylalkyloxy, cyano, aminocarbonylalkoxy, aminocarbonylamino, aminocarbonylaminoalkyl, haloalkyl, $SO_2NR^7R^9$, wherein all said substitutions may be optionally substituted with one or more of the following: halogen, $C_1$–$C_{10}$-alkyl, amino, alkylamino, dialkylamino, aminoalkyl, aminoacyl, carboxyl, carboalkoxy, carboaryloxy, carboalkylaryloxy, hydroxy, $C_1$–$C_{10}$-alkoxy;

L is selected from the group consisting of $C_1$–$C_{10}$-alkylene, $C_2$–$C_{10}$-alkenylene, $C_2$–$C_{10}$-alkynylene, and —$(CH_2)_m$—D—$(CH_2)_n$—;

D is selected from the group consisting of O, S, SO, $SO_2$, $SO_2NR^7$, $NR^7SO_2$, $NR^8$, $POOR^7$, $PON(R^7)_2$, $POOR^7NR^7$, $NR^7POOR^7$, C(O), C(O)O;

$R^7$ is hydrogen, $C_1$–$C_{10}$— alkyl, or aryl;

$R^8$ is hydrogen, $C_1$–$C_{10}$-alkyl, $COR^9$, or $CO^2R^9$;

$R^9$ is $C_1$–$C_{10}$-alkyl, or aryl;

m=0 to 7;

n=0 to 5;

wherein L may optionally be substituted by one or more of the following: $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, $S(O)R^9$, $S(O)_2R^9$, halogen, nitro, amino, alkylamino, dialkylamino, aminoalkyl, dialkylaminoalkyl, arylamino, aminoaryl, alkylaminoaryl, acylamino, carboxyl, carboalkoxy, carboaryloxy, carboarylalkyloxy, cyano, aminocarbonylalkoxy, aminocarbonylamino, aminocarbonylaminoalkyl, haloalkyl, $SO_2NR^7R^9$, $C_3$–$C_{10}$-cycloalkyl, $C_4$–$C_{10}$-heterocyclyl, aryl, heteroaryl, lactonyl, lactamyl, amidino, isourea, isothiourea, guanidino, substituted guanidino, wherein all said substitutions may be optionally substituted with one or more of the following: $C_1$–$C_{10}$-alkyl, amino, alkylamino, dialkylamino, aminoalkyl, aminoacyl, carboxyl, carboalkoxy, carboaryloxy, carboalkylaryloxy, hydroxy, $C_1$–$C_{10}$-alkoxy, nitro, amidino, guanidino, substituted guanidino, isourea, isothiourea and p=0 to 4

A is selected from the group consisting of O, $NR^7$, $(CH_2)_q$, CH=CH;

q is 1 to 2;

B is selected from the group consisting of $(CH_2)_v$, CH=CH;

v=1 to 2;

$R^2$, $R^3$ and $R^4$ are independently selected from hydrogen $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, $S(O)R^9$, $S(O)_2R^9$, halogen, nitro, amino, alkylamino, dialkylamino, aminoalkyl, dialkylaminoalkyl, arylamino, aminoaryl, alkylaminoaryl, acylamino, carboxyl, carboalkoxy, carboaryloxy, carboarylalkyloxy, cyano, aminocarbonylalkoxy, aminocarbonylamino, aminocarbonylaminoalkyl, haloalkyl, $SO_2NR^7R^9$, wherein all said substitutions may be optionally substituted with one or more of the following: halogen, $C_1$–$C_{10}$-alkyl, amino, alkylamino, dialkylamino, aminoalkyl, aminoacyl, carboxyl, carboalkoxy, carboaryloxy, carboalkylaryloxy, hydroxy, $C_1$–$C_{10}$-alkoxy, and $R^2$, $R^3$ may optionally be taken together to form an exocyclic double bond, $C_3$–$C_{10}$-alicyclic hydrocarbon, $C_4$–$C_{10}$-heterocyclyl or aromatic hydrocarbon and said optionally formed unit may be optionally substituted with one or more of the following: $C_1$–$C_{10}$-alkyl, $C_2$–$C_{10}$-alkenyl, $C_2$–$C_{10}$-alkynyl which may be optionally substituted with carboxyl, carboalkoxy, carboaryloxy, carboxyalkylaryloxy and $C_1$–$C_{10}$-alkoxy; and $R^5$, $R^6$ are independently selected from the group consisting of hydrogen, hydroxy, and alkylalkoxy, wherein aryl wherever occurring means a 5- or 6-membered single aromatic radical which may include 0 to 4 heteroatoms, with the proviso that when X=S, A=$(CH_2)_q$, B=$(CH_2)_v$, q+v=2, or one of A or B is HC=CH and the other is not present, $R^2$, $R^3$, $R^4$ are H, then $R^1$ is not

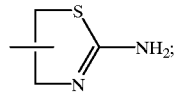

with the further proviso that when B is HC=CH and A is HC=CH, then X cannot be $(CH_2)_2$ where p=0;

and with the further provis that when X is $(CH_2)_p$, p=1, A=$(CH_2)_q$ and B=$(CH_2)_v$, where q, v is 1, $R^2$–$R^6$ are H, L is $CH_2$, $R^1$ is not phenyl.

2. The compound as recited in claim 1 wherein:

$R^1$ is selected from the group consisting of $C_3$–$C_{10}$-cycloalkyl, $C_4$–$C_{10}$-heterocyclyl, and aryl, which may optionally be substituted by one or more of $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, $S(O)R^9$, $S(O)_2R^9$, amino, amidino, alkylamino, aminoalkyl, aminoaryl, carboxyl, carboalkoxy, carboaryloxy, aminocarbonylalkoxy, aminocarbonylamino, $SO_2NR^7R^9$, wherein all said substitutions may be optionally substituted with one or more of the following: $C_1$–$C_{10}$-alkyl, amino, alkylamino, aminoalkyl, aminoacyl, carboxyl, carboalkoxy, carboaryloxy, carboalkylaryloxy, hydroxy, $C_1$–$C_{10}$-alkoxy, and L is selected from the group consisting of $C_1$–$C_{10}$-alkylene, $C_2$–$C_{10}$-alkenylene, $C_2$–$C_{10}$-alkynylene, and —$(CH_2)_m$—D—$(CH_2)_n$—;

D is O, S, SO, $SO_2$, $NR^8$, C(O), C(O)O or $POOR^7$;

$R^7$ is hydrogen, $C_1$–$C_{10}$-alkyl, or aryl;

$R^8$ is hydrogen, $C_1$–$C_{10}$-alkyl, $COR^9$, or $CO_2R^9$;

$R^9$ is $C_1$–$C_{10}$-alkyl, or aryl;

m=0 to 4;

n=0 to 3;

wherein L may optionally be substituted by one or more of $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, S(O)$R^9$, S(O)$_2R^9$, amino, alkylamino, aminoalkyl, arylamino, aminoaryl, carboxyl, carboalkoxy, carboaryloxy, aminocarbonylalkoxy, aminocarbonylamino, SO$_2$NR$^7$R$^9$, cycloalkyl, heterocyclyl, aryl, heteroaryl, lactonyl, amidino, isourea, isothiourea, guanidino, substituted guanidino wherein all said substitutions may be optionally substituted with one or more of the following: $C_1$–$C_{10}$-alkyl, amino, alkylamino, aminoalkyl, aminoacyl, carboxyl, carboalkoxy, carboaryloxy, carboalkylaryloxy, hydroxy, $C_1$–$C_{10}$-alkoxy, nitro, amidino, guanidino, substituted guanidino, isourea, isothiourea, and X is selected from the group consisting of NH, O, S, (CH$_2$)$_p$, or CH=CH;

p=0 to 3;

A is selected from the group consisting of O, NR$^7$, (CH$_2$)$_q$, CH=CH;

q=1 to 2;

B is selected from the group consisting of (CH$_2$)$_v$, CH=CH;

v=1 to 2;

$R^2$, $R^3$, and $R^4$ are independently selected from hydrogen, $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, S(O)$R^9$, S(O)$_2R^9$, amino, alkylamino, aminoalkyl, arylamino, aminoaryl, carboxyl, carboalkoxy, carboaryloxy, aminocarbonylalkoxy, aminocarbonylamino, SO$_2$NR$^7$R$^9$, wherein all said substitutions may be optionally substituted with one or more of the following: $C_1$–$C_{10}$-alkyl, amino, alkylamino, aminoalkyl, aminoacyl, carboxyl, carboalkoxy, carboaryloxy, carboalkylaryloxy, hydroxy, and $C_1$–$C_{10}$-alkoxy and $R^2$, $R^3$, may optionally be taken together to form an exocyclic double bond, $C_3$–$C_{10}$-alicyclic hydrocarbon, $C_4$–$C_{10}$-heterocyclyl or aromatic hydrocarbon;

$R^5$, $R^6$ are independently selected from the group consisting of hydrogen, hydroxy, and alkyloxy.

3. The compound as recited in claim 1 wherein:

$R^1$ is selected from the group consisting of $C_3$–$C_{10}$-cycloalkyl, $C_4$–$C_{10}$-heterocyclyl, and aryl, which may optionally be substituted by one or more of $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, S(O)$R^9$, S(O)$_2R^9$, amino, aminoalkyl, aminoaryl, carboxyl, carboalkoxy, carboaryloxy, aminocarbonylalkoxy, aminocarbonylamino, SO$_2$NR$^7$R$^9$, wherein all said substitutions may be optionally substituted with one or more of the following: $C_1$–$C_{10}$-alkyl, amino, aminoalkyl, aminoacyl, carboxyl, carboalkoxy, carboaryloxy, hydroxy, $C_1$–$C_{10}$-alkoxy, and L is selected from the group consisting of $C_1$–$C_{10}$-alkylene, $C_2$–$C_{10}$-alkenylene, $C_2$–$C_{10}$-alkynylene, and —(CH$_2$)$_m$—D—(CH$_2$)$_n$—;

D is selected from the group consisting of O, S, SO, SO$_2$, NR$^8$, C(O), C(O)O;

$R^7$ is H, $C_1$–$C_{10}$-alkyl, or aryl;

$R^8$ is H, $C_1$–$C_{10}$-alkyl, COR$^9$, or CO$_2$R$^9$;

$R^9$ is $C_1$–$C_{10}$-alkyl, or aryl;

m=0 to 4;

n=0 to 3;

wherein L may optionally be substituted by one or more of $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, S(O)$R^9$, S(O)$_2R^9$, amino, aminoalkyl, aminoaryl, carboxyl, carboalkoxy, carboaryloxy, aminocarbonylalkoxy, aminocarbonylamino, SO$_2$NR$^7$R$^9$, $C_3$–$C_{10}$-cycloalkyl, $C_4$–$C_{10}$-heterocyclyl, aryl, heteroaryl, lactonyl, amidino, guanidino, substituted guanidino, wherein all said substitutions may be optionally substituted with one or more of the following: $C_1$–$C_{10}$-alkyl, amino, aminoalkyl, aminoacyl, carboxyl, carboalkoxy, carboaryloxy, hydroxy, $C_1$–$C_{10}$-alkoxy, nitro, amidino, guanidino, substituted guanidino;

X is selected from the group consisting of NH O, S, (CH$_2$)$_p$, and CH=CH;

p=0 to 3;

A is selected from the group consisting of O, NR$^7$, (CH$_2$)$_q$, CH=CH;

q=1;

B is selected from the group consisting of (CH$_2$)$_v$, CH=CH;

v=1;

$R^2$, $R^3$, and $R^4$ are independently selected from hydrogen, $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, S(O)$R^9$, S(O)$_2R^9$, amino, aminoalkyl, aminoaryl, carboxyl, carboalkoxy, carboaryloxy, aminocarbonylalkoxy, aminocarbonylamino, SO$_2$NR$^7$R$^9$, wherein all said substitutions may be optionally substituted with one or more of the following: $C_1$–$C_{10}$-alkyl, amino, aminoalkyl, aminoacyl, carboxyl, carboalkoxy, carboaryloxy, hydroxy, $C_1$–$C_{10}$-alkoxy, and $R^5$, $R^6$ are independently selected from the group consisting of hydrogen, hydroxy, and alkyloxy.

4. The compound as recited in claim 1 wherein:

$R^1$ is selected from the group consisting of $C_3$–$C_{10}$-cycloalkyl, $C_4$–$C_{10}$-heterocyclyl, and aryl, which may optionally be substituted by one or more of $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, amino, aminoalkyl, aminoaryl, carboxyl, carboalkoxy, carboaryloxy, aminocarbonylalkoxy, aminocarbonylamino, wherein all said substitutions may be optionally substituted with one or more of the following: $C_1$–$C_{10}$-alkyl, amino, aminoalkyl, aminoacyl, carboxyl, carboalkoxy, carboaryloxy, hydroxy, $C_1$–$C_{10}$-alkoxy, and L is selected from the group consisting of $C_1$–$C_{10}$-alkylene, $C_2$–$C_{10}$-alkenylene, $C_2$–$C_{10}$-alkynylene, which may optionally be substituted by one or more of the following: $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, amino, aminoalkyl, aminoaryl, carboxyl, carboalkoxy, carboaryloxy, aminocarbonylalkoxy, aminocarbonylamino, wherein all said substitutions may be optionally substituted with one or more of the following: $C_1$–$C_{10}$-alkyl, amino, aminoalkyl, aminoacyl, carboxyl, carboalkoxy, carboaryloxy, hydroxy, $C_1$–$C_{10}$-alkoxy, nitro, amidino, guanidino, substituted guanidino;

X is selected from the group consisting of NH, O, S, (CH$_2$)$_p$, CH=CH;

p=0 to 3;

A is selected from the group consisting of CH$_2$, CH=CH;

B is selected from the group consisting of CH$_2$, CH=CH;

$R^2$, $R^3$, and $R^4$ are independently selected from hydrogen, $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, amino, aminoalkyl, aminoaryl, carboxyl, carboalkoxy, carboaryloxy, aminocarbonylalkoxy, aminocarbonylamino, wherein all said substitutions may be optionally substituted with one or more of the following: $C_1$–$C_{10}$-alkyl, amino, aminoalkyl, aminoacyl, carboxyl, carboalkoxy, carboaryloxy, hydroxy, $C_1$–$C_{10}$-alkoxy, and $R^5$, $R^6$ are independently selected from the group consisting of hydrogen, hydroxy, and alkyloxy.

5. The compound as recited in claim 1 wherein:

$R^1$ is selected from the group consisting of $C_3$–$C_{10}$-cycloalkyl, $C_4$–$C_{10}$-heterocyclyl, and aryl which may optionally be substituted by one or more of $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, amino, aminoalkyl, aminoaryl, carboxyl, carboalkoxy, carboaryloxy wherein all said substitutions may be optionally substituted with one or more of the following: $C_1$–$C_{10}$-alkyl, amino, aminoalkyl, aminoacyl, carboxyl, carboalkoxy, carboaryloxy, hydroxy, $C_1$–$C_{10}$-alkoxy, and L is selected from the group consisting of a linker group such as alkylene, alkenylene, alkynylene, which may optionally be substituted by one or more of $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, amino, aminoalkyl, carboxyl, carboalkoxy, carboaryloxy wherein all said substitutions may be optionally substituted with one or more of the following: $C_1$–$C_{10}$-alkyl, amino, aminoalkyl, aminoacyl, carboxyl, carboalkoxy, carboaryloxy, hydroxy, $C_1$–$C_{10}$-alkoxy, nitro, amidino, guanidino, substituted guanidino and X is selected from the group consisting of $(CH_2)_p$, and CH=CH;

p=0 to 3;

A is selected from the group consisting of $CH_2$, and CH=CH;

B is selected from the group consisting of $CH_2$, and CH=CH;

$R^2$, $R^3$, and $R^4$ are independently selected from hydrogen, $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, amino, aminoalkyl, carboxyl, carboalkoxy, carboaryloxy wherein all said substitutions may be optionally substituted with one or more of the following: $C_1$–$C_{10}$-alkyl, amino, aminoalkyl, aminoacyl, carboxyl, carboalkoxy, carboaryloxy, hydroxy, and $C_1$–$C_{10}$-alkoxy; and $R^5$, $R^6$ are independently selected from the group consisting of hydrogen, hydroxy, and alkyloxy.

6. The compound as defined in claim 1 wherein the compound is selected from the group consisting of hexahydro-7-(phenylmethyl) -2H-azepin-2-imine, monohydrochloride;

hexahydro-3-(phenylmethyl)-2H-azepin-2-imine, monohydrochloride;

7-(cyclohexylmethyl)hexahydro-2H-azepin-2-imine, monohydrochloride;

3-(cyclohexylmethyl)hexahydro-2H-azepin-2-imine, monohydrochloride;

(±)-hexahydro-7-(phenylmethyl)-2H-azepin-2-imine, monohydrochloride;

(−)-hexahydro-7-(phenylmethyl)-2H-azepin-2-imine, monohydrochloride;

hexahydro-7-[(oxiran-2-yl)methyl]-2H-azepin-2-imine, monohydrochloride;

7-[(1,4-benzodioxan-2-yl)methyl]hexahydro-2H-azepin-2-imine, monohydrochloride;

hexahydro-7-[2-methoxy-3-(2-methoxyphenoxy)propyl]-2H-azepin-2-imine, monohydrochloride;

hexahydro-a-[(2-hydroxyphenoxy)methyl)-7-imino-1H-azepine-2-ethanol, monohydrochloride;

a-[(2-acetyloxyphenoxy)methyl]hexahydro-7-imino-1H-azepine-2-ethanol acetate(ester), monohydrochloride;

hexahydro-7-(3-phenyl-2-propenyl)-2H-azepin-2-imine, monohydrochloride;

hexahydro-7-(3-phenylpropyl)-2H-azepin-2-imine, monohydrochloride;

hexahydro-7-[(tetrahydro-2-furanyl)methyl]-2H-azepin-2-imine, monohydrochloride;

hexahydro-3-[(tetrahydro-2-furanyl)methyl]-2H-azepin-2-imine, monohydrochloride;

7-[(2-furanyl)methyl]hexahydro-2H-azepin-2-imine, monohydrochloride;

3-[(2-furanyl)methyl]hexahydro-2H-azepin-2-imine, monohydrochloride;

hexahydro-7-[(2-thienyl)methyl]-2H-azepin-2-imine, monohydrochloride;

hexahydro-3-[(2-thienyl)methyl]-2H-azepin-2-imine, monohydrochloride;

(±)(trans) 4-methyl-5-(phenylmethyl)pyrrolidin-2-imine, monohydrochloride;

octahydro-8-(3-phenyl-2-propenyl)azepin-2-imine, monohydrochloride;

octahydro-8-(3-phenylpropyl)azepin-2-imine, monohydrochloride;

methyl 2-[2-(hexahydro-7-imino-1H-azepin-2-yl)ethyl]benzoate, monohydrochloride;

methyl 2-[2-(hexahydro-7-imino-1H-azepin-2-yl)ethyl]benzoate, monohydrochloride;

methyl 2-[2-(hexahydro-2-imino-1H-azepin-3-yl)ethyl]benzoate, monohydrochloride;

methyl 2-[2-(hexahydro-2-imino-1H-azepin-3-yl)ethyl]benzoate, monohydrochloride;

methyl 3-[2-(hexahydro-7-imino-1H-azepin-2-yl)ethenyl]benzeneacetate, monohydrochloride;

6-(phenylmethyl)piperidin-2-imine, monohydrochloride;

6-(cyclohexylmethyl)piperidin-2-imine, monohydrochloride;

6-(3-phenyl-2-propenyl)piperidin-2-imine, monohydrochloride;

6-(3-phenylpropyl)piperidin-2-imine, monohydrochloride;

7-[2-(1,3-dioxolan-2-yl)ethyl]hexahydro-2H-azepin-2-imine, monohydrochloride;

7-[2-(1,3-dioxan-2-yl)ethyl]hexahydro-2H-azepin-2-imine, monohydrochloride;

7-[[4,5-dihydro-3-(trifluoromethyl)isoxazol-5-yl]methyl]hexahydro-2H-azepin-2-imine, monohydrochloride;

7-[[4,5-dihydro-3-(trifluoromethyl)isoxazol-4-yl]methyl]hexahydro-2H-azepin-2-imine, monohydrochloride;

hexahydro-7-[[3-(trifluoromethyl)isoxazol-5-yl]methyl]-2H-azepin-2-imine, monohydrochloride;

hexahydro-7-[[3-(trifluoromethyl)isoxazol-4-yl]methyl]-2H-azepin-2-imine, monohydrochloride;

hexahydro-7-[(3-phenylisoxazol-4-yl)methyl]-2H-azepin-2-imine, monohydrochloride;

hexahydro-7-[(3-phenylisoxazol-5-yl)methyl]-2H-azepin-2-imine, monohydrochloride;

7-[[4,5-dihydro-1-phenyl-3-(trifluoromethyl)-1H-pyrazol-5-yl]methyl]-hexahydro-2H-azepin-2-imine, monohydrochloride;

7-[[4,5-dihydro-1-phenyl-3-(trifluoromethyl)-1H-pyrazol-4-yl]methyl]-hexahydro-2H-azepin-2-imine, monohydrochloride;

hexahydro-7-[[1-phenyl-3-(trifluoromethyl)-1H-pyrazol-5-yl]methyl]-2H-azepin-2-imine, monohydrochloride;

hexahydro-7-[[1-phenyl-3-(trifluoromethyl)-1H-pyrazol-4-yl]methyl]-2H-azepin-2-imine, monohydrochloride;

7-[[4,5-dihydro-1,3-diphenyl-1H-pyrazol-4-yl]methyl]hexahydro-2H-azepin-2-imine, monohydrochloride;

7-[((1,3-diphenyl-1H-pyrazol-5-yl))methyl]hexahydro-2H-azepin-2-imine, monohydrochloride;

hexahydro-7-[[1-phenyl-3-(trifluoromethyl)-1H-1,2,4-triazol-5-yl]methyl]-2H-azepin-2-imine, monohydrochloride;

hexahydro-7-[2-(2-nitrophenyl)ethenyl]-2H-azepin-2-imine, monohydrochloride;

2-[[2-(hexahydro-7-imino-2H-azepin-2-yl)ethyl] benzenamine, dihydrochloride;

methyl 2-[3-(hexahydro-7-imino-1H-azepin-2-yl)-1-propenyl]-5-nitrobenzoate, monohydrochloride;

methyl 5-amino-2-[3-(hexahydro-7-imino-1H-azepin-2-yl)-1-propenyl]benzoate, dihydrochloride;

hexahydro-7-[2-(3-methoxyphenyl)ethenyl]-2H-azepin-2-imine, monohydrochloride;

hexahydro-7-[2-(3-methoxyphenyl)ethyl]-2H-azepin-2-imine, monohydrochloride;

7-[2-(3-furanyl)ethyl]hexahydro-2H-azepin-2-imine, monohydrochloride;

hexahydro-7-[2-(2-thienyl)ethenyl]-2H-azepin-2-imine, monohydrochloride;

hexahydro-7-[2-(2-thienyl)ethyl]-2H-azepin-2-imine, monohydrochloride;

methyl 5-[3-(hexahydro-7-imino-1H-azepin-2-yl)-1-propenyl]furan-2-carboxylate, monohydrochloride;

methyl 5-[3-(hexahydro-7-imino-1H-azepin-2-yl)propyl]furan-2-carboxylate, monohydrochloride;

hexahydro-7-[2-(2-thiazolyl)ethenyl]-2H-azepin-2-imine, monohydrochloride;

hexahydro-7-[2-(2-thiazolyl)ethyl]-2H-azepin-2-imine, monohydrochloride;

1,5,6,7-tetrahydro-7-(phenylmethyl)-2H-azepin-2-imine, monohydrochloride;

7-[(4,5-dihydro-3-phenylisoxazolyl-5-yl)methyl]hexahydro-2H-azepin-2-imine, monotrifluoroacetic acid salt;

7-[(2,6-dichlorophenyl)methyl]-hexahydro-2H-azepin-2-imine;

7-[(4-fluorophenyl)methyl]hexa-hydro-2H-azepin-2-imine;

7-[(4-fluorophenyl)methyl]hexa-hydro-2H-azepin-2-imine;

7-[(2,4-difluorophenyl)methyl]-hexahydro-2H-azepin-2-imine;

7-[(2,3,4,5-pentafluorophenyl)-methyl]hexahydro-2H-azepin-2-imine;

hexahydro-7-[[4-(trifluoro-methyl)phenyl]methyl]-2H-azepin-2-imine;

hexahydro-7-[[3-(trifluoro-methyl)phenyl]methyl]-2H-azepin-2-imine;

7-[(2-biphenylyl)methyl]hexa-hydro-2H-azepin-2-imine;

hexahydro-7-[(2-nitrophenyl)-methyl]-2H-azepin-2-imine;

hexahydro-7-[(4-nitrophenyl)-methyl]-2H-azepin-2-imine;

4-[(hexahydro-7-imino-2H-azepin-2-yl)methyl]benzeneacetic acid;

7-[(5-chlorothien-2-yl)methyl]-hexahydro-2H-azepin-2-imine;

7-[(3,5-dimethylisoxazol-4-yl)methyl]hexahydro-2H-azepin-2-imine;

hexahydro-7-[(tetrahydro-2H-pyran-2-yl)methyl]-1H-azepin-2-imine monohydrochloride;

hexahydro-3-[(tetrahydro-2H-pyran-2-yl)methyl]-2H-azepin-2-imine;

hexahydro-7-(2-phenylethyl)-1H-azepin-2-imine, monohydrochloride;

hexahydro-7-[2-(4-nitrophenyl)ethyl]-1H-azepin-2-imine, monohydrochloride;

hexahydro-7-[2-(4-methoxyphenyl)ethyl]-1H-azepin-2-imine, monohydrochloride;

7-[3-(5-(1,3-dioxolan-2-yl)thien-2-yl)-2-propenyl] hexahydro-2H-azepin-2-imine, monohydrochloride;

5-[3-(hexahydro-7-imino-1H-azepin-2-yl)-1-propenyl]thiophene-2-carboxamide, monohydrochloride;

methyl 2-[3-(hexahydro-7-imino-1H-azepin-2-yl)-1-propenyl]-5-methoxybenzoate, monohydrochloride;

methyl hexahydro-7-imino-b-(4-methylphenyl)-1H-azepine-2-propanoate, monohydrochloride;

methyl hexahydro-2-imino-b-(4-methylphenyl)-1H-azepine-3-propanoate, monohydrochloride;

methyl 3-[4-(trifluoromethyl)phenyl]propenoate methyl hexahydro-7-imino-b-(4-(trifluoromethyl)phenyl]-1H-azepine-2-propanoate, monohydrochloride;

(2-nitroethenyl)benzene hexahydro-7-(2-nitro-1-phenylethyl)-2H-azepin-2-imine, monohydrochloride;

3-(2-furanyl)propenenitrile b-(2-furanyl)hexahydro-7-imino-1H-azepine-2-propanenitrile, monohydrochloride;

methyl 3-(2-furanyl)propenoatemethyl β-(2-furanyl) hexahydro-7-imino-1H-azepine-2-propanoate, monohydrochloride;

(ethenylsulfonyl)benzene hexahydro-7-[2-phenylsulfonyl)ethyl]-2H-azepin-2-imine, monohydrochloride;

hexahydro-7-imino-β-phenyl-1H-azepine-2-ethanamine, bis(trifluoroacetate)salt;

N-[2-(hexahydro-7-imino-1H-azepin-2-yl)-2-phenylethyl]methanesulfonamide, monohydrochloride;

γ-(2-furanyl)hexahydro-7-imino-1H-azepine-2-propanamine, dihydrochloride;

N-[3-(2-furanyl)-3-(hexahydro-7-imino-1H-azepin-2-yl)propyl)methanesulfonamide, monohydrochloride;

methyl-β-(2,3-dihydroxypropyl)hexahydro-7-imino-1H-azepine-2-butanoate, monohydrochloride;

4-[(hexahydro-7-imino-1H-azepin-2-yl)-methyl]-3,4,5,6-tetrahydro-6O-hydroxy-2H-pyran-2-one, monohydrochloride;

hexahydro-7-[(4-morpholinyl)methyl]-2H-azepin-2-imine, dihydrochloride;
hexahydro-2-imino-7-[(4-morpholinyl)methyl]-1H-azepin-3-ol, dihydrochloride;
5-[(hexahydro-7-imino-1H-azepin-2-yl)methyl]4,5-dihydroisoxazol-3-amine, dihydrochloride;
5-[(hexahydro-7-imino-1H-azepin-2-yl)methyl]-1-methylpyrazolidin-3-one, dihydrochloride;
5-[(hexahydro-7-imino-1H-azepin-2-yl)methyl]-1,2-dihydro-3H-pyrazol-3-one, dihydrochloride;
(±) (cis) 4-methyl-5-(phenylmethyl)pyrrolidin-2-imine, monohydrochloride;
(±) (trans) 4-methyl-5-(phenylmethyl)pyrrolidin-2-imine, monohydrochloride;
(±) (cis) 5-(phenylmethyl)-4-(trifluoromethyl)pyrrolidin-2-imine, monohydrochloride;
(±) (trans) 5-(phenylmethyl)-4-(trifluoromethyl)pyrrolidin-2-imine, monohydrochloride;
4,4-dimethyl-5-(phenylmethyl)pyrrolidin-2-imine, monohydrochloride;
5-(phenylmethyl)pyrrolidin-2-imine, monohydrochloride;
(±) (cis) 5-[(1,3-dioxolan-2-yl)methyl]-4-(trifluoromethyl)pyrrolidin-2-imine, monohydrochloride;
(±) (trans) 5-[(1,3-dioxolan-2-yl)methyl]-4-(trifluoromethyl)pyrrolidin-2-imine, monohydrochloride;
(±) (trans) 2-[2-hydroxy-3-[5-imino-3-(trifluoromethyl)pyrrolidin-2-yl]propyl]oxazole-4-carboxylic acid, monohydrochloride;
(±) (cis) 2-(2-hydroxy-3-(5-imino-3-(trifluoromethyl)pyrrolidin-2-yl]propyl]oxazole-4-carboxylic acid, monohydrochloride;
(±) ethyl (trans) 2-[3-[5-imino-3-(trifluoromethyl)pyrrolidin-2-yl]propyl]oxazole-4-carboxylate, monohydrochloride;
(±) ethyl (cis) 2-(3-(5-imino-3-(trifluoromethyl)pyrrolidin-2-yl)propyl]oxazole-4-carboxylate, monohydrochloride;
(±) (trans) 2-[3-[5-imino-3-(trifluoromethyl)pyrrolidin-2-yl]propyl]oxazole-4-carboxylic acid, monohydrochloride;
(±) (cis) 2-[3-[5-imino-3-(trifluoromethyl)pyrrolidin-2-yl]propyl]oxazole-4-carboxylic acid, monohydrochloride;
(±) (cis) 5-[(4-methoxyphenyl)methyl]-3-methylpyrrolidin-2-imine, monohydrochloride;
(±) (trans) 5-[(4-methoxyphenyl)methyl]-3-methylpyrrolidin-2-imine, monohydrochloride;
hexahydro-3-[[(methoxyphenyl)methyl]thio]-2H-azepin-2-imine, trifluoroacetate salt;
2-[2-(2-iminohexahydro-1H-azepin-3-yl)ethyl-1-methylpyridinium chloride, monohydrochloride;
hexahydro-3-(2-(1-methylpiperidin-2-yl)ethyl]-2H-azepin-2-imine, dihydrochloride;
ethyl 5-[(hexahydro-2-imino-1H-azepin-3-yl)methyl]-4,5-dihydroisoxazole-3-carboxylate, trifluoroacetate salt;
cyclohexyl hexahydro-7-iminoazepine-2-carboxylate, monohydrochloride;
phenylmethyl hexahydro-7-iminoazepine-2-carboxylate, monohydrochloride;
hexahydro-7-[3-(phenylmethoxy)propyl]-2H-azepin-2-imine, trifluoroacetate salt;
N-[2-(hexahydro-7-imino-1H-azepin-2-yl)ethyl]benzenimidamide, bis(trifluoroacetate)salt;
N-[2-(hexahydro-7-imino-1H-azepin-2-yl)ethyl]-3,4,5,6-tetrahydro-2H-azepin-7-amine, bis(trifluoroacetate)salt;
N-[2-(hexahydro-7-imino-1H-azepin-2-yl)ethyl]-2,3,4,5-tetrahydropyridin-6-amine, bis (trifluoroacetate)salt;
N-[2-(hexahydro-7-imino-1H-azepin-2-yl)ethyl]-3,4-dihydro-2H-pyrrol-5-amine, bis(trifluoroacetate)salt;
N-[2-(hexahydro-7-imino-1H-azepin-2-yl)ethyl]benzenesulfonamide, trifluoroacetate salt;
N-[2-(hexahydro-7-imino-1H-azepin-2-yl)ethyl]benzenemethanesulfonamide, trifluoroacetate salt;
N-[2-(hexahydro-7-imino-1H-azepin-2-yl)ethyl]morpholin-4-amine, bis(trifluoroacetate)salt;
N-[2-(hexahydro-7-imino-1H-azepin-7-yl)ethyl]pyridin-2-methanamine, tris(trifluoroacetate)salt;
N-[2-(hexahydro-7-imino-1H-azepin-2-yl)ethyl]pyridin-3-methanamine, tris(trifluoroacetate)salt;
N-[2-(hexahydro-7-imino-1H-azepin-2-yl)ethyl]pyridin-4-methanamine, tris(trifluoroacetate) salt;
1-[2-(hexahydro-7-imino-1H-azepin-2-yl)ethyl]-1H-imidazole, bis(trifluoroacetate)salt;
1-[2-(hexahydro-7-imino-1H-azepin-2-yl)ethyl]-1H-1,2,4-triazole, bis(trifluoroacetate)salt;
4-[2-(hexahydro-7-imino-1H-azepin-2-yl)ethyl]-4H-1,2,4-triazole, bis(trifluoroacetate)salt;
1-[2-(hexahydro-7-imino-1H-azepin-2-yl)ethyl)-1H-tetrazole, trifluoroacetate salt;
methyl 1-[2-(hexahydro-7-imino-1l-azepin-2-yl)ethyl]pyrrolidine-2-carboxylate, bis(trifluoroacetate)salt;
4-[2-(hexahydro-7-imino-1H-azepin-2-yl)ethyl]morpholine, bis(trifluoroacetate)salt;
1-[2-(hexahydro-7-imino-1H-azepin-2-yl)ethyl]piperazine, bis(trifluoroacetate)salt;
1-[2-(hexahydro-7-imino-1H-azepin-2-yl)ethyl]-4-methylpiperazine, tris(trifluoroacetate)salt;
hexahydro-7-(2-nitro-1-phenyl)-2H-azepin-2-imine,
N-[2-(hexahydro-7-imino-1H-azepin-2-yl)-2-phenylethyl]guanidine, bis(trifluoroacetate)salt;
hexahydro-N-(hexahydro-1H-azepin-2-ylidene)-7-imino-β-phenyl-1H-azepine-2-ethanamine, bis(trifluoroacetate) salt;
hexahydro-7-(2-nitro-1-phenylpropyl)-2H-azepin-2-imine, trifluoroacetate salt;
hexahydro-7-imino-α-methyl-β-phenyl-1H-azepine-2-ethanamine, bis(trifluoroacetate)salt;
hexahydro-7-imino-α-methyl-β-phenyl-1H-azepine-2-ethanamine, bis(trifluoroacetate)salt;
hexahydro-7-imino-α-methyl-β-cyclohexyl-1H-azepine-2-ethanamine, bis(trifluoroacetate)salt;
7-(1-(1,3-benzodioxol-5-yl)-2-nitropropyl]hexahydro-2H-azepin-2-imine, trifluoroacetate salt;
β-(1,3-benzodioxol-5-yl)hexahydro-7-imino-α-methyl-1H-azepine-2-ethanamine, bis(trifluoroacetate)salt;
hexahydro-7-[2-nitro-1-(2-thienyl)ethyl]-2H-azepine, trifluoroacetate salt;
hexahydro-7-imino-β-(2-thienyl)-1H-azepine-2-ethanamine, bis(trifluoroacetate)salt;
hexahydro-7-imino-β-(3-thienyl)-1H-azepine-2-ethanamine, bis(trifluoroacetate)salt;

hexahydro-7-imino-β-(2-furanyl)-1H-azepine-2-ethanamine, bis(trifluoroacetate)salt;

hexahydro-N-(hexahydro-1H-azepin-2-ylidene-7-imino-β-(2-thienyl)-1H-azepine-2-ethanamine, bis(trifluoroacetate)salt;

hexahydro-7-imino-N-(2-pyrrolidinylidene)-β-(2-thienyl)-1H-azepine-2-ethanamine, bis(trifluoroacetate)salt;

hexahydro-7-[1-(1H-indol-3-yl)-2-nitroethyl]-2H-α-azepin-2-imine, trifluoroacetate salt;

hexahydro-7-imino-β-(1H-indol-3-yl)-1H-azepine-2-ethanamine, bis(trifluoroacetate) salt;

hexahydro-7-[(2-nitrophenyl)methyl]-2-azepin-2-imine, monohydrochloride;

2-[(hexahydro-7-imino-1H-azepin-2-yl)methyl]benzenamine, dihydrochloride;

2-[(hexahydro-7-imino-1H-azepin-2-yl)methyl]cyclohexanamine, dihydrochloride;

hexahydro-7-[(4-nitrophenyl)methyl]-2H-azepin-2-imine, monohydrochloride;

4-(hexahydro-7-imino-1H-azepin-2-yl)methyl]benzenamine, dihydrochloride;

hexahydro-7-[[4-(trifluoromethyl)phenyl]methyl]-2H-azepin-2-imine, monohydrochloride;

7-[(4-fluorophenyl)methyl]hexahydro-2H-azepin-2-imine, monohydrochloride;

hexahydro-7-[[3-(trifluoromethyl)phenyl]methyl]-2H-azepin-2-imine, monohydrochloride;

7-[(2,4-difluorophenyl)methyl]hexahydro-2H-azepin-2-imine, monohydrochloride;

7-[(2,6-dichlorophenyl)methyl]hexahydro-2H-azepin-2-imine, monohydrochloride;

hexahydro-7-[3-(2-thienyl)-2-propenyl]-2H-azepin-2-imine, monohydrochloride;

methyl α-[[(3,4-dihydro-2H-pyrrol-5-yl)amino]methyl]hexahydro-7-imino-1H-azepine-2-acetate, bis(trifluoroacetate)salt;

4,5-dihydro-5-[(hexahydro-7-imino-1H-azepin-2-yl)methyl]isoxazole-3-carboxylic acid, monohydrochloride;

ethyl 4,5-dihydro-5-[(hexahydro-7-imino-1H-azepin-2-yl)methyl]isoxazole-3-carboxylate, trifluoroacetate salt;

4,5-dihydro-5-[(hexahydro-7-imino-1H-azepin-2-yl)methyl]isoxazole-3-carboxamide, trifluoroacetate salt;

3-amino-5-[(hexahydro-7-imino-1H-azepine-2-yl)methyl]-tetrahydrofuran-2-one, bis(trifluoroacetate) salt;

7-[2-(2,2-dimethyldioxolan-4-yl)ethyl]hexahydro-2H-azepin-2-imine, monohydrochloride;

hexahydro-7-[2-(4-pyridinyl)ethyl]-2H-azepin-2-imine, monohydrochloride;

4-[2-(hexahydro-7-imino-1H-azepin-2-yl)ethyl]pyridinium-1-oxide, bis(trifluoroacetate)salt;

4-[2-(hexahydro-7-imino-1H-azepin-2-yl)ethyl]-1-methylpyridinium chloride, monohydrochloride salt;

hexahydro-7-(2-(2-pyridinyl)ethyl]-2H-azepin-2-imine, monohydrochloride;

2-[2-(hexahydro-7-imino-1H-azepin-2-yl)ethyl]-1-methylpyridinium chloride, bis trifluoroacetate salt;

hexahydro-7-[2-(1-methylpiperidin-2-yl)ethyl]-2H-azepin-2-imine, dihydrochloride;

hexahydro-7-[2-(2-piperidinyl)ethyl]-2H-azepin-2-imine, dihydrochloride;

hexahydro-7-[2-(4-piperidinyl)ethyl]-2H-azepin-2-imine, dihydrochloride;

hexahydro-7-[2-(4-piperidinyl)ethyl]-2H-azepin-2-imine, dihydrochloride;

hexahydro-7-[2-(1-(methylsulfonyl)piperidin-2-yl]ethyl]-2H-azepin-2-imine, trifluoroacetate salt;

3-(hexahydro-7-imino-1H-azepin-2-yl)-1-(4-morpholinyl)propan-1-one, trifluoroacetate salt;

6-(phenylmethyl)piperidin-2-imine, monohydrochloride;

6-(cyclohexylmethyl)piperidin-2-imine, monohydrochloride;

trans-N-[3-(5-imino-3-methylpyrrolidin-2-yl)ethyl]phenylmethylamine, dihydrochloride;

N-[2-(hexahydro-7-imino-1H-azepin-2-yl)ethyl]-4,5-dihydro-1H-imidazol-2-amine, bis(trifluoroacetate) salt;

N-[2-(hexahydro-7-imino-1H-azepin-2-yl)ethyl]-1,4,5,6-tetrahydropyrimidin-2-amine, bis(trifluoroacetate)salt;

N-[2-(hexahydro-7-imino-1-H-azepin-2-yl)ethyl]-3,4-dihydro-4-methyl-2H-pyrrol-5-amine, bis(trifluoroacetate)salt;

N-[2-(hexahydro-7-imino-1-H-azepin-2-yl)ethyl]-3,4-dihydro-2-methyl-2H-pyrrol-5-amine, bis(trifluoroacetate)salt;

(±) cis-5-imino-3-methyl-N-(phenylmethyl)pyrrolidine-2-ethanamine, dihydrochloride;

(±) trans-5-imino-N-(phenylmethyl)-3-(trifluoromethyl)pyrrolidine-2-ethanamine, dihydrochloride;

(±) cis-5-imino-N-(phenylmethyl)-3-(trifluoromethyl)pyrrolidine-2-ethanamine, dihydrochloride;

(±) trans-5-imino-3-methyl-N-[(2-thienyl)methyl]pyrrolidine-2-ethanamine, dihydrochloride;

(±) cis-5-imino-N-[(2-thienyl)methyl]-3-(trifluoromethyl)-pyrrolidine-2-ethanamine, dihydrochloride;

(±) cis-5-imino-3-methyl-N-[(2-thienyl)methyl]pyrrolidine-2-ethanamine, dihydrochloride;

(±) trans-5-imino-N-[(2-thienyl)methyl]-3-(trifluoromethyl)-pyrrolidine-2-ethanamine, dihydrochloride;

(±) trans-5-imino-3-methyl-α-phenylpyrrolidine-2-ethanamine, dihydrochloride;

(±) cis-5-imino-3-methyl-α-phenylpyrrolidine-2-ethanamine, dihydrochloride;

(±) trans-5-imino-3-methyl-N-(phenylmethyl)pyrrolidine-2-propanamine, dihydrochloride;

(±) cis-5-imino-3-methyl-N-(phenylmethyl)pyrrolidine-2-propanamine, dihydrochloride;

(±) trans-5-imino-a,3-dimethyl-N-(phenylmethyl)pyrrolidine-2-propanamine, dihydrochloride;

(±) cis-5-imino-a,3-dimethyl-N-(phenylmethyl)pyrrolidine-2-propanamine, dihydrochloride;

hexahydro-7-imino-α-[[(3,4-dihydro-2H-pyrrol-5-yl)amino]methyl]-1H-azepine-2-acetamide, bis(trifluoroacetate)salt;

β-cyclopropylhexahydro-7-imino-1H-azepine-2-ethanamine, bis(trifluoroacetate)salt;

hexahydro-7-imino-α-(1H-imidazol-5-yl)-1H-azepine-2-ethanamine, bis(trifluoroacetate)salt;

4-[(hexahydro-7-imino-1H-azepin-2-yl)methyl]cyclohexanamine, dihydrochloride;

α-aminohexahydro-7-imino-β-phenyl-1H-azepine-2-propanoic acid, dihydrochloride;

α-aminohexahydro-7-amino-β-(2-thienyl)-1H-azepine-2-propanoic acid, dihydrochloride;

α-(aminomethyl)hexahydro-7-imino-1H-azepine-2-acetonitrile, bis(trifluoroacetate)salt;

5-imino-3-methylene-N-(phenylmethyl)pyrrolidine-2S-ethanamine, dihydrochloride;

β-ethynylhexahydro-7-imino-N-(3,4-dihydro-2H-pyrrol-5-yl)-1H-azepine-2-ethanamine, bis(trifluoroacetate) salt;

hexahydro-β-(1H-imidazol-1-yl)-7-imino-N-(3,4-dihydro-2H-pyrrol-5-yl)-1H-azepine-2-ethanamine, bis(trifluoroacetate)salt;

3-[[2-(hexahydro-7-imino-1H-azepin-2-yl)-2-(2-thienyl) ethyl]amino]alanine, trihydrochloride.

7. A pharmaceutical composition comprising a compound of claim 1, 2, 3, 4, 5 or 6 or a compound of claim 1 wherein X is $(CH_2)_p$ p=1, A is $(CH_2)_q$, B is $(CH_2)_v$, q, v=1, $R^2$, $R^3$, $R^4$, $R^6$ are H, L is $CH_2$, $R^1$ is phenyl and together with at least one non-toxic pharmaceutical acceptable carrier.

8. A compound having the formula:

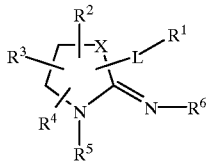

and salts and pharmaceutically acceptable esters thereof, wherein:

$R^1$ is selected from the group consisting of $C_3$–$C_{10}$-cycloalkyl, $C_4$–$C_{10}$-heterocyclyl, and aryl, which may optionally be substituted by one or more of $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, amino, aminoalkyl, aminoaryl, carboxyl, carboalkoxy, carboaryloxy, aminocarbonylalkoxy, aminocarbonylamino, wherein all said substitutions may be optionally substituted with one or more of the following $C_1$–$C_{10}$-alkyl, amino, aminoalkyl, aminoacyl, carboxyl, carboalkoxy, carboaryloxy, hydroxy, $C_1$–$C_{10}$-alkoxy, and L is selected from the group consisting of $C_1$–$C_{10}$-alkylene, $C_2$–$C_{10}$-alkenylene, $C_2$–$C_{10}$-alkynylene, which may optionally be substituted by one or more of the following: $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, amino, aminoalkyl, aminoaryl, carboxyl, carboalkoxy, carboaryloxy, aminocarbonylalkoxy, aminocarbonylamino, wherein all said substitutions may be optionally substituted with one or more of the following: $C_1$–$C_{10}$-alkyl, amino, aminoalkyl, aminoacyl, carboxyl, carboalkoxy, carboaryloxy, hydroxy, $C_1$–$C_{10}$-alkoxy, nitro, amidino, guanidino, substituted guanidino:

X is selected from the group consisting of NH, O, S $(CH_2)_p$, CH=CH;

p=0 to 3;

$R^2$, $R^3$, and $R^4$ are independently selected from hydrogen, $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, amino, aminoalkyl, aminoaryl, carboxyl, carboalkoxy, carboaryloxy, aminocarbonylalkoxy, aminocarbonylamino, wherein all said substitutions may be optionally substituted with one or more of the following: $C_1$–$C_{10}$-alkyl, amino, aminoalkyl, aminoacyl, carboxyl, carboalkoxy, carboaryloxy, hydroxy, $C_1$–$C_{10}$-alkoxy, and $R^5$, $R^6$ are independently selected from the group consisting of hydrogen, hydroxy, and alkyloxy, except the compounds wherein X is S, $R^2$, $R^3$, $R^4$ are H and $R^1$ is

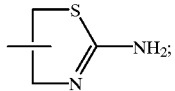

and except the compound wherein X is $(CH_2)_p$, p is 1, $R^2$–$R^6$ are H, L is $CH_2$, $R^1$ is phenyl.

9. A compound having the formula

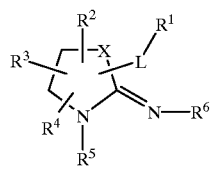

and salts, pharmaceutically-acceptable esters thereof, wherein:

$R^1$ is selected from the group consisting of $C_3$–$C_{10}$-cycloalkyl, $C_4$–$C_{10}$-heterocyclyl, and aryl, which may optionally be substituted by one or more of $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, amino, aminoalkyl, aminoaryl, carboxyl, carboalkoxy, carboaryloxy, aminocarbonylalkoxy, aminocarbonylamino, wherein all said substitutions may be optionally substituted with one or more of the following: $C_1$–$C_{10}$-alkyl, amino, aminoalkyl, aminoacyl, carboxyl, carboalkoxy, carboaryloxy, hydroxy, $C_1$–$C_{10}$-alkoxy, and L is selected from the group consisting of $C_1$–$C_{10}$-alkylene, $C_2$–$C_{10}$-alkenylene, $C_2$–$C_{10}$-alkynylene, which may optionally be substituted by one or more of the following: $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, amino, aminoalkyl, aminoaryl, carboxyl, carboalkoxy, carboaryloxy, aminocarbonylalkoxy, aminocarbonylamino, wherein all said substitutions may be optionally substituted with one or more of the following: $C_1$–$C_{10}$-alkyl, amino, aminoalkyl, aminoacyl, carboxyl, carboalkoxy, carboaryloxy, hydroxy, $C_1$–$C_{10}$-alkoxy, nitro, amidino, guanidino, substituted guanidino;

X is selected from the group consisting of $(CH_2)_p$;

p=1 to 3;

$R^2$, $R^3$, and $R^4$ are independently selected from hydrogen, $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, amino, aminoalkyl, aminoaryl, carboxyl, carboalkoxy, carboaryloxy, aminocarbonylalkoxy, aminocarbonylamino, wherein all said substitutions may be optionally substituted with one or more of the following: $C_1$–$C_{10}$-alkyl, amino, aminoalkyl, aminoacyl, carboxyl, carboalkoxy, carboaryloxy, hydroxy, $C_1$–$C_{10}$-alkoxy, and $R^5$, $R^6$ are independently selected from the group consisting of hydrogen, hydroxy, and alkyloxy.

10. The compound as defined in claim 9 wherein the compound is selected from a preferred group consisting of N-[2-(hexahydro-7-imino-1H-azepin-2-yl)ethyl]-3,4-dihydro-2H-pyrrol-5-amine, bis(trifluoroacetate)salt; hexahydro-7-imino-β-phenyl-1H-azepine-2-ethanamine, bis(trifluoroacetate)salt; hexahydro-7-imino-β-(2-thienyl)-1H-azepine-2-ethanamine, bis(trifluoroacetate)salt; hexahydro-7-imino-β-(3-thienyl)-1H-azepine-2-ethanamine, bis(trifluoroacetate)salt; hexahydro-7-imino-β-(2-furanyl)-1H-azepine-2-ethanamine, bis(trifluoroacetate)salt; N-(2-(hexahydro-7-imino-1H-azepin-2-yl)-2-phenylethyl)guanidine, bis(trifluoroacetate)salt; 4,5-dihydro-5-[(hexahydro-7-imino-1H-azepin-2-yl)methyl]isoxazole-3-carboxylic acid, monohydrochloride; 7-[(4,5-dihydro-3-phenylisoxazolyl-5-yl)methyl]hexahydro-2H-azepine-2-imine, monotrifluoroacetic acid salt; hexahydro-7-[2-(4-pyridinyl)ethyl]-2H-azepin-2-imine, monohydrochloride; hexahydro-7-[2-(1-methylpiperidin-2-yl)ethyl]-2H-azepin-2-imine, dihydrochloride; hexahydro-7-[2-(2-piperidinyl)ethyl]-2H-azepin-2-imine, dihydrochloride; [2-(hexahydro-7-imino-1H-azepin-2-yl)ethyl]-1H-tetrazole, trifluoroacetate salt; N-[2-(hexahydro-7-imino-1H-azepin-2-yl)ethyl]-3,4,5,6-tetrahydro-2H-azepin-7-amine, bis(trifluoroacetate)salt; N-[2-(hexahydro-7-imino-1H-azepin-2-yl)ethyl]-2,3,4,5-tetrahydropyridin-6-amine, bis(trifluoroacetate)salt; hexahydro-N-(hexahydro-1H-azepin-2-ylidene)-7-imino-β-phenyl-1H-azepine-2-ethanamine, bis(trifluoroacetate)salt; hexahydro-N-(hexahydro-1H-azepin-2-ylidene)-7-imino-β-(2-thienyl)-1H-azepine-2-ethanamine, bis(trifluoroacetate)salt; N-[2-(hexahydro-7-imino-1H-azepin-2-yl)ethyl]-4,5-dihydro-1H-imidazol-2-amine, bis(trifluoroacetate)salt, N-[2-(hexahydro-7-imino-1H-azepin-2-yl)ethyl]-1,4,5,6-tetrahydropyrimidin-2-amine, bis(trifluoroacetate)salt; 2-[(hexahydro-7-imino-1H-azepin-2-yl)methyl]benzenamine, dihydrochloride; N-[2-(hexahydro-7-imino-1H-azepin-2-yl)ethyl]-3,4-dihydro-2-methyl-2-pyrrol-5-amine, bis(trifluoroacetate)salt; N-[2-(hexahydro-7-imino-1H-azepin-2-yl)ethyl]-3,4-dihydro-4-methyl-2H-pyrrol-5-amine, bis(trifluoroacetate)salt; 2-[(hexahydro-7-imino-1H-azepin-2-yl)methyl]cyclohexanamine, dihydrochloride; 6-(cyclohexylmethyl)piperidin-2-imine, monohydrochloride; (±)(trans) 4-methyl-5-(phenylmethyl)pyrrolidin-2-imine, monohydrochloride; trans-N-[3-(5-imino-3-methylpyrrolidin-2-yl)propyl]benzenamine, dihydrochloride.

11. The compound as in claim 9 wherein the compound is selected from a most preferred group consisting of hexahydro-7-[2-(2-piperidinyl)ethyl]-2H-azepin-2-imine, dihydrochloride; N-[2-(hexahydro-7-imino-1H-azepin-2-yl)ethyl]-3,4-dihydro-2H-pyrrol-5-amine, bis(trifluoroacetate)salt; hexahydro-7-imino-β-phenyl-1H-azepine-2-ethanamine, bis(trifluoroacetate) salt; 1-[2-(hexahydro-7-imino-1H-azepin-2-yl)ethyl]-1H-tetrazole, trifluoroacetate salt; hexahydro-7-imino-β-(2-thienyl)-1H-azepine-2-ethanamine, bis(trifluoroacetate)salt; trans-N-[3-(5-imino-3-methylpyrrolidin-2-yl)ethyl])phenylmethylamine, dihydrochloride; hexahydro-7-imino-N-(2-pyrrolidinylidene)-β-(2-thienyl)-1H-azepine-2-ethanamine, bis(trifluoroacetate)salt; hexahydro-N-(hexahydro-1H-azepin-2-ylidene)-7-imino-β-phenyl-1-H-azepine-2-ethanamine, bis(trifluoroacetate)salt; and 2-[(hexahydro-7-imino-1H-azepin-2-yl)methyl]cyclohexanamine, dihydrochloride.

12. The compound as in claim 11 wherein the compound is hexahydro-7-[2-(2-piperidinyl)ethyl]-2H-azepin-2-imine, dihydrochloride.

13. The compound as in claim 11 wherein the compound is N-[2-(hexahydro-7-imino-1H-azepin-2-yl)ethyl]-3,4-dihydro-2H-pyrrol-5-amine, bis(trifluoroacetate)salt.

14. The compound as in claim 11 wherein the compound is hexahydro-7-imino-β-phenyl-1H-azepine-2-ethanamine, bis(trifluoroacetate)salt.

15. The compound as in claim 11 wherein the compound is 1-[2-(hexahydro-7-imino-1H-azepin-2-yl)ethyl]-1H-tetrazole, trifluoroacetate salt.

16. The compound as in claim 11 wherein the compound is trans-N-[3-(5-imino-3-methylpyrrolidin-2-yl)ethyl]phenylmethylamine, dihydrochloride.

17. The compound as in claim 11 wherein the compound is hexahydro-7-imino-β-(2-thienyl)-1H-azepine-2-ethanamine, bis(trifluoroacetate)salt.

18. The compound as in claim 11 wherein the compound is hexahydro-N-(hexahydro-1H-azepin-2-ylidene)-7-imino-β-phenyl-1H-azepine-2-ethanamine, bis(trifluoroacetate) salt.

19. The compound as in claim 11 wherein the compound is hexahydro-7-imino-N-(2-pyrrolidinylidene)-β-(2-thienyl)-1H-azepine-2-ethanamine, bis(trifluoroacetate)salt.

20. The compound as in claim 11 wherein the compound is 2-[(hexahydro-7-imino-1H-azepin-2-yl)methyl]cyclohexanamine, dihydrochloride.

21. A method of inhibiting nitric oxide synthesis in a subject in need of such inhibition by administering a therapeutically effective amount of a compound of claim 1, 2, 3, 4, 5 or 6 wherein X is $(CH_2)_p$, p=1, A is $(CH_2)_q$, q=1, B is $(CH_2)_v$, v=1, $R^2$, $R^3$, $R^4$, $R^6$ are H, L is $CH_2$, and $R^1$ is phenyl.

22. A method of selectively inhibiting nitric oxide synthesis produced by inducible NO synthase over NO produced by the constitutive forms of NO synthase in a subject in need of such inhibition by administering a therapeutically effective amount of a compound of claim 1, 2, 3, 4, 5 or 6 wherein X is $(CH_2)_p$, p=1, A is $(CH_2)_q$, q=1, B is $(CH_2)_v$, v=1, $R^2$, $R^3$, $R^4$, $R^6$ are H, L is $CH_2$, and $R^1$ is phenyl.

23. A method of lowering nitric oxide levels in a subject in need of such by administering a therapeutically effective amount of a compound of claim 1, 2, 3, 4, 5 or 6 wherein X is $(CH_2)_p$, p=1, A is $(CH_2)_q$, q=1, B is $(CH_2)_v$, v=1, $R^2$, $R^3$, $R^4$, $R^6$ are H, L is $CH_2$, and $R^1$ is phenyl.

24. A method of lowering nitric oxide levels in a subject in need of such by administering a therapeutically effective amount of a pharmaceutical composition comprising a compound of claim 1, 2, 3, 4, 5, or 6 and together with at least one non-toxic pharmaceutical acceptable carrier wherein X is $(CH_2)_p$, p=1, A is $(CH_2)_q$, q=1, B is $(CH_2)_v$, v=1, $R^2$, $R^3$, $R^4$, $R^6$ are H, L is $CH_2$, and $R^1$ is phenyl.

* * * * *